(12) United States Patent
Vicker et al.

(10) Patent No.: US 7,230,020 B2
(45) Date of Patent: Jun. 12, 2007

(54) 11β-HYDROXYSTEROID DEHYDROGENASE INHIBITORS

(75) Inventors: Nigel Vicker, Maidenhead (GB); Su Xiangdong, Bath (GB); Dharshini Ganeshapillai, Slough (GB); Atul Purohit, Harrow (GB); Michael John Reed, London (GB); Barry Victor Lloyd Potter, Bath (GB)

(73) Assignee: Sterix Limited, Berkshire (GB)

( * ) Notice: Subject to any disclaimer, the term of this patent is extended or adjusted under 35 U.S.C. 154(b) by 118 days.

(21) Appl. No.: 10/970,064

(22) Filed: Oct. 22, 2004

(65) Prior Publication Data

US 2005/0227987 A1   Oct. 13, 2005

Related U.S. Application Data

(60) Provisional application No. 60/513,217, filed on Oct. 23, 2003.

(30) Foreign Application Priority Data

Oct. 23, 2003   (GB) ................... 0324792.1

(51) Int. Cl.
  *A61K 31/423* (2006.01)
  *A61K 31/426* (2006.01)
  *C07D 263/56* (2006.01)
  *C07D 277/64* (2006.01)
(52) U.S. Cl. ............... 514/367; 514/375; 548/170; 548/217
(58) Field of Classification Search ............... None
  See application file for complete search history.

(56) References Cited

U.S. PATENT DOCUMENTS

| 4,659,738 A * | 4/1987 | Miller et al. ........... 514/514 |
| 2004/0137472 A1* | 7/2004 | Kole ............... 435/6 |

FOREIGN PATENT DOCUMENTS

| EP | 1 378 751 A2 | 1/2004 |
| GB | 822947 A | 11/1959 |
| GB | 828963 A | 2/1960 |
| GB | 1198941 A | 7/1970 |
| WO | WO 01/90090 A1 | 11/2001 |
| WO | WO 01/90092 A1 | 11/2001 |
| WO | WO 03/043999 A1 | 5/2003 |
| WO | WO 03/044000 A1 | 5/2003 |
| WO | WO 03/044009 A1 | 5/2003 |

OTHER PUBLICATIONS

Sener et al., "Synthesis and microbiological activity of some novel 5-benzamido- and 5-phenylacetamido- substituted 2-phenylbenzoxazole derivatives," IL Farmco, vol. 55, pp. 397-405 (2000).*
Sener E. A. et al., *Il Farmaco* (2000) vol. 55 pp. 397-405.
Chan M. F. et al., *Bioorganic and Medical Chemistry Letters* (1996) vol. 6, No. 20, pp. 2393-2398.
Stein P. D. et al., *J Medicinal Chemistry* (1995) vol. 38 No. 8, pp. 1344-1354.
Hammond M.L. et al., *J Medicinal Chemistry* (1990) vol. 33, No. 3, pp. 908-918.
Yoshida Y. et al., *Bioorganic and Medical Chemistry* (1999) vol. 7, No. 11, pp. 2647-2666.
Grehn L et al., *Tetrahedron* (1999) vol. 55, No. 15, pp. 4843-4852.
Database Beilstein: Beilstein Registry No. 6416404 (Abuzar et al., *Z. Naturforsch. B. Anorg. Chem. Org. Chem.* (1981) vol. 36, No. 1, pp. 108-111).
Database Beilstein: Beilstein Registry No. 2784754 (2001).
Jensen K.A. et al., *Acta Chemica Scandinavica* (1974) vol. 28, pp. 1-4.

* cited by examiner

*Primary Examiner*—Kamal A. Saeed
*Assistant Examiner*—Andrew B. Freistein
(74) *Attorney, Agent, or Firm*—Steptoe & Johnson LLP

(57) ABSTRACT

A compound having Formula I $$R_1—Z—R_2 \text{ Formula I}$$

wherein $R_1$ is an optionally substituted phenyl ring; $R_2$ is or comprises an optionally substituted aromatic ring; and Z is —X—Y—L— or —Y—X—L— wherein either X is selected from —S(=O)(=O)— and —C(=O)—; and Y is —NR$_3$—; or X is selected from —S(=O)(=O)— and —S—, and Y is —C(R$_4$)(R$_5$)—; L is an optional linker; and $R_3$, $R_4$ and $R_5$ are each independently selected from H and hydrocarbyl; and wherein when $R_2$ comprises the following structural moiety

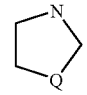

wherein Q is an atom selected from the group consisting of S, O, N and C; the compound is selected from compounds of the formulae $R_1$—C(=O)—NR$_3$—L—R$_2$; $R_1$—S(=O)(=O)—C(R$_4$)(R$_5$)—L—R$_2$; $R_1$—S—C(R$_4$)(R$_5$)—L—R$_2$; $R_1$—NR$_3$—S(=O)(=O)—L—R$_2$; $R_1$—NR$_3$—C(=O)—L—R$_2$; $R_1$—C(R$_4$)(R$_5$)—S(=O)(=O)—L—R$_2$; and $R_1$—C(R$_4$)(R$_5$)—S—L—R$_2$.

10 Claims, 25 Drawing Sheets

11β-HYDROXYSTEROID DEHYDROGENASE INHIBITORS

This application claims the benefit of priority from U.S. Provisional Application No. 60/513,217, filed Oct. 23, 2003, and United Kingdom Application No. 0324792.1, filed Oct. 23, 2003, both of which are incorporated herein by reference in their entirety.

FIELD OF INVENTION

The present invention relates to a compound. In particular the present invention provides compounds capable of inhibiting 11β-hydroxysteroid dehydrogenase (11β-HSD).

INTRODUCTION

The Role of Glucocorticoids

Glucocorticoids are synthesised in the adrenal cortex from cholesterol. The principle glucocorticoid in the human body is cortisol. This hormone is synthesised and secreted in response to the adrenocortictrophic hormone (ACTH) from the pituitary gland in a circadian, episodic manner, but the secretion of this hormone can also be stimulated by stress, exercise and infection. Cortisol circulates mainly bound to transcortin (cortisol binding protein) or albumin and only a small fraction is free (5-10%) for biological processes [1].

Cortisol has a wide range of physiological effects, including regulation of carbohydrate, protein and lipid metabolism, regulation of normal growth and development, influence on cognitive function, resistance to stress and mineralocorticoid activity. Cortisol works in the opposite direction compared to insulin meaning a stimulation of hepatic gluconeogenesis, inhibition of peripheral glucose uptake and increased blood glucose concentration. Glucocorticoids are also essential in the regulation of the immune response. When circulating at higher concentrations glucocorticoids are immunosuppressive and are used pharmacologically as anti-inflammatory agents.

Glucocorticoids like other steroid hormones are lipophilic and penetrate the cell membrane freely. Cortisol binds, primarily, to the intracellular glucocorticoid receptor (GR) that then acts as a transcription factor to induce the expression of glucocorticoid responsive genes, and as a result of that protein synthesis.

The Role of the 11β-HSD Enzyme

The conversion of cortisol (F) to its inactive metabolite cortisone (E) by 11β-HSD was first described in the 1950's, however it was not until later that the biological importance for this conversion was suggested [2]. In 1983 Krozowski et al. showed that the mineralocorticoid receptor (MR) has equal binding affinities for glucocorticoids and mineralocorticoids [3]. Because the circulating concentration of cortisol is a 100 times higher than that of aldosterone and during times of stress or high activity even more, it was not clear how the MR remained mineralocorticoid specific and was not constantly occupied by glucocorticoids. Earlier Ulick et al. [4] had described the hypertensive condition known as, "apparent mineralocorticoid excess" (AME), and observed that whilst secretion of aldosterone from the adrenals was in fact low the peripheral metabolism of cortisol was disrupted. These discoveries lead to the suggestion of a protective role for the enzymes. By converting cortisol to cortisone in mineralocorticoid dependent tissues 11β-HSD enzymes protects the MR from occupation by glucocorticoids and allows it to be mineralcorticoid specific. Aldosterone itself is protected from the enzyme by the presence of an aldehyde group at the C-18 position.

Congenital defects in the 11β-HSD enzyme results in over occupation of the MR by cortisol and hypertensive and hypokalemic symptoms seen in AME.

Localisation of the 11β-HSD showed that the enzyme and its activity is highly present in the MR dependent tissues, kidney and parotid. However in tissues where the MR is not mineralocorticoid specific and is normally occupied by glucocorticoids, 11 β-HSD is not present in these tissues, for example in the heart and hippocampus [5]. This research also showed that inhibition of 11 β-HSD caused a loss of the aldosterone specificity of the MR in these mineralocorticoid dependent tissues.

It has been shown that two iso-enzymes of 11 β-HSD exist. Both are members of the short chain alcohol dehydrogenase (SCAD) superfamily which have been widely conserved throughout evolution. 11 β-HSD type 2 acts as a dehydrogenase to convert the secondary alcohol group at the C-11 position of cortisol to a secondary ketone, so producing the less active metabolite cortisone. 11 β-HSD type 1 is thought to act mainly in vivo as a reductase, that is in the opposite direction to type 2 [6] [see below]. 11 β-HSD type 1 and type 2 have only a 30% amino acid homology.

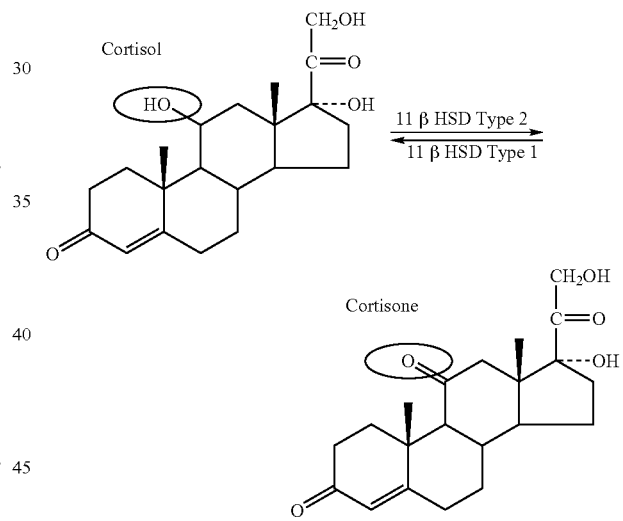

The intracellular activity of cortisol is dependent on the concentration of glucocorticoids and can be modified and independently controlled without involving the overall secretion and synthesis of the hormone.

The Role of 11 β-HSD Type 1

The direction of 11 β-HSD type 1 reaction in vivo is generally accepted to be opposite to the dehydrogenation of type 2. In vivo homozygous mice with a disrupted type 1 gene are unable to convert cortisone to cortisol, giving further evidence for the reductive activity of the enzyme [7]. 11 β-HSD type 1 is expressed in many key glucocorticoid regulated tissues like the liver, pituitary, gonad, brain, adipose and adrenals, however, the function of the enzyme in many of these tissues is poorly understood [8].

The concentration of cortisone in the body is higher than that of cortisol, cortisone also binds poorly to binding globulins, making cortisone many times more biologically available. Although cortisol is secreted by the adrenal cortex, there is a growing amount of evidence that the intracellular conversion of E to F may be an important mechanism in regulating the action of glucocorticoids [9].

It may be that 11 β-HSD type 1 allows certain tissues to convert cortisone to cortisol to increase local glucocorticoid activity and potentiate adaptive response and counteracting the type 2 activity that could result in a fall in active glucocorticoids [10]. Potentiation of the stress response would be especially important in the brain and high levels of 11 β-HSD type 1 are found around the hippocampus, further proving the role of the enzyme. 11 β-HSD type 1 also seems to play an important role in hepatocyte maturation [8]. Another emerging role of the 11 β-HSD type 1 enzyme is in the detoxification process of many non-steroidal carbonyl compounds, reduction of the carbonyl group of many toxic compounds is a common way to increase solubility and therefore increase their excretion. The 11 β-HSD type 1 enzyme has recently been shown to be active in lung tissue [11]. Type 1 activity is not seen until after birth, therefore mothers who smoke during pregnancy expose their children to the harmful effects of tobacco before the child is able to metabolically detoxify this compound.

The Role of 11 β-HSD Type 2

As already, stated earlier the 11 β-HSD type 2 converts cortisol to cortisone, thus protecting the MR in many key regulatory tissues of the body. The importance of protecting the MR from occupation by glucocorticoids is seen in patients with AME or liquorice intoxification. Defects or inactivity of the type 2 enzyme results in hypertensive syndromes, and research has shown that patients with an hypertensive syndrome have an increased urinary excretion ratio of cortisol:cortisone. This along with a reported increase in the half life of radiolabelled cortisol suggests a reduction of 11 β-HSD type 2 activity [12].

Rationale for the Development of 11 β-HSD Inhibitors

As said earlier cortisol opposes the action of insulin meaning a stimulation of hepatic gluconeogenesis, inhibition of peripheral glucose uptake and increased blood glucose concentration. The effects of cortisol appear to be enhanced in patients suffering from glucose intolerance or diabetes mellitus. Inhibition of the enzyme 11 β-HSD type 1 would increase glucose uptake and inhibit hepatic gluconeogenesis, giving a reduction in circulatory glucose levels. The development of a potent 11 β-HSD type 1 inhibitor could therefore have considerable therapeutic potential for conditions associated with elevated blood glucose levels.

An excess in glucocorticoids can result in neuronal dysfunctions and also impair cognitive functions. A specific 11 β-HSD type 1 inhibitor might be of some importance by reducing neuronal dysfunctions and the loss of cognitive functions associated with ageing, by blocking the conversion of cortisone to cortisol.

Glucocorticoids also have an important role in regulating part of the immune response [13]. Glucocorticoids can suppress the production of cytokines and regulate the receptor levels. They are also involved in determining, whether T-helper (Th) lymphocytes progress into either Th1 or Th2 phenotype. These two different types of Th cells secrete a different profile of cytokines, Th2 is predominant in a glucocorticoid environment. By inhibiting 11 β-HSD type 1, Th1 cytokine response would be favoured. It is also possible to inhibit 11 β-HSD type 2, thus by inhibiting the inactivation of cortisol, it may be possible to potentiate the anti-inflammatory effects of glucocorticoids.

Aspects of the invention are defined in the appended claims.

SUMMARY ASPECTS OF THE PRESENT INVENTION

In one aspect the present invention provides a compound having Formula I

   Formula I wherein $R_1$ is an optionally substituted phenyl ring; $R_2$ is or comprises an optionally substituted aromatic ring; and Z is —X—Y—L— or —Y—X—L— wherein either X is selected from —S(=O)(=O)— and —C(=O)—, and Y is —$NR_3$—; or X is selected from —S(=O)(=O)— and —S—, and Y is —C($R_4$)($R_5$)—; L is an optional linker; and $R_3$, $R_4$ and $R_5$ are each independently selected from H and hydrocarbyl; and wherein when $R_2$ comprises the following structural moiety

wherein Q is an atom selected from the group consisting of S, O, N and C; the compound is selected from compounds of the formulae $R_1$—C(=O)—$NR_3$—L—$R_2$; $R_1$—S(=O)(=O)—C($R_4$)($R_5$)—L—$R_2$; $R_1$—S—C($R_4$)($R_5$)—L—$R_2$; $R_1$—$NR_3$—S(=O)(=O)—L—$R_2$; $R_1$—$NR_3$—C(=O)—L—$R_2$; $R_1$—C($R_4$)($R_5$)—S(=O)(=O)—L—$R_2$; and $R_1$—C($R_4$)($R_5$)—S—L—$R_2$.

In one aspect the present invention provides a pharmaceutical composition comprising
(i) a compound having Formula I

   Formula I wherein $R_1$ is an optionally substituted phenyl ring; $R_2$ is or comprises an optionally substituted aromatic ring; and Z is —X—Y—L— or —Y—X—L— wherein either X is selected from —S(=O)(=O)— and —C(=O)—, and Y is —$NR_3$—; or X is selected from —S(=O)(=O)— and —S—, and Y is —C($R_4$)($R_5$)—; L is an optional linker; and $R_3$, $R_4$ and $R_5$ are each independently selected from H and hydrocarbyl; and wherein when $R_2$ comprises the following structural moiety

wherein Q is an atom selected from the group consisting of S, O, N and C; the compound is selected from compounds of the formulae $R_1$—C(=O)—$NR_3$—L—$R_2$; $R_1$—S(=O)(=O)—C($R_4$)($R_5$)—L—$R_2$; $R_1$—S—C($R_4$)($R_5$)—L—$R_2$; $R_1$—$NR_3$—S(=O)(=O)—L—$R_2$; $R_1$—$NR_3$—C(=O)—L—$R_2$; $R_1$—C($R_4$)($R_5$)—S(=O)(=O)—L—$R_2$; and $R_1$—C($R_4$)($R_5$)—S—L—$R_2$.
(ii) optionally admixed with a pharmaceutically acceptable carrier, diluent, excipient or adjuvant, or mixtures thereof.

In one aspect the present invention provides a compound for use in medicine wherein the compound has Formula I

   Formula I wherein $R_1$ is an optionally substituted phenyl ring; $R_2$ is or comprises an optionally substituted aromatic ring; and Z is —X—Y—L— or —Y—X—L— wherein either X is selected from —S(=O)(=O)— and —C(=O)—, and Y is —NR₃—; or X is selected from —S(=O)(=O)— and —S—, and Y is —C(R₄)(R₅)—; L is an optional linker; and R₃, R₄ and R₅ are each independently selected from H and hydrocarbyl; and wherein when R₂ comprises the following structural moiety

wherein, Q is an atom selected from the group consisting of S, O, N and C; the compound is selected from compounds of the formulae R₁—C(=O)—NR₃—L—R₂; R₁—S(=O)(=O)—C(R₄)(R₅)—L—R₂; R₁—S—C(R₄)(R₅)—L—R₂; R₁—NR₃—S(=O)(=O)—L—R₂; R₁—NR₃—C(=O)—L—R₂; R₁—C(R₄)(R₅)—S(=O)(=O)—L—R₂; and R₁—C(R₄)(R₅)—S—L—R₂.

In one aspect the present invention provides a use of a compound in the manufacture of a medicament for use in the therapy of a condition or disease associated with 11β—HSD, wherein the compound has Formula I

 R₁—Z—R₂          Formula I wherein R₁ is an optionally substituted phenyl ring; R₂ is or comprises an optionally substituted aromatic ring; and Z is —X—Y—L— or —Y—X—L— wherein either X is selected from —S(=O)(=O)— and —C(=O)—, and Y is —NR₃—; or X is selected from —S(=O)(=O)— and —S—, and Y is —C(R₄)(R₅)—; L is an optional linker; and R₃, R₄ and R₅ are each independently selected from H and hydrocarbyl; and wherein when R₂ comprises the following structural moiety

wherein Q is an atom selected from the group consisting of S, O, N and C; the compound is selected from compounds of the formulae R₁—C(=O)—NR₃—L—R₂; R₁—S(=O)(=O)—C(R₄)(R₅)—L—R₂; R₁—S—C(R₄)(R₅)—L—R₂; R₁—NR₃—S(=O)(=O)—L—R₂; R₁—NR₃—C(=O)—L—R₂; R₁—C(R₄)(R₅)—S(=O)(=O)—L—R₂; and R₁—C(R₄)(R₅)—S—L—R₂.

SOME ADVANTAGES

One key advantage of the present invention is that the compounds of the present invention can act as 11β-HSD inhibitors. The compounds may inhibit the interconversion of inactive 11-keto steroids with their active hydroxy equivalents. Thus present invention provides methods by which the conversion of the inactive to the active form may be controlled, and to useful therapeutic effects which may be obtained as a result of such control. More specifically, but not exclusively, the invention is concerned with interconversion between cortisone and cortisol in humans.

Another advantage of the compounds of the present invention is that they may be potent 11β-HSD inhibitors in vivo.

Some of the compounds of the present invention are also advantageous in that they may be orally active.

The present invention may provide for a medicament for one or more of (i) regulation of carbohydrate metabolism, (ii) regulation of protein metabolism, (iii) regulation of lipid metabolism, (iv) regulation of normal growth and/or development, (v) influence on cognitive function, (vi) resistance to stress and mineralocorticoid activity.

Some of the compounds of the present invention may also be useful for inhibiting hepatic gluconeogenesis. The present invention may also provide a medicament to relieve the effects of endogenous glucocorticoids in diabetes mellitus, obesity (including centripetal obesity), neuronal loss and/or the cognitive impairment of old age. Thus, in a further aspect, the invention provides the use of an inhibitor of 11β-HSD in the manufacture of a medicament for producing one or more therapeutic effects in a patient to whom the medicament is administered, said therapeutic effects selected from inhibition of hepatic gluconeogenesis, an increase in insulin sensitivity in adipose tissue and muscle, and the prevention of or reduction in neuronal loss/cognitive impairment due to glucocorticoid-potentiated neurotoxicity or neural dysfunction or damage.

From an alternative point of view, the invention provides a method of treatment of a human or animal patient suffering from a condition selected from the group consisting of: hepatic insulin resistance, adipose tissue insulin resistance, muscle insulin resistance, neuronal loss or dysfunction due to glucocorticoid potentiated neurotoxicity, and any combination of the aforementioned conditions, the method comprising the step of administering to said patient a medicament comprising a pharmaceutically active amount of a compound in accordance with the present invention.

Some of the compounds of the present invention may be useful for the treatment of cancer, such as breast cancer, as well as (or in the alternative) non-malignant conditions; such as the prevention of auto-immune diseases, particularly when pharmaceuticals may need to be administered from an early age.

DETAILED ASPECTS OF THE PRESENT INVENTION

As previously mentioned, in one aspect the present invention provides a compound having Formula I defined above.

As previously -mentioned, in one aspect the present invention provides a pharmaceutical composition comprising
(i) a compound having Formula I defined above
(ii) optionally admixed with a pharmaceutically acceptable carrier, diluent, excipient or adjuvant, or mixtures thereof.

As previously mentioned, in one aspect the present invention provides a compound having Formula I defined above, for use in medicine.

As previously mentioned, in one aspect the present invention provides a use of a compound having Formula I defined above in the manufacture of a medicament for use in the therapy of a condition or disease associated with 11β-HSD.

In one aspect the present invention provides a use of a compound having Formula I defined above in the manufacture of a medicament for use in the therapy of a condition or disease associated with adverse 11β-HSD levels.

In one aspect the present invention provides a use of a compound having Formula I defined above in the manufacture of a pharmaceutical for modulating 11β-HSD activity.

In one aspect the present invention provides a use of a compound having Formula I defined above in the manufacture of a pharmaceutical for inhibiting 11β-HSD activity.

In one aspect the present invention provides a method comprising (a) performing a 11β-HSD assay with one or more candidate compounds having Formula I defined above; (b) determining whether one or more of said candidate compounds is/are capable of modulating 11β-HSD activity; and (c) selecting one or more of said candidate compounds that is/are capable of modulating 11β-HSD activity.

In one aspect the present invention provides a method comprising (a) performing a 11β-HSD assay with one or more candidate compounds having Formula I defined above; (b) determining whether one or more of said candidate compounds is/are capable of inhibiting 11β-HSD activity; and (c) selecting one or more of said candidate compounds that is/are capable of inhibiting 11β-HSD activity.

In one aspect the present invention provides
a compound identified by the above method,
the use of the said compound in medicine,
a pharmaceutical composition comprising the said compound, optionally admixed with a pharmaceutically acceptable carrier, diluent, excipient or adjuvant, or mixtures thereof,
use of the said compound in the manufacture of a medicament for use in the therapy of a condition or disease associated with 11β-HSD, and
use of the said compound in the manufacture of a medicament for use in the therapy of a condition or disease associated with adverse 11β-HSD levels.

For ease of reference, these and further aspects of the present invention are now discussed under appropriate section headings. However, the teachings under each section are not necessarily limited to each particular section.

Preferable Aspects

Compound

As previously mentioned, in one aspect the present invention provides a compound having Formula I $$R_1—Z—R_2 \quad\quad \text{Formula I}$$

wherein $R_1$ is an optionally substituted phenyl ring; $R_2$ is or comprises an optionally substituted aromatic ring; and Z is —X—Y—L— or —Y—X—L— wherein either X is selected from —S(=O)(=O)— and —C(=O)—, and Y is —NR$_3$—; or X is selected from —S(=O)(=O)— and —S—, and Y is —C(R$_4$)(R$_5$)—; L is an optional linker; and $R_3$, $R_4$ and $R_5$ are each independently selected from H and hydrocarbyl; and wherein when $R_2$ comprises the following structural moiety

wherein Q is an atom selected from the group consisting of S, O, N and C; the compound is selected from compounds of the formulae R$_1$—C(=O)—NR$_3$—L—R$_2$; R$_1$—S(=O)(=O)—C(R$_4$)(R$_5$)—L—R$_2$; R$_1$—S—C(R$_4$)(R$_5$)—L—R$_2$; R$_1$—NR$_3$—S(=O)(=O)—L—R$_2$; R$_1$—NR$_3$—C(=O)—L—R$_2$; R$_1$—C(R$_4$)(R$_5$)—S(=O)(=O)—L—R$_2$; and R$_1$—C(R$_4$)(R$_5$)—S—L—R$_2$.

It will be readily appreciated that references to the structural moiety

wherein Q is an atom selected from the group consisting of S, O, N and C, include the following structural moieties

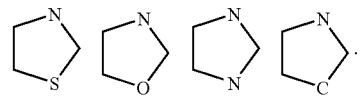

The structural moiety may be saturated or may include unsaturation, such as one or more double bonds.

Thus, references to the structural moiety

include structural moieties such as

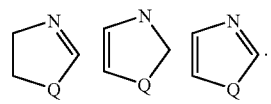

The structural moiety may be substituted. The structural moiety may be part of a polycyclic system such as

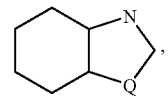

for example

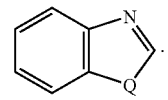

$R_1$ and $R_2$ $R_1$ is an optionally substituted phenyl ring and $R_2$ is or comprises an optionally substituted aromatic ring. $R_1$ and $R_2$ are referred to collectively as the ring systems.

$R_1$ is an optionally substituted phenyl ring.

$R_1$ may be substituted or unsubstituted. Preferably $R_1$ is substituted.

$R_1$ may be substituted with one or more hydrocarbyl substituents. Preferably the substituents are selected from hydrocarbon groups, oxyhydrocarbon groups, halogens, amines and amides. More preferably the substituents are selected from aromatic hydrocarbon groups, alkyl groups, oxyalkyl groups, halogens, amines and amides, such as from aromatic hydrocarbon groups, alkyl groups, oxyalkyl groups and halogens.

In a highly preferred aspect the substituents are selected from phenyl groups, $C_{1-5}$alkyl groups, oxy-$C_{1-5}$-alkyl groups, chloro, bromo and iodo. More preferably the substituents are selected from phenyl, methyl, ethyl, propyl, O-methyl, O-ethyl, O-propyl and chloro.

Preferably $R_1$ is selected from the following:

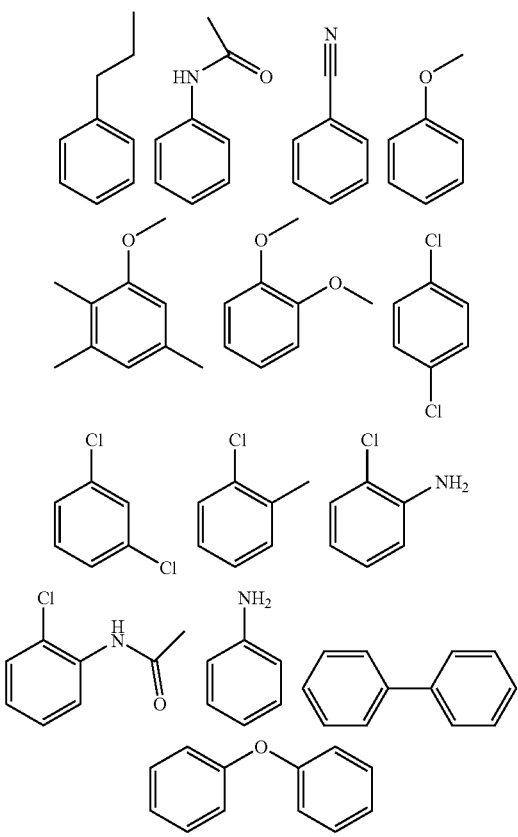

Preferably $R_1$ is or comprises a group selected from the following wherein—indicates the point of attachment to Z.

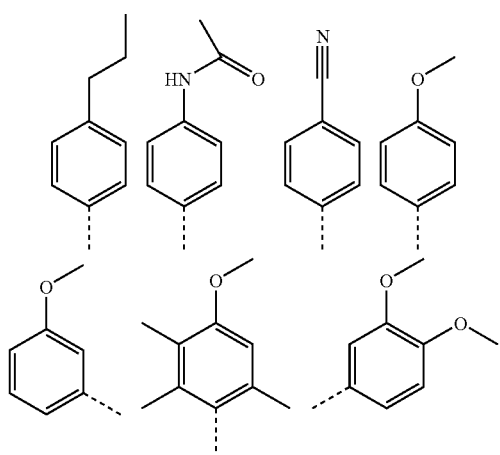

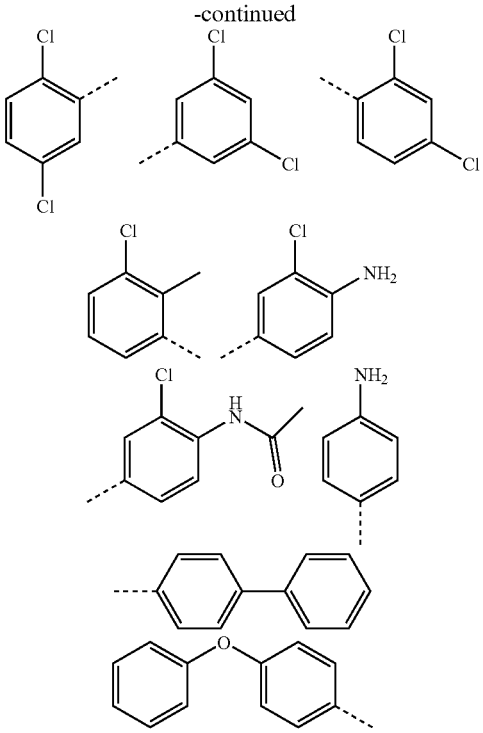

More preferably $R_1$ is selected from the following:

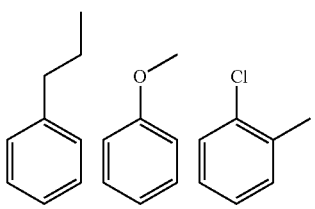

$R_2$ is or comprises an optionally substituted aromatic ring. Preferably the optionally substituted aromatic ring is a five or six membered ring. In one aspect preferably $R_2$ is an optionally substituted five membered aromatic ring. In another aspect preferably $R_2$ is an optionally substituted six membered aromatic ring.

In one preferred aspect, the optionally substituted aromatic ring is a heterocyclic ring. Preferably $R_2$ is an optionally substituted five or six membered aromatic heterocyclic ring.

Preferably the optionally substituted aromatic ring is a heterocyclic ring comprising a carbon and a hetero atom selected from O, S and N. More preferably the optionally substituted aromatic ring is a heterocyclic ring comprising a carbon and a hetero atom selected from O and N.

Preferably $R_2$ is or comprises:

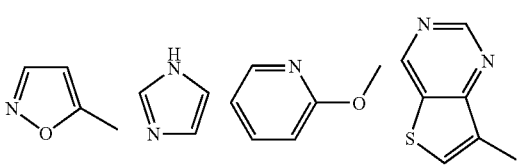

-continued

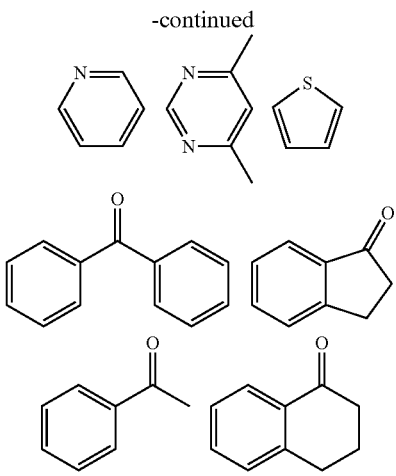

Preferably $R_2$ is

Preferably $R_2$ is or comprises a group selected from the following wherein—indicates the point of attachment to Z.

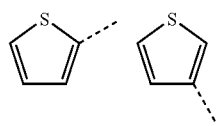

In one preferred aspect, $R_2$ is an optionally substituted five membered heterocyclic aromatic ring. In this aspect preferably $R_2$ is or comprises:

In this aspect more preferably $R_2$ is or comprises:

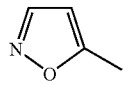

In one preferred aspect the optionally substituted aromatic ring is a carbocyclic ring.

$R_2$ may be substituted or unsubstituted. Preferably $R_2$ is substituted, more preferably $R_2$ is a substituted aromatic carbocyclic ring.

In one aspect the substituents are selected from hydrocarbon groups, oxyhydrocarbon groups, halogens, amines and amides. More preferably the substituents are selected from aromatic hydrocarbon groups, alkyl groups, oxyalkyl groups, halogens, amines and amides, such as from aromatic hydrocarbon groups, alkyl groups, oxyalkyl groups and halogens.

In one aspect $R_2$ is substituted with two or more substituents. In a preferred aspect $R_2$ is substituted with two or more substituents and the two or more substituents together form a ring which is fused to the carbocyclic ring of $R_2$.

Preferably the carbocyclic ring is a five or six membered aromatic carbocyclic ring. More preferably the carbocyclic ring is a phenyl ring.

In a preferred aspect $R_2$ is a substituted phenyl ring. Preferably $R_2$ is substituted with two or more substituents and the two or more substituents together form a ring which is fused to the phenyl ring of $R_2$.

In this aspect preferably $R_2$ comprises the following structure:

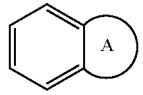

wherein A represents a heterocyclic ring, preferably a five or six membered heterocyclic ring.

Thus, in one aspect preferably $R_2$ comprises the following structure:

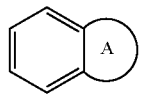

wherein A represents a five membered heterocyclic ring. In this aspect preferably $R_2$ is or comprises a group selected from the following:

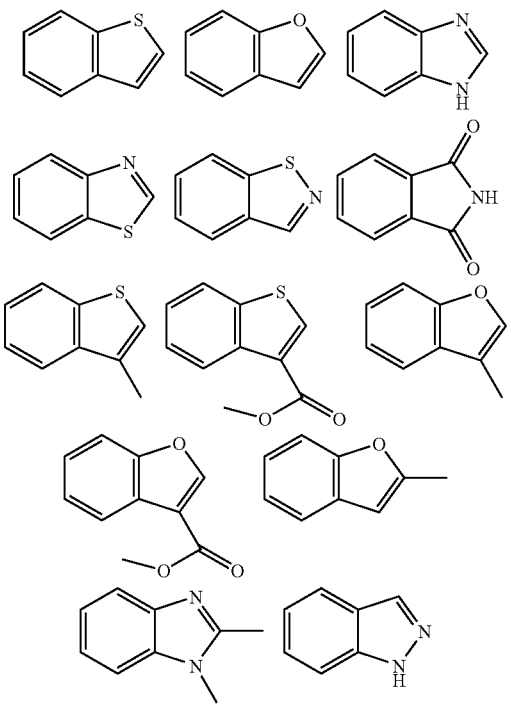

-continued

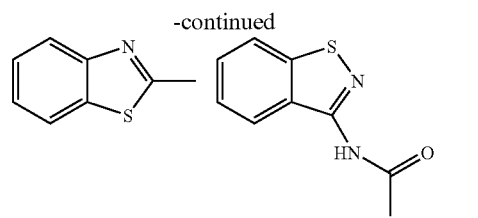

More preferably R₂ is or comprises a group selected from the following:

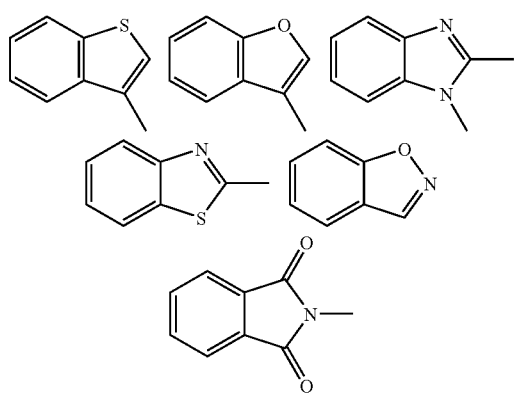

In another preferred aspect R₂ comprises the following structure:

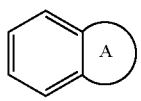

wherein A represents a six membered heterocyclic ring. In this aspect preferably R₂ is or comprises a group selected from the following:

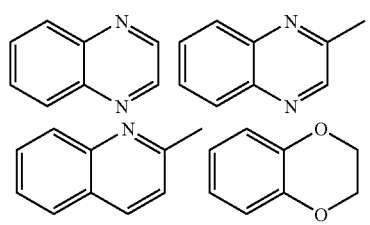

-continued

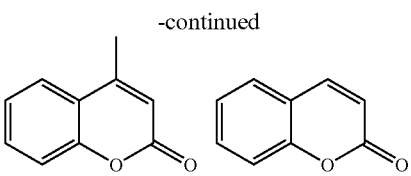

More preferably R₂ is or comprises a group selected from the following:

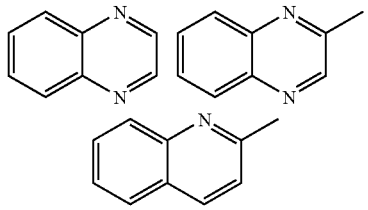

In one preferred aspect R₂ is or comprises a group selected from the following:

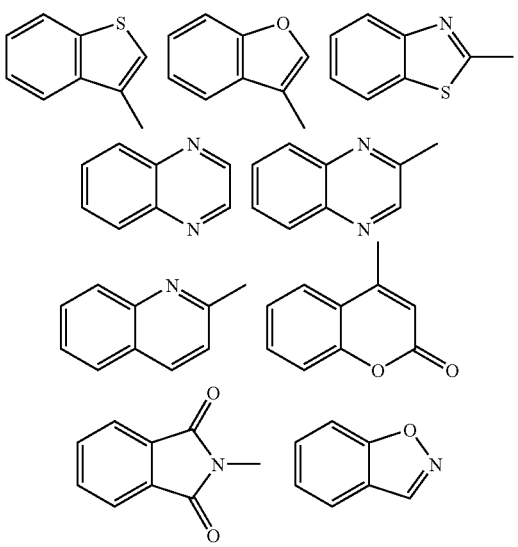

In another preferred aspect R₂ is or comprises a group selected from the following:

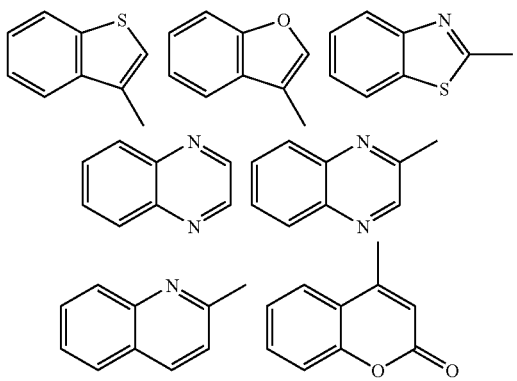

-continued

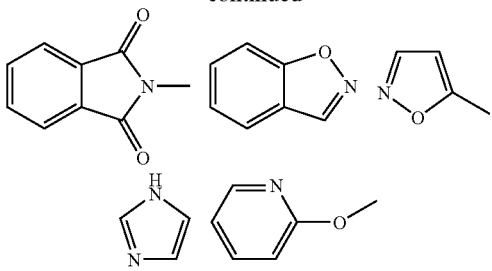

Preferably R₂ is or comprises a group selected from the following wherein—indicates the point of attachment to Z.

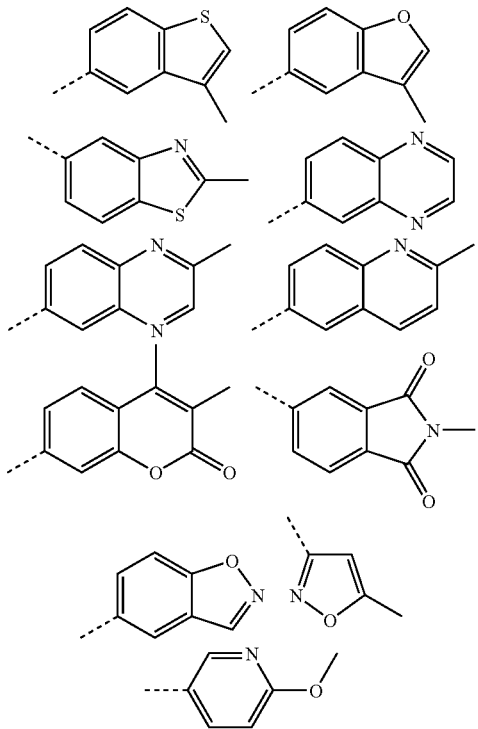

Preferably in this aspect, R₁ is a substituted phenyl and Z is —S(=O)(=O)NH— or —NHS(=O)(=O)—.

The compound of the present invention may have substituents other than those of the ring systems show herein. Furthermore the ring systems herein are given as general formulae and should be interpreted as such. The absence of any specifically shown substituents on a given ring member indicates that the ring member may substituted with any moiety of which H is only one example. Each ring system may contain one or more degrees of unsaturation, for example, in some aspects one or more rings of a ring system is aromatic. Each ring system may be carbocyclic or may contain one or more hetero atoms.

The compound of the invention, in particular the ring systems of the compound of the invention may contain substituents other than those show herein. By way of example, these other substituents may be one or more of: one or more halo groups, one or more O groups, one or more hydroxy groups, one or more amino groups, one or more sulphur containing group(s), one or more hydrocarbyl group(s)—such as an oxyhydrocarbyl group.

In general terms the ring systems of the present compounds may contain a variety of non-interfering substituents. In particular, the ring systems may contain one or more hydroxy, alkyl especially lower ($C_1$-$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$-$C_6$) alkoxy, e.g. methoxy, ethoxy, propoxy etc., alkinyl, e.g. ethinyl, or halogen, e.g. fluoro substituents.

X, Y and L

As previously mentioned, Z in Formula I is —X—Y—L— or —Y—X—L—; wherein either X is selected from —S(=O)(=O)— and —C(=O)—, and Y is —NR₃—; or X is selected from —S(=O)(=O)— and —S—, and Y is —C(R₄)(R₅)—; L is an optional linker; and R₃, R₄ and R₅ are each independently selected from H and hydrocarbyl.

In one preferred aspect, X is —C(=O)—. In this aspect preferably Z is selected from —C(=O)—NR₃—, —C(=O)—NR₃—L—, —NR₃—C(=O)—, and —NR₃—C(=O)—L—.

In one preferred aspect, X is —S(=O)(=O)—. In this aspect preferably Z is selected from —S(=O)(=O)—NR₃—, —S(=O)(=O)—NR₃—L—, —NR₃—S(=O)(=O)—, —NR₃—S(=O)(=O)—L—, —S(=O)(=O)—C(R₄)(R₅)—, —S(=O)(=O)—C(R₄)(R₅)—L—, —C(R₄)(R₅)—S(=O)(=O)— and —C(R₄)(R₅)—S(=O)(=O)—L—.

In one preferred aspect, X is —S—. In this-aspect preferably Z is selected from —S—C(R₄)(R₅)—, —S—C(R₄)(R₅)—L—, —C(R₄)(R₅)—S— and —C(R₄)(R₅)—S—L—.

In one preferred aspect, Y is —NR₃—. In this aspect preferably Z is selected from —C(=O)—NR₃—, —C(=O)—NR₃—L—, —NR₃—C(=O)—, —NR₃—C(=O)—L—, —S(=O)(=O)—NR₃—, —S(=O)(=O)—NR₃—L—, —NR₃—S(=O)(=O)— and —NR₃—S(=O)(=O)—L—.

In another preferred aspect, Y is —C(R₄)(R₅)—. In this aspect preferably Z is selected from —S(=O)(=O)—C(R₄)(R₅)—, —S(=O)(=O)—C(R₄)(R₅)—L—, —C(R₄)(R₅)—S(=O)(=O)— and —C(R₄)(R₅)—S(=O)(=O)—L—, —S—C(R₄)(R₅)—, —S—C(R₄)(R₅)—L—, —C(R₄)(R₅)—S— and —C(R₄)(R₅)—S—L—.

In one preferred aspect, X is —S(=O)(=O)— and Y is —NR₃—. In this aspect preferably Z is —S(=O)(=O)NR₃— or —NR₃S(=O)(=O)—, such as —S(=O)(=O)NH— or —NHS(=O)(=O)—

In one preferred aspect, X is —S(=O)(=O)— and Y is —C(R₄)(R₅)—. In this aspect preferably Z is —S(=O)(=O)C(R₄)(R₅)— or —C(R₄)(R₅)S(=O)(=O)—, such as —S(=O)(=O)CH₂— or —CH₂S(=O)(=O)—

In one preferred aspect, X is —S— and Y is —C(R₄)(R₅)—. In this aspect preferably Z is —SC(R₄)(R₅)— or —C(R₄)(R₅)S—, such as —SCH₂— or —CH₂S—

L is an optional linker. In one aspect L is present. L may be any suitable group, for example L may a hydrocarbyl group or a hetero atom, in particular L may be a hydrocarbon group such a $C_{1-10}$ alkyl group. In one aspect, L is selected from —C(=O)—, —S(=O)(=O)—, —S—, —NR₃—, —[C(R₄)(R₅)]ₙ—, —C₆H₄— and combination thereof, wherein R₃, R₄ and R₅ are each independently selected from H and hydrocarbyl and wherein n is an integer from 1 to 10, preferably from 1 to 5, more preferably 1 or 2. In one preferred aspect, L is selected from —C(=O)—, —S(=O)(=O)—, —S—, —NR₃—, —C(R₄)(R₅)—, —C₆H₄— and combinations thereof, wherein $R_3$, $R_4$ and $R_5$ are each independently selected from H and hydrocarbyl. In these aspects X—Y is preferably S(=O)(=O)$NR_3$— or —$NR_3$S(=O)(=O)—, such as —S(=O)(=O)NH— or —NHS(=O)(=O)—.

In a preferred aspect, L is selected from —$NR_3$—C(=O)—C($R_4$)($R_5$)—S— and —S(=O)(=O)—$NR_3$—$NR_3$—C(=O)—. In these aspects X—Y is preferably S(=O)(=O)$NR_3$— or —$NR_3$S(=O)(=O)—, such as —S(=O)(=O)NH— or —NHS(=O)(=O)—.

In a highly preferred aspect, L is selected from —NH—C(=O)—$CH_2$—S— and —S(=O)(=O)—NH—NH—C(=O)—. In these aspects X—Y is preferably S(=O)(=O)$NR_3$— or —$NR_3$S(=O)(=O)—, such as —S(=O)(=O)NH— or —NHS(=O)(=O)—.

$R_3$, $R_4$ and $R_5$

As previously mentioned, Z in Formula I is —X—Y—L— or —Y—X—L—; wherein either X is selected from —S(=O)(=O)— and —C(=O)—, and Y is —$NR_3$—; or X is selected from —S(=O)(=O)— and —S—, and Y is —C($R_4$)($R_5$)—; L is an optional linker; and $R_3$, $R_4$ and $R_5$ are each independently selected from H and hydrocarbyl.

The term "hydrocarbyl group" as used herein means a group comprising at least C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

A typical hydrocarbyl group is a hydrocarbon group. Here the term "hydrocarbon" means anyone of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

In some aspects of the present invention, one or more hydrocarbyl groups is independently selected from optionally substituted alkyl group, optionally substituted haloalkyl group, aryl group, alkylaryl group, alkylarylakyl group, and an alkene group.

In some aspects of the present invention, one or more hydrocarbyl groups is independently selected from $C_1$-$C_{10}$ alkyl group, such as $C_0$-$C_6$ alkyl group, and $C_1$-$C_3$ alkyl group. Typical alkyl groups include $C_1$ alkyl, $C_2$ alkyl, $C_3$ alkyl, $C_4$ alkyl, $C_5$ alkyl, $C_7$ alkyl, and $C_8$ alkyl.

In some aspects of the present invention, one or more hydrocarbyl groups is independently selected from $C_1$-$C_{10}$ haloalkyl group, $C_1$-$C_6$ haloalkyl group, $C_1$-$C_3$ haloalkyl group, $C_1$-$C_{10}$ bromoalkyl group, $C_1$-$C_6$ bromoalkyl group, and $C_1$-$C_3$ bromoalkyl group. Typical haloalkyl groups include: $C_1$ haloalkyl, $C_2$ haloalkyl, $C_3$ haloalkyl, $C_4$ haloalkyl, $C_5$ haloalkyl, $C_7$ haloalkyl, $C_8$ haloalkyl, $C_1$ bromoalkyl, $C_2$ bromoalkyl, $C_3$ bromoalkyl, $C_4$ bromoalkyl, $C_5$ bromoalkyl, $C_7$ bromoalkyl, and $C_8$ bromoalkyl.

In some aspects of the present invention, one or more hydrocarbyl groups is independently selected from aryl groups, alkylaryl groups, alkylarylalkyl groups, —$(CH_2)_{1-10}$-aryl, —$(CH_2)_{1-10}$—Ph, —$(CH_2)_{1-10}$—Ph—$C_{1-10}$ alkyl, —$(CH_2)_{1-5}$—Ph, —$(CH_2)_{1-5}$—Ph—$C_{1-5}$ alkyl, —$(CH_2)_{1-3}$—Ph, —$(CH_2)_{1-3}$—Ph—$C_{1-3}$ alkyl, —$CH_2$—Ph, and —$CH_2$—Ph—C($CH_3$)$_3$. The aryl groups may contain a hetero atom. Thus the aryl group or one or more of the aryl groups may be carbocyclic or heterocyclic. Typical hetero atoms include O, N and S, in particular N.

In some aspects of the present invention, one or more hydrocarbyl groups is independently selected from —$(CH_2)_{1-10}$-cycloalkyl, —$(CH_2)_{1-10}$—$C_{3-10}$cycloalkyl, —$(CH_2)_{1-7}$—$C_{3-7}$cycloalkyl, —$(CH_2)_{1-5}$—$C_{3-5}$cycloalkyl, —$(CH_2)_{1-3}$—$C_{3-5}$cycloalkyl, and —$CH_2$—$C_3$cycloalkyl.

In some aspects of the present invention, one or more hydrocarbyl groups is independently selected from alkene groups. Typical alkene groups include $C_1$-$C_{10}$ alkene group, $C_1$-$C_6$ alkene group, $C_1$-$C_3$ alkene group, such as $C_1$, $C_2$, $C_3$, $C_4$, $C_5$, $C_6$, or $C_7$ alkene group. In a preferred aspect the alkene group contains 1, 2 or 3 C=C bonds. In a preferred aspect the alkene group contains 1 C=C bond. In some preferred aspect at least one C=C bond or the only C=C bond is to the terminal C of the alkene chain, that is the bond is at the distal end of the chain to the ring system.

In some aspects of the present invention, one or more hydrocarbyl groups is independently selected from oxyhydrocarbyl groups.

The term "oxyhydrocarbyl" group as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

In one embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Typically, the oxyhydrocarbyl group is of the formula $C_{1-6}O$ (such as a $C_{1-3}O$).

In a preferred aspect, $R_3$ is selected from H and hydrocarbon groups. Preferably, $R_3$ is selected from H and alkyl groups, preferably from H and $C_{1-10}$alkyl groups, preferably from H and $C_{1-5}$alkyl groups. In a highly preferred aspect, $R_3$ is H.

In a preferred aspect, $R_3$ may be equivalent to —L—$R_2$ wherein L and $R_2$ are independently selected from the possibilities defined herein. In this aspect the present compound contains two groups of the formula —L—$R_2$ wherein each L and $R_2$ are selected independently of each other. However in one aspect, each of L and $R_2$ may be the same as the other of L and R$_2$ present in the compound. Examples of compounds meeting such requirements are shown below.

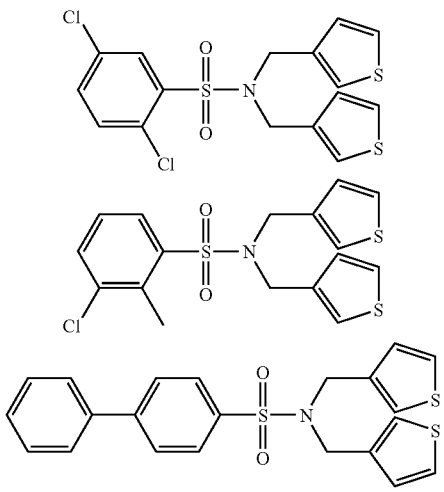

In a preferred aspect, R$_4$ and R$_5$ are independently selected from H and hydrocarbon groups. Preferably R$_4$ and R$_5$ are independently selected from H and alkyl groups, preferably independently selected from H and C$_{1-10}$alkyl groups, preferably independently selected from H and C$_{1-5}$alkyl groups. In a preferred aspect at least one of R$_4$ and R$_5$ is H. In a highly preferred aspect, R$_4$ and R$_5$ are both H.

Further Aspects

For some applications, preferably the compounds have a reversible action.

For some applications, preferably the compounds have an irreversible action.

In one embodiment, the compounds of the present invention are useful for the treatment of breast cancer.

The compounds of the present invention may be in the form of a salt.

The present invention also covers novel intermediates that are useful to prepare the compounds of the present invention. For example, the present invention covers novel alcohol precursors for the compounds. The present invention also encompasses a process comprising precursors for the synthesis of the compounds of the present invention.

Steroid Dehydrogenase

11β Steroid dehydrogenase may be referred to as "11β-HSD" or "HD" for short.

In some aspects of the invention 11β-HSD is preferably 11p-HSD Type 1.

In some aspects of the invention 11β-HSD is preferably 11β-HSD Type 2.

Steroid Dehydrogenase Inhibition

It is believed that some disease conditions associated with HD activity are due to conversion of a inactive, cortisone to an active, cortisol. In disease conditions associated with HD activity, it would be desirable to inhibit HD activity.

Here, the term "inhibit" includes reduce and/or eliminate and/or mask and/or prevent the detrimental action of HD.

HD Inhibitor

In accordance with the present invention, the compound of the present invention is capable of acting as an HD inhibitor.

Here, the term "inhibitor" as used herein with respect to the compound of the present invention means a compound that can inhibit HD activity—such as reduce and/or eliminate and/or mask and/or prevent the detrimental action of HD. The HD inhibitor may act as an antagonist.

The-ability of compounds to inhibit steroid dehydrogenase activity can be assessed using the suitable biological assay presented in the Examples section.

It is to be noted that the compound of the present invention may have other beneficial properties in addition to or in the alternative to its ability to inhibit HD activity.

Therapy

The compounds of the; present invention may be used as therapeutic agents—i.e. in therapy applications.

The term "therapy" includes curative effects, alleviation effects, and prophylactic effects.

The therapy may be on humans or animals, preferably female animals.

Pharmaceutical Compositions

In one aspect, the present invention provides a pharmaceutical composition, which comprises a compound according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may, be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Combination Pharmaceutical

The compound of the present invention may be used in combination with one or more other active agents, such as one or more other pharmaceutically active agents.

By way of example, the compounds of the present invention may be used in combination with other 11β-HSD inhibitors and/or other inhibitors such as an aromatase inhibitor (such as for example, 4hydroxyandrostenedione (4-OHA)), and/or a steroid sulphatase inhibitors such as EMATE and/or steroids—such as the naturally occurring sterneurosteroids dehydroepiandrosterone sulfate (DHEAS) and pregnenolone sulfate (PS) and/or other structurally similar organic compounds.

In addition, or in the, alternative, the compound of the present invention may be used in combination with a biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. For some applications, preferably, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)— such as TNF-α; Interferon alpha, beta and gamma; TGF-β. For some applications, preferably the cytokine is tumour necrosis factor (TNF). For some applications, the TNF may be any type of TNF—such as TNF-α, TNF-β, including derivatives or mixtures thereof. More preferably the cytokine is TNF-α. Teachings on TNF may be found in the art—such as WO-A-98/08870 and WO-A-98/13348.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration. Depending upon the need, the agent may be administered at a dose of from 0.01 to 30 mg/kg body weight, such as from 0.1 to 10 mg/kg, more preferably from 0.1 to 1 mg/kg body weight.

By way of further example, the agents of the present invention maybe administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Thus, for pharmaceutical administration, the compounds of the present invention can be formulated in any suitable manner utilising conventional pharmaceutical formulating techniques and pharmaceutical carriers, adjuvants, excipients, diluents etc. and usually for parenteral administration. Approximate effective dose rates may be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

Cell Cycling

The compounds of the present invention may be useful in the method of treatment of a cell cycling disorder.

As discussed in "Molecular Cell Biology" 3rd Ed. Lodish et al. pages 177-181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10-20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x; and when in $G_2$ (or M), it has 2x of DNA.

The stages of mitosis and cytokinesis in an animal cell are as follows.
(a) Interphase. The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.
b) Early prophase. Centrioles, each with a newly formed daughter centriole, begin moving toward opposite poles of the cell; the chromosomes can be seen as long threads. The nuclear membrane begins to disaggregate into small vesicles.
(c) Middle and late prophase. Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles. Some spindle fibres reach from pole to pole; most go to chromatids and attach at kinetochores.
(d) Metaphase. The chromosomes move toward the equator of the cell, where they become aligned in the equatorial plane. The sister chromatids have not yet separated.
(e) Anaphase. The two sister chromatids separate into independent chromosomes. Each contains a centromere that is linked by a spindle fibre to one pole, to which it moves. Thus one copy of each chromosome is donated to each daughter cell. Simultaneously, the cell elongates, as do the pole-to-pole spindles. Cytokinesis begins as the cleavage furrow starts to form.
(f). Telophase. New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase.
(g) Interphase. Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling may result in cancer. Reduced cell cycling may result in degenerative conditions. Use of the compound of the present invention may provide a means to treat such disorders and conditions.

Thus, the compound of the present invention may be suitable for use in the treatment of cell, cycling disorders such as cancers, including hormone dependent and hormone independent cancers.

In addition, the compound of the present invention may be suitable for the treatment of cancers such as breast cancer, ovarian cancer, endometrial cancer, sarcomas, melanomas, prostate cancer, pancreatic cancer etc. and other solid tumours.

For some applications, cell cycling is inhibited and/or prevented and/or arrested, preferably wherein cell cycling is prevented and/or arrested. In one aspect cell cycling may be inhibited and/or prevented and/or arrested in the $G_2$/M phase. In one aspect cell cycling may be irreversibly prevented and/or inhibited and/or arrested, preferably wherein cell cycling is irreversibly prevented and/or arrested.

By the term "irreversibly prevented and/or inhibited and/or arrested" it is meant after application of a compound of the present invention, on removal of the compound the effects of the compound, namely prevention and/or inhibition and/or arrest of cell cycling, are still observable. More particularly by the-term "irreversibly prevented and/or inhibited and/or arrested" it is meant that when assayed in accordance with the cell cycling assay protocol presented herein, cells treated with a compound of interest show less growth after Stage 2 of the protocol I than control cells. Details on this protocol are presented below.

Thus, the present invention provides compounds which: cause inhibition of growth of oestrogen receptor positive (ER+) and ER negative (ER−) breast cancer cells in vitro by preventing and/or inhibiting and/or arresting cell cycling; and/or cause regression of nitroso-methyl urea (NMU)-induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay

Protocol 2

Procedure

Stage 1

MCF-7 breast cancer cells are seeded into multi-well culture plates at a density of 105 cells/well. Cells were allowed to attach and grown until about 30% confluent when they are treated as follows:

Control—no treatment
Compound of Interest (COI) 20 μM

Cells are grown for 6 days in growth medium containing the COI with changes of medium/COI every 3 days. At the end of this period cell numbers were counted using a Coulter cell counter.

Stage 2

After treatment Of cells for a 6-day period with the COI cells are re-seeded at a density of $10^4$ cells/well. No further treatments are added. Cells are allowed to continue to grow for a further 6 days in the presence of growth medium. At the end of this period cell numbers are again counted.

Cancer

As indicated, the compounds of the present invention may be useful in the treatment of a cell cycling disorder. A particular cell cycling disorder is cancer.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

We believe that the compound of the present invention provides a means for the treatment of cancers and, especially, breast cancer.

In addition or in the alternative the compound of the present invention may be useful in the blocking the growth of cancers including leukaemias and solid tumours such as breast, endometrium, prostate, ovary and pancreatic tumours.

Other Therapies

As previously mentioned, in one aspect the present invention provides use of a compound as described herein in the manufacture of a medicament for use in the therapy of a condition or disease associated with 11β-HSD.

Conditions and diseases associated with 11β-HSD have been reviewed in Walker, E. A,; Stewart, P. M.; *Trends in Endocrinology and Metabolism,* 2003, 14 (7), 334-339.

In a preferred aspect; the condition or disease is selected from the group consisting of:
 metabolic disorders, such as diabetes and obesity
 cardiovascular disorders, such as hypertension
 glaucoma
 inflammatory disorders, such as arthritis or asthma
 immune disorders
 bone disorders, such as osteoporosis
 cancer
 intrauterine growth retardation
 apparent mineralocorticoid excess syndrome (AME)
 polycystic ovary syndrome (PCOS)
 hirsutism
 acne
 oligo- or amenorrhea
 adrenal cortical adenoma and carcinoma
 Cushing's syndrome
 pituitary tumours
 invasive carcinomas
 breast cancer; and
 endometrial cancer.

It is also to be understood that the compound/composition of the present invention may have other important medical implications.

For example, the compound or composition of the present invention may be useful in the treatment of the disorders listed in WO-A-99/52890—viz .

In addition, or in the alternative, the compound or composition of the present invention may be useful in the treatment of the disorders listed in WO-A-98/05635. For ease of reference, part of that list is now provided: diabetes including Type II diabetes, obesity, cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endoscierosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as anti-microbials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveo-retinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, sub-acute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of -muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Summary

In summation, the present invention provides compounds for use as steroid dehydrogenase inhibitors, and pharmaceutical compositions for the same.

Broad Aspects

In one broad aspect the present invention provides a compound having Formula I

   Formula I wherein Z is —X—Y—L— or —Y—X—L—; $R_1$ is an aromatic ring; $R_2$ is or comprises a ring; X is selected from —C(=O)—, —S(=O)(=O)— and —S—; Y is selected from —$NR_3$— and —C($R_4$)($R_5$)—; L is an optional linker; $R_3$, $R_4$ and $R_5$ are each independently selected from H and hydrocarbyl.

In one broad aspect the present invention provides a pharmaceutical composition comprising
(i) a compound having Formula I

   Formula I wherein Z is —X—Y—L— or —Y—X—L—; $R_1$ is an aromatic ring; $R_2$ is or comprises a ring; X is selected from —C(=O)—, —S(=O)(=O)— and —S—; Y is selected from —$NR_3$— and —C($R_4$)($R_5$)—; L is an optional linker; $R_3$, $R_4$ and $R_5$ are each independently selected from H and hydrocarbyl;
(ii) optionally admixed with a pharmaceutically acceptable carrier, diluent, excipient or adjuvant, or mixtures thereof.

In one broad aspect the present invention provides a compound for use in medicine wherein the compound has Formula I

   Formula I wherein Z is —X—Y—L— or —Y—X—L—; $R_1$ is an aromatic ring; $R_2$ is or comprises a ring; X is selected from —C(=O)—, —S(=O)(=O)— and —S—; Y is selected from —$NR_3$— and —C($R_4$)($R_5$)—; L is an optional linker; $R_3$, $R_4$ and $R_5$ are each independently selected from H and hydrocarbyl.

In one broad aspect the present invention provides a use of a compound in the manufacture of a medicament for use in the therapy of a condition or disease associated with 11β-HSD, wherein the compound has Formula I

   Formula I wherein Z is —X—Y—L— or —Y—X—L—; $R_1$ is an aromatic ring; $R_2$ is or comprises a ring; X is selected from —C(=O)—, —S(=O)(=O)— and —S—; Y is selected from —$NR_3$— and —C($R_4$)($R_5$)—; L is an optional linker; $R_3$, $R_4$ and $R_5$ are each independently selected from H and hydrocarbyl.

In these broad aspects, $R_1$ is an aromatic ring. Preferably $R_1$ is a five or six membered aromatic ring, more preferably a six membered aromatic ring. Preferably, $R_1$ is a carbocyclic ring. In a highly preferred aspect, $R_1$ is an optionally substituted phenyl ring.

In these broad aspects, $R_2$ is or comprises a ring, preferably an aromatic ring, more preferably an optionally substituted aromatic ring.

In one broad aspect $R_2$ comprises the following structure:

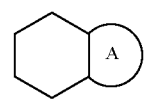

wherein A represents a heterocyclic ring, preferably a five or six membered heterocyclic ring.

In these broad aspects X is selected from —C(=O)—, —S(=O)(=O)— and —S—; and Y is selected from —NR$_3$— and —C(R$_4$)(R$_5$)—. In a preferred aspect -either X is selected from —S(=O)(=O)— and —C(=O)—, and Y is —NR$_3$—; or X is selected from —S(=O)(=O)— and —S—, and Y is —C(R$_4$)(R$_5$)—.

BRIEF DESCRIPTION OF THE FIGURES

The present invention will be described in further detail by way of example only with reference to the accompanying figures in which:

FIG. 9(A) shows the effect of protein; FIG. 9(B) shows the effect of cortisone; and FIG. 9(C) shows the effect of Tween-80.

Figure 1:
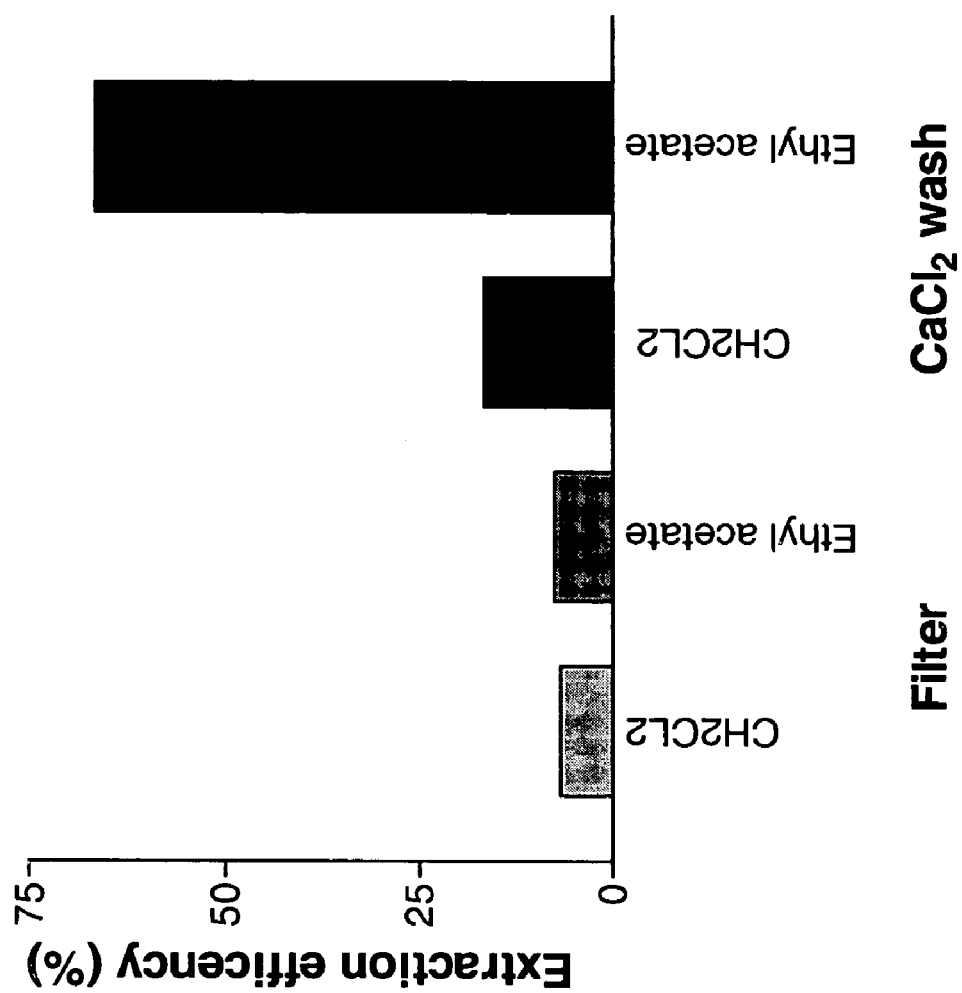
FIG. 1 is a graph showing extraction efficiencies obtained with four extraction methods.

The present invention will now be described in further detail in the following examples.

EXAMPLES

The present invention will now be described only by way of example.

Biological Assays

Standard Operating Procedure for the 11β-Hydroxysteroid Dehydrogenase Type 1 cortisol Radioimmunoassay (11β HSD1 Cortisol RIA).

Reagents

Cortisone, Cortisol (Hydrocortisone), NADPH, Glucose-6-phosphate, Glycyrrhetinic acid (GA), Dextran coated charcoal (C6197) and DMSO were obtained from Sigma Aldrich, Carbenoxolone was obtained from ICN Biomedicals, Product 215493001, $^3$H-conisone was obtained from American Radiolabelled Compounds Inc, Product ART-743, $^3$H-cortisol was obtained from NEN, Product NET 396, $^{14}$C-cortisol was obtained from NEN, Product NEC 163, human hepatic microsomes were obtained from XenoTech, product H0610/Lot 0210078, rat hepatic microsomes were obtained from XenoTech, SPA beads were obtained from Amersham, Product RPNQ0017, the Immunoassay kit was obtained from Assay Designs, Product 900-071, the Immunologicals Direct anti-cortisol antibody was Product OBT 0646, the Sigma anti-cortisol antibody was Product C8409 and the Immunotech antibody was supplied by Beckman, Product IMBULK3 6D6.

Buffer Solutions

Buffer 1, from Barf et al., (2002) [14]: 30 mM Tris-HCL, pH 7.2, containing 1 mM EDTA, Buffer 2, from the Sterix protocol: PBS (pH 7.4) containing 0.25M sucrose Buffer 3, from the Sigma RIA protocol: 50 mM Tris-HCL, pH 8, containing 0.1 M NaCl and 0.1% gelatin Stop solution, from Barf et al., (2002) [14]: 1 mM Glycyrrhetinic acid in 100% DMSO Enzyme assays were carried out in the presence of 181 µM NADPH, 1 mM Glucose-6-Phosphate and cortisone concentrations indicated for each experiment.

Enzyme Assay Buffer 30 mM Tris-HCL, pH 7.2 containing 1 mM EDTA.

Antibody Binding Buffer 50 mM Tris-HCL, pH 8, containing 0.1 M NaCl and 0.1% gelatin.

Compound Preparation

Prepare 10 mM stock solutions in 100% DMSO at 100 times the required assay concentration. Dilute into assay buffer 1 in 25. Also dilute neat DMSO 1 in 25 into assay buffer for controls.

Substrate Preparation

Prepare a solution of cortisone in ethanol 600 times the required assay concentration (175 nM). Dilute this 1 in 50 into assay buffer.

Prepare NADPH as a 1.8 mg/ml solution in assay buffer.

Prepare G-6-P as a 3.65 mg/ml solution in assay buffer.

Mix these 3solutions 1:1:1 to make a solution of sufficient volume for 25 µl additions to each sample. Add 0.5 µCi tritiated cortisone per 25 µl and mix the solution well.

Microsome Preparation
Dilute stock 20 mg/ml solution 1 in 100 with assay buffer.

Antibody Preparation
Dilute stock antibody solution to 17 μg/ml in antibody binding buffer.

Dextran Coated Charcoal Preparation
Make a 20 mg/ml solution in antibody binding buffer and chill on ice.

Enzyme Assay
To a u-bottom polypropylene 96 well plate add:
25 μl compound dilution or diluted DMSO to controls, NSB's and blanks
10 μl 1 mM GA in DMSO (enzyme stop solution) to blanks
25 μl substrate mixture to all samples
50 μl diluted microsomes to all samples
Incubate plate for 30 min at 37° C. shaking p0 Add 10 μl enzyme stop solution to all wells except the blanks
Add 100 μl antibody solution to all wells except the NSB's, add antibody binding buffer to these wells
Incubate at 37° C. for 1 h
Chill plate on ice for 15 min
Add 50 μl/well charcoal solution and mix with an 8-channel pipette (4-5 aspirations)
Chill the plate on ice
Centrifuge at 4° C., 2000×g for 15 min
Transfer 100 μl supernatant into an Optiplate, also add 25 μl substrate mixture to 2 empty wells to indicate counting efficiency
Add 200 μl Microscint-40 to all wells and count on a Topcount Radioimmunoassay
The 11β HSD1 enzyme assay was carried out following the standard operating procedure described above in u-bottom polypropylene 96 well plates or 1.5 ml Eppendorf tubes as indicated for each experiment. Subsequent to stopping the enzyme reaction, 100 μl antibody prepared in buffer 3 unless otherwise indicated was added to test samples and 100 μl buffer 3 was added to the NSB samples. The samples were incubated for 1 hour at 37° C. and the chilled on ice for 15 mins. Dextran coated charcoal (50 μl/sample) prepared to the indicated concentration in buffer 3 was added and the samples were mixed (vortex for tubes and aspiration 5 times with an 8-channel pipette for 96 well plates) and chilled for a further 10 min. The samples were centrifuged at 2000×g for 15 min at 4° C. to pellet the charcoal. Aliquots of the supernatant (100 μl) were transferred to an Optiplate and counted on the Topcount in 150-200 μl Microscint 40. In some experiments, aliquots of supernatant were transferred to scintillation vials and counted on the Tricarb LSC in 5 ml Ultima Gold scintillant.

Inhibition Data

| STX No. | Structure | % inhibition of Human 11β HSD1 @10 μM typical sd ± 5% N = 2 |
|---|---|---|
| 990 | 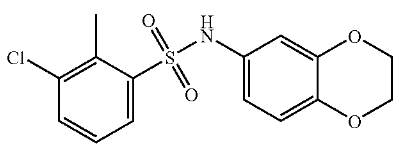 | 73.3 |
| 472 | 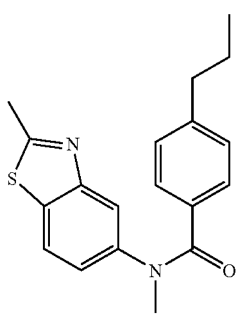 | 71.4 |
| 956 | 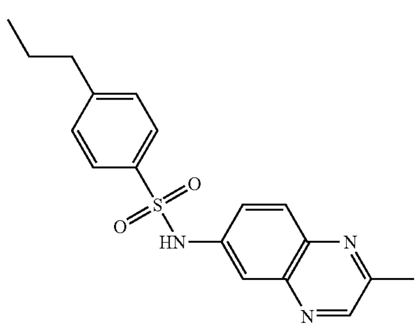 | 64.8 |

-continued

Inhibition Data

| STX No. | Structure | % inhibition of Human 11β HSD1 @10 μM typical sd ± 5% N = 2 |
|---|---|---|
| 1015 | 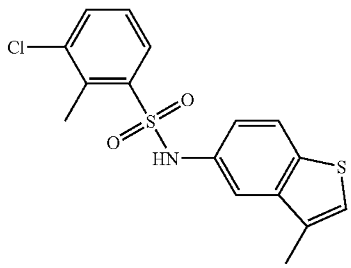 | 64.6 |
| 1033 | 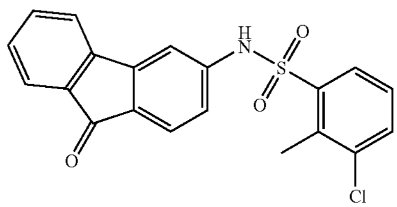 | 62.6 |
| 980 | 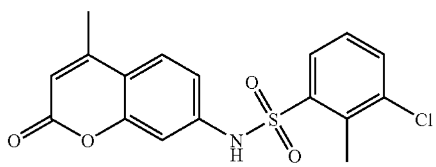 | 61.2 |
| 955 | 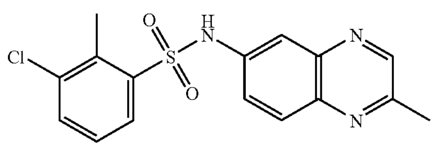 | 60.8 |
| 972 | 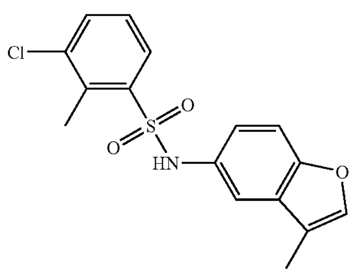 | 59.2 |
| 958 | 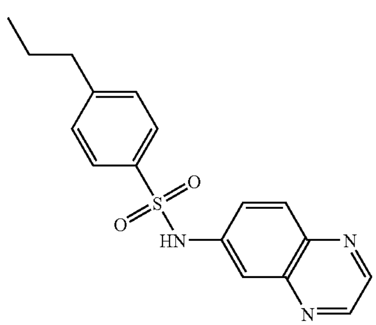 | 58.1 |

-continued
Inhibition Data
| STX No. | Structure | % inhibition of Human 11β HSD1 @10 μM typical sd ± 5% N = 2 |
|---|---|---|
| 988 | 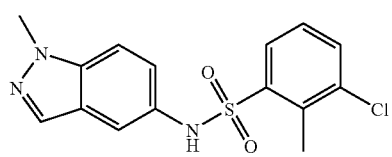 | 56 |
| 957 | 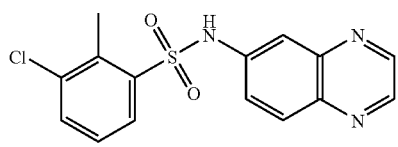 | 55.5 |
| 577 | 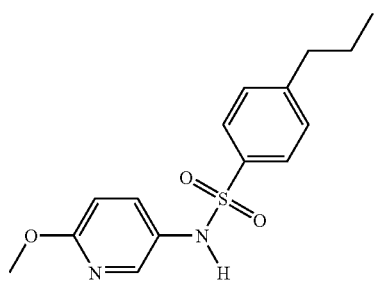 | 54.6 |
| 979 | 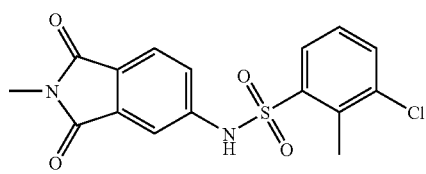 | 54.1 |
| 471 | 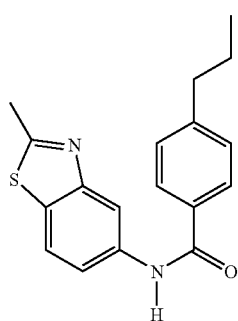 | 53.7 |

-continued
Inhibition Data
| STX No. | Structure | % inhibition of Human 11β HSD1 @10 μM typical sd ± 5% N = 2 |
|---|---|---|
| 555 | 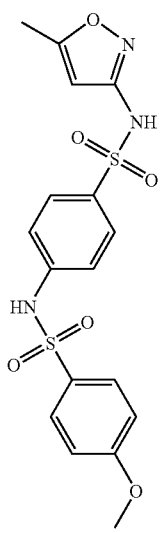 | 53.0 |
| 557 | 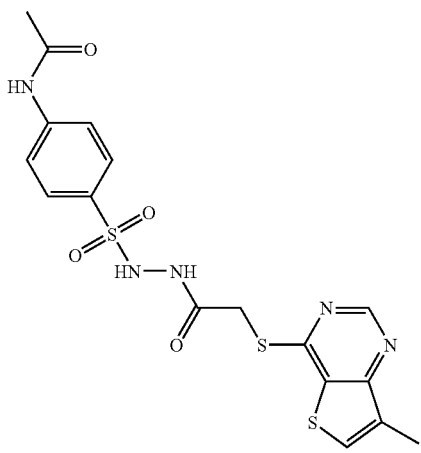 | 51.3 |
| 971 | 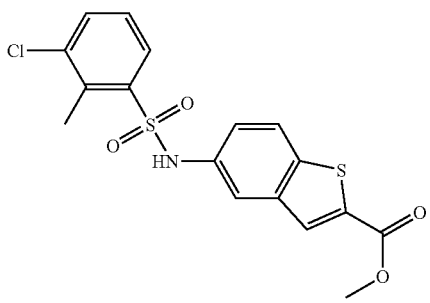 | 49.6 |

-continued
Inhibition Data
| STX No. | Structure | % inhibition of Human 11β HSD1 @10 μM typical sd ± 5% N = 2 |
|---|---|---|
| 646 | 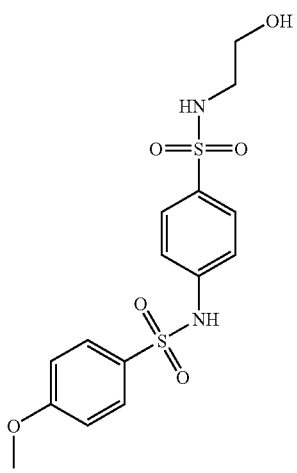 | 48.5 |
| 576 | 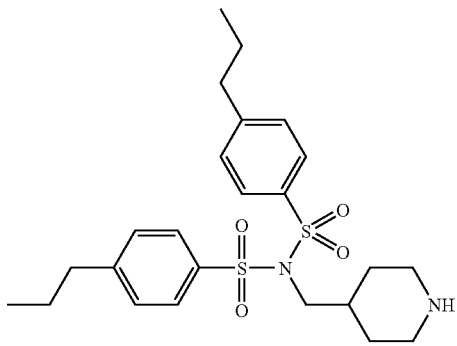 | 47.7 |
| 556 | 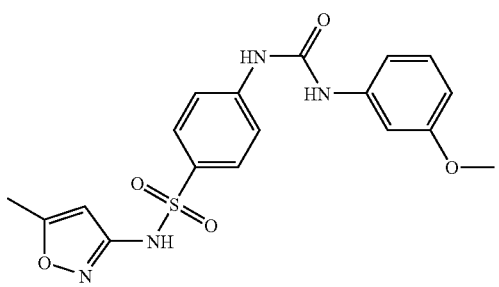 | 46.2 |
| 1031 | 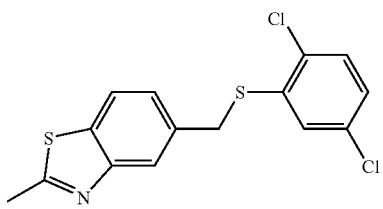 | 45.6 |

-continued
Inhibition Data
| STX No. | Structure | % inhibition of Human 11β HSD1 @10 μM typical sd ± 5% N = 2 |
|---|---|---|
| 520 | 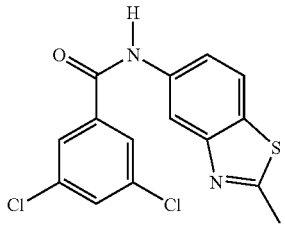 | 43.5 |
| 823 | 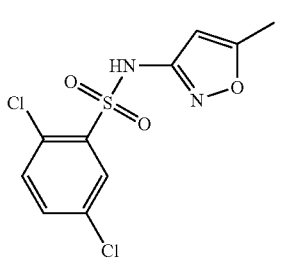 | 42.9 |
| 936 | 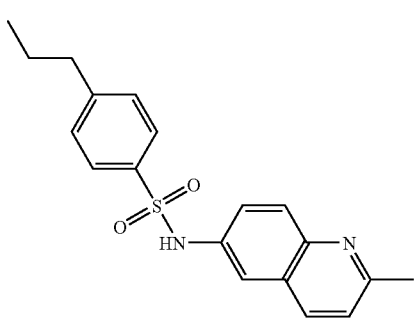 | 42.3 |
| 645 | 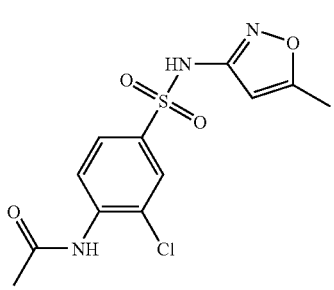 | 42.0 |
| 983 | 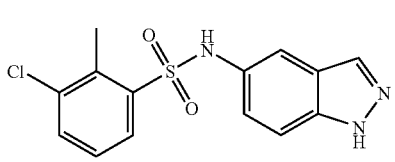 | 41.9 |

-continued
Inhibition Data
| STX No. | Structure | % inhibition of Human 11β HSD1 @10 μM typical sd ± 5% N = 2 |
|---|---|---|
| 702 | 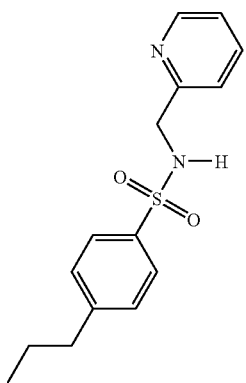 | 37.6 |
| 644 | 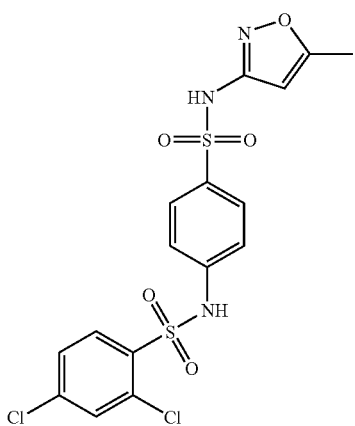 | 37.1 |
| 937 | 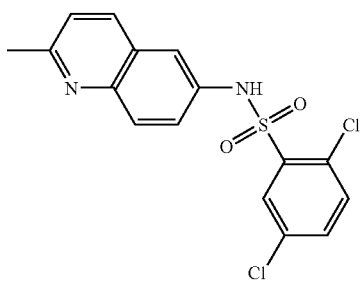 | 36.6 |
| 608 | 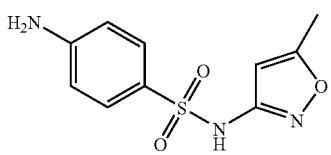 | 36.1 |

-continued
Inhibition Data
| STX No. | Structure | % inhibition of Human 11β HSD1 @10 μM typical sd ± 5% N = 2 |
|---|---|---|
| 653 | 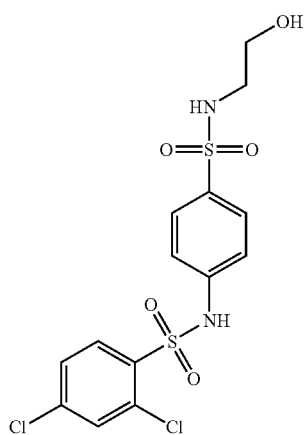 | 36.4 |
| 647 | 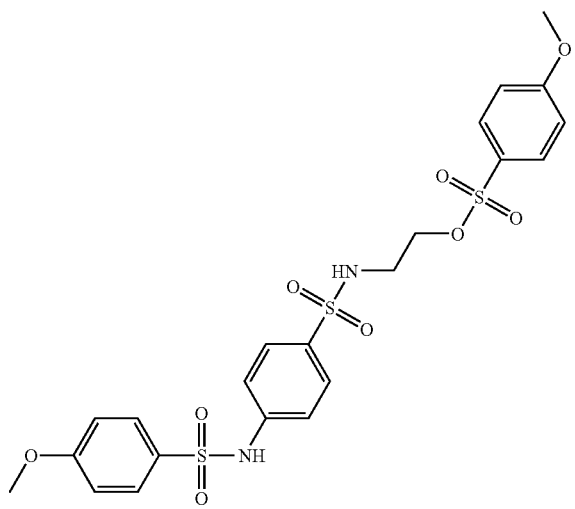 | 34.5 |
| 973 | 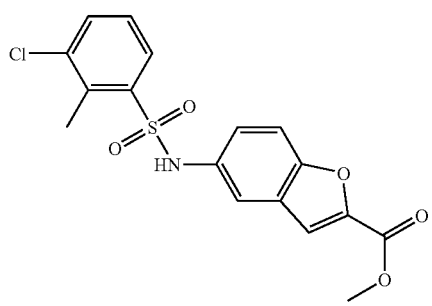 | 33.1 |

-continued

Inhibition Data

| STX No. | Structure | % inhibition of Human 11β HSD1 @10 μM typical sd ± 5% N = 2 |
|---|---|---|
| 654 | 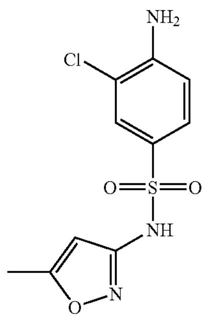 | 32.1 |
| 652 | 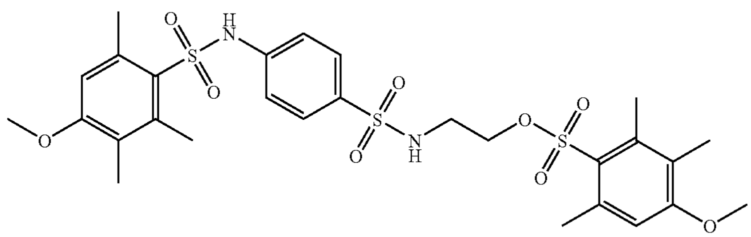 | 31.8 |
| 558 | 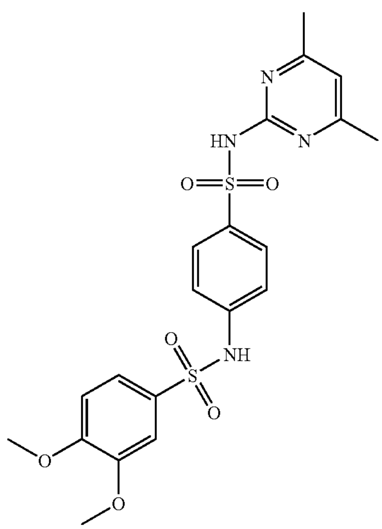 | 31.2 |
| 929 | 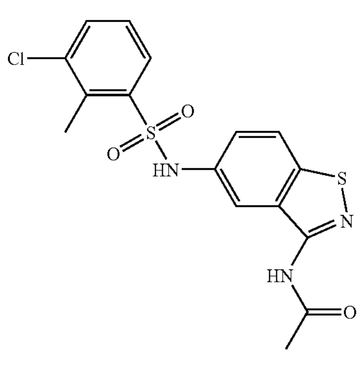 | 31.0 |

-continued

Inhibition Data

| STX No. | Structure | % inhibition of Human 11β HSD1 @10 μM typical sd ± 5% N = 2 |
|---|---|---|
| 1038 | 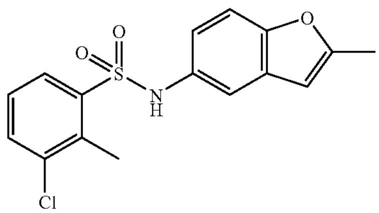 | 28.7 |
| 920 | 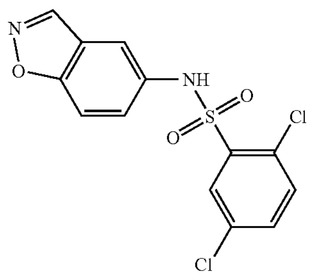 | 27.5 |
| 649 | 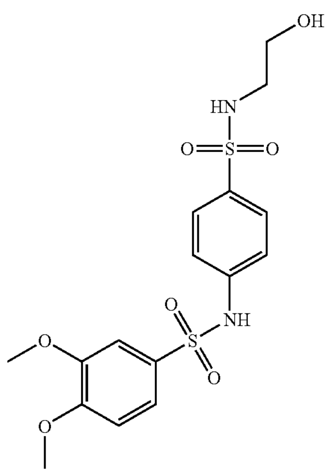 | 26.3 |
| 919 | 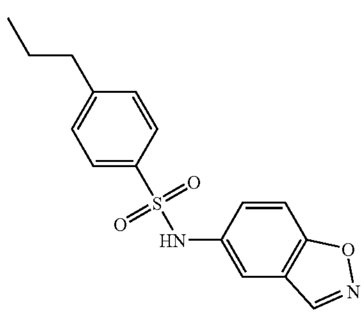 | 25.4 |

-continued

Inhibition Data

| STX No. | Structure | % inhibition of Human 11β HSD1 @10 μM typical sd ± 5% N = 2 |
|---|---|---|
| 876 | 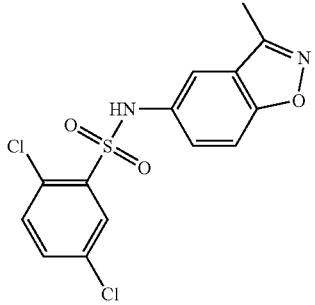 | 23.6 |
| 825 | 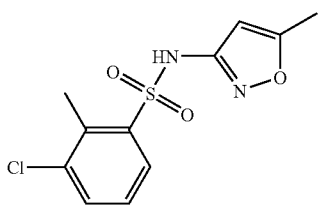 | 23.2 |
| 606 | 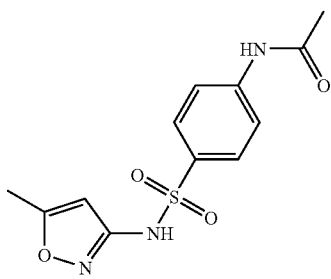 | 22.1 |
| 935 | 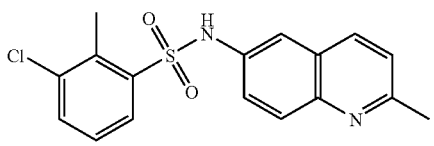 | 20.7 |

Chemistry Experimental Section and Compound Examples

General. All chemicals were either purchased from the Aldrich Chemical Co. (Gillingham, UK), Lancaster Synthesis (Morecambe, UK) or ACROS Organics (Loughborough, UK). All organic solvents of A.R. grade were supplied by Fisher Scientific (Loughborough, UK).

Thin layer chromatography (TLC) was performed on precoated plates (Merck TLC aluminium sheets silica gel 60 $F_{254}$, Art. No. 5554). Compounds were visualised by either viewing under UV light or treating with an ethanolic solution of phosphomolybdic acid (PMA) followed by heating.

Flash chromatography was carried out using Sorbsil C60 silica gel or Isolute® pre-packed Flash Si columns from Argonaut Technologies. Parallel synthesis was performed on either Radleys Carousel reaction stations or Radleys Green-House parallel synthesisers. Solvent removal from parallel syntheses was performed on a GeneVac DD4 evaporation system. NMR spectra were recorded with a JEOL GX-270 or Varian-Mercury-400 spectrometer, and chemical shifts are reported in parts per million (ppm, δrelative to tetramethylsilane (TMS) as an internal standard. Mass spectra were recorded at the Mass Spectrometry Service Centre, University of Bath. FAB-MS were carried out using m-nitrobenzyl alcohol (NBA) as the matrix. High performance liquid chromatography (HPLC) analysis was performed with a Waters Delta 600 liquid chromatograph with a Waters 996 photodiode Array Detector using a Waters Radialpack C18, 8×100 mm column. Melting points (Mp) were measured with a Reichert-Jung ThermoGalen Kofler block or a Sanyo Gallenkamp melting point apparatus and are uncorrected.

Synthesis of Benzofuran and Benzo[b]thiophene Derivatives

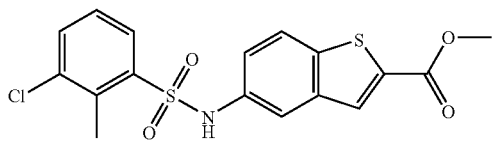
STX 971

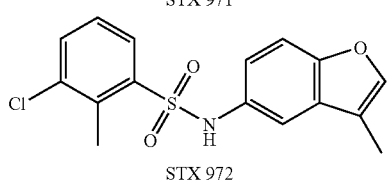
STX 972

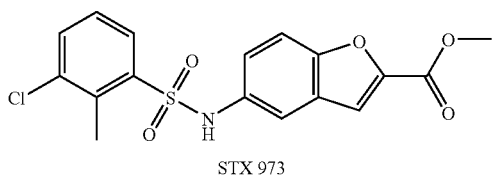
STX 973

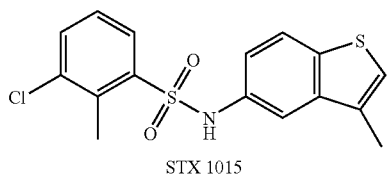
STX 1015

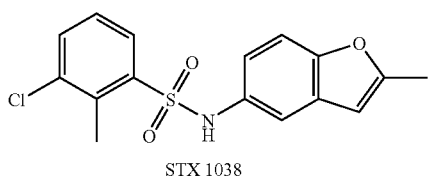
STX 1038

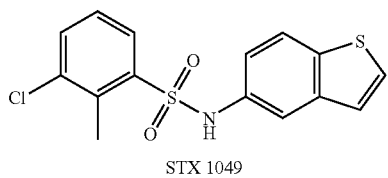
STX 1049

Synthesis of 5-(3-chloro-2-methyl-benzenesulfony-lamino)-benzo[b]thiophene-2-carboxylic acid methyl ester, STX 971 (KRB01096)

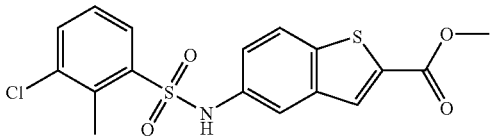

5-amino-benzo[b]thiophene-2-carboxylic acid methyl ester (KRB01094): To a solution of 5-nitro-benzo[b]thiophene-2-carboxylic acid methyl ester [15] (130 mg, 0.548 mmol) in methanol (30 mL) was added 5% palladium on carbon (20 mg) and the mixture was stirred under 1 atm $H_2$ for 2 h. The mixture was filtered through celite and the filtrate evaporated. The residue was passed through a silica column to afford 5-amino-benzo[b]thiophene-2-carboxylic acid methyl ester as a pale yellow solid (94 mg, 83%), single spot at $R_f$ 0.75 (95:5 dichloromethane:methanol). $^1$H NMR (CDCl$_3$): δ 7.86 (1H, s), 7.61 (1H, d, J=8.7 Hz), 7.11 (1H, d, J=2.2 Hz), 6.88(1H, dd, J=8.7, 2.5 Hz), 3.91 (3H, s), 3.76 (2H, s, N—H$_2$) [16].

To a solution of 3-chloro-2-methylbenzenesulphonyl chloride (46 mg, 0.20 mmol) in dichloromethane (2 mL) was added pyridine (40 μL, 0.48 mmol) and the mixture was stirred under N$_2$ for 5 min, after which time 5-amino-benzo[b]thiophene-2-carboxylic acid methyl ester (40 mg, 0.19 mmol) was added. The resulting mixture was stirred for 2 h at room temperature, then saturated NaHCO$_3$ solution (6 mL) was added and the mixture was extracted into ethyl acetate (12 mL). The organic phase was washed with brine, dried (Na$_2$SO$_4$), filtered and evaporated to give a residue that was purified using flash chromatography to afford a pale yellow solid (65 mg, 85%), single spot at $R_f$ 0.52 (2:1 hexane:ethyl acetate). mp 173.6-174.2° C., HPLC purity 99% ($t_R$ 2.13 min in 10% water-acetonitrile). $^1$H NMR (CDCl$_3$): δ 7.91 (1H, s), 7.88 (1H, d, J=7.9 Hz), 7.70 (1H, d, J=8.7 Hz), 7.55-7.52 (2H, m), 7.18 (1H, t, J=8.0 Hz), 7.12 (1H, dd, J=8.7, 2.2 Hz), 6.98 (1H, s, N—H), 3.92 (3H, s), 2.73(3H, s). LCMS: 394.12 (M–). FAB-MS (MH+, C$_{17}$H$_{14}$ClNO$_4$S$_2$): calcd 395.0053, found 395.0045.

Synthesis of 3-chloro-2-methyl-N-(3-methyl-benzofuran-5-yl)-benzenesulfonamide, STX 972 (KRB01097)

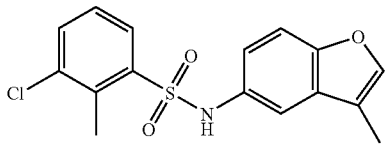

5-amino-3-methyl-benzofuran (KRB01095): To a solution of 3-methyl-5-nitro-benzofuran [17] (135 mg, 0.762 mmol) in methanol (30 mL) was added 5% palladium on carbon (30 mg) and the mixture was stirred under 1 atm H$_2$ for 8 h. The mixture was filtered through celite and the filtrate evaporated. The residue was passed through a silica plug to afford 5-amino-3-methyl-benzofuran as a pale pink oil (85 mg, 76%), single spot at $R_f$ 0.28 (2:1 hexane:ethyl acetate). $^1$H NMR (CDCl$_3$): δ 7.31 (1H, s), 7.22 (1H, d, J=8.7 Hz), 6.78 (1H, d, J=2.5 Hz), 6.66 (1H, dd, J=8.7, 2.5 Hz), 3.60 (2H, s, N—H$_2$), 2.16 (3H, s).

To a solution of 3-chloro-2-methylbenzenesulphonyl chloride (128 mg, 0.571 mmol) in dichloromethane (3 mL) was added pyridine (110 μL, 1.36 mmol) and the mixture was stirred under N$_2$ for 5 min, after which time 5-amino-3-methyl-benzofuran (80 mg, 0.54 mmol) was added. The resulting mixture was stirred for 2 h at room temperature, then saturated NaHCO$_3$ solution (8 mL) was added and the mixture was extracted into ethyl acetate (15 mL). The organic phase was washed with brine, dried (Na$_2$SO$_4$), filtered and evaporated to give a residue that was purified using flash chromatography to afford a yellow solid (159 mg, 87%), single spot at R$_f$ 0.65 (2:1 hexane:ethyl acetate). mp 119.5-120.1° C., HPLC purity 99% (t$_R$ 2.22 min in 10% water-acetonitrile). $^1$H NMR (CDCl$_3$): δ 7.82 (1H, d, J=7.9 Hz), 7.54 (1H, d, J=7.9 Hz), 7.38 (1H s), 7.28-7.22 (2H, m), 7.15 (1H, t, J=8.0 Hz), 6.83 (1H, dd, J=8.7, 2.2 Hz), 6.56 (1H, s, N—H, 2.72 (3H, s), 2.15 (3H, s). LCMS: 334.07 (M–). FAB-MS (MH+, C$_{16}$H$_{14}$ClNO$_3$S): calcd 335.0383, found 335.0383.

Synthesis of 5-(3-chloro-2-methyl-benzenesulfonylamino)-benzofuran-2-carboxylic acid methyl ester. STX 973 (KRB01100):

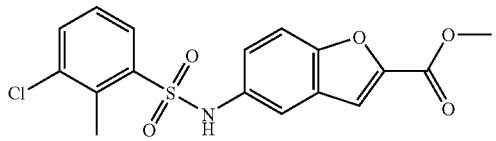

5-nitro-benzofuran-2-carboxylic acid methyl ester (KRB01098): To a suspension of NaH (258 mg, 60% dispersion in mineral oil, 6.46 mmol) in anhydrous DMF (10 mL) was added methyl glycolate (420 μL, 5.39 mmol) dropwise. After 10 min, a solution of 2-chloro-5-nitrobenzaldehyde (1.00 g, 5.39 mmol) in anhydrous DMF (3 mL) was added and the resulting solution was stirred at room temperature for 1 h followed by 100° C. for 5 h. After cooling, the mixture was poured into 1N HCl (50 mL) and the resulting precipitate filtered and washed with water. The solid was purified by flash chromatography (4:1 hexane:ethyl acetate) and then recrystallized from hexane/ethyl acetate to yield 5-nitro-benzofuran-2-carboxylic acid methyl ester as yellow needles (450 mg, 37%). mp 168.0-168.4° C. $^1$H NMR (CDCl$_3$): δ 8.65 (1H, d, J=2.2 Hz), 8.37 (1H, dd, J=9.0, 2.2 Hz), 7.70 (1H, d, J=9.1 Hz), 7.64 (1H, s), 4.01 (3H, s).

5-amino-benzofuran-2-carboxylic acid methyl ester (KRB01099): To a solution of 5-nitrobenzofuran-2-carboxylic acid methyl ester (100 mg, 0.452 mmol) in methanol (20 mL) was added 5% palladium on carbon (20 mg) and the mixture was stirred under 1 atm H$_2$ for 4h. The mixture was filtered through celite and the filtrate evaporated. The residue was passed through a silica plug to afford 5-amino-benzofuran-2-carboxylic acid methyl ester as an orange solid (87 mg, ~100%), single spot at R$_f$ 0.34 (1:1 hexane:ethyl acetate). mp 112.4-113.0° C. $^1$H NMR (CDCl$_3$): δ 7.36 (1H, s), 7.36 (1H, d, J=8.2 Hz), 6.89 (1H, d, J=2.2 Hz), 6.83 (1H, dd, J=8.2, 2.2 Hz), 3.95 (3H, s), 3.66 (2H, s, N—H$_2$).

To a solution of 3-chloro-2-methylbenzenesulphonyl chloride (99 mg, 0.44 mmol) in dichloromethane (3 mL) was added pyridine (85 μL, 1.05 mmol) and the mixture was stirred under N$_2$ for 5 min, after which time 5-amino-benzofuran-2-carboxylic acid methyl ester (80 mg, 0.42 mmol) was added. The resulting mixture was stirred for 2 h at room temperature, then saturated NaHCO$_3$ solution (10 mL) was added and the mixture was extracted into ethyl acetate (15 mL). The organic phase was washed with brine, dried (Na$_2$SO$_4$), filtered and evaporated to give a residue that was purified using flash chromatography to afford an off-white solid (122 mg, 77%), single spot at R$_f$ 0.47 (2:1 hexane:ethyl acetate). mp 139.4-140.1° C., HPLC purity 99+% (t$_R$ 1.90 min in 10% water-acetonitrile). $^1$H NMR (CDCl$_3$): δ 7.83 (1H, d, J=7.9 Hz), 7.55 (1H, d, J=7.9 Hz), 7.44 (1H, d, J=9.0 Hz), 7.42 (1H, s), 7.39 (1H, d, J=2.2 Hz), 7.17 (1H, t, J=8.0 Hz), 7.05 (1H, dd, J8.7, 2.2 Hz), 6.65 (1H, s, N—H), 3.95 (3H, s), 2.72 (3H, s). LCMS: 378.16. FAB-MS (MH+, C$_{17}$H$_{14}$ClNO$_5$S): calcd 379.0281, found 379.0281.

Synthesis of 3-chloro-2-methyl-N-(3-methyl-benzo[b]thiophen-5-yl)-benzenesulfonamide, STX 1015 (KRB01108)

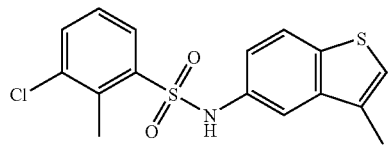

3-methyl-benzo[b]thiophen-5-ylamine (KRB01106): To a solution of 3-methyl-5-nitro-benzo[b]thiophene [18] (95 mg, 0.492 mmol) in methanol (20 mL) was added 5% palladium on carbon (20 mg) and the mixture was stirred under 1 atm H$_2$ for 8.5h. The mixture was filtered through celite and the filtrate evaporated. The residue was passed through a silica plug to afford 3-methyl-benzo[b]thiophen-5-ylamine as a dark orange solid (31 mg, 39%), single spot at R$_f$ 0.31 (4:1 hexane:ethyl acetate). $^1$H NMR (CDCl$_3$): δ 7.60 (1H, d, J=8.4 Hz), 7.02 (1H, s), 7.00 (1H, d, J=2.2 Hz), 6.79 (1H, dd, J=8.4, 2.2 Hz), 2.37 (3H, s).

To a solution of 3-chloro-2-methylbenzenesulphonyl chloride (43 mg, 0.19 mmol) in dichloromethane (2 mL) was added pyridine (40 μL, 0.46 mmol) and the mixture Was stirred under N$_2$ for 5 min, after which time 3-methyl benzo[b]thiophen-5-ylamine (30 mg, 0.18 mmol) was added. The resulting mixture was stirred for 2 h at room temperature, then saturated NaHCO$_3$ solution (10 mL) was added and the mixture was extracted into ethyl acetate (15 mL). The organic phase was washed with brine, dried (Na$_2$SO$_4$), filtered and evaporated to give a residue that was purified using flash chromatography to afford a pale brown solid (30 mg, 46%), single spot at R$_f$ 0.39 (3:1 hexane:ethyl acetate). mp 152.6-1.53.0° C., HPLC purity 99% (t$_R$ 2.42 min in 10% water-acetonitrile). $^1$H NMR (CDCl$_3$): δ 7.90 (1H, d, J=7.9 Hz), 7.65 (1H, d, J=8.7 Hz), 7.53 (1H, d, J=7.9 Hz), 7.37 (1H, d, J=2.0 Hz), 7.16 (1H, t, J=7.9 Hz), 7.07 (1H, s), 7.02 (1H, dd; J8.7, 2.0 Hz), 2.74 (3H, s), 2.32 (3H, s). LCMS: 350.09. FAB-MS (MH+, C$_{16}$H$_{14}$ClNO$_2$S$_2$): calcd 351.0155, found 351.0155.

Synthesis of 3-chloro-2-methyl-N-(2-methyl-benzofuran-5-yl)-benzenesulfonamide, STX-1038 (KRB01114)

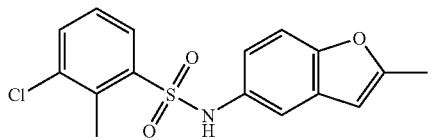

5-amino-2-methylbenzofuran (KRB01112): To a solution of 2-methyl-5-nitro-benzofuran [19] (125 mg, 0.706 mmol) in methanol (20 mL) was added 5% palladium on carbon (20 mg) and the mixture was stirred under 1 atm $H_2$ for 4 h. The mixture was filtered through celite and the filtrate evaporated. The residue was passed through a silica plug to afford 5-amino-2-methyl benzofuran as a red-brown oil (78 mg, 75%), single spot at $R_f$ 0.45 (1:1 hexane:ethyl acetate). $^1$H NMR (CDCl$_3$): δ 7.17 (1H, d, J=8.7 Hz), 6.75 (1H, d, J=2.5 Hz), 6.57 (1H, dd, J8.7, 2.5 Hz), 6.20 (1H, s), 3.53 (2H, s, NH$_2$), 2.39 (3 H, s).

To a solution of 3-chloro-2-methylbenzenesulphonyl chloride (112 mg, 0.499 mmol) in dichloromethane (3 mL) was added pyridine (95 μL, 1.2 mmol) and the mixture was stirred under N$_2$ for 5 min, after which time 5-amino-2-methyl benzofuran (70 mg, 0.48 mmol) was added. The resulting mixture was stirred for 2 h at room temperature, then saturated NaHCO$_3$ solution (10 mL) was added and the mixture was extracted into ethyl acetate (1.5 mL). The organic phase was washed with brine, dried (Na$_2$SO$_4$), filtered and evaporated to give a residue that was purified using flash chromatography to afford a pale brown solid (120 mg, 75%), single spot at $R_f$ 0.51 (3:1 hexane:ethyl acetate). mp 123.2-123.6° C., HPLC purity 98% ($t_R$ 3.14 min in 10% water-acetonitrile). $^1$H NMR (CDCl$_3$): δ 7.81 (1H, d, 3J=7.7 Hz), 7.52 (1H, d, J=7.7 Hz), 7.21 (1H, d, J=8.7 Hz), 7.16-7.11 (2H, m), 6.78 (1H, dd, J=8.7, 2.2 Hz), 6.48 (1H, s, N—H), 6.27 (1H, s), 2.70 (3H, s), 2.40 (3H, s); LCMS: 334.13. FAB-MS (MH+, C$_{16}$H$_{14}$ClNO$_3$S): calcd 335.0383, found 335.0381.

Synthesis of N-benzo[b]thiophen-5-yl-3-chloro-2-methyl-benzenesulfonamide, STX 1049 (KRB01121)

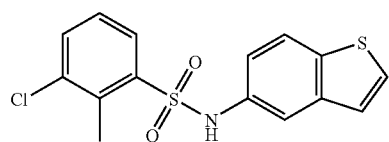

To a solution of 3-chloro-2-methylbenzenesulphonyl chloride (47 mg, 0.21 mmol) in dichloromethane (2 mL) was added pyridine (40 μL, 0.50 mmol) and the mixture was stirred under N$_2$ for 5 min, after which time 5-amino-benzo[b]thiophene [20] (30 mg, 0.20 mmol) was added. The resulting mixture was stirred for 2 h at room temperature, then saturated NaHCO$_3$ solution (10 mL) was added and the mixture was extracted into ethyl acetate (15 mL). The organic phase was washed with brine, dried (Na$_2$SO$_4$), filtered and evaporated to give a residue that was purified using flash chromatography to afford a dark brown solid (50 mg, 74%), single spot at $R_f$ 0.58 (3:1 hexane:ethyl acetate). mp 108.5-109.0° C., HPLC purity 99% ($t_R$ 2.20 min in 10% water-acetonitrile). $^1$H NMR (CDCl$_3$): δ 7.87 (1H, d, J=7.9 Hz), 7.70 (1H, d, J=8.7 Hz), 7.54-7.51 (2H, m), 7.44 (1H, d, J=5.4 Hz), 7.21 (1H, d, J=5.4 Hz), 7.16 (1H, t, J=7.9 Hz), 6.98 (1H, dd, J=8.7, 2.2 Hz), 6.73 (1H, s, N—H), 2.74 (3H, s). LCMS: 336.07. FAB-MS (MH+, C$_{15}$H$_{12}$ClNO$_2$S$_2$): calcd 336.9998, found 337.0004.

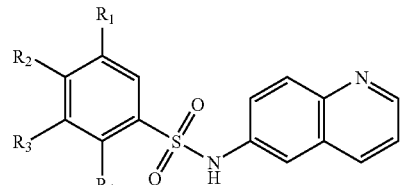

STX 932: $R_1$ = $R_2$ = H, $R_3$ = Cl, $R_4$ = Me
STX 933: $R_1$ = $R_3$ = $R_4$ = H, $R_2$ = n-propyl
STX 934: $R_1$ = $R_4$ = Cl, $R_2$ = $R_3$ = H

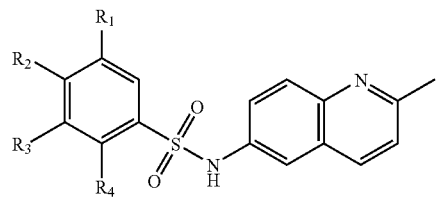

STX 935: $R_1$ = $R_2$ = H, $R_3$ = Cl, $R_4$ = Me
STX 936: $R_1$ = $R_3$ = $R_4$ = H, $R_2$ = n-propyl
STX 937: $R_1$ = $R_4$ = Cl, $R_2$ = $R_3$ = H

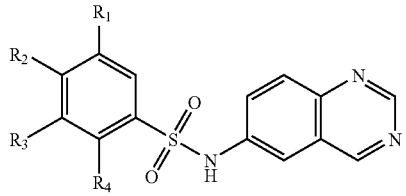

STX 943: $R_1$ = $R_2$ = H, $R_3$ = Cl, $R_4$ = Me
STX 944: $R_1$ = $R_3$ = $R_4$ = H, $R_2$ = n-propyl

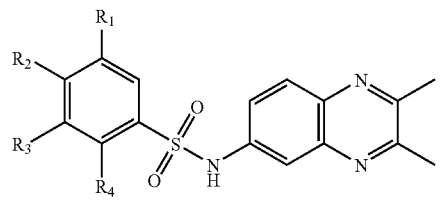

STX 953: $R_1$ = $R_2$ = H, $R_3$ = Cl, $R_4$ = Me
STX 954: $R_1$ = $R_3$ = $R_4$ = H, $R_2$ = n-propyl

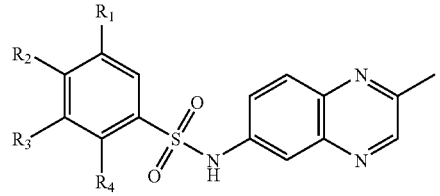

STX 955: $R_1$ = $R_2$ = H, $R_3$ = Cl, $R_4$ = Me
STX 956: $R_1$ = $R_3$ = $R_4$ = H, $R_2$ = n-propyl -continued

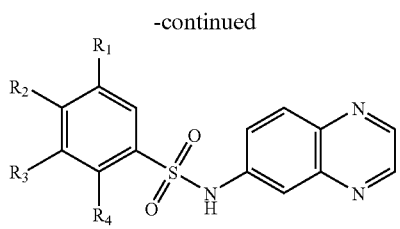

STX 957: R$_1$ = R$_2$ = H, R$_3$ = Cl, R$_4$ = Me
STX 958: R$_1$ = R$_3$ = R$_4$ = H, R$_2$ = n-propyl Synthesis of 3-chloro-2-methyl-N-quinolin-6-yl-benzenesulfonamide, STX 932 (KRB01058)

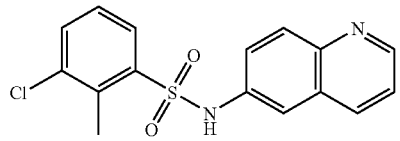

To a solution of 3-chloro-2-methylbenzenesulphonyl chloride (164 mg, 0.728 mmol) in dichloromethane (4 mL) was added pyridine (140 μL, 1.74 mmol) and the mixture was stirred under N$_2$ for 5 min, after which time 6-aminoquinoline (100 mg, 0.694 mmol) was added. The resulting mixture was stirred for 2 h at room temperature, then saturated NaHCO$_3$ solution (10 mL) was added and the mixture was extracted into ethyl acetate (20 mL). The organic: phase was washed with brine, dried (Na$_2$SO$_4$), filtered and evaporated to give a residue that was purified using flash chromatography to afford a pale pink solid (48 mg, 21%), single spot at R$_f$ 0.71 (ethyl acetate). mp 228.0-228.5° C., HPLC purity 99+% (t$_R$ 2.43 min in 10% water-acetonitrile). $^1$H NMR (CDCl$_3$): δ 8.83 (1H, dd, J=4.2, 1.7 Hz), 7.98 (3H, m), 7.54 (1H, d, J=7.9 Hz), 7.48 (1H, d, J=2.7 Hz), 7.39-7.32 (2H, m), 7.20 (1H, t, J=7.9 Hz), 7.05 (1H, s, N—H), 2.75 (3H, s). LCMS: 331.16 (M−). FAB-MS (MH+, C$_{16}$H$_{13}$ClN$_2$O$_2$S): calcd 333.0464, found 333.0461.

Synthesis of 4-propyl-N-quinolin-6-yl-benzenesulfonamide, STX 933 (KRB01059)

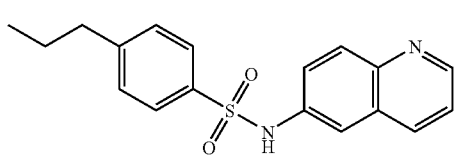

To a solution of 4n-propylbenzenesulphonyl chloride (159 mg, 0.728 mmol) in dichloromethane (4 mL) was added pyridine (140 μL, 1.74 mmol) and the mixture was stirred under N$_2$ for 5 min, after which time 6-aminoquinoline (100 mg, 0.694 mmol) was added. The resulting mixture was stirred for 2 h at room temperature, then saturated NaHCO$_3$ solution (10 mL) was added and the mixture was extracted into ethyl acetate (20 mL). The organic phase was washed with brine, dried (Na$_2$SO$_4$), filtered and evaporated to give a residue that was purified using flash chromatography to afford a white solid (210 mg, 93%), single spot at R$_f$ 0.71 (ethyl acetate). mp 180.1-180.7° C., HPLC purity 99+% (t$_R$ 2.37 min in 10% water-acetonitrile). $^1$H NMR (CDCl$_3$): δ 8.83 (1H, dd, J=4.2, 1.7 Hz), 8.05 (1H, d, J=8.4 Hz), 7.97 (1H, d, J=9.2 Hz), 7.70 (2H, d, J=8.2 Hz), 7.57 (1H, d, J=2.5 Hz), 7.40-7.34 (2H, m), 7.22 (2H, m), 6.85 (1H, s, N—H), 2.57 (2H, t, J=7.2 Hz), 1.57 (2H, sextet, J=7.2 Hz), 0.87 (3H, t, J=7.3 Hz). LCMS: 325.23 (M−). FAB-MS (MH+, C$_{18}$H$_{18}$N$_2$O$_2$S): calcd 327.1167, found 327.1167.

Synthesis of 2,5-dichloro-N-guinolin-6-yl-benzenesulfonamide, STX 934 (KRB01060)

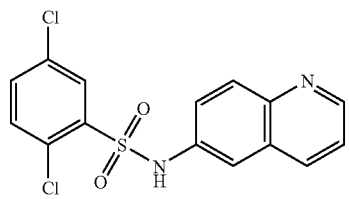

To a solution of 2,5-dichlorobenzenesulphonyl chloride (179 mg, 0.728 mmol) in dichloromethane (4 mL) was added pyridine (140 μL, 1.74 mmol) and the mixture was stirred under N$_2$ for 5 min, after which time 0.6-aminoquinoline (100 mg, 0.694 mmol) was added. The resulting mixture was stirred for 2 h at room temperature, then saturated NaHCO$_3$ solution (10 mL) was added and the mixture was extracted into ethyl acetate (20 mL). The organic phase was washed with brine, dried (Na$_2$SO$_4$), filtered and evaporated to give a residue that was purified using flash chromatography to afford a white solid (168, mg, 69%), single spot at R$_f$ 0.74 (ethyl acetate). mp 213.4-213.8° C., HPLC purity 99+% (t$_R$ 2.28 min in 10% water-acetonitrile). $^1$H NMR (CDCl$_3$): δ 8.85 (1H, dd, J=4.2, 1.5 Hz), 8.09 (1H, d, J=8.4 Hz), 8.03-8.00 (2H, m), 7.62 (1H, d, J=2.5 Hz), 7.56 (1H, s, N—H), 7.47-7.38 (4H, m). LCMS: 351.10 (M−). FAB-MS (MH+, C$_{15}$H$_{10}$Cl$_2$N$_2$O$_2$S): calcd 352.9918, found 352.9922.

Synthesis of 3-chloro-2-methyl-N-(2-methyl-quinolin-6-yl)-benzenesulfonamide, STX 935 (KRB01061)

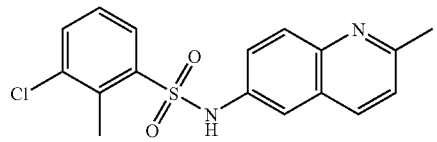

To a solution of 3-chloro-2-methylbenzenesulphonyl chloride (149 mg, 0.664 mmol) in dichloromethane (4 mL) was added pyridine (130 μL, 1.58 mmol) and the mixture was stirred under N$_2$ for 5 min, after which time 6-amino-2-methylquinoline (100 mg, 0.632 mmol) was added. The resulting mixture was stirred for 90 min at room temperature, then saturated NaHCO$_3$ solution (10 mL) was added and the mixture was extracted into ethyl acetate (20 mL). The organic phase was washed with brine, dried (Na$_2$SO$_4$), filtered and evaporated to give a residue that was purified using flash chromatography to afford an off-white solid (148 mg, 68%), single spot at R$_f$ 0.64 (ethyl acetate). mp 178.1-

178.4° C., HPLC purity 99+% ($t_R$ 2.27 min in 10% water-acetonitrile). $^1$H NMR (CDCl$_3$): δ 7.93-7.89 (3H, m), 7.53 (1H, d, J=8.2 Hz), 7.44 (1H, d, J=2.5 Hz), 7.31-7.24 (2H, m), 7.18 (1H, t, J=8.1 Hz), 2.73 (3H, s), 2.69 (3H, s). LCMS: 345.17 (M−). FAB-MS (MH+, C$_{17}$H$_{15}$ClN$_2$O$_2$S): calcd 347.0621, found 347.0622.

Synthesis of N-(2-methyl-quinolin-6-yl)-4-propyl-benzenesulfonamide, STX 936 (KRB01062)

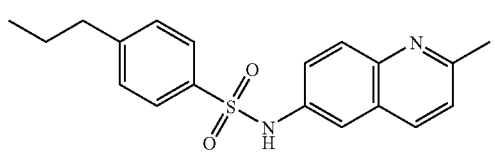

To a solution- of 0.4n-propylbenzenesulphonyl chloride (145 mg, 0.664 mmol) in dichloromethane (4 mL) was added pyridine (130 μL, 1.58 mmol) and the mixture was stirred- under N$_2$ for 5 min, after which time 6-amino-2-methylquinoline (100 mg, 0.632 mmol) was added. The resulting mixture was stirred for 1 h at room temperature, then saturated NaHCO$_3$ solution (10 mL) was added and the mixture was extracted into ethyl acetate (20 mL). The organic phase was washed with brine, dried (Na$_2$SO$_4$), filtered and evaporated to give a residue that was purified using flash chromatography to afford an off-white solid (186 mg, 86%), single spot at $R_f$ 0.70 (ethyl acetate). mp 173.7-174.0° C., HPLC purity 99+% ($t_R$ 2.32 min in 10% water-acetonitrile). $^1$H NMR (CDCl$_3$): δ 7.94 (1H, d, J=8.4 Hz), 7.89 (1H, d, J=9.2 Hz), 7.67 (2H, d, J=8.4 Hz), 7.54 (1H, d, J=2.5 Hz), 7.31 (1H, dd, J=8.9, 2.5 Hz), 7.25 (1H, d, J=8.4 Hz), 7.19 (2H, d, J=8.4 Hz), 7.07 (1H, s, N—H), 2.70 (3H, s), 2.56 (2H, t, J=7.5 Hz), 1.58 (2H, sextet, J=7.4 Hz), 0.87 (3H, t, J=7.4 Hz). LCMS: 339.24 (M−). FAB-MS (MH+, C$_{19}$H$_{20}$N$_2$O$_2$S): calcd 341.1323, found 341.1324.

Synthesis of 2,5-dichloro-N-(2-methyl-quinolin-6-yl)-benzenesulfonamide. STX 937 (KRB01063)

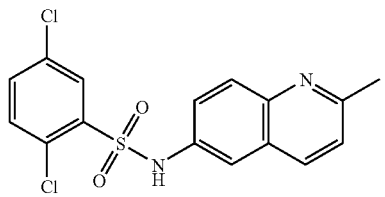

To a solution of 2,5-dichlorobenzenesulphonyl chloride (163 mg, 0.664 mmol) in dichloromethane (4 mL) was added pyridine (130 μL, 1.58 mmol) and the mixture was stirred under N$_2$ for 5 min, after which time 6-amino-2-methylquinoline (100 mg, 0.632 mmol) was added. The resulting mixture was stirred for 2 h at room temperature, then saturated NaHCO$_3$ solution (10 mL) was added and the mixture was extracted into ethyl acetate (20 mL). The organic phase was washed with brine, dried (Na$_2$SO$_4$), filtered and evaporated to give a residue that was purified using flash chromatography to afford an off-white solid (120 mg, 52%), single spot at $R_f$ 0.68 (ethyl acetate). mp 124.6-125.0° C., HPLC purity 99+% ($t_R$ 2.22 min in 10% water-acetonitrile). $^1$H NMR (CDCl$_3$): δ 7.98 (1H, d, 2.2 Hz), 7.94 (1H, d, J=8.4 Hz), 7.88 (1H, d, J=8.9 Hz), 7.57 (1H, d, J=2.2 Hz), 7.45-7.35 (3H, m), 7.27-7.24 (2H, m), 2.68 (3H, s). LCMS: 365.10 (M−). FAB-MS (MH+, C$_{16}$H$_{12}$Cl$_2$N$_2$O$_2$S): calcd 367.0075, found 367.0074.

Synthesis of 3-chloro-2-methyl-N-quinazolin-6-yl-benzenesulfonamide, STX 943 (KRB01068)

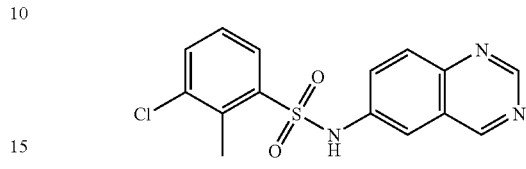

To a solution of 3-chloro-2-methylbenzenesulphonyl chloride (163 mg, 0.723 mmol) in dichloromethane (4 mL) was added pyridine (140 μL, 1.72 mmol) and the mixture was stirred under N$_2$ for 5 min, after which time 6-amino-quinazoline [21] (100 mg, 0.689 mmol) was added. The resulting mixture was stirred for 4 h at room temperature, then saturated NaHCO$_3$ solution (10 mL) was added and the mixture was extracted into ethyl acetate (20 mL). The organic phase was washed with brine, dried (Na$_2$SO$_4$), filtered and evaporated to give a residue that was purified using flash chromatography to afford a pale yellow solid (55 mg, 24%), single spot at $R_f$ 0.56 (ethyl acetate). mp>270° C. (appeared to decompose at about 150° C.), HPLC purity 98% ($t_R$ 2.06 min in 10% water-acetonitrile). $^1$H NMR (CDCl$_3$): δ 9.28 (1H, s), 9.25 (1H, s), 7.98 (1H, d, J=4.4 Hz), 7.95 (1H, d, J=5.2 Hz), 7.59-7.53 (3H, m), 7.25-7.20 (1H, m), 2.76 (3H, s). LCMS: 332.11 (M−). FAB-MS (MH+, C$_{15}$H$_{12}$ClN$_3$O$_2$S): calcd 334.0417, found 334.0420.

Synthesis of 4-propyl-N-quinazolin-6-yl-benzenesulfonamide, STX 944 (KRB01069)

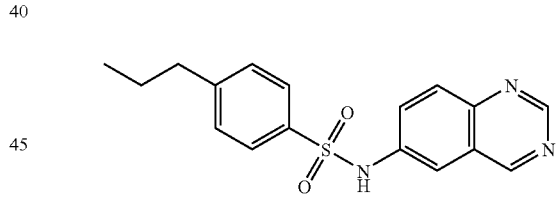

To a solution of 4n-propylbenzenesulphonyl chloride (151 mg, 0.723 mmol) in dichloromethane (4 mL) was added pyridine (140 μL, 1.72 mmol) and the mixture was stirred under N$_2$ for 5 min, after which time 6-amino-quinazoline (100 mg, 0.689 mmol) was added. The resulting mixture was stirred for 4 h at room temperature, then saturated NaHCO$_3$ solution (10 mL) was added and the mixture was extracted into ethyl acetate (20 mL). The organic phase was washed with brine, dried (Na$_2$SO$_4$), filtered and evaporated to give a residue that was purified using flash chromatography to afford a pale yellow solid (47 mg, 21%), single spot at $R_f$ 0.57 (ethyl acetate). mp 202.1-202.6° C., HPLC purity 96% ($t_R$ 2.14 min in 10% water-acetonitrile). $^1$H NMR (CDCl$_3$): δ 9.30 (1H, s), 9.24 (1H, s), 7.99-7.92 (2H, m), 7.77 (2H, d, J=8.4 Hz), 7.68-7.63 (2H, m), 7.23 (1H, d, J=7.7 Hz), 2.57 (2H, t, J=7.6 Hz), 1.57 (2H, sextet, J=7.6 Hz), 0.87 (3H, t, J=7.4 Hz). LCMS: 326.24 (M−). FAB-MS (MH+, C$_{17}$H$_{17}$N$_3$O$_2$S): calcd 328.1119, found 328.1118.

Synthesis of 3-chloro-N-(2.3-dimethyl-quinoxalin-6-yl)-2-methyl-benzenesulfonamide. STX 953 (KRB01074)

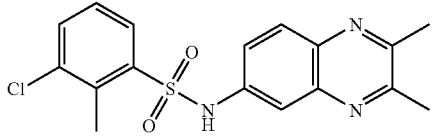

To a solution of 3-chloro-2-methylbenzenesulphonyl chloride (109 mg, 0.485 mmol) in dichloromethane (3 mL) was added pyridine (90 µL, 1.2 mmol) and the mixture was stirred under $N_2$ for 5 min, after which time 6-amino-2,3-dimethylquinoxaline [22] (80 mg, 0.46 mmol) was added. The resulting mixture was stirred for 6 h at room temperature, then saturated $NaHCO_3$ solution (8 mL) was added and the mixture was extracted into ethyl acetate (15 mL). The organic phase was washed with brine, dried ($Na_2SO_4$), filtered and evaporated to give a residue that was purified using flash chromatography to afford an off-white solid (152 mg, 91%), single spot at $R_f$ 0.70 (ethyl acetate). mp 225.3-225.7° C. HPLC purity 99+% ($t_R$ 2.29 min in 10% water-acetonitrile). $^1$H NMR ($CDCl_3$): δ 7.99 (1H, d, 4=7.9. Hz), 7.85 (1H, d, J=9.2 Hz), 7.54-7.52 (2H, m), 7.40 (1H, dd, J=9.1, 2.6 Hz), 7.21 (1H, t, J=7.9 Hz), 6.95 (1H, s, N—H, 2.75 (3H, s), 2.67 (6H, s). LCMS: 360.24 (M–). FAB-MS (MH+, $C_{17}H_{16}ClN_3O_2S$): calcd 362.0730, found 362.0732.

Synthesis of N-(2.3-dimethyl-quinoxalin-6-yl)-4-propyl-benzenesulfonamide, STX 954 (KRB01075)

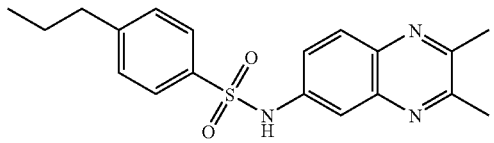

To a solution of 0.4n-propylbenzenesulphonyl chloride (106 mg, 0.485 mmol) in dichloromethane (3 mL) was added pyridine (90 µL, 1.2 mmol) and the mixture was stirred under. $N_2$ for 5 min, after which time 6-amino-2,3-dimethylquinoxaline (80 mg, 0.46 mmol) was added. The resulting mixture was stirred for 6 h at room temperature, then saturated $NaHCO_3$ solution (8 mL) was added and the mixture was extracted into ethyl acetate (15 mL). The organic phase was washed with brine, dried ($Na_2SO_4$), filtered and evaporated to give a residue that was purified using flash chromatography to afford an off-white solid (147 mg, 90%), single spot at $R_f$ 0.69 (ethyl acetate). mp 198.4-198.8° C., HPLC purity 99+% ($t_R$ 2.39 min in 10% water-acetonitrile). $^1$H NMR ($CDCl_3$): δ 7.86 (1H, d, J=8.9 Hz), 7.72 (2H, d, Jz;8.4 Hz), 7.56 (1H, d, J=2.5 Hz), 7.48 (1H, dd, J9.2, 2.5 Hz), 7.20 (2H, d, J=7.9 Hz), 6.82 (1H, s, N—H, 2.67 (6H, s), 2.56 (2H, t, J=7.5 Hz), 1.57 (2H, sextet, J=7.4 Hz), 0.87 (3H, t, J=7.4 Hz). LCMS: 354.31 (M–). FAB-MS (MH+, $C_{19}H_{21}N_3O_2S$): calcd 356.1432, found 356.1433.

Synthesis of 3-chloro-N-(2-methyl-quinoxalin-6-yl)-2-methyl-benzenesulfonamide, STX 955 (KRB01079)

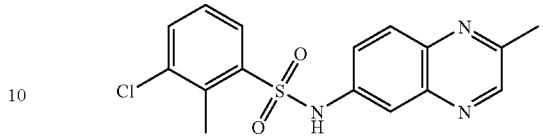

6-amino-2-methylquinoxaline (KRB01078): To a solution of 2-methyl-6-nitroquinoxaline [23] (500 mg, 2.64 mmol) in methanol (22 mL) was added 10% palladium on carbon (50 mg) and the mixture was stirred under 1 atm $H_2$ for 4 h. The mixture was filtered through celite and the filtrate evaporated. The residue was passed through a silica plug and evaporated to afford 6-amino-2-methylquinoxaline as a yellow solid (376 mg, 89%), single spot at $R_f$ 0.33 (ethyl acetate). mp 163-164° C. ([23] 164-165° C.). $^1$H NMR ($CDCl_3$): δ 8.57 (1H, s), 7.78 (1H, d, J=8.4 Hz), 7.17-7.12 (2H, m), 4.11 (2H, s —$NH_2$), 2.67 (3H, s).

To a solution of 3-chloro-2-methylbenzenesulphonyl chloride (119 mg, 0.528 mmol) in dichloromethane (3 mL) was added pyridine (100 µL, 1.26 mmol) and the mixture was stirred under $N_2$ for 5 min, after which time 6-amino-2-methylquinoxaline (80 mg, 0.50 mmol) was added. The resulting mixture was stirred for 5 h. at room temperature, then saturated $NaHCO_3$ solution (8 mL) was added and the mixture was extracted into ethyl acetate (15 mL). The organic phase was washed with brine, dried ($Na_2SO_4$), filtered and evaporated to give a residue that was purified using flash chromatography to afford a pale pink solid (161 mg, 92%), single spot at $R_f$ 0.67 (ethyl acetate). mp 158.7-159.3° C., HPLC purity 99+% ($t_R$ 2.23 min in 10% water-acetonitrile). $^1$H NMR ($CDCl_3$): δ 8.66 (1H, s), 8.02 (1H, d, J=7.7 Hz), 7.89 (1H, d, J=8.9 Hz), 7.61 (1H, d, J=2.5 Hz), 7.55 (1H, d, J=8.2 Hz), 7.46 (11H, dd, J=8.9, 2.5 Hz), 7.23 (1H, t, J=7.9 Hz), 7.08 (1H, s, N—H), 2.76 (3H, s), 2.71 (3H, s). LCMS: 346.11 (M–). FAB-MS (MH+, $C_{16}H_{14}ClN_3O_2S$): calcd 348.0573, found 348.0589.

Synthesis of N-(2-methyl-quinoxalin-6-yl)-4-propyl-benzenesulfonamide, STX 956 (KRB01080)

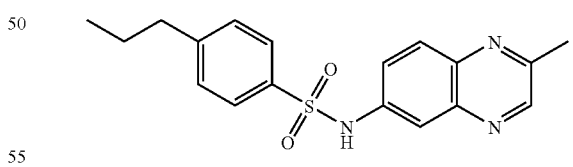

To a solution of 4n-propylbenzenesulphonyl chloride (115 mg, 0.528 mmol) in dichloromethane (3 mL) was added pyridine (100 µL, 1.26 mmol) and the mixture was stirred under $N_2$ for 5 min, after which time 6-amino-2-methylquinoxaline (80 mg, 0.50 mmol) was added. The resulting mixture was stirred for 2 h at room temperature, then saturated $NaHCO_3$ solution (8 mL) was added and the mixture was extracted into ethyl acetate (15 mL). The organic phase was washed with brine, dried ($Na_2SO_4$), filtered and evaporated to give a residue that was purified using flash chromatography to afford a white solid (168 mg, 95%), single spot at $R_f$ 0.72 (ethyl acetate). mp 135.6-136.2° C., HPLC purity 99+% ($t_R$ 2.23 min in 10% water-acetonitrile). $^1$H NMR (CDCl$_3$): δ 8.66 (1H, s), 7.89 (1H, di-J=9.2 Hz), 7.77 (2H, d, J=8.4 Hz), 7.67 (1H, d, J=2.5 Hz), 7.54 (1H, dd, J=8.9, 2.5 Hz), 7.22 (2H, d, J=8.4 Hz), 2.71 (3H, s), 2.56 (2H, t, J=7.7 Hz), 1.58 (2H, sextet, J=7.7 Hz), 0.87 (3H, t, J=7.4 Hz). LCMS: 340.25 (M−). FAB-MS (MH+, C$_{18}$H$_{19}$N$_3$O$_2$S): calcd 342.1276, found 342.1290.

Synthesis of 3-chloro-2-methyl-N-quinoxalin-6-yl-benzenesulfonamide, STX 957

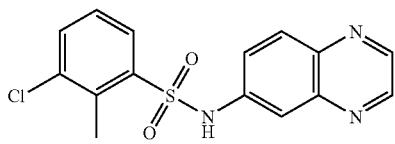

6-aminoquinoxaline (KRB01083): To a solution of 6-nitroquinoxaline [24] (500 mg, 2.86 mmol) in methanol (20 mL) was added 10% palladium on carbon (50 mg) and the mixture was stirred under 1 atm H$_2$ for 4 h. The mixture was filtered through celite and the filtrate evaporated. The residue was passed through a silica plug and evaporated to afford 6-aminoquinoxaline as a yellow solid (342 mg, 82%), single spot at $R_f$ 0.32 (ethyl acetate). $^1$H NMR (CDCl$_3$): δ 8.65 (1H, d, J=1.7 Hz), 8.55 (1H, d, J=1.7 Hz), 7.87 (1H, d, J=8.9 Hz), 7.18 (1H, dd, J=8.9, 2.5 Hz), 7.13 (1H, d, J=2.5 Hz), 4.20 (2H, br.s, —NH$_2$) [25].

To a solution of 3-chloro-2-methylbenzenesulphonyl chloride (147 mg, 0.651 mmol) in dichloromethane (4 mL) was added pyridine (125 µL, 1.55 mmol) and the mixture was stirred under N$_2$ for 5 min, after which time 6-aminoquinoxaline (90 mg, 0.62 mmol) was added. The resulting mixture was stirred for 5 h at room temperature, then saturated NaHCO$_3$ solution (10 mL) was added and the mixture was extracted into ethyl acetate (20 mL). The organic phase was washed with brine, dried (Na$_2$SO$_4$), filtered and evaporated to give a residue that was purified using flash chromatography to afford a pale yellow solid (180 mg, 87%), single spot at $R_f$ 0.60 (ethyl acetate). mp 166.5-166.9° C., HPLC purity 99+% ($t_R$ 2.15 min in 10% water-acetonitrile). $^1$H NMR (CDCl$_3$): δ 8.77 (1H, d, J=1.7 Hz), 8.74 (1H, d, J=1.7 Hz), 8.06 (1H, d, J=8.2 Hz), 8.00 (1H, d, J=9.2 Hz), 7.66 (1H, d, J=2.5 Hz), 7.56 (1H, d, J=7.9 Hz), 7.50 (1H, dd, J=9.1, 2.6 Hz), 7.28-7.22 (1H, obscured under CHCl$_3$), 2.76 (3H, s). LCMS: 332.24 (M−). FAB-MS (MH+, C$_{15}$H$_{12}$ClN$_3$O$_2$S): calcd 334.0417, found 334.0433.

Synthesis of 4-propyl-N-guinoxalin-6-yl-benzenesulfonamide, STX 958 (KRB01085)

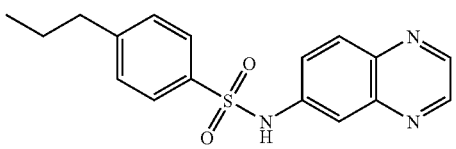

To a solution of 4n-propylbenzenesulphonyl chloride (142 mg, 0.651 mmol) in dichloromethane (4 mL) was added pyridine (125 µL, 1.55 mmol) and the mixture was stirred under N$_2$ for 5 min, after which time 6-aminoquinoxaline (90 mg, 0.62 mmol) was added. The resulting mixture was stirred for 4 h at room temperature, then saturated NaHCO$_3$ solution (10 mL) was added and the mixture was extracted into ethyl acetate (20 mL). The organic phase was washed with brine, dried (Na$_2$SO$_4$), filtered and evaporated to give a residue that was purified using flash chromatography to afford an off-white solid (190 mg, 94%), single spot at $R_f$ 0.66 (ethyl acetate). mp 198.4-198.9° C., HPLC purity 99+% ($t_R$ 2.22 min in 10% water-acetonitrile). $^1$H NMR (CDCl$_3$): δ 8.77 (1H, d, J=1.7 Hz), 8.73 (1H, d, J=1.7 Hz), 8.00 (1H, d, J=8.9 Hz), 7.80 (2H, d, J=8.2 Hz), 7.71 (1H, d, J=2.5 Hz), 7.59 (1H, dd, J=8.9, 2.5 Hz), 7.23 (2H, obscured under CHCl$_3$), 2.57 (2H, t, J=7.6 Hz), 1.58 (2H, sextet, J=7.5 Hz), 0.87 (3H, t, J=7.4 Hz). LCMS: 326.24 (M−). FAB-MS (MH+, C$_{17}$H$_{17}$N$_3$O$_2$S): calcd 328.1119, found 328.1136.

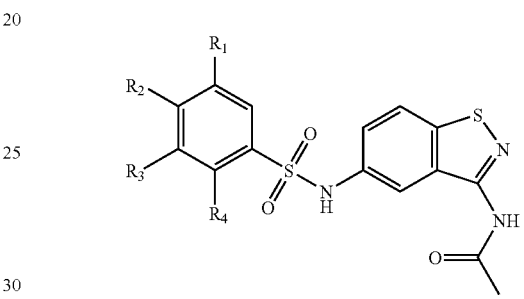

STX 929: $R_1 = R_2 = H$, $R_3 = Cl$, $R_4 = Me$
STX 930: $R_1 = R_3 = R_4 = H$, $R_2 = $ n-propyl
STX 931: $R_1 = R_4 = Cl$, $R_2 = R_3 = H$ Synthesis of N-acetyl-N-(5-amino-benzo[d]isothiazol-3-yl)-acetamide (KRB01050)

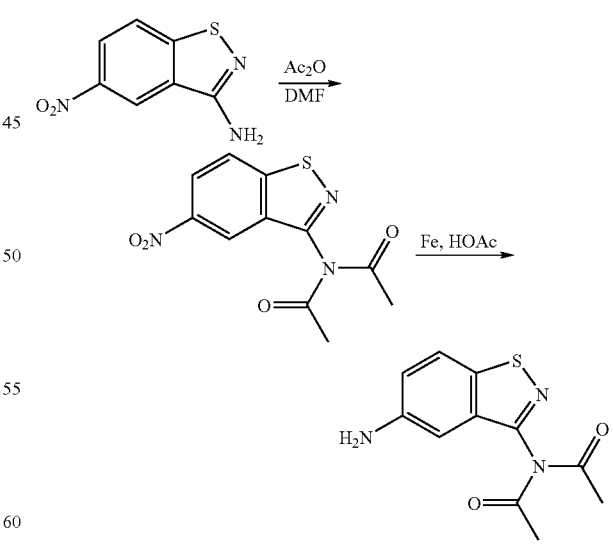

N-acetyl-N-(5-nitro-benzo[d]isothiazol-3-yl)-acetamide (KRB01049): To a solution of 3-amino-5-nitrobenzisothiazole (1.00 g, 5.12 mmol) in DMF (20 mL) was added acetic anhydride (1 mL) and triethylamine (1 mL) and the resulting solution was stirred for 4 h. The yellow precipitate was filtered, washed quickly with cold ethyl acetate, and dried in vacuo (1.139 g, 80%). ¹H NMR (CDCl₃): δ 9.20 (1H, d, J=2.5 Hz), 8.87 (1H, d, J=9.4 Hz), 8.55 (1H, dd, J=9.4, 2.5 Hz), 2.69 (3H, s), 2.63 (3H, s).

N-acetyl-N-(5-amino-benzo[d]isothiazol-3-yl)-acetamide: To a suspension of N-acetyl-N-(5-nitro-benzo[d]isothiazol-3-yl)-acetamide (1.133 g, 4.06 mmol) in a 1:1 acetic acid:ethyl acetate solution (70 mL) at 50° C. was added iron powder (680 mg, 12.2 mmol). The resulting mixture was stirred at 50° C. for 5 h, then cooled, poured into saturated sodium bicarbonate and extracted into ethyl acetate. The organic layers were combined, washed with water and then brine, dried (MgSO₄), filtered, and evaporated. The residue was purified using flash chromatography on silica to afford the desired amine as an orange solid (383 mg, 38%), single spot at $R_f$ 0.30 (1:1 dichloromethane:ethyl acetate). mp 213.0-214.2° C. ¹H NMR (CDCl₃): δ 8.56 (1H, d, J=9.2 Hz), 7.48 (d, J=2.7 Hz), 7.14 (1H, dd, J=9.2, 2.7 Hz), 2.62 (3H, s), 2.56 (3H, s).

Synthesis of N-[5-(3-chloro-2-methyl-benzenesulfonylamino)-benzo[d]isothiazol-3-yl]-acetamide, STX 929 (KRB01055)

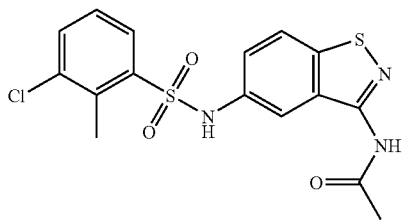

To a solution of 3-chloro-2-methylbenzenesulphonyl chloride (95 mg, 0.42 mmol) in dichloromethane (3 mL) was added pyridine (80 μL, 1.0 mmol) and the mixture was stirred under N₂ for 5 minutes, at which time N-acetyl-N-(5-amino-benzo[d]isothiazol-3-yl)-acetamide (100 mg, 0.401 mmol) was added. The resulting mixture was stirred for 4 heat room temperature. 5% NaHCO₃ solution (8 mL) was added and the mixture was extracted into ethyl acetate (15 mL). The organic phase was washed with brine, dried (Na₂SO₄), filtered and evaporated to give a residue that was purified using flash chromatography to afford a yellow solid (82 mg, 47%), single spot at $R_f$ 0.71 (1:1 hexane:ethyl acetate). This solid was stirred in a solution of 1:1 THF:6N HCl (6 mL) for 1:6 h. The solution was then made slightly basic by the addition of Na₂CO₃, and extracted into ethyl acetate (15 mL). The organic layer was dried (MgSO₄), filtered, and evaporated. The residue was purified using flash chromatography to afford a dark brown solid (32 mg, 44%), single spot at $R_f$ 0.84 (ethyl acetate). mp 142-1460C, HPLC purity 96% ($t_R$ 2.34 min in 10% water-acetonitrile). ¹H NMR (d₆ DMSO): 612.32 (1H, s), 10.61 (1H, s), 7.93-7.88 (2H, m), 7.68 (1H, d, J=8.2 Hz), 7.47 (1H, d, J=9.4 Hz), 7.34 (1H, t, J=8.1 Hz), 7.13 (1H, dd, J=9.4, 2.2 Hz), 2.68 (3H, s), 2.34 (3H, s). LCMS: 394.18 (M−). FAB-MS (MH+, C₁₆H₁₄ClN₃O₃S₂): calcd 396.0243, found 396.0238.

Synthesis of N-[5-(4-propyl-benzenesulphonylamino)-benzo[d]isothiazol-3-yl]-acetamide, STX 930 (KRB01056)

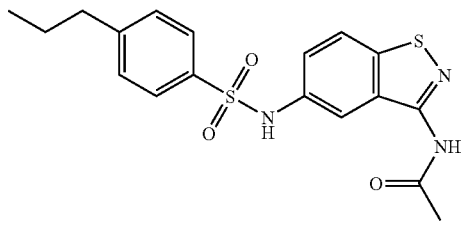

To a solution of 4n-propylbenzenesulphonyl chloride (92 mg, 0.42 mmol) in dichloromethane (3 mL) was added pyridine (80 μL, 1.0 mmol) and the mixture was stirred under N₂ for 5 minutes, at which time N-acetyl-N-(5-amino-benzo[d]isothiazol-3-yl)-acetamide (100 mg 0.401 mmol) was added. The resulting mixture was stirred for 3 h at room temperature. 5% NaHCO₃ solution (8 mL) was added and the mixture was extracted into ethyl acetate (15 mL). The organic phase was washed with brine, dried (Na₂SO₄), filtered and evaporated to give a residue that was purified using flash chromatography to afford a yellow solid (115 mg, 66%), single spot at $R_f$ 0.66 (1:1 hexane:ethyl acetate). This solid was stirred in a solution of 1:1 THF:6N HCl (6 mL) for 6 h. The solution was then made slightly basic by the addition of Na₂CO₃, and extracted into ethyl acetate (15 mL). The organic layer was dried (MgSO₄), filtered, and evaporated. The residue was purified using flash chromatography to afford a pale brown solid (88 mg, 91%), single spot at $R_f$ 0.71 (ethyl acetate). mp 254.3-255.0° C., HPLC purity 99+% ($t_R$ 2.32 min in 10% water-acetonitrile). ¹H NMR (d₆ DMSO): δ 12.35 (1H, s), 10.23 (1H, s), 7.94 (1H, d, J=2.0 Hz), 7.70 (2H, d, J=8.2 Hz), 7.43 (1H, d, J=9.4 Hz), 7.33 (2H, d, J=8.2 Hz), 7.08 (1H, dd, J=9.4, 2.0 Hz), 2.50 (2H, t, J=7.4 Hz), 2.35 (3H, s), 1.53 (2H, sextet, J=7.4 Hz), 0.82 (3H, t, J=7.3 Hz). LCMS: 388.25 (M−). FAB-MS (MH+, C₁₈H₁₉N₃O₃S₂): calcd 390.0946, found 390.0941.

Synthesis of N-[5-(2.5-dichloro-benzenesulphonylamino)-benzo[d]isothiazol-3-yl]-acetamide, STX 931 (KRB01057)

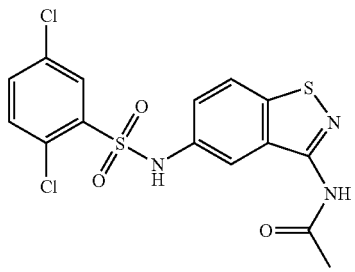

To a solution of 2,5-dichlorobenzenesulphonyl chloride (103 mg, 0.421 mmol) in dichloromethane (3 mL) was added pyridine (80 μL, 1.0 mmol) and the mixture was stirred under N₂ for 5 minutes, at which time N-acetyl-N-(5-amino-benzo[d]isothiazol-3-yl)-acetamide (100 mg, 0.401 mmol) was added. The resulting mixture was stirred for 6 h at room temperature. 5% NaHCO₃ solution (8 mL)

was added and the mixture was extracted into ethyl acetate (15 mL). The organic phase was washed with brine, dried ($Na_2SO_4$), filtered and evaporated to give a residue that was purified using flash chromatography to afford a yellow solid (114 mg, 62%), single spot at $R_f$ 0.74 (1:1 hexane:ethyl acetate). This solid was stirred in a solution of 1:1 THF:6N HCl (6 mL) for 5 h. The solution was then made slightly basic by the addition of $Na_2CO_3$, and extracted into ethyl acetate (15 mL). The organic layer was dried ($MgSO_4$), filtered, and evaporated. The residue was purified using flash chromatography to afford a pale brown solid (28 mg, 29%), single spot at $R_f$ 0.64 (ethyl acetate). mp 169-172° C., HPLC purity 99+% ($t_R$ 2.85 min in 10% water-acetonitrile). $^1$H NMR ($d_6$ DMSO): δ 12.34 (1H, s), 10.84 (1H, s), 8.12 (1H, d, J=1.7 Hz), 7.89 (1H, d, J=1.7 Hz), 7.68 (2H, m), 7.49 (1H, d, J=9.4 Hz), 7.18 (1H, dd, J=9.4, 2.0 Hz), 2.35 (3H, s). LCMS: 414.11 (M−). FAB-MS (MH+, $C_{15}H_{11}Cl_2N_3O_3S_2$): calcd 415.9697, found 415.9697.

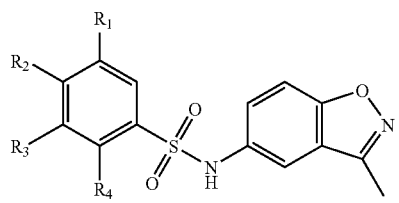

STX 874: $R_1 = R_2 = H$, $R_3 = Cl$, $R_4 = Me$
STX 875: $R_1 = R_3 = R_4 = H$, $R_2 = $ n-propyl
STX 876: $R_1 = R_4 = Cl$, $R_2 = R_3 = H$

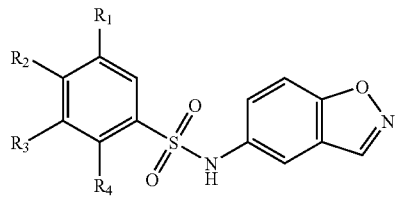

STX 918: $R_1 = R_2 = H$, $R_3 = Cl$, $R_4 = Me$
STX 919: $R_1 = R_3 = R_4 = H$, $R_2 = $ n-propyl
STX 920: $R_1 = R_4 = Cl$, $R_2 = R_3 = H$ Synthesis of 3-chloro-2-methyl-N-(3-methyl-benzo[d]isoxazol-5-yl)-benzenesulfonamide, STX 874 (KRB01027)

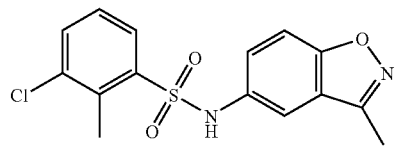

To a solution of 3-chloro-2-methylbenzenesulphonyl chloride (128 mg, 0.567 mmol) in dichloromethane (3 mL) was added pyridine (110 μL, 1.35 mmol) and the mixture was stirred under $N_2$ for 5 min, after which time 5-amino-3-methyl-1,2-benzisoxazole [26] (80 mg, 0.54 mmol) was added. The resulting mixture was stirred for 4 h at, room temperature, then saturated $NaHCO_3$ solution (8 mL) was added and the mixture was extracted into ethyl acetate (15 mL). The organic phase was washed with brine, dried ($Na_2SO_4$), filtered and evaporated to give a residue that was purified using flash chromatography to afford a white solid (88 mg, 48%), single spot at $R_f$ 0.58 (1:1 hexane:ethyl acetate). mp 162.8-163.2° C., HPLC purity 99+% ($t_R$ 2.26 min in 10% water-acetonitrile). $^1$H NMR ($CDCl_3$): δ 7.80 (1H, dd, J=7.9, 1.3 Hz), 7.55 (1H, dd, J=8.1, 1.1 Hz), 7.38 (2H, m), 7.17 (1H, t, J=8.1 Hz), 7.10 (1H, dd, J=8.8, 2.2 Hz), 6.72 (1H, s, N−H), 2.72 (3H, s), 2.50 (3H, s). LCMS: 320.00 (M−$CH_3$). FAB-MS (MH+, $C_{15}H_{13}ClN_2O_3S$): calcd 337.0413, found 337.0422.

Synthesis of N-(3-methyl-benzo[d]isozazol-5-yl)-4-propyl-benzenesulfonamide, STX 875 (KRB01028)

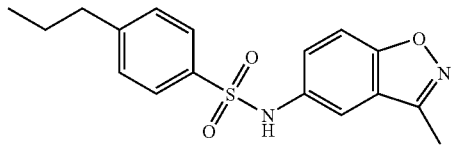

To a solution of 4n-propylbenzenesulphonyl chloride (124 mg, 0.567 mmol) in dichloromethane (3 mL) was added pyridine (110 μL, 1.35 mmol) and the mixture was stirred under $N_2$ for 5 min, after which time 5-amino-3-methyl-1,2-benzisoxazole (80 mg, 0.54 mmol) was added. The resulting mixture was stirred for 3 h at room temperature, then saturated $NaHCO_3$ solution (8 mL) was added and the mixture was extracted into ethyl acetate (15 mL). The organic phase was washed with brine, dried ($Na_2SO_4$), filtered and evaporated to give a residue that was purified using flash chromatography to afford a pale pink solid (150 mg, 84%), single spot at $R_f$ 0.62 (1:1 hexane:ethyl acetate). mp 119.5-120.0° C., HPLC purity 99+% ($t_R$ 2.29 min in 10% water-acetonitrile). $^1$H NMR ($CDCl_3$): δ 7.57 (2H, d, J=8.4 Hz), 7.40 (1H, d, J=2.2 Hz), 7.37 (1H, d, J=8.8 Hz), 7.20 (2H, d, J=8.4 Hz), 7.10 (1H, dd, J=8.8, 2.2 Hz), 6.71 (1H, s, N−H, 2.59 (2H, t, 2.51 (3H, s), 1.59 (2H, sextet, J=7.5 Hz), 0.88 (3H, t, J=7.5 Hz). LCMS: 314.07 (M−$CH_3$). FAB-MS (MH+, $C_{17}H_{18}N_2O_3S$): calcd 331.1116, found 331.1117.

Synthesis of 2.5-dichloro-N-(3-methyl-benzo[d]isozazol-5-yl)-benzenesulfonamide. STX 876 (KRB01030)

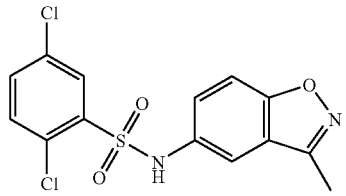

To a solution of 2,5-dichlorobenzenesulphonyl chloride (105 mg, 0.428 mmol) in dichloromethane (3 mL) was added pyridine (100 μL, 1.02 mmol) and the mixture was stirred under $N_2$ for 5 min, after which time 5-amino-3-methyl-1,2-benzisoxazole (60 mg, 0.41 mmol) was added. The resulting mixture was stirred for 2 h at room temperature, then saturated $NaHCO_3$ solution (8 mL) was added and the mixture was extracted into ethyl acetate (15 mL). The organic phase was washed with brine, dried ($Na_2SO_4$), filtered and evaporated to give a residue that was purified using flash chromatography to afford a yellow solid (100 mg, 68%), single spot at $R_f$ 0.62 (1:1 hexane:ethyl acetate). mp 229.4-230.0° C., HPLC purity 94% ($t_R$ 2.18 min in 10% water-acetonitrile). $^1$H NMR (CDCl$_3$): δ 7.89 (1H, d, J=2.2 Hz), 7.43 (4H, m), 7.22 (1H, m), 7.09 (1H, s, N—H, 2.54 (3H, s). LCMS: 340.06 (M–CH$_3$). FAB-MS (MH+, C$_{14}$H$_{10}$Cl$_2$N$_2$O$_3$S): calcd 356.9867, found 356.9860.

Synthesis of N-benzo[d]isoxazol-5-yl-3-chloro-2-methyl-benzenesulfonamide, STX 918 (KRB01046)

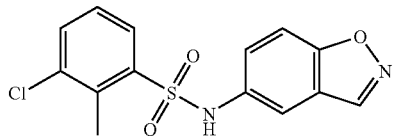

To a solution of. 3-chloro-2-7methylbenzenesulphonyl chloride (176 mg, 0.783 mmol) in dichloromethane (4 mL) was added pyridine (150 µL, 1.86 mmol) and the mixture was stirred under N$_2$ for 5 min, after which time 5-amino-1,2-benzisoxazole [27] (100 mg, 0.746 mmol) was added. The resulting mixture was stirred for 2 h at room temperature, then saturated NaHCO$_3$ solution (10 mL) was added and the mixture was extracted into ethyl acetate (20 mL). The organic phase was washed with brine, dried (Na$_2$SO$_4$), filtered and evaporated to give a residue that was purified using flash chromatography to afford a white solid (178 mg, 74%), single spot at $R_f$ 0.69 (1:1 hexane:ethyl acetate). mp 111.9-112.4° C., HPLC purity 97% ($t_R$ 2.44 min in 10% water-acetonitrile). $^1$H NMR (CDCl$_3$): δ 8.62 (1H, d, J=1.0 Hz), 7.81 (1H, dd, J7.9, 1.2 Hz), 7.55 (1H, dd, J=7.9, 1.0 Hz), 7.45 (2H, m), 7.17 (2H, m), 6.77 (1H, s, N–H), 2.72 (3H, s). LCMS: 321.01 (M–) FAB-MS (MH+, C$_{14}$H$_{11}$ClN$_2$O$_3$S): calcd 323.0257, found 323.0271.

Synthesis of N-benzo[d]isoxazol-5-yl-4-propyl-benzenesulfonamide, STX 919 (KRB01047)

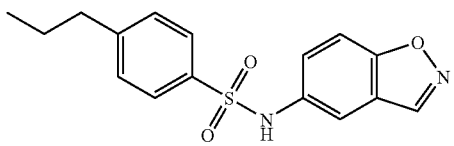

To a solution of 4n-propylbenzenesulphonyl chloride (171 mg, 0.783 mmol) in dichloromethane (4 mL).was added pyridine (150 µL, 1.86 mmol) and the mixture was stirred under. N$_2$ for 5 min, after which time 5-amino-1,2-benzisoxazole (100 mg, 0.746 mmol) was added. The resulting mixture was stirred for 2 h at room temperature, then saturated NaHCO$_3$ solution (10 mL) was added and the mixture was extracted into ethyl acetate (20 mL). The organic phase was washed with brine, dried (Na$_2$SO$_4$), filtered and evaporated to give a residue that was purified using flash chromatography to afford a white solid (170 mg, 72%), single spot at $R_f$ 0.68 (1:1 hexane:ethyl acetate). mp 130.0-130.6° C., HPLC purity 99+% ($t_R$ 2.44 min in 10% water-acetonitrile). $^1$H NMR (CDCl$_3$): δ 8.62 (1H, d, J=1.0 Hz), 7.60 (2H, d, J=8.4 Hz), 7.48 (2H, m), 7.19 (3H, m), 6.86 (1H, s, N–H), 2.58 (2H, t, J=7.5 Hz), 1.58 (2H, sextet, J=7.4 Hz), 0.88 (3H, t, J=7.4 Hz). LCMS: 315.14 (M–). FAB-MS (MH+, C$_{16}$H$_{16}$N$_2$O$_3$S): calcd 317.0960, found 317.0962.

Synthesis of N-benzo[d]isoxazol-5-yl-2,5-dichloro-benzenesulfonamide, STX 920 (KRB01048)

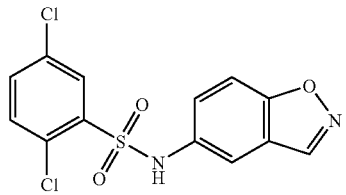

To a solution of 2,5-dichlorobenzenesulphonyl chloride (192 mg, 0.783 mmol), in dichloromethane (4 mL) was added pyridine (150 µL, 1.86 mmol) and the mixture was stirred under N$_2$ for 5 min, after which time 5-amino-1,2-benzisoxazole (100 mg, 0.746 mmol) was added. The resulting mixture was stirred for 2 h at room temperature, then saturated NaHCO$_3$ solution (10 mL) was added and the mixture was extracted into ethyl acetate (20 mL). The organic phase was washed with brine, dried (Na$_2$SO$_4$), filtered and evaporated to give a residue that was purified using flash chromatography to afford a white solid (174 mg, 68%), single spot at $R_f$ 0.68 (1:1 hexane:ethyl acetate). mp 172.9-173.6° C., HPLC purity 99+% ($t_R$ 2.41 min in 10% water-acetonitrile). $^1$H NMR (CDCl$_3$): δ 8.64 (1H, s), 7.89 (1H, d, J=2.2 Hz), 7.56-7.28 (5H, m). LCMS: 341.07 (M–). FAB-MS (MH+, C$_{13}$H$_8$Cl$_2$N$_2$O$_3$S): calcd 342.9711, found 342.9710.

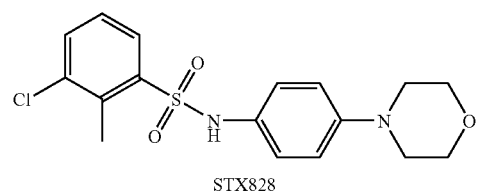

STX828

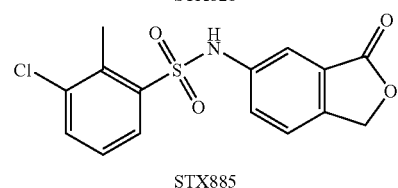

STX885

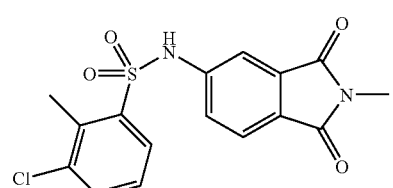

STX979

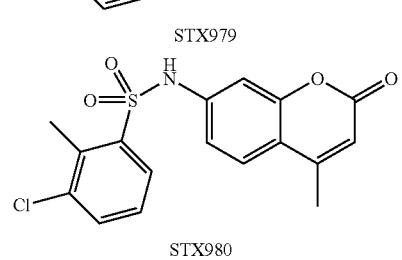

STX980

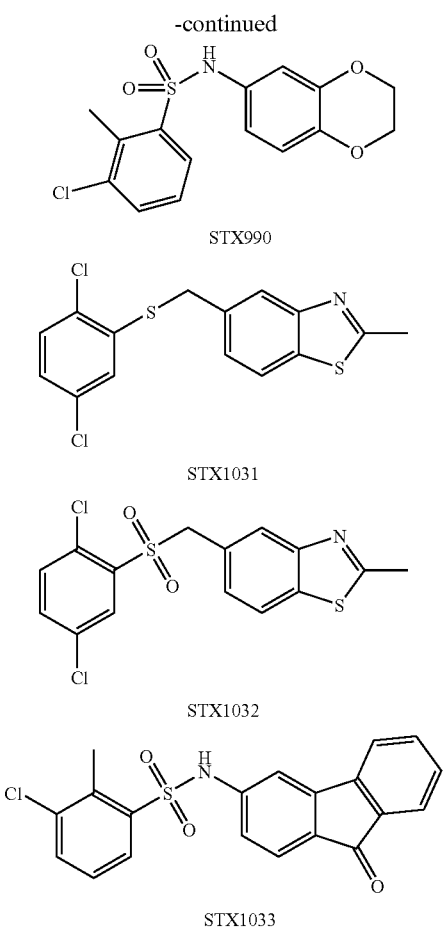

General Method for Arylsulphonamide Formation:

To a solution arylsulphonyl chloride (1.1 eq.) in DCM were added pyridine (2.2 eq.) and catalytic amount of DMAP, followed by the corresponding amine (1 eq.). The reaction mixture was stirred at rt under nitrogen for 4-16 h, then partitioned between ethyl acetate and 5% sodium bicarbonate after TLC showed the completion of the reaction. The organic layer was washed with brine, dried over sodium sulphate, and concentrated in vacuo to give crude product as solid or thick syrup. The compound was then purified by flash chromatography (Methanol-DCM gradient elution) to give desired arylsulphonamide as crystalline solid. Yield ranges from 40-90%.

3-Chloro-2-methyl-N-(4-morpholin-4-yl-phenyl)-benzenesulfonamide (STX828, XDS01161)

Off-white crystalline solid. TLC single spot at $R_f$ 0.70 (70% ethyl acetate/hexane); HPLC purity >99% ($t_R$ 1.8 min in 4% water-methanol); $^1$H NMR (400 MHz, DMSO): δ 10.1 (1H, s, NH), 7.77 (1H, dd, J=8.2, 1.2 Hz, ArH), 7.70 (1H, dd, J=8.2, 1.2 Hz, ArH), 7.34 (1H, t, J.=8.2 Hz, ArH), 6.78-6.92 (4H, m, ArH), 3.67 (4H, t, J=5.1 Hz, N(CH$_2$)$_2$), 2.99 (4H, t, J=5.1 Hz, O(CH$_2$)$_2$), 2.60 (3H, s, CH$_3$); APCI-MS 365 (M–H$^+$); FAB-HRMS calcd for C$_{17}$H$_{20}$ClN$_2$O$_3$S (MH$^+$) 367.0883, found 367.0854.

3-Chloro-2-methyl-N-(3-oxo-1,3-dihydro-isobenzofuran-5-yl)-benzenesulfonamide (STX885, XDS01179)

White crystalline solid. TLC single spot at $R_f$ 0.60 (20% ethyl acetate/hexane); HPLC purity >99% ($t_R$ 2.2 min in 10% water-methanol); $^1$H NMR (270 MHz, DMSO): δ 11.0 (1H, s, NH), 7.84 (1H, d, J=7.9 Hz, ArH), 7.66 (1H, d, J=7.9 Hz, ArH), 7.49 (1H, d, J=8.5 Hz, ArH), 7.31-7.46 (3H, m, ArH), 5.22 (2H, s, CH$_2$), 2.57 (3H, s, CH$_3$); APCI-MS 338 (M+H$^+$); FAB-HRMS calcd for C$_{15}$H$_{13}$ClNO$_4$S (MH$^+$) 338.0254, found 338.0270.

3-Chloro-2-methyl-N-(2-methyl-1,3-dioxo-2,3-dihydro-1H-isoindol-5-yl)-benzenesulfonamide (STX979, XDS01180)

Yellow crystalline solid. TLC single spot at $R_f$ 0.82 (20% ethyl acetate/hexane); HPLC purity >99% ($t_R$ 2.1 min in 10% water-methanol); $^1$H NMR (270 MHz, DMSO): δ 11.5 (1H, s, NH), 7.98 (1H, d, J=7.9 Hz, ArH), 7.76 (1H, d, J=8.3 Hz, ArH), 7.73 (1H, d, J=8.3 Hz, ArH), 7.45 (1H, t, J=8.3 Hz, ArH ), 7.41 (1H, s, ArH), 7.39 (1H, d, J=7.9 Hz, ArH ),2.94 (3H, s, NCH$_3$), 2.64 (3H, s, CH$_3$); APCI-MS 363 (M–H$^+$); FAB-HRMS calcd for C$_{16}$H$_{14}$ClN$_2$O$_4$S (MH$^+$) 365.0363, found 365.0375.

3-Chloro-2-methyl-N-(4-methyl-2-oxo-2H-chromen-7-yl)-benzenesulfonamide (STX980, XDS02018)

White crystalline solid. TLC single spot at $R_f$ 0.78 (6% methanol/DCM); HPLC purity >99% ($t_R$ 2.1 min in 10% water-methanol); $^1$H NMR (270 MHz, DMSO): δ 11.3 (1H, s, NH), 8.03 (1H, d, J=7.9 Hz, ArH), 7.76 (1H, d, J=7.9 Hz, ArH), 7.65 (1H, d, J=8.6 Hz, ArH), 7.46 (1H, t, J=7.9 Hz, ArH), 7.07 (1H, dd, J=8.6, 1.8 Hz, ArH), 6.98 (1H, d, J=1.5 Hz, ArH), 6.24 (1H,'s, 3-H), 2.69 (3H, s, CH$_3$), 2.33 (3H, s, CH$_3$); APCI-MS 362 (M–H+); FAB-HRMS calcd for C$_{17}$H$_{15}$ClNO$_4$S (MH$^+$) 364.0410, found 364.0414.

3-Chloro-N-(2,3-dihydro-benzo[0.41]dioxin-6-yl)-2-methyl-benzenesulfonamide (STX990, XDS02039)

White crystalline solid. TLC single spot at $R_f$ 0.78 (30% ethyl acetate/DCM); HPLC purity 94% ($t_R$ 2.3 min in 10% water-methanol); $^1$H NMR (270 MHz, DMSO): δ 10.3 (1H, s, NH), 7.82 (1H, d, J=7.9 Hz, ArH), 7.72 (1H, dd, J=7.9, 1.0 Hz, ArH), 7.39 (1H, t, J=7.9 Hz, ArH ), 6.72 (1H, d, J=8.4 Hz, ArH ), 6.49-6.55 (2H, m, ArH), 4.15 (4H, s, (CH$_2$)$_2$), 2.62 (3H, s, CH$_3$); APCI-MS 338 (M–H$^+$); FAB-HRMS calcd for C$_{15}$H$_{15}$ClNO$_4$S (MH$^+$) 340.0410, found 340.0387.

3-Chloro-2-methyl-N-(9-oxo-9H-fluoren-3-yl)-benzenesulfonamide (STX1033, XDS02074)

Yellow solid. TLC single spot at $R_f$ 0.55 (8% ethyl acetate/DCM); HPLC purity >99% (tR 2.5 min in 20% water-methanol); $^1$H NMR (270 MHz, DMSO): δ 10.3 (1H, s, NH), 7.82 (1H, d, J=7.9 Hz, ArH), 7.72(1H, dd, J=7.9, 1.0 Hz, ArH), 7.39 (1H, t, J=7.9 Hz, ArH), 6.72 (1H, d, J=8.4 Hz, ArH ), 6.49-6.55 (2H, m, ArH), 4.15 (4H, s, (CH$_2$)$_2$), 2.62 (3H, s, CH$_3$); APCI-MS 382 (M–H$^+$); FAB-HRMS calcd for C$_{20}$H$_{15}$ClNO$_3$S (MH$^+$) 384.0461; found 384.0457.

5-(2,5-Dichloro-phenylsulfanylmethyl)-2-methyl-benzothiazole (STX1031. XDS02072)

To a solution of 2,5-dichlorobenzothiol (179 mg, 1.0 mmol) in absolute ethanol (3 mL) were added: 5-(bromomethyl)-2-methylbenzothiazole (182 mg, 0.75 mmol) and triethylamine (0.15 mL). After stirred at rt for 3h, the mixture was partitioned between ethyl acetate and 1% KOH solution. The organic phase was washed with brine, dried over sodium sulphate and concentrated in vacuo to give a residue that was subjected to flash chromatography. Colorless needles (220 mg, 86%) were obtained. TLC single spot at $R_f$ 0.55° (5% ethyl acetate/DCM); HPLC purity >99% ($t_R$ 6.8 min in 20% water-methanol); $^1$H NMR (270 MHz, DMSO): δ 8.00 (1H, d, J=8.1 Hz, ArH), 7.97 (1H, s, ArH), 7.53 (1H, d, J=2.5 Hz, ArH ), 7.46-7.49 (2H, m, ArH), 7.24 (1H, dd, J=8.1, 2.5 Hz, ArH), 4.54 (2H, s, $CH_2$), 2.79 (3H, s, $CH_3$); APCI-MS 338 ($M^+$); FAB-HRMS calcd for $C_{15}H_{12}Cl_2NS_2$ ($MH^+$) 339.9788, found 339.9779.

5-(2,5-Dichloro-benzenesulfonylmethyl)-2-methyl-benzothiazole 4STX1032, XDS02075)

To a solution of 5-(2,5-Dichloro-phenylsulfanylmethyl)-2-methylbenzothiazole (STX1031, 125 mg, 0.367 mmol) in DCM (5 mL) was added 3-cholroperoxybenzoic acid (370 mg, 2.14 mmol). The, mixture was stirred at rt for 2h, then partitioned between DCM and saturated sodium carbonate solution. The organic phase was washed with brine, dried over sodium sulphate and concentrated to give a residue that was purified with flash chromatography. White crystals (55 mg, 40%) were obtained after recrystallization from DCM. TLC single spot at $R_f$ 0.20 (5% ethyl acetate/DCM); HPLC purity 97% ($t_R$ 3.0 min in 20% water-methanol); $^1$H NMR (270 MHz, DMSO): δ 7.99 (1H, d, J=8.2 Hz, ArH), 7.82-7.83 (2H, m, ArH), 7.77 (1H, s, ArH), 7.69 (1H, d, J=2.5 Hz, ArH ), 7.23 (1H, dd,v,J 8.2,1.5 Hz, ArH), 5.07 (2H, s, $CH_2$), 2.79 (3H, s, $CH_3$); APCI-MS 370 ($M^+$); FAB-HRMS calcd for $C_{15}H_{12}Cl_2NO_2S_2$ ($MH^+$) 371.9686, found 371.9691.

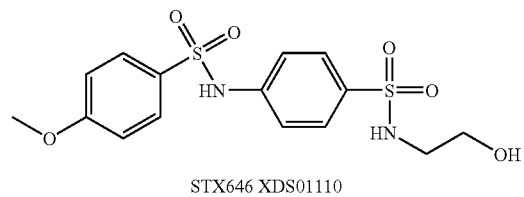

STX646 XDS01110

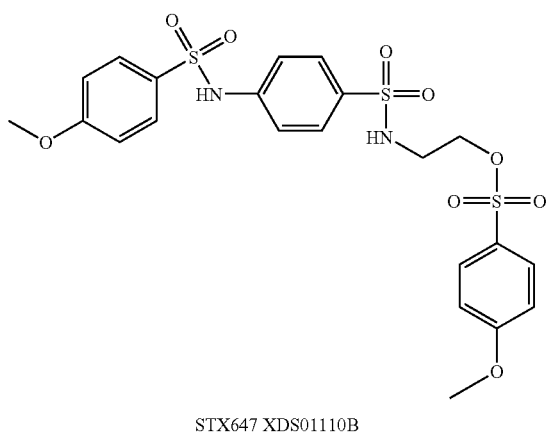

STX647 XDS01110B

-continued

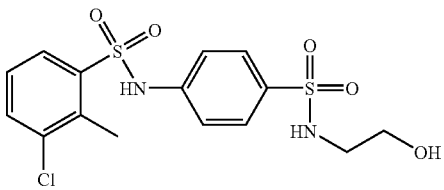

STX648 XDS01111

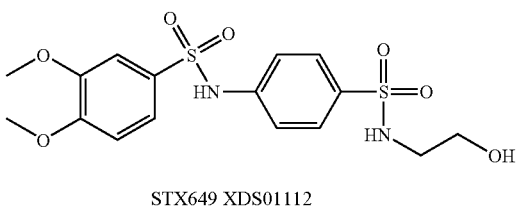

STX649 XDS01112

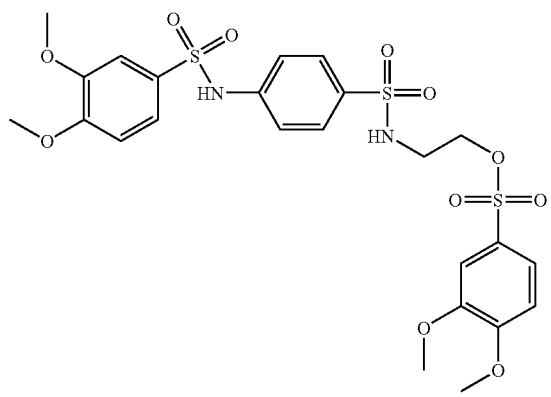

STX650 XDS01112B

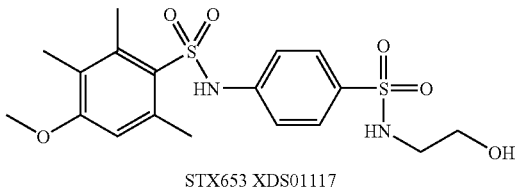

STX653 XDS01117

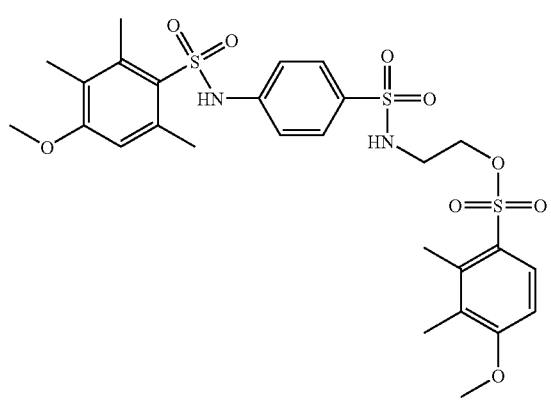

STX652 XDS01117B

-continued

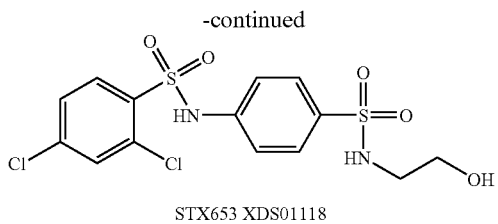

STX653 XDS01118

General Method for coupling 4-amino-N-(2-hydroxyethyl)benzenesulfonamide with arylsulphonyl chloride (STX646-STX653)

To a solution arylsulphonyl chloride (1.1 eq.) in DCM were added pyridine (10 eq.) and A4-amino-N-(2-hydroxyethyl)-benzenesulfonamide (1 eq.). The reaction mixture was stirred at rt under nitrogen for 20 h, then partitioned between DCM and 1% HCl solution. The organic layer was washed with brine, dried over sodium sulphate, and concentrated in vacuo to give crude oily product, which was seperated by flash chromatography (ethyl acetate-DCM gradient elution) to give arylsulphonamide (STX646, 648, 649, 651, 653) and arylsulphonamide arylsulphonic acid ester (STX647, 650, 652) in 10:1 ratio.

N-[4-(2-Hydroxyethylsulfamoyl)phenyl]-4'-methoxybenzenesulfonamide (STX646. XDS01110)

White foam . TLC single spot at $R_f$ 0.21 (50% DCM-ethyl acetate); HPLC purity >99% ($t_R$ 2.0 min in 10% water-methanol); $^1$H NMR (400 MHz, DMSO): δ 10.8 (1H, s, NH), 7.76 (2H, m, ArH), 7.64 (2H, d, J=9 Hz, ArH), 7.46 (1H, t, J=5.9 Hz, NH), 7.24 (2H, d, J=9 Hz, ArH), 7.08 (2H, m, ArH), 4.66 (1H, t, J=5.5 Hz, OH), 3.80 (3H, s, OCH$_3$), 3.30 (2H, m, OCH$_2$), 2.72 (2H, m, NCH$_2$); FAB-MS 387 (MH$^+$); FAB-HRMS calcd for $C_{15}H_{19}N_2O_6S_2$ (MH$^+$) 387.0685, found 387.0685.

4-Methoxy-benzenesulfonic acid 2-[4-(4-methoxy-benzenesulfonylamino)-benzenesulfonylamino]ethyl ester (STX647, XDS01110B)

White foam TLC single spot at $R_f$ 0.62 (50% DCM-ethyl acetate); HPLC purity >99% (tR 1.6 min methanol); $^1$H NMR (400 MHz, DMSO): δ 10.8 (1H, s, NH), 7.82 (1H, t, J=5.9 Hz, NH), 7.75-7.81 (4H, m, ArH), 7.59 (2H, d, J=9 Hz, ArH), 7.22-7.25 (2H, 2d, J=9 Hz, ArH), 7.17 (2H, m, ArH), 7.08 (2H, m, ArH), 3.88 (2H, m, OCH$_2$), 3.87 (3H, s, OCH$_3$), 3.79 (3H, s, OCH$_3$), 2.90 (2H, q, J=5.9 Hz, NCH$_2$); FAB-MS 557 (MH$^+$); FAB-HRMS calcd for $C_{22}H_{25}N_2O_9S_3$ (MH$^+$) 557.0722, found 557.0717.

N-[4-(2-Hydroxyethylsulfamoyl)Phenyl]-2'-methyl-3'-chlorobenzenesulfonamide (STX648. XDS01111)

White foam. TLC single spot at $R_f$ 0.28 (50% DCM-ethyl acetate); HPLC purity >99% ($t_R$ 1.7 min in methanol); $^1$H NMR (400 MHz, DMSO): δ 11.2 (1H, s, NH), 7.96 (1H, dd, J=8.2, 1.1 Hz, ArH), 7.75 (1H, dd, J=8.2, 1.1 Hz, ArH), 7.65 (2H, m, ArH), 7.46 (1H, t, J=8.2 Hz, ArH ), 7.44 (1H, t, J=6.4 Hz, NH), 7.22 (1H, m, ArH ), 4.66 (1H, t, J=5.8 Hz, OH), 3.32 (2H, m, OCH$_2$), 2.71 (2H, m, NCH$_2$), 2.65 (3H, s, CH$_3$); APCI-MS 405 (MH$^+$); FAB-HRMS calcd for $C_{15}H_{18}ClN_2O_5S_2$ (MH$^+$) 405.0345, found 405.0334.

N-[4-(2-Hydroxyethylsulfamoyl)phenyl]-3',4'-dimethoxy .Benzene Sulfonamide (STX649, STX01112)

White foam. TLC single spot at $R_f$ 0.17 (50% DCM-ethyl acetate); HPLC purity >99% ($t_R$ 1.6 min in methanol); $^1$H NMR (400 MHz, DMSO): δ 10.7 (1H, s, NH), 7.64 (2H, d, J=8.6 Hz, ArH), 7.46 (1H, t, J=6.4 Hz, NH), 7.39 (1H, dd, J=8.5, 2.3 Hz, ArH), 7.28 (1H, d, J=2.3 Hz, ArH), 7.26 (2H, d, J=8.6 Hz, ArH), 7.08 (1H, d, J=8.5 Hz, ArH ), 4.66 (1H, t, J=5.4 Hz, OH), 3.79 (3H, s, OCH$_3$), 3.77 (3H, s, OCH$_3$), 3.33 (2H, m, OCH$_2$), 2.71 (2H, m, NCH$_2$); FAB-MS 417 (MH$^+$); FAB-HRMS calcd for $C_{16}H_{21}N_2O_7S_2$ (MH$^+$) 417.0790, found 417.0783.

3,4-Dimethoxybenzenesulfonic acid 2-[4-(3,4-dimethoxybenzenesulfonylamino)-benzenesulfonylamino]ethyl ester (STX650, XDS01112B)

White foam TLC single spot at $R_f$ 0.50 (50% DCM-ethyl acetate); HPLC purity >99% ($t_R$ 1.6 min in methanol); $^1$H NMR (400 MHz, DMSO): δ 10.7 (1H, s, NH), 7.80(1H, t, J=5.9 Hz, NH), 7.60 (2H, d, J=8.9 Hz, ArH), 7.38-7.45 (2H, m ArH), 7.23-7.29 (4H, m ArH), 7.17 (2H, d, J=8.6 Hz, ArH), 7.07 (2H, d, J=8.6 Hz, ArH), 3.92 (2H, t, J=5.1 Hz, OCH$_2$), 3.87 (3H, s, OCH$_3$), 3.84 (3H, s, OCH$_3$), 3.79 (3H, s, OCH$_3$), 3.76 (3H, s, OCH$_3$), 2.90 (2H, q, J=5.9 Hz, NCH$_2$); FAB-MS 617 (M–H$^+$); FAB-HRMS calcd for $C_{24}H_{29}N_2O_{11}S_3$ (MH$^+$) 617.0933, found 617.0926.

N-[4-(2-Hydroxyethylsulfamoyl)phenyl]-2',3', 6'-trimethyl-4'-methoxy-benzenesulfonamide (STX651, XDS01117)

White solid. TLC single spot at $R_f$ 0.28 (60% DCM-ethyl acetate); HPLC purity >99% A($t_R$ 1.6 min in methanol); $^1$H NMR (400 MHz, DMSO): δ 10.8 (1H, s, NH), 7.60 (2H, d, J=8.9 Hz, ArH), 7.41 (1H, t, J=5.8 Hz, NH), 7.07 (2H, d, J=8.9 Hz, ArH), 6.83 (1H, s, ArH), 4.65 (1H, broad, OH), 3.81 (3H, s, OCH$_3$), 3.33 (2H, m, OCH$_2$), 2.70 (2H, m, NCH$_2$), 2.65 (3H, s CH$_3$), 2.53 (3H, s CH$_3$), 2.05 (3H, s CH$_3$); FAB-MS 429 (MH$^+$); FAB-HRMS calcd for $C_{18}H_{25}N_2O_6S_2$ (MH$^+$) 429.1154, found 429.1143.

4-Methoxy-2,3,6-trimethylbenzenesulfonic acid 2-[4-(4-methoxy-2,3,6-trimethyl-benzenesulfonylamino)benzenesulfonylamino]ethyl ester (STX652, XDS01117B)

White foam TLC single spot at $R_f$ 0.80 (60% DCM-ethyl acetate); HPLC purity >99% ($t_R$ 1.7 min in methanol); $^1$H NMR (400 MHz, DMSO): δ 10.8 (1H, s, NH), 7.72(1H, t, J=5.9 Hz, NH), 7.56 (2H, d, J=9 Hz, ArH), 7.03 (2H, d, J=9 Hz, ArH), 6.89 (1H, s, ArH), 6.84 (1H, s, ArH), 3.86 (3H, s, OCH$_3$), 3.80 (5H, m, OCH$_3$, and OCH$_2$), 2.89 (2H, m, NCH$_2$), 2.65 (3H, s CH$_3$), 2.54 (3H, s CH$_3$), 2.52 (3H, s CH$_3$), 2.42 (3H, s CH$_3$), 2.08 (3H, s CH$_3$), 2.03 (3H, s CH$_3$); FAB-MS 641 (MH$^+$); FAB-HRMS calcd for $C_{28}H_{37}N_2O_9S_3$ (MH$^+$) 641.1661, found 641.1642.

N-[4-(2-Hydroxy-ethylsulfamoyl)-phenyl]-2',4'-dichlorobenzenesulfonamide (STX653, XDS01118)

White crystalline solid. TLC single spot at $R_f$ 0.36 (60% DCM-ethyl acetate); HPLC purity 5>99% ($t_R$ 1.9 min in 4% water-methanol); $^1$H NMR (400 MHz, DMSO): δ 11.3 (1H, s, NH), 8.11 (1H, d, J=8.2 Hz, ArH), 7.88 (1H, d, J=2.3 Hz, ArH), 7.62-7.68 (3H, m, ArH), 7.47 (1H, t, J=5.8 Hz, NH), 7.23 (2H, d, J=8.6 Hz, ArH), 4.66 (1H, t, J=5.9 Hz, OH), 3.33 (2H, m, OCH$_2$), 2.71 (2H, m, NCH$_2$); FAB-MS 424.9 (MH$^+$); FAB-HRMS calcd for C$_{14}$H$_{15}$Cl$_2$N$_2$O$_5$S$_2$ (MH$^+$) 424.9799, found 424.9800
-continued
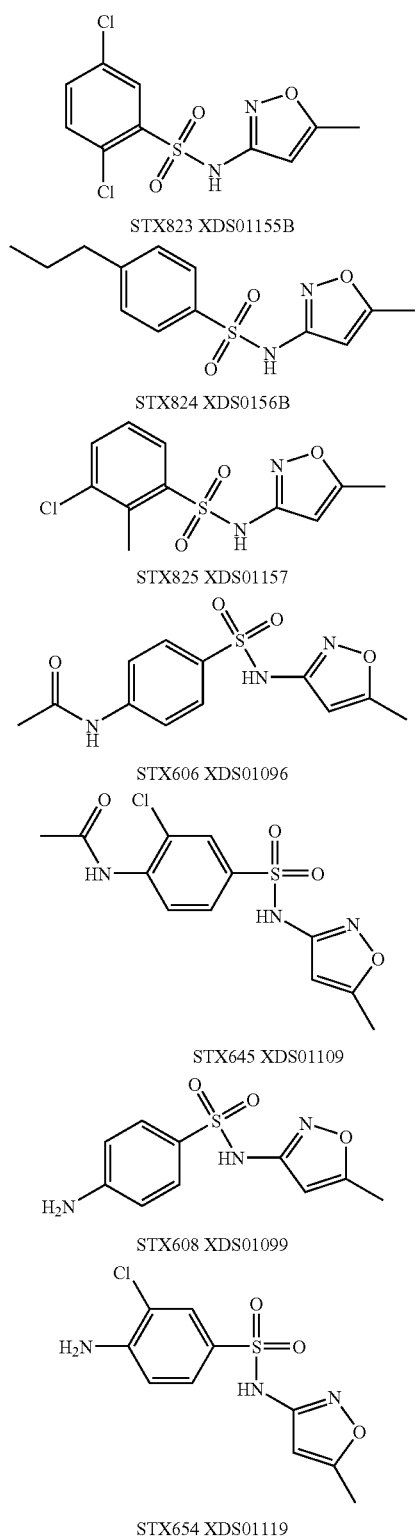
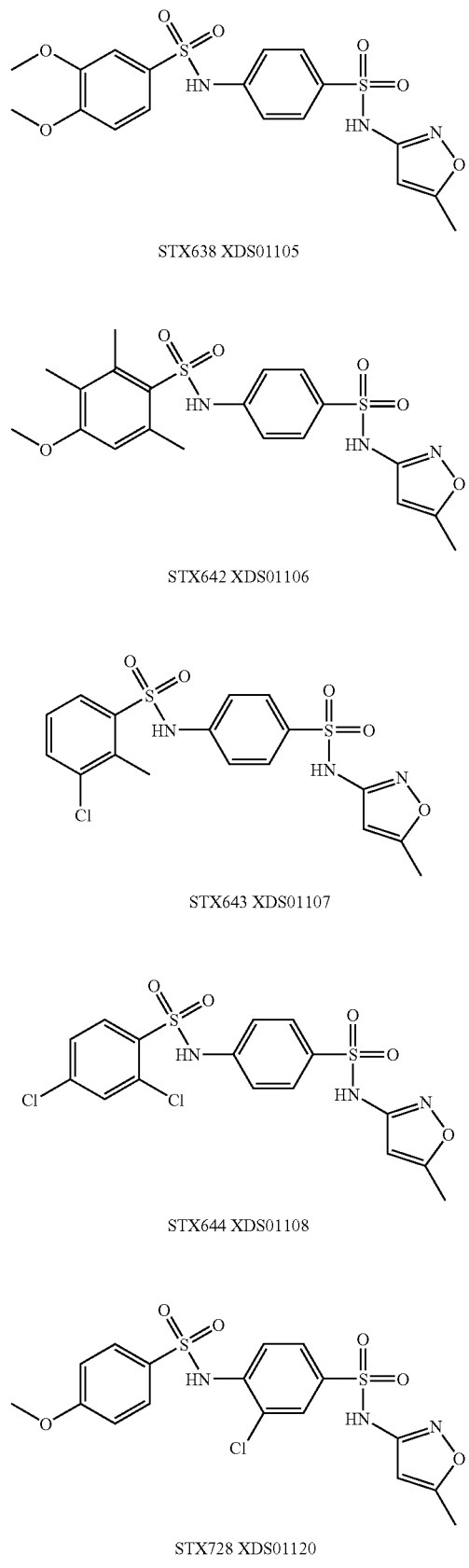

-continued

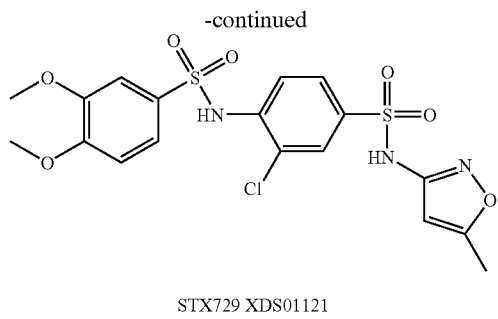

STX729 XDS01121

General Method for Coupling 3-amino-5-methylisooxazole with arylsulphonyl chloride (STX606, STX645, STX823-825)

To a solution arylsulphonyl chloride (1.1 eq.) in DCM were added pyridine (1.2 eq.) and 3-amino-5-methylisooxazole (1 eq.). The reaction mixture was stirred at rt under nitrogen for 24 h, then partitioned between ethyl acetate and 5% sodium bicarbonate solution. The organic layer was washed with 1% HCl solution and brine, dried over sodium sulphate, and concentrated in vacuo to give crude product that was purified by flash chromatography (ethyl acetate-DCM gradient elution) to give arylsulphonamide as white or off-white crystalline solid (Yield 50-80%).

2,5-Dichloro-N-(5-methylisoxazol-3-yl)benzenesulphonamide (STX823 XDS01155B)

White crystalline solid. TLC single spot at $R_f$ 0.45 (10% ethyl acetate-DCM); HPLC purity as rotational isomers >99% ($t_R$ 2.2 min in 15% water-methanol); $^1$H NMR (270 MHz, DMSb-d6): δ 12.0 (1H,s, NH), 8.01 (1H, d, J=2 Hz, ArH), 7.78 (1H, dd, J=8.0, 2.0 Hz, ArH), 7.71 (1H, d, J=8.0 Hz, ArH), 6.04 (1H, s, ArH), 2.27 (3H, s, CH$_3$); APCI-MS 306 (M$^+$); FAB-HRMS calcd for C$_{10}$H$_9$Cl$_2$N$_2$O$_3$S (MH$^+$) 306.9711, found 306.9718.

N-(5-Methylisoxazol-3-yl)-4-propylbenzenesulphonamide (STX824 XDS01156B)

White crystalline solid. TLC single spot at $R_f$ 0.65 (10% ethyl acetate-DCM); HPLC purity >99% ($t_R$ 2.2 min in 10% water-methanol); $^1$H NMR (270 MHz, DMSO-d$_6$): δ 11.3 (1H, s, NH), 7.72 (2H, d, J=8.1 Hz, ArH), 7.38 (2H, d, J=8.1 Hz, ArH), 6.10 (1H, s, ArH), 2.58 (2H, t, J=8.0 Hz, CH$_2$), 2.25 (3H, s, CH$_3$), 1.53 (2H, t, J=7.9 Hz, CH$_2$), 0.83 (3H, t, J=7.9 Hz, CH$_3$); APCI-MS 281 (MH$^+$); FAB-HRMS calcd for C$_{13}$H$_{17}$N$_2$O$_3$S (MH$^+$) 281.0960, found 281.0970.

3-Chloro-2-methyl-N-(5-methylisoxazol-3-yl)benzenesulphonamide (STX825 XDS01157)

White crystalline solid. TLC single spot at $R_f$ 0.50 (10% ethyl acetate-DCM); HPLC purity as rotational isomers >99% ($t_R$ 2.4 min in 15% water-methanol); $^1$H NMR (270 MHz, DMSO-d$_6$): δ 11.8 (1H, s, NH), 7.91 (1H, d, J=8.1 Hz, ArH), 7.76 (1H, d, J=8.1 Hz, ArH), 7.43 (1H, t, J=8.1 Hz, ArH), 6.01 (1H, s, ArH), 2.61 (3H, s, CH$_3$), 2.26 (3H, s, CH$_3$); FAB-MS 286 (M+); FAB-HRMS calcd for C$_{11}$H$_{12}$ClN$_2$O$_3$S (MH$^+$) 287.0257, found 287.0258.

N-(5-methylisoxazol-3-yl)-4-acetamidobenzenesulphonamide (STX606, XDS01096)

White solid. Mp 220-222° C. (lit [28], 225-228° C.); TLC single spot at $R_f$ 0.62 (10% ethyl acetate-DCM); HPLC purity 99% ($t_R$ 1.7 min in methanol); $^1$H NMR (270 MHz, DMSO-d6): δ 11.3 (1H, s, NH), 10.4 (1H, s, AcNH), 7.76 (4H, s, ArH), 6.12 (1H, s, ArH), 2.29 (3H, s, CH$_3$), 2.07 (3H, s, COCH$_3$); FAB-MS 296 (MH$^+$); FAB-HRMS calcd for C$_{12}$H$_{14}$N$_3$O$_4$S (MH$^+$) 296.0705, found 296.0701.

N-(5-methylisoxazol-3-yl)-3-chloro-4-acetamidobenzenesulphonamide (STX645, XDS01109)

White solid. TLC single spot at $R_f$ 0.52 (6% methanol-DCM); HPLC purity as rotational isomers >99% ($t_R$ 1.7 min in 4% water-methanol); $^1$H NMR (400 MHz, DMSO-d$_6$): δ 11.5 (1H, s, NH), 9.78 (1H, s, AcNH), 8.10 (1H, d, J=8.2 Hz, ArH), 7.90 (1H, s, ArH), 7.77 (1H, d, J=8.2 Hz, ArH), 6.15 (1H, s, ArH), 2.31 (3H, s, CH$_3$), 2.16 (3H, s, COCH$_3$); FAB-MS 330 (MH$^+$); FAB-HRMS calcd for C$_{12}$H$_{13}$ClN$_3$O$_4$S (MH$^+$) 330.0315, found 330.0321.

4-Amino-N-(5-methyl-isoxazol-3-yl)-benzenesulphonamide (STX608, XDS01099)

The solution of N-(5-methylisoxazol-3-yl)-4-acetamidobenzenesulphonamid (3.4 g, 11.5 mmol) in 10% NaOH solution (15 mL) was stirred at 809C for 1 h, cooled to rt and neutralized to pH. 6 with acetic acid. The precipitate was washed with water, dried in vacuo to yield off-white solid (2,8 g, 96%). Mp167-169° C. (lit [29], 168-171° C.); TLC single spot at $R_f$ 0.39 (6% methanol-DCM); HPLC purity >99% ($t_R$ 1.6 min in 4% water-*methanol*); $^1$H NMR (400 MHz, CD$_3$OD): δ 7.54 (2H, m, ArH), 6.63 (2H, m, ArH), 6.08 (1H, s, ArH), 2.30 (3H, s, CH$_3$); FAB-MS 254 (MH$^+$); FAB-HRMS calcd for C$_{10}$H$_{12}$N$_3$O$_3$S (MH$^+$) 254.0599, found 254.0605.

4-Amino-3-chloro-N-(5-methylisoxazol-3-yl)benzenesulphonamide (STX654. XDS01119)

The compound was prepared as described above. White solid (370 mg, 94%) was obtained. TLC single spot at $R_f$ 0.58 (30% ethyl acetate-DCM); HPLC purity >99% ($t_R$ 1.7 min in methanol); $^1$H NMR (400 MHz, DMSO-d$_6$): δ 11.1 (1H, s, NH), 7.60 (1H, d, J=2.3 Hz, ArH), 7.45 (1H, dd, J=8.5, 2.3 Hz, ArH),6.82 (1H, d, J=8.5 Hz, ArH),), 6.23 (2H, s, NH$_2$), 6.10 (1H, s, ArH), 2.29 (3H, s, CH$_3$); FAB-MS 288 (MH$^+$); FAB-HRMS calcd for C$_{10}$H$_{10}$ClN$_3$O$_3$S (MH$^+$) 288.0210, found 288.0213.

General Method for coupling 4-Amino-N-(5-methyl-isoxazol-3-yl)-benzenesulphonamide or 4-Amino-3-chloro-N-(5-methylisoxazol-3-yl)benzenesulphonamide with arylsulphonyl chloride (STX638, 642-644, 728, 729)

To a solution arylsulphonyl chloride (1.1 eq.) in DCM were added pyridine (1.3 eq.) and catalytic amount of DMAP, followed by the amine (1 eq.). The reaction mixture was stirred at rt or 40° C. under nitrogen for 24-48 h, then partitioned between DCM and water after TLC showed completion of the reaction. The organic layer was washed with 3% HCl solution and brine, dried over magnesium sulphate, and concentrated in vacuo to give crude product that was purified by recrystallization from ethyl acetate- DCM or by flash chromatography (ethyl acetate-DCM gradient elution) to give arylsulphonamide as white or off-white crystalline solid (Yield 40–80%).

N-[4-(5-Methyl-isoxazol-3-ylsulfamoyl)phenyl]-3', 4'-dimethoxy-benzenesulphonamide (STX638, XDS01105)

White crystalline solid. TLC single spot at $R_f$ 0.30 (6% methanol-DCM); HPLC purity as rotational isomers >99% ($t_R$ 1.7 min in 4% water-methanol); $^1$H NMR (400 MHz, DMSO-d6): δ 11.3 (1H, s, NH), 10.8 (1H, s, NH), 7.71 (2H, d, J=8.2 Hz, ArH), 7.41 (1H, m, ArH), 7.38 (3H, m, ArH), 7.07 (1H, d, J=8.6 Hz, ArH), 6.08 (1H, s, ArH), 3.79 (3H, s, OCH$_3$), 3.74 (3H, s, OCH$_3$), 2.28 (3H, s, CH$_3$); FAB-MS 454 (MH$^+$); FAB-HRMS calcd for $C_{18}H_{20}N_3O_7S_2$ (MH$^+$) 454.0743, found 454.0746.

N-[4-(5-Methyl-isoxazol-3-ylsulfamoyl)-phenyl]-2', 3',6'-trimethyl-4'-methoxy-benzenesulfonamide (STX642, XDS01106)

White crystalline solid. TLC single spot at $R_f$ 0.60 (10% methanol-DCM); HPLC purity as rotational isomers >99% ($t_R$ 1.8 min in 4% water-methanol); $^1$H NMR (400 MHz, DMSO-d6): δ 11.3 (1H; s, NH), 10.9 (1H, s, NH), 7.67 (2H, d, J=9.0 Hz, ArH), 7.04 (2H, d, J=9.0 Hz, ArH), 6.83 (1H, s, ArH), 6.06 (1H, s, ArH), 3.81 (3H, s, OCH$_3$), 2.64 (3H, s, CH$_3$), 2.27 (3H, s, CH$_3$), 2.03 (3H, s, CH$_3$); FAB-MS 466 (MH$^+$); FAB-HRMS calcd for $C_{20}H_{24}N_3O_6S_2$ (MH$^+$) 466.1107, found 466.1109.

N-[4-(5-Methyl-isoxazol-3-ylsulfamoyl)-phenyl]-2'-methyl-3'-chlorobenzenesulfonamide (STX643, XDS01107)

White crystalline solid. TLC single spot at $R_f$ 0.56 (10% methanol-DCM); HPLC purity as rotational isomers >99% ($t_R$ 2.0 min in 4% water-methanol); $^1$H NMR (400 MHz, DMSO-d6): δ 11.3 (2H, s, NH), 7.97 (1H, d, J=8.2 Hz, ArH), 7.75 (1H, d, J=8.2 Hz, ArH), 7.71 (2H, d, J=8.6 Hz, ArH), 7.43 (1H, t, J=8.2 Hz, ArH), 7.21 (2H, .m, ArH), 6.08 (1H, s, ArH), 2.62 (3H, s, CH$_3$), 2.28 (3H, s, CH$_3$); FAB-MS 442 (MH$^+$); FAB-HRMS calcd for $C_{17}H_{17}ClN_3O_5S_2$ (MH$^+$) 442.0298, found 442.0297.

N-[4-(5-Methyl-isoxazol-3-ylsulfamoyl)phenyl]-2', 4'-dichlorobenzenesulfonamide (STX644, XDS01108)

White crystalline solid. TLC single spot at $R_f$ 0.60 (10% methanol-DCM); HPLC purity as rotational isomers >99% ($t_R$ 2.2 min in 10% water-methanol); $^1$H NMR (400 MHz, DMSO-d$_6$): δ 11.5 (1H, s, NH), 11.3 (1H, s, NH), 8.12 (1H, d, J=8.5 Hz, ArH), 7.88 (1H, s, ArH), 7.72 (2H, d, J=8.6 Hz, ArH), 7.65 (1H, d, J=8.5 Hz, ArH), 7.23 (2H, d, J=8.6 Hz, ArH), 6.08 (1H, s, ArH), 2.29 (3H, s, CH$_3$); FAB-MS 462 (MH$^+$); FAB-HRMS calcd for $C_{16}H_{14}Cl_2N_3O_5S_2$ (MH$^+$) 461.9752, found 461.9756.

3-Chloro-4-(4-methoxybenzenesulfonylamino)-N-(5-methylisoxazol-3-yl)-benzenesulfonamide (STX728, XDS01120)

Off-white solid. TLC single spot at $R_f$ 0.64 (30% ethyl acetate-DCM); HPLC purity >99% ($t_R$ 1.8 min in 10% water-methanol); $^1$H NMR (400 MHz, DMSO-d$_6$): δ 11.5 (1H, s, NH), 10.4 (1H, s, NH), 7.80 (1H, d, J=2.0 Hz, ArH), 7.70–7.76 (3H, m, ArH), 7.52 (1H, d, J=8.0 Hz, ArH), 7.08 (2H, d, J=8.0 Hz, ArH), 6.13 (1H, s, ArH), 3.82 (3H, s, OCH$_3$), 2.30 (3H, s, CH$_3$); FAB-MS 458 (MH$^+$); FAB-HRMS calcd for $C_{17}H_{17}ClN_3O_6S_2$ (MH$^+$) 458.0247, found 458.0245.

3-Chloro-4-(3,4-dimethoxybenzenesulfonylamino)-N-(5-methylisoxazol-3-yl)-benzenesulfonamide (STX729, XDS01121)

White crystalline solid. TLC single spot at $R_f$ 0.49 (25% ethyl acetate-DCM); HPLC purity as rotational isomers >99% ($t_R$ 1.8 min in methanol); $^1$H NMR (270 MHz, DMSO-d6): δ 11.5 (1H, s, NH), 10.3 (1H, s, NH), 7.77 (1H, d, J=2.1 Hz, ArH), 7.69 (1H, dd, J=8.2, 2.1 Hz ArH), 7.48 (1H, d, J=8.2 Hz, ArH), 7.36 (1H, dd, J=8.6, 2.2 Hz, ArH), 7.23 (1H, d, J=2.2 Hz, ArH), 7.05 (1H, d, J=8.6 Hz, ArH), 6.07 (1H, s, ArH), 3.77 (3H, s, OCH$_3$), 3.67 (3H, s, OCH$_3$), 2.25 (3H, s, CH$_3$); FAB-MS 488 (MH$^+$); FAB-HRMS calcd for $C_{18}H_{19}CN_3O_7S_2$ (MH$^+$) 488.0353, found 488.0360.

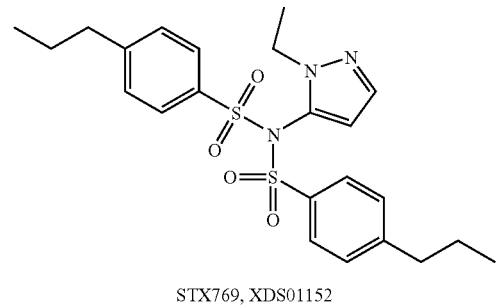

STX769, XDS01152

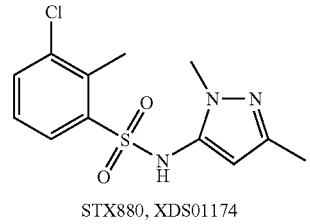

STX880, XDS01174

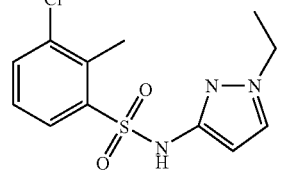

STX881, XDS01175C

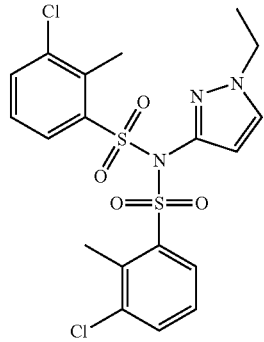

STX882, XDS01075B

-continued

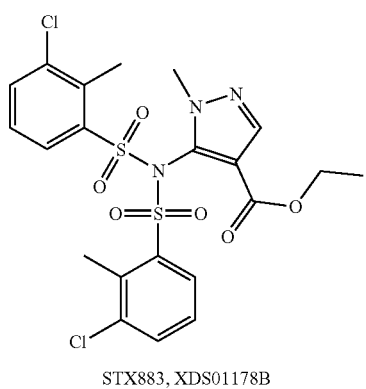

STX883, XDS01178B

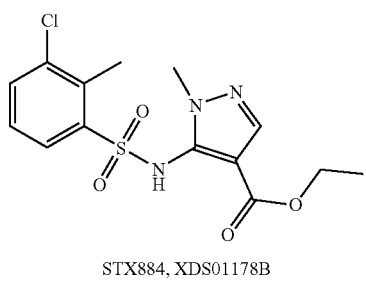

STX884, XDS01178B

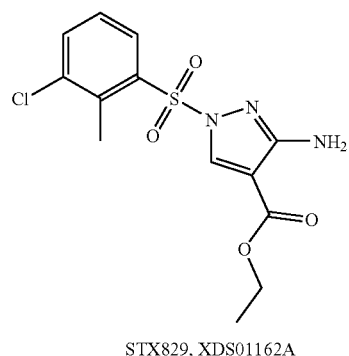

STX829, XDS01162A

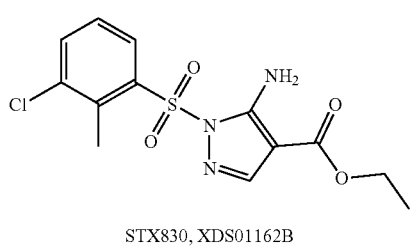

STX830, XDS01162B

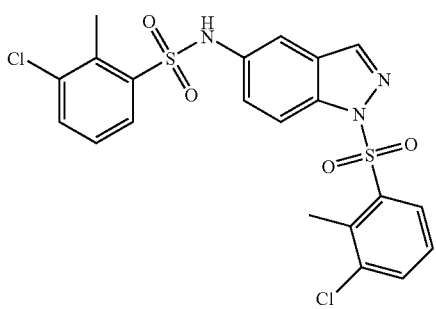

STX826, XDS01159

-continued

STX983, XDS02021B

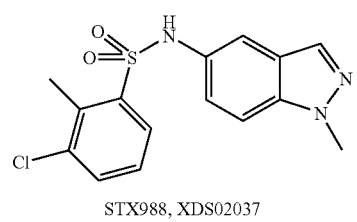

STX988, XDS02037

⑦ indicates text missing or illegible when filed

General Method for Synthesis of Arylsulphonamide and N-arylsulphonyl Arylsulphonamide (STX769, STX829-830, STX880-884)

To a solution arylsulphonyl chloride (1.05 eq.) in DCM were added pyridine (2.1 eq.) and the amine (1 eq.). The reaction mixture was stirred at rt or 40° C. under nitrogen for 4-14 h, then partitioned between ethyl acetate and 5% sodium bicarbonate solution after TLC showed completion of the reaction. The organic layer was washed with brine, dried over sodium sulphate, and concentrated in vacuo to give crude product that was separated by flash chromatography (ethyl acetate-DCM gradient elution) to give arylsulphonamide and N-arylsulphonyl arylsulphonamide as white or off-white solid (Yield 30-80%).

N-(2-N-ethyl-2H-pyrazol-3-yl)-N-(4-n-propylphenylsulphonyl)-4-n-propylbenzenesulfonamide (STX769, XDS01152)

White powder. TLC single spot at $R_f$ 0.71 (10% ethyl acetate-DCM); HPLC purity 99% ($t_R$ 4.1 min in 10% water-methanol); $^1$H NMR (400 MHz, DMSO-$d_6$): δ 7.62-7.66 (4H, m, ArH), 7.56 (1H, d, J=2.3 Hz, ArH), 7.47-7.50 (4H, m, ArH), 5.93 (1H, d, J=2.2 Hz, ArH), 3.66 (2H, q, J=7.0 Hz, NCH$_2$), 2.68 (4H, t J=7.8 Hz, CH$_2$) 1.63(4H, m, 2×CH$_2$), 1.18 (3H, t, J=7.0 Hz, CH$_3$), 0.90 (6H, t, J=7.6 Hz, 2×CH$_3$); FAB-MS 476 (MH$^+$); FAB-HRMS calcd for $C_{23}H_{30}N_3O_4S_2$ (MH$^+$) 476.1678, found 476.1682.

N-(2,5-dimethyl-2H-pyrazol-3-yl)-3-Chloro-2-methylbenzenesulfonamide (STX880, XDS01174)

White crystalline solid. TLC single spot at $R_f$ 0.76 (10% methanol-DCM); HPLC purity as rotational isomers 96% ($t_R$ 2.0 min in 20% water-methanol); $^1$H NMR (270 MHz, DMSO-d6): δ 7.75 (2H, d, J=8.2 Hz, ArH), 7.37 (1H, d, J=8.1 Hz, ArH), 5.49 (1H, s, ArH), 3.48 (3H, s, CH$_3$), 2.61 (3H, s, CH$_3$), 1.98 (3H, s, CH$_3$); APCI-MS 300 (MH$^+$); FAB-HRMS calcd for $C_{12}H_{15}ClN_3O_2S$ (MH$^+$) 300.0573, found 300.0572.

N-(1-Ethyl-1H-pyrazol-3-yl)-3-Chloro-2-methylbenzenesulfonamide (STX881, XDS01175C)

White solid. TLC single spot at $R_f$ 0.80 (10% methanol-DCM); HPLC purity as rotational isomers 95% ($t_R$ 2.0 min in 20% water-methanol); $^1$H NMR (270 MHz, DMSO-$d_6$): δ 10.5 (1H, s, NH), 7.71 (1H, d, J=8.1 Hz, ArH), 7.68 (1H, d, J=8.1 Hz, ArH), 7.32 (1H, t, J=8.1 Hz, ArH), 7.24 (1H, broad s, ArH), 5.57 (1H, d, J=1.8 Hz, ArH), 3.88 (2H, q, J=7.3 Hz, CH$_2$), 2.57 (3H, s, CH$_3$), 1.10 (3H, t, J=7.3 Hz, CH$_3$); APCI-MS 300 (MH$^+$); FAB-HRMS calcd for C$_{12}$H$_{15}$ClN$_3$O$_2$S (MH$^+$) 300.0573, found 300.0583.

N-(1-Ethyl-1H-pyrazol-3-yl)-N-(3-chloro-2-methylphenylsulphonyl)-3-chloro-2-methylbenzenesulfonamide (STX882, XDS01175B)

Colorless oil. TLC single spot at $R_f$ 0.82 (20% ethyl acetate-DCM); HPLC purity 98% ($t_R$ 4.5 min in 20% water-methanol); $^1$H NMR (270 MHz, CDCl$_3$): δ 7.95 (2H, d, J=8.1 Hz, ArH), 7.70 (2H, d, J=8.1 Hz, ArH), 7.56 (1H, d, J=2.1 Hz, ArH), 7.32 (2H, t, J=8.1 Hz, ArH), 6.21 (1H, d, J=1.8 Hz, ArH), 3.71 (2H, q, J=7.3 Hz, CH$_2$), 2.47 (6H, s, 2×CH$_3$), 1.28 (3H, t, J=7.3 Hz, CH$_3$); APCI-MS 488 (MH$^+$); FAB-HRMS calcd for C$_{19}$H$_{20}$Cl$_2$N$_3$O$_4$S$_2$ (MH$^+$) 488.0272, found 488.0263.

5-(N-3-Chloro-2-methylphenylsulphonyl-[3-Chloro-2-methyl-benzenesulfonylamino])-1-methyl-1H-pyrazole-4-carboxylic acid ethyl ester (STX883, XDS01178A)

White crystalline solid. TLC single spot at $R_f$ 0.81 (20% ethyl acetate-DCM); HPLC purity 93% ($t_R$ 2.2 min in 15% water-methanol); $^1$H NMR (270 MHz, CDCl$_3$): δ 8.09 (2H, dd, J=8.1, 1.5 Hz, ArH), 7.95 (1H, s, ArH), 7.63 (2H, dd, J=8.1, 1.3 Hz, ArH), 7.30 (2H, t, J=8.1 Hz, ArH), 3.88 (2H, q, J=7.0 Hz, CH$_2$), 3.54 (3H, s, CH$_3$), 2.29 (6H, s, 2×CH$_3$), 0.96 (3H, t, J=7.3 Hz, CH$_3$); FAB-MS 546 (MH$^+$); FAB-HRMS calcd for C$_{21}$H$_{22}$Cl$_2$N$_3$O$_6$S$_2$ (MH$^+$) 546.0327, found 546.0320.

5-(3-Chloro-2-methyl-benzenesulfonylamino)-1-methyl-1H-pyrazole-4-carboxylic acid ethyl ester (STX884, XDS01178B)

Off-white solid. TLC single spot at $R_f$ 0.49 (20% ethyl acetate-DCM); HPLC purity 91% ($t_R$ 2.0 min in 20% water-methanol); $^1$H NMR (270 MHz, CDCl$_3$): δ 7.60 (1H, s, ArH), 7.58 (1H, dd, J=7.9, 2.0 Hz, ArH), 7.50 (1H, dd, J=8.0, 2.0 Hz, ArH), 7.09 (1H, t, J=8.1 Hz, ArH), 3.91 (3H, s, CH$_3$), 3.90 (2H, q, J=7.0 Hz, CH$_2$), 2.50 (3H, s, CH$_3$), 1.05 (3H, t, J=7.0 Hz, CH$_3$); APCI-MS 358 (MH$^+$); FAB-HRMS calcd for C$_{14}$H$_{17}$ClN$_3$O$_4$S (MH$^+$) 358.0628, found 358.0640.

3-Amino-1-(3-chloro-2-methylbenzenesulfonyl)-1H-pyrazole-4-carboxylic acid ethyl ester (STX829, XDS01162A)

White crystalline solid. TLC single spot at $R_f$ 0.25 (DCM); HPLC purity >99% ($t_R$ 2.0 min in 4% water-methanol); $^1$H NMR (270 MHz, DMSO-$d_6$): δ 8.62 (1H, s, ArH), 7.95 (1H, d, J=8.2 Hz, ArH), 7.86(1H, d, J=8.2 Hz, ArH), 7.48 (1H, t, J=8.2 Hz, ArH), 5.95 (2H, s, NH$_2$), 4.17 (2H, q, J=7.0 Hz, CH$_2$), 2.49 (3H, s, CH$_3$), 1.21 (3H, t, J=7.0 Hz, CH$_3$); APCI-MS 0.344 (MH$^+$); FAB-HRMS calcd for C$_{13}$H$_{15}$ClN$_3$O$_4$S (MH$^+$) 344.0472, found 344.0477.

5-Amino-1-(3-chloro-2-methyl-benzenesulfonyl)-1H-pyrazole-4-carboxylic acid ethyl ester (STX830, XDS01162B)

Off-white crystalline solid. TLC single spot at $R_f$ 0.30 (DCM); HPLC purity 91% ($t_R$ 2.0 min in 4% water-methanol); $^1$H NMR (270 MHz, DMSO-$d_6$): 657.97 (1H, d, J=8.0 Hz, ArH), 7.87 (1H,d, J=8.0 Hz, ArH), 7.77 (1H, s, ArH), 7.50 (1H, t,J=8.0 Hz,ArH),703 (2H, s, NH$_2$), 4.14 (2H, q, J=6.9 Hz, CH$_2$), 2.50 (3H, s, CH$_3$), 1.18 (3H, t, J=6.9 Hz, CH$_3$); FAB-MS 344 (MH$^+$); FAB-HRMS calcd for C$_{13}$H$_{15}$ClN$_3$O$_4$S (MH$^+$) 344.0472, found 344.0472.

N-[1-(3-Chloro-2-methylbenzenesulfonyl)-1H-indazol-5-yl]-3-chloro-2-methylbenzenesulfonamide (STX826, XDS01159)

Off-white foam. TLC single spot at $R_f$ 0.65 (10% ethyl acetate-DCM); HPLC purity 96% ($t_R$ 2.2 min in 15% water-methanol); $^1$H NMR (270 MHz, DMSO-$d_6$): δ 10.7 (1H, s, NH), 9.01 (1H, s, 3-H), 8.05 (1H, d, J=8.1 Hz, ArH), 7.84 (1H, d, J=8.0 Hz, ArH), 7.80 (1H, d, J=8.0 Hz, ArH), 7.62 (1H, d, J=8.0 Hz, ArH), 7.51 (1H, d, J=8.0 Hz, ArH), 7.49 (1H, t, J=8.0 Hz, ArH), 7.29 (1H, t, J=8.0 Hz, ArH), 7.24 (1H, d, J=1.1 Hz, ArH), 7.11 (1H, dd, J=8.0, 1.2 Hz, ArH), 2.36 (6H, s, 2×CH$_3$); APCI-MS 510 (MH$^+$); FAB-HRMS calcd for C$_{21}$H$_{18}$Cl$_2$N$_3$O$_4$S$_2$ (MH$^+$) 510.0116, found 510.0106.

3-Chloro-N-(1H-indazol-5-yl)-2-methyl-benzenesulfonamide (STX983, XDS02021B)

Off-white solid. TLC single spot at $R_f$ 0.46 (6% methanol-DCM); HPLC purity >99% ($t_R$2.0 min in 10% water-methanol); $^1$H NMR (270 MHz, DMSO-$d_6$): δ 10.4 (1H, s, NH), 7.99 (1H, s, 3-H), 7.79 (1H, d, J=7.9 Hz, ArH), 7.68 (1H, d, J=7.9 Hz, ArH), 7.43 (1H, d, J=8.9 Hz, ArH), 7.41 (1H, s, ArH), 7.32 (1H, t, J=8.0 Hz, ArH), 7.08 (1H, d, J=8.9 Hz, ArH), 2.64 (3H, s, CH$_3$); APCI-MS 322 (MH$^+$); FAB-HRMS calcd for C$_{14}$H$_{13}$ClN$_3$O$_2$S (MH$^+$) 322.0417, found 322.0417.

3-Chloro-2-methyl-N-(1-methyl-1H-indazol-5-yl)-benzenesulfonamide (STX988, XDS02037)

Off-white solid. TLC single spot at $R_f$ 0.46 (7% methanol-DCM); HPLC purity 96% ($t_R$ 2.2 min in 10% water-methanol); $^1$H NMR (270 MHz, DMSO-$d_6$): δ 10.4 (1H, s, NH), 7.95 (1H; s, 3-H), 7.78 (1H, d, J=7.9 Hz, ArH), 7.68 (1H, d, J=7.9 Hz, ArH), 7.52 (1H, d, J=9.0 Hz, ArH), 7.40 (1H, J=2.0 Hz, ArH), 7.31 (1H, t, J=7.9 Hz, ArH), 7.12 (1H, dd, J=9.0, 2.0 Hz, ArH), 3.97 (3H, s, NCH$_3$), 2.65 (3H, s, CH$_3$); APCI-MS 336 (MH$^+$); FAB-HRMS calcd for C$_{15}$H$_{15}$ClN$_3$O$_2$S (MH$^+$) 336.0573, found 336.0575

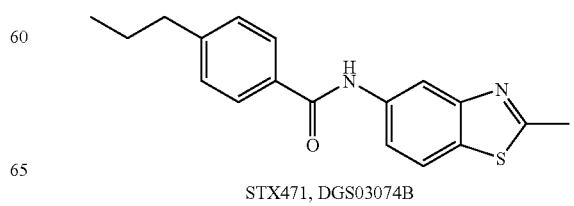

STX471, DGS03074B

-continued

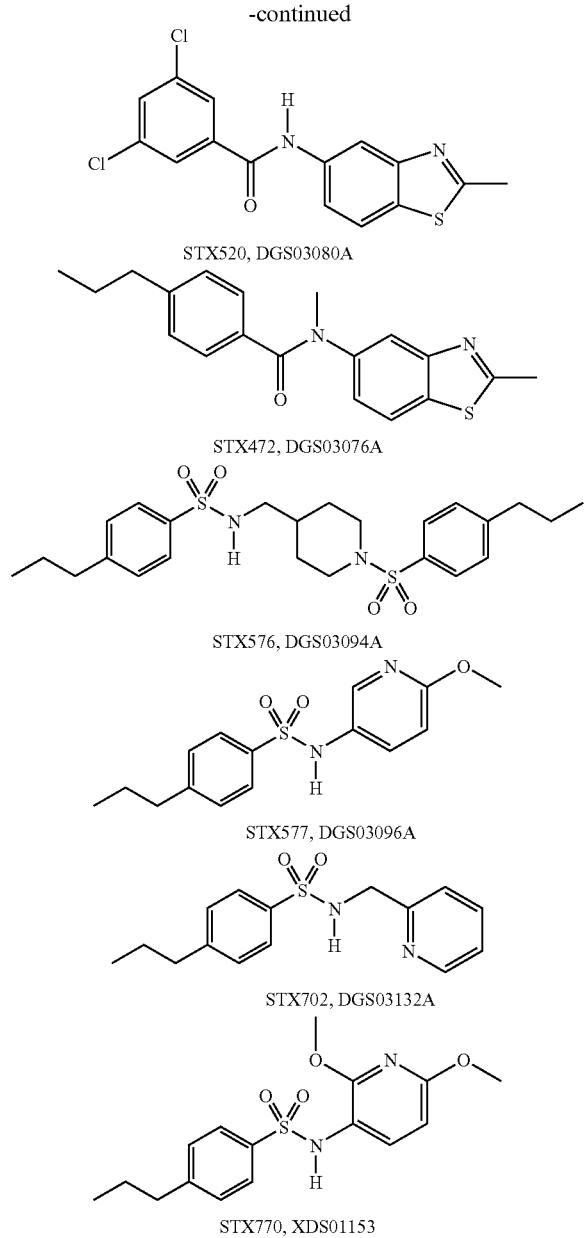

N-(2-Methylbenzothiazol-5-yl)-4-propylbenzamide
(STX471, DGS03074B)

To a solution of 5-amino-2-methylbenzothiazole (150 mg, 0.91 mmol) in THF (1 mL) was added triethylamine (5 mL). After stirring at rt for 15 min. 4-propylbenzoyl chloride(200 mg, 1.09 mmol) was added. The mixture was kept stirring at rt for 1 h, extracted with ethyl acetate. The organic phase was washed with brine, dried over sodium sulphate and concentrated in vacuo to yield a white solid that was recrystallized from ethyl acetate to give white needles (216 mg, 76%). mp 148-149° C.; TLC single spot at $R_f$ 0.56 (60% ethyl acetate-hexane); HPLC purity 99% ($t_R$ 3.1 min in 10% water-methanol); $^1$H NMR (400 MHz, DMSO-$d_6$): δ 10.3 (1H, s, NH), 8.41 (1H, d, J=2.0 Hz, ArH), 7.88-7.96 (3H, m, ArH), 7.50 (1H, dd, J=9.0, 2.3 Hz, ArH), 7.33-7.36 (1H, m, ArH), 2.78 (3H, s, CH$_3$), 2.63 (2H, t J=: 7.4 Hz, CH$_2$) 1.62(2H, m, CH$_2$), 0.98 (3H, t, J=7.4 Hz, CH$_3$); FAB-MS 311 (MH$^+$); FAB-HRMS calcd for C$_{18}$H$_{19}$N$_{20}$S (MH$^+$) 311.1218, found 311.1227.

3,5-Dichloro-N-(2-methylbenzothiazol-5-yl)-benzamide (STX520, DGS03080A)

STX520 was synthesized as described for STX471. White crystalline solid (166 mg, 54%) was obtained. mp 194° C.; TLC single spot at $R_f$ 0.76 (60% ethyl acetate-hexane); HPLC purity 97% ($t_R$ 1.6 min in 4% water-methanol); $^1$H NMR (400 MHz, DMSO-$d_6$): δ 10.6 (1H, s, NH), 8.40 (1H, d, J=2.0 Hz, ArH), 7.99-8.02 (3H, m, ArH), 7.89-7.90 (1H, m, ArH), 7.74 (1H, dd, J=8.9, 2.3 Hz, ArH), 2.80 (3H, s, CH$_3$); FAB-MS 337 (MH$^+$); FAB-HRMS calcd for C$_{15}$H$_{11}$Cl$_2$N$_2$OS (MH$^+$) 336.9969, found 336.9972.

N-Methyl-N-(2-methylbenzothiazol-5-yl)-4-propylbenzamide (STX472, DGS03076A)

To a solution of N-(2-methylbenzothiazol-5-yl)-4-propylbenzamide (130 mg, 0.4 mmol) in DMF (5 mL) was added sodium hydride (17 mg, 0.44 mmol), followed by methyl iodide (85 mg, 059 mmol). The mixture was stirred at rt overnight, partitioned between water and ethyl acetate. The organic phase was washed with brine, dried over sodium sulphate and concentrated to give a residue that wad purified with flash chromatography (ethyl acetate-hexane gradient elution). A thick syrup (41 mg, 26% was obtained. $^1$H NMR (400 MHz, CDCl$_3$): δ 7.61-7.79 (3H, m, ArH), 7.22-7.26 (2H, m, ArH), 6.92-7.02 (2H, m, ArH), 3.54 (3H, s, CH$_3$) 2.81 (3H, s, CH$_3$), 2.45 (2H, t J=7.4 Hz, CH$_2$) 1.52 (2H, m, CH$_2$), 0.83 (3H, t, .J=7.4 Hz, CH$_3$); FAB-MS 325 (MH$^+$); FAB-HRMS calcd for C$_{19}$H$_{21}$N$_2$OS (MH$^+$) 325.1375, found 325.1992.

General Method for Synthesis of Arylsulphonamide (, STX576-577, STX702, STX770)

To a solution of amine (1 eq.) in DMF was added Et$_3$N (5 eq.), followed by corresponding sulphonyl chloride (1.2 eq.). The reaction mixture was stirred at rt under N$_2$ overnight, poured into water after TLC showed completion of the reaction, and extracted with ethyl acetate, dried (MgSO$_4$), concentrated under reduced pressure to give the desired sulphonamide as crystalline solid or as a thick syrup. The crude compound was then purified by flash chromatography using EtOAc/hexane (3:2) or CH$_2$Cl$_2$/EtOAc (4:1) as eluent to give crystalline solid. Yield 20-80%.

4-Propyl-N-[1-(4-propylbenzenesulfonyl)-piperidin-4-ylmethyl]-benzenesulfonamide (STX576, DGS03094A)

White solid. mp 158-159° C.; TLC single spot at$R_f$ 0.59 (20% ethyl acetate-DCM); HPLC purity 99% ($t_R$ 2.0 min in 4% water-methanol); $^1$H NMR (400 MHz, DMSO-$d_6$): δ 7.60-7.66 (4H, m, ArH), 7.55 (1H, broad, NH), 7.35-7.45 (4H, m, ArH), 3.55-3.58 (2H, dd, J=7.2, 2.3 Hz, CH$_2$), 2.56-2.67 (6H, m, 3×CH$_2$), 2.04-2.10 (2H, m, CH$_2$), 1.54-1.65 (6H, m, 3×CH$_2$), 1.23 (1H, m, CH), 1.02-1.11 (2H, m, CH$_2$), 0.85-0.89 (6H, m, 2×CH$_3$); FAB-MS 479 (MH$^+$).

N-(6-Methoxypyridin-3-yl)-4-propylbenzenesulfonamide (STX577, DGS03096A)

White solid. mp 93-94° C.; TLC single spot at $R_f$ 0.54 (20% ethyl acetate-DCM); HPLC purity 99% ($t_R$ 2.0 min in 4% water-methanol); $^1$H NMR (400 MHz, DMSO-d$_6$): δ 10.0 (1H, s, NH), 7.77 (1H, d, J=2.7 Hz, ArH), 7.56-7.59 (2H, m, ArH), 7.35-7.38 (3H, m, ArH), 6.72 (1H, m, ArH), 3.75 (3H, s, OCH$_3$), 2.59 (2H, t, J=7.4 Hz, CH$_2$), 1.61 (2H, m, CH$_2$), 0.85 (3H, t, J=; 7.4 Hz, CH$_3$); FAB-MS 307 (MH$^+$); FAB-HRMS calcd for C$_{15}$H$_{19}$N$_2$O$_3$S (MH$^+$) 307.1048, found 307.1061.

4-Propyl-N-(pyridin-2-yl-methyl)-benzenesulfonamide (STX702, DGS03132A)

White crystalline solid. mp 109° C.; TLC single spot at $R_f$ 0.50 (20% ethyl acetate-DCM); HPLC purity >99% ($t_R$ 1.8 min in 4% water-methanol); $^1$H NMR (400 MHz, DMSO-d$_6$): δ 8.41 (1H, m, ArH), 8.19 (1H, s, NH), 7.66-7.72 (3H, m, ArH), 7.31-7.37 (3H, m, ArH), 7.22 (1H, m, ArH), 4.06 (2H, s, CH$_2$), 2.61 (2H, t, J=7.0 Hz, CH$_2$), 1.60 (2H, m, CH$_2$), 0.88 (3H, t, J=7.4 Hz, CH$_3$); FAB-MS 291 (MH$^+$); FAB-HRMS calcd for C$_{15}$H$_{19}$N$_2$O$_2$S (MH$^+$) 291.1167, found 291.1164.

N-(2,6-Dimethoxypyridin-3-yl)-4-propylbenzenesulfonamide (STX770, XDS01153)

Off-white crystalline solid. TLC single spot at $R_f$ 0.37 (30% ethyl acetate-hexane); HPLC purity 98% ($t_R$ 2.7 min in 10% water-methanol); $^1$H NMR (400 MHz, DMSO-d$_6$): δ 9.39 (1H, s, NH), 7.48-7.54 (2H, m, ArH), 7.42 (1H, d, J=8.8 Hz, ArH), 7.33 (2H, d, J=8.6 Hz, ArH), 6.30 (1H, d, J=8.8 Hz, ArH), 3.76 (3H, s, OCH$_3$), 3.45 (3H, s, OCH$_3$), 2.60 (2H, t, J=7.8 Hz, CH$_2$), 1.55 (2H, sextet, J=7.8 Hz, CH$_2$), 0.88 (3H, t, J=7.8 Hz, CH$_3$); FAB-MS 291 (MH$^+$); FAB-HRMS calcd for C$_{16}$H$_{21}$N$_2$O$_4$S (MH$^+$) 337.1222, found 337.1222.

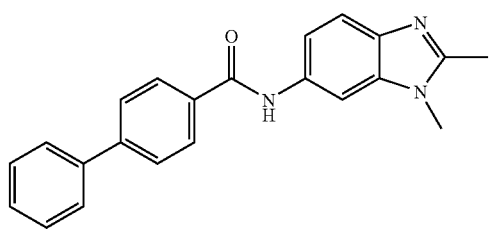

STX1129, JWS01109

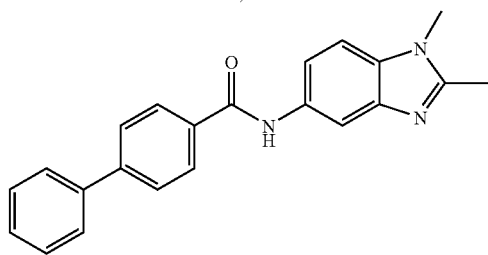

STX1130, JWS01111

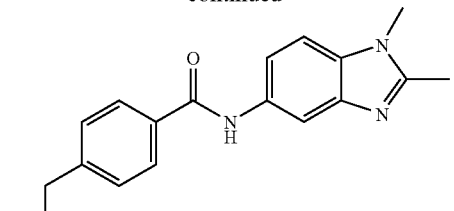

STX1131, JWS01113

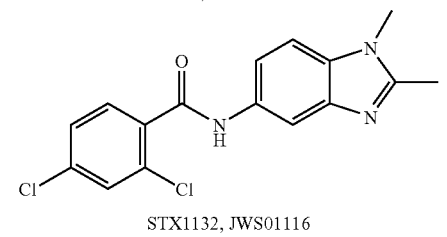

STX1132, JWS01116

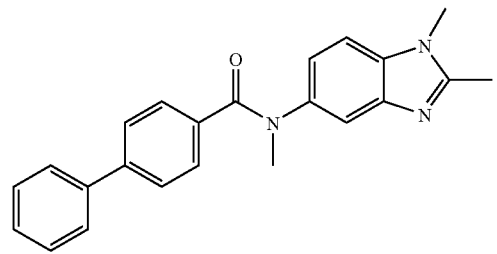

STX1133, XDS02112

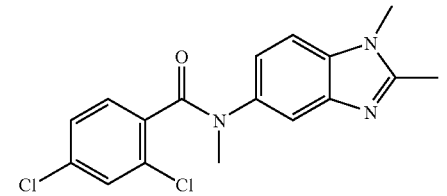

STX1134, XDS02113

General Method for Benzamide Formation:

To a solution of substituted benzoyl chloride (1.2 eq.) in THF-triethylamine (1:4) was added the corresponding amine (1 eq.). The reaction mixture was stirred at rt under nitrogen for 16 h, partitioned between DCM and 5% sodium bicarbonate after TLC showed completion of the reaction. The organic layer was washed with brine, dried over sodium sulphate, and concentrated in vacuo to give crude product as solid or thick syrup. The compound was then purified by flash chromatography (Methanol-DCM gradient elution) to give desired N-benzimidazole aryl amide as crystalline solid. Yield ranges from 60-80%.

Biphenyl-4-carboxylic acid (1,2-dimethyl-3H-benzoimidazol-6-yl)-amide (STX1129. JWS01109)

Off-white solid. Mp 270-270.3° C.; TLC single spot at $R_f$ 0.52 (10% methanol/DCM); HPLC purity 98% ($t_R$ 2.2 min in 20% water-methanol); $^1$H NMR (400 MHz, DMSO): δ 10.3 (1H, s, NH), 8.05-8.10 (3H, m, ArH), 7.82 (2H, d, J=8.2 Hz, ArH), 7.75 (2H, dd, J=8.1, 1.2 Hz, ArH), 7.38-7.52 (5H, m, ArH), 3.70 (3H, s, NCH$_3$), 2.52 (3H, s, CH$_3$); FAB-MS 342 (MH$^+$); FAB-HRMS calcd for C$_{22}$H$_{20}$N$_3$O (MH$^+$) 342.1606, found 342.1615.

Biphenyl-4-carboxylic acid (1,2-dimethyl-3H-benzoimidazol-5-yl)-amide (STX1130, JWS01112)

Off-white solid. Mp 272-274° C.; TLC single spot at $R_f$ 0.52 (10% methanol/DCM); HPLC purity 98% ($t_R$ 2.2 min in 20% water-methanol); $^1$H NMR (400 MHz, DMSO): δ 10.2 (1H, s, NH), 8.06 (2H, d, J=8.2 Hz, ArH), 7.95 (1H, d, J=2.0 Hz, ArH), 7.82 (2H, d, J=8.2 Hz, ArH), 7.74 (2H, dd, J=8.2, 1.9 Hz, ArH), 7.48-7.56 (5H, m, ArH), 3.72 (3H, s, NCH$_3$), 2.52 (3H, s, CH$_3$); FAB-MS 342 (MH$^+$); FAB-HRMS calcd for C$_{22}$H$_{20}$N$_3$O (MH$^+$) 342.1606, found 342.1611.

N-(1,2-Dimethyl-1H-benzoimidazol-5-yl)-4-propyl-benzamide (STX1131, JWS01113)

Off-white solid. Mp 214-218° C.; TLC single spot at $R_f$ 0.43 (10% methanol/DCM); HPLC purity >99% ($t_R$ 2.2 min in 20% water-methanol); $^1$H NMR (400 MHz, DMSO): δ 10.1 (1H, s, NH), 7.95 (1H, d, J=1.5 Hz, ArH), 7.87 (2H, d, J=8.2 Hz, ArH), 7.51 (1H, dd, J=8.5, 2.0 Hz, ArH), 7.39 (1H, d, J=8.2 Hz, ArH), 7.32 (2H, d, J=8.5 Hz, ArH), 3.70 (3H, s, NCH$_3$), 2.63 (2H, t, J=7.1 Hz, CH$_2$), 2.50 (3H, s, CH$_3$), 1.62 (2H, sextet, J=7.2 Hz, CH$_2$), 0.91 (3H, t, J=7.3 Hz, CH$_2$); FAB-MS 308 (MH$^+$); FAB-HRMS calcd for C$_{19}$H$_{22}$N$_3$O (MH$^+$) 308.1763, found 308.1778.

2,4-Dichloro-N-(1,2-dimethyl-1H-benzoimidazol-5-yl)-benzamide (STX1132, JWS01116)

light yellow solid. Mp 275-277° C.; TLC single spot at $R_f$ 0.43 (10% methanol/DCM); HPLC purity >99% ($t_R$ 2.0 min in 10% water-methanol); $^1$H NMR (400 MHz, DMSO): δ 10.4 (1H, s, NH), 7.92 (1H, d, J=2.0 Hz, ArH), 7.74 (1H, d, J=1.9 Hz, ArH), 7.62 (1H, d, J=8.2 Hz, ArH), 7.53 (1H, dd, J=8.2, 2.0 Hz, ArH), 7.39-7.42 (2H, m, ArH), 3.70 (3H, s, NCH$_3$), 2.50 (3H, s, CH$_3$); FAB-MS 334 (MH$^+$); FAB-HRMS calcd for C$_{16}$H$_{14}$Cl$_2$N$_3$O (MH$^+$) 334.0514, found 334.0517

Biphenyl-4-carboxylic acid (1,2-dimethyl-3H-benzoimidazol-5-yl)-N-methyl-amide (STX1133, XDS02112)

White crystals. Mp 213-214.5° C.; TLC single spot at $R_f$ 0.79 (10% methanol/DCM); HPLC purity 99% ($t_R$ 2.2 min in 20% water-methanol); $^1$H NMR (270 MHz, DMSO): δ 7.58 (2H, m, ArH), 7.30-7.50 (9H, m, ArH), 7.07 (1H, dd, J=8.1, 1.9 Hz, ArH), 3.65 (3H, s, NCH$_3$), 3.29 (3H, s, NCH$_3$), 2.45 (3H, s, CH$_3$); APCI-MS 356 (MH$^+$).

2,4-Dichloro-N-(1,2-dimethyl-1H-benzoimidazol-5-yl)-N-methyl-benzamide (STX1134, XDS02113)

White crystals. Mp 245-247° C.; TLC single spot at $R_f$ 0.70 (10% methanol/DCM); HPLC purity >99% ($t_R$ 2.2 min in 10% water-methanol); $^1$H NMR (270 MHz, DMSO): δ 7.44 (1H, d, J=2.0 Hz, ArH), 7.41 (1H, broad, W$_{1/2}$=1.7 Hz, ArH), 7.39 (1H, d, J=8.2 Hz, ArH), 7.35 (1H, d, J=8.5 Hz, ArH), 7.22 (1H, dd, J=8.2, 1.9 Hz, ArH), 7.09 (1H, dd, J=8.5, 1.9 Hz, ArH), 3.64 (3H, s, NCH$_3$), 3.39 (3H, s, NCH$_3$), 2.45 (3H, s, CH$_3$); APCI-MS 348 (MH$^+$).

The compounds shown in the following table were synthesised in the manner described.

| STX CODE | COMPOUND CODE | STRUCTURE |
| --- | --- | --- |
| 1264 | XDS03019 | 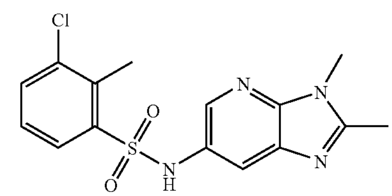 |
| 1317 | XDS03047B | 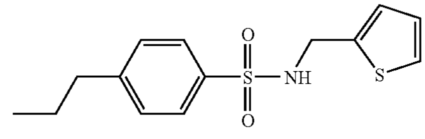 |
| 1318 | XDS03048 | 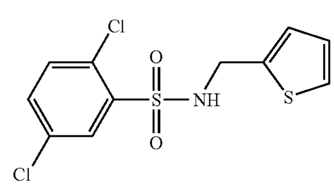 |
| 1319 | XDS03049 | 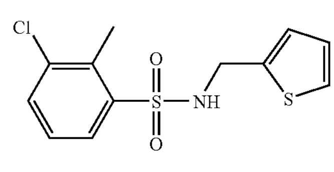 |

-continued
| STX CODE | COMPOUND CODE | STRUCTURE |
|---|---|---|
| 1320 | XDS03050 | 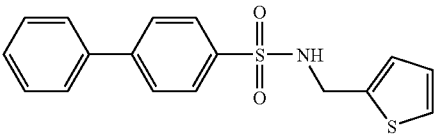 |
| 1321 | XDS03051 | 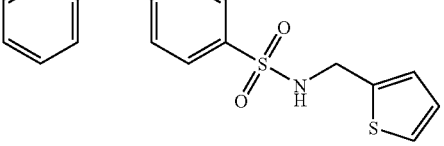 |
| 1327 | XDS03061A | 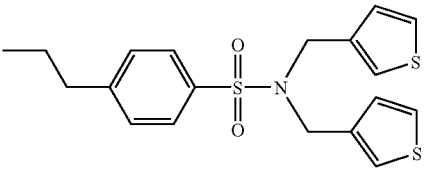 |
| 1328 | XDS03061B | 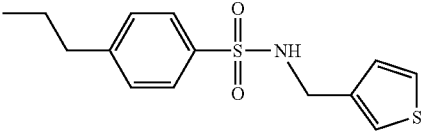 |
| 1329 | XDS03062A | 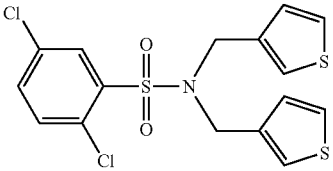 |
| 1330 | XDS03062B | 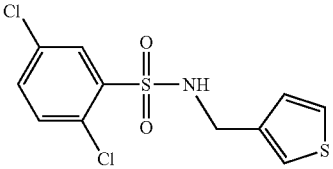 |
| 1331 | XDS03063A | 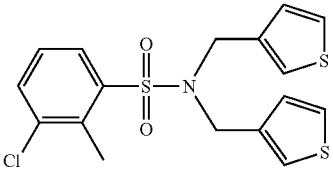 |
| 1332 | XDS03063B | 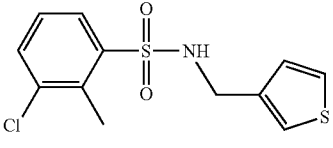 |
| 1333 | XDS03064A | 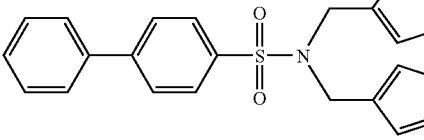 |

-continued

| STX CODE | COMPOUND CODE | STRUCTURE |
|---|---|---|
| 1334 | XDS03064B | 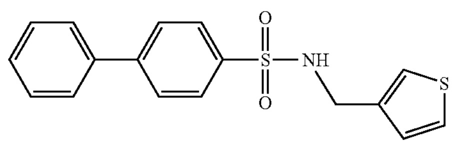 |
| 1335 | XDS03065 | 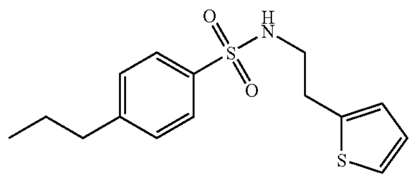 |
| 1336 | XDS03066 | 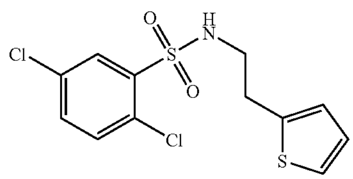 |
| 1337 | XDS03067 | 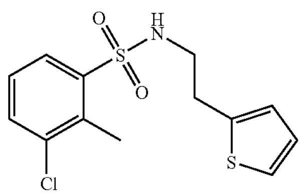 |
| 1338 | XDS03068 | 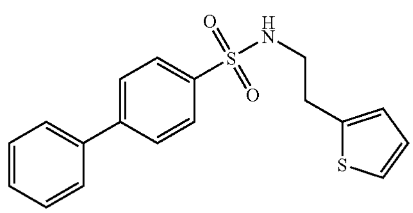 |
| 1339 | XDS03070 | 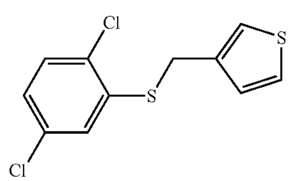 |
| 1340 | XDS03071B | 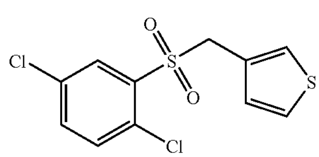 |
| 1355 | CCM01002 | 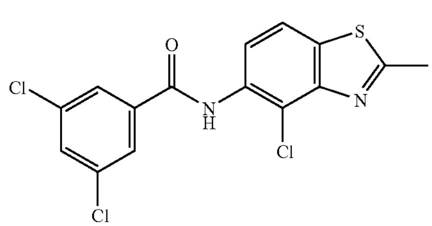 |

-continued
| STX CODE | COMPOUND CODE | STRUCTURE |
|---|---|---|
| 1356 | CCM01003 | 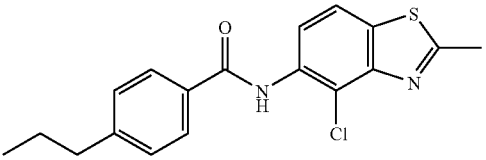 |
| 1357 | CCM01004 | 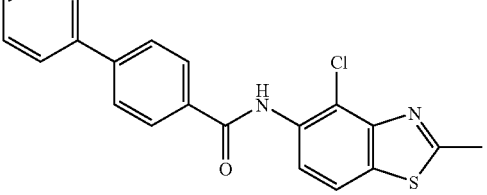 |
| 1358 | CCM01006 | 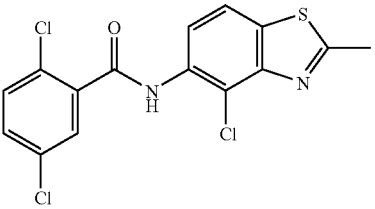 |
| 1363 | CCM01008 | 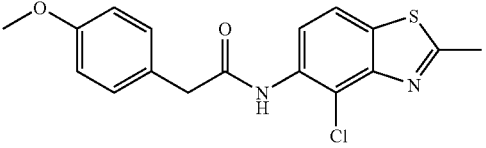 |
| 1364 | CCM01009 | 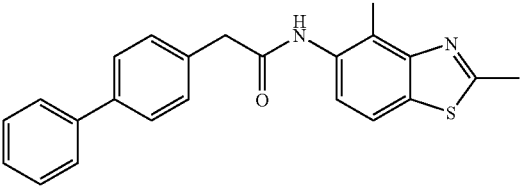 |
| 1365 | CCM01010 | 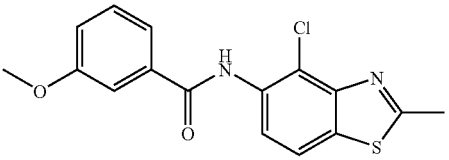 |
| 1366 | CCM01011 | 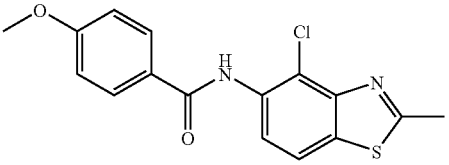 |
| 1367 | CCM01012 | 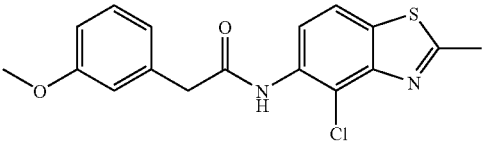 |

-continued
| STX CODE | COMPOUND CODE | STRUCTURE |
|---|---|---|
| 1376 | CCM01013 | 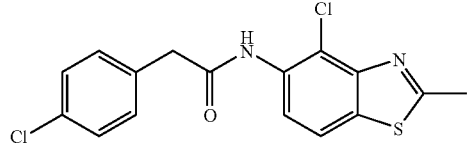 |
| 1377 | CCM01015 | 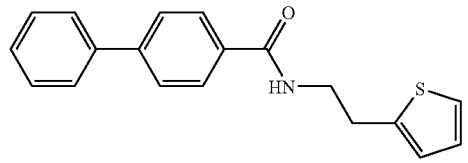 |
| 1378 | CCM01016 | 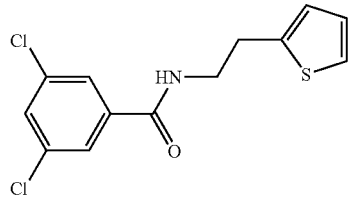 |
| 1379 | CCM01017 | 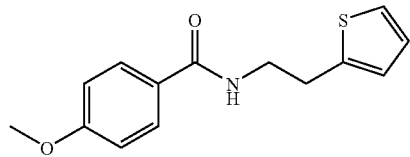 |
| 1380 | CCM01018 | 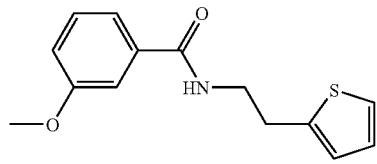 |
| 1381 | CCM01020 | 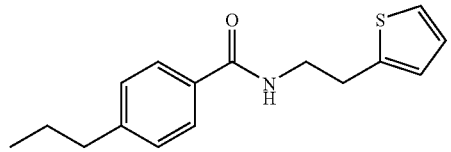 |
| 1382 | CCM01021 | 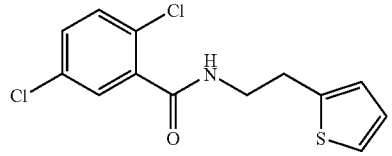 |
| 1396 | CCM01022 | 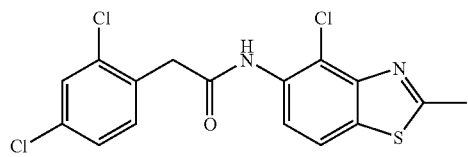 |

-continued

| STX CODE | COMPOUND CODE | STRUCTURE |
|---|---|---|
| 1397 | CCM01023 | 2,5-dichloro-N-(1-oxo-2,3-dihydro-1H-inden-5-yl)benzamide |
| 1398 | CCM01024 | N-(1-oxo-2,3-dihydro-1H-inden-5-yl)-[1,1'-biphenyl]-4-carboxamide |
| 1399 | CCM01025 | 3,5-dichloro-N-(1-oxo-2,3-dihydro-1H-inden-5-yl)benzamide |
| 1400 | CCM01026 | 4-propyl-N-(1-oxo-2,3-dihydro-1H-inden-5-yl)benzamide |
| 1401 | CCM01027 | 4-methoxy-N-(1-oxo-2,3-dihydro-1H-inden-5-yl)benzamide |
| 1402 | CCM01028 | 3-methoxy-N-(1-oxo-2,3-dihydro-1H-inden-5-yl)benzamide |
| 1405 | XDS03101 | 4-propyl-N-(thiophen-2-ylmethyl)benzamide |
| 1406 | XDS03102 | 3,5-dichloro-N-(thiophen-2-ylmethyl)benzamide |

-continued
| STX CODE | COMPOUND CODE | STRUCTURE |
|---|---|---|
| 1407 | XDS03103 | 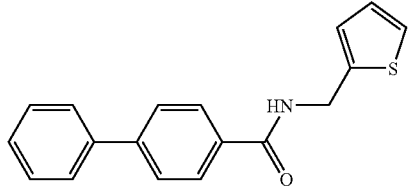 |
| 1408 | XDS03104 | 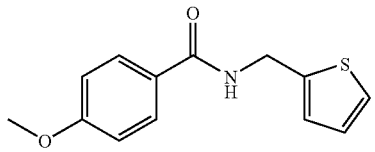 |
| 1409 | XDS03105 | 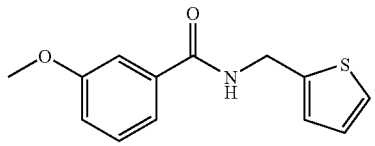 |
| 1414 | XDS03111 | 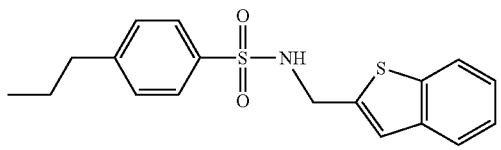 |
| 1415 | XDS03112 | 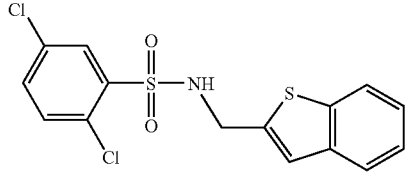 |
| 1416 | XDS03113 | 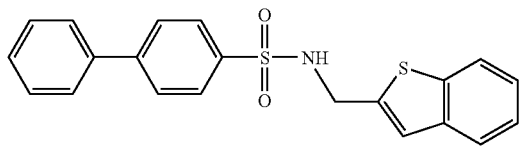 |
| 1417 | XDS03114 | 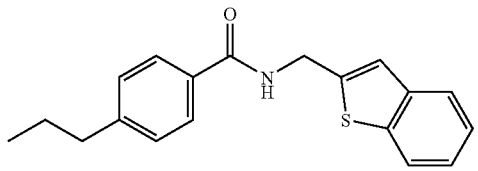 |
| 1418 | XDS03115 | 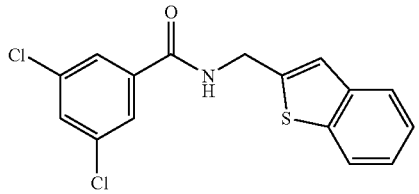 |

-continued

| STX CODE | COMPOUND CODE | STRUCTURE |
|---|---|---|
| 1419 | XDS03116 | 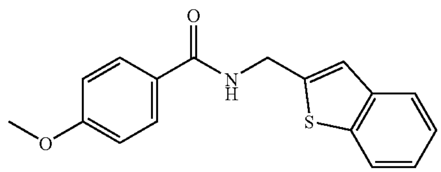 |
| 1430 | CCM01029 | 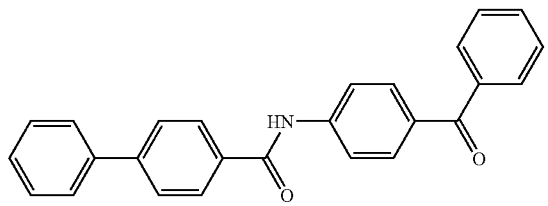 |
| 1431 | CCM01031 | 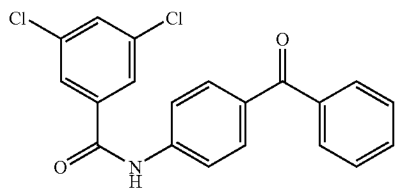 |
| 1432 | CCM01032 | 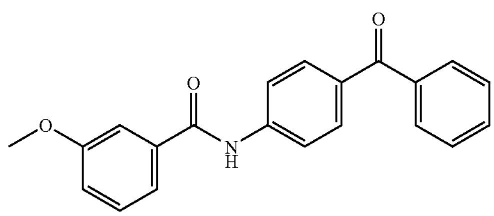 |
| 1433 | CCM01034 | 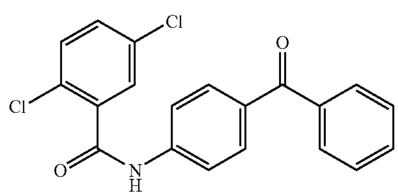 |
| 1434 | CCM01036 | 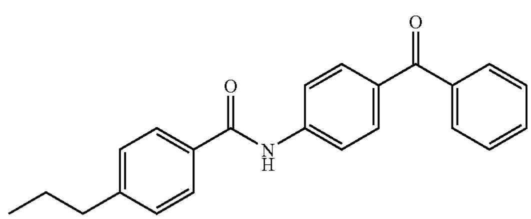 |
| 1435 | CCM01037 | 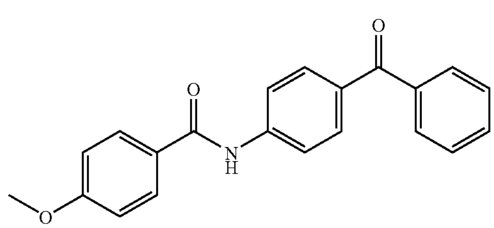 |

-continued

| STX CODE | COMPOUND CODE | STRUCTURE |
|---|---|---|
| 1445 | CCM01038 | 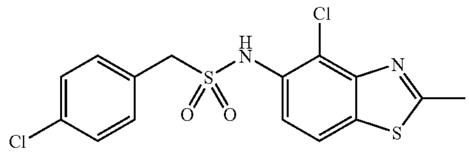 |
| 1446 | CCM01029 | 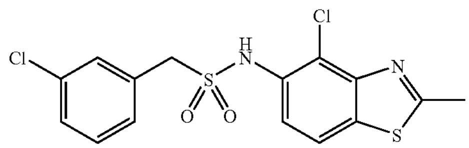 |
| 1461 | CCM01040A | 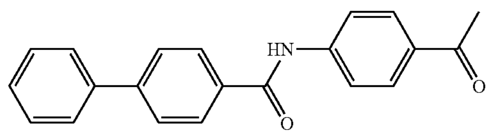 |
| 1462 | CCM01041 | 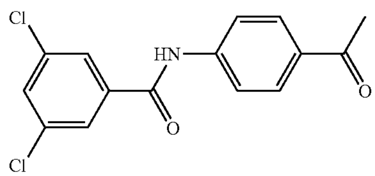 |
| 1463 | CCM01042 | 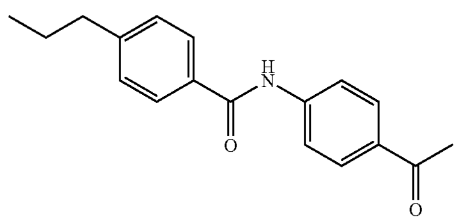 |
| 1464 | CCM01043 | 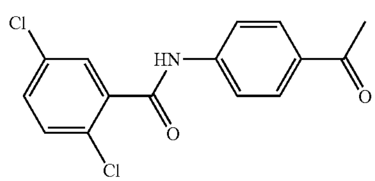 |
| 1465 | CCM01044 | 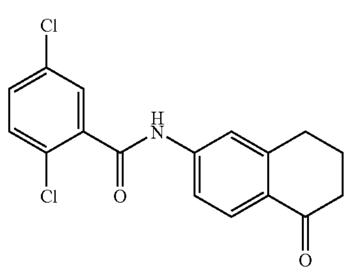 |
| 1468 | CCM01047 | 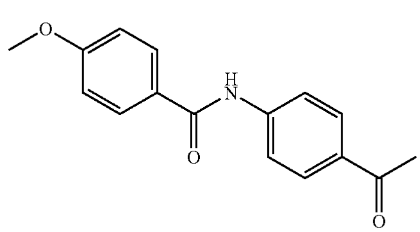 |

| STX CODE | COMPOUND CODE | STRUCTURE |
|---|---|---|
| 1469 | CCM01048 | 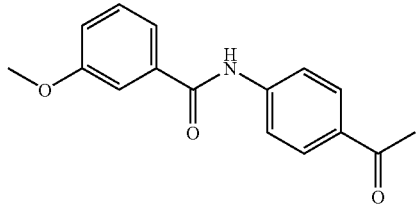 |
| 1470 | CCM01049 | 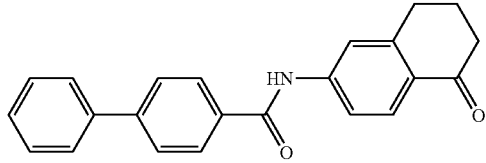 |
| 1472 | CCM01050 | 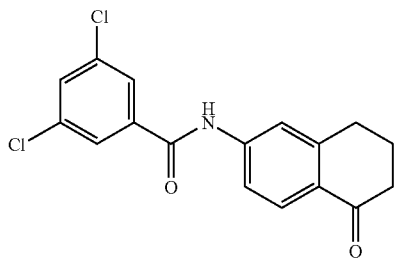 |
| 1473 | CCM01051 | 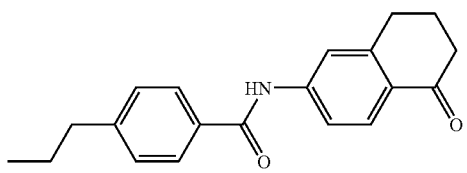 |
| 1474 | CCM01052 | 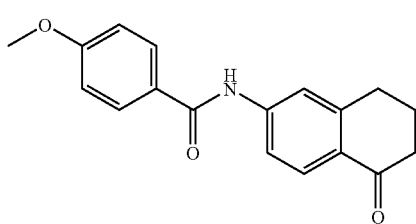 |
| 1475 | CCM01052 | 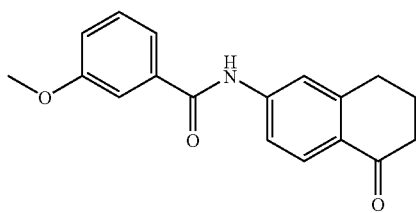 |
Synthesis of N-(2-thiopheneethyl)-benzamide derivatives
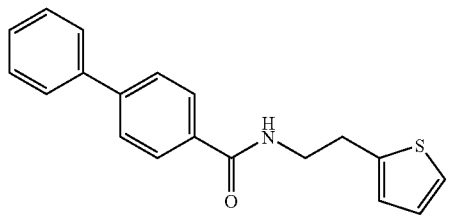

-continued

| STX CODE | COMPOUND CODE | STRUCTURE |
|---|---|---|
| STX1377, CCM01015 | | |
| STX1378, CCM01016 | | |
| STX1379, CCM01017 | | |
| STX1380, CCM01018 | | |
| STX1381, CCM01020 | | |
| STX1382, CCM01021 | | |

General method for synthesis of
N-(2-thiopheneethyl)-benzamide derivatives
(STX1377-1382)

Method A: to a stirred solution of the amine (n mmol) in THF are added triethylamine (1.2 n mmol) and the acyl chloride (1.2 n mmol) at room temperature. After completion, ethyl acetate and water are added. The aqueous layer is extracted by ethyl acetate. The combined organic layers are washed with brine, dried (MgSO4), filtered and evaporated under reduce pressure. The crude product is then purified to give the amide.

Method B: A solution of the acid (3n mmol) in thionyl chloride is refluxed 3 hours. Thionyl chloride is then removed under reduced pressure. The crude product is diluted in dry THF and added to a solution of the amine (n mmol) and triethylamine in THF. After completion, ethyl acetate and water are added. The aqueous layer is extracted by EtOAc. The combined organic layers are then washed with brine, dried (MgSO4), filtered and evaporated under reduce pressure. The crude product is purified to give the amide.

Biphenyl-4-carboxylic acid (2-thiophen-2-yl-ethyl)-amide (STX1377, CCM01015)

Reaction of 2-thiopheneethylamine (50 μL, 0.42 mmol) in THF (2.5 mL) with 4-biphenylcarbonyl chloride (120 mg, 0.55 mmol) in presence of triethylamine (78 μL, 0.55 mmol) according to method A gave biphenyl-4-carboxylic acid (2-thiophen-2-yl-ethyl)-amide (70 mg, 0.23 mmol, 55% yield) as a grey powder after crystallisation in hexane/EtOAc.

$R_f$:0.4 (EtOAc/DCM 5/95); M.p.:164-166° C.; $^1$H NMR (270 MHz, CDCl$_3$) $\delta_H$ 3.16 (t, 2H, J=6.6 Hz, CH$_2$Ar), 3.71-3.77 (m, 2H, CH$_2$NH), 6.27 (bs, 1H, NH), 6.88 (bs, 1H, H$_{Ar}$), 6.95-6.98 (m, 1H, H$_{Ar}$), 7.17 (d, 1H, J=4.7 Hz, H$_{Ar}$thiophene), 7.36-7.47 (m, 3H, H$_{Ar}$), 7.57-7.64 (m, 4H, H$_{Ar}$), 7.77 (d, 2H, J=8.1 Hz, H$_{Ar}$); $^{13}$C NMR (400 MHz, CDCl$_3$) δ$_C$ 30.0 (CH$_2$), 41.4 (CH$_2$), 124.2 (CH$_{Ar}$), 125.6 (CH$_{Ar}$), 127.2 (2*CH$_{Ar}$), 127.3 (CH$_{Ar}$), 127.4 (CH$_{Ar}$), 128.0 (CH$_{Ar}$), 129.0 (CH$_{Ar}$), 133.2 (C$_q$), 140.0 (C$_q$), 141.3 (C$_q$), 144.3 (C$_q$), 167.7 (C=O); LC/MS (AP−) m/z305.8 (M−H); t$_R$=2.3 min (99.6%); HRMS (FAB+) Calculated for C$_{19}$H$_{17}$NOS 307.1031; Found 307.1016.

3,5-Dichloro-N-(2-thiophen-2-yl-ethyl)-benzamide (STX1378, CCM01016)

Reaction of 2-thiopheneethylamine (50 μL, 0.42 mmol) in THF (2.5 mL) with 3,5-dichlorobenzoyl chloride (120 mg, 0.57 mmol) in presence of triethylamine (78 μL, 0.55 mmol) according to method A gave 3,5-dichloro-N-(2-thiophen-2-yl-ethyl)-benzamide (118 mg, 0.39 mmol, 92% yield) as a white powder after purification by chromatography on silica gel (eluent: EtOAc/hexane 2/8).

R$_f$:0.3 (EtOAc/hexane 2/8); M.p.:100-102° C.; $^1$H NMR (270 MHz, CDCl$_3$) δ$_H$ 3.13 (t, 2H, J=6.4 Hz, CH$_2$—Ar), 3.69 (dt, 2H, J=6.4, 6.4 Hz, CH$_2$NH), 6.24 (bs, 1H, NH), 6.85 (dd, 1H, J=1.0, 3.5 Hz, H$_{Ar}$thiophene), 6.96 (dd, 1H, J=3.5, 5.2 Hz, H$_{Ar}$thiophene), 7.18 (dd, 1H, J=1.0, 5.2 Hz, H$_{Ar}$thiophene), 7.45 (t, 1H, J=2.0 Hz, H$_{Ar}$), 7.56 (d, 2H, J=2.0 Hz, H$_{Ar}$); LC/MS (AP−) m/z 297.8 (M−H); t$_R$=2.5 min (99.3%); HRMS (FAB+) Calculated for C$_{13}$H$_{11}$Cl$_2$NOS 298.9938; Found 298.9934

4-Methoxy-N-(2-thiophen-2-yl-ethyl)-benzamide (STX1379, CCM01017)

Reaction of 2-thiopheneethylamine (50 μL, 0.42 mmol) in THF (2.5 mL) with p-anisoyl chloride(74 μL, 0.57 mmol) in presence of triethylamine (78 μL, 0.55 mmol) according to method A gave 4-methoxy-N-(2-thiophen-2-yl-ethyl)-benzamid (105 mg,0.40 mmol, 95% yield) as a white powder after purification by chromatography on silica gel (eluent: EtOAc/hexane 5/95 to 20/80).

R$_f$: 0.4 (EtOAc/DCM 1/9); M.p.: 109-111° C.; $^1$H NMR (270 MHz, CDCl$_3$) δ$_H$ 3.13 (t, 2H, J=6.4 Hz, CH$_2$Ar), 3.69 (dt, 2H, J=6.4, 6.4 Hz, CH$_2$NH), 3.82 (s, 3H, OCH$_3$), 6.19 (bs, 1H, NH), 6.85-6.90 (m, 3H, H$_{Ar}$), 6.94 (dd, 1H, J=3.5, 5.4 Hz, H$_{Ar}$thiophene), 7.16 (dd, 1H, J=1.2, 5.4 Hz, H$_{Ar}$thiophene), 7.65-7.70 (m, 2H, H$_{Ar}$); LC/MS (AP−) m/z 259.9 (M−H); t$_R$=2.0 min (95.4%); HRMS (FAB+) Calculated for C$_{14}$H$_{15}$NO$_2$S 261.0824; Found 261.0826.

3-Methoxy-N-(2-thiophen-2-yl-ethyl)-benzamide (STX1380, CCM01018)

Reaction of-2-thiopheneethylamine (50 μL, 0.42 mmol) in THF (2.5 mL) with m-anisoyl chloride (74 μL, 0.57 mmol) in presence of triethylamine (78 μL, 0.55 mmol) according to method A gave 3-methoxy-N-(2-thiophen-2-yl-ethyl)-benzamide (100 mg, 0.38 mmol, 90% yield) as a yellow wax after purification on silica gel (eluent: EtOAc/hexane 5/95 to 20/80).

R$_f$: 0.3 (EtOAc/DCM 5/95); $^1$H NMR (270 MHz, CDCl$_3$) δ$_H$ 3.13 (t, 2H, J=6.4 Hz, CH$_2$Ar), 3.70 (dt, 2H, J=6.4, 6.4 Hz, CH$_2$NH), 3.81 (s, 3H, OCH$_3$), 6.27 (bs, 1H, NH), 6.85 (dd, 1H, J=1.2, 3.4 Hz, H$_{Ar}$thiophene), 6.94 (dd, 1H, J=3.5, 5.2 Hz, H$_{Ar}$thiophene), 7.00 (ddd, 1H, J=1.3, 2.8, 8.2 Hz, H$_{Ar}$), 7.16 (dd, 1H, J=1.2, 5.2. Hz, H$_{Ar}$thiophene), 7.19 (ddd, 1H, J=1.3, 1.3, 7.7 Hz, H$_{Ar}$), 7.24-7.32 (m, 2H, H$_{Ar}$); LC/MS (AP−) m/z 259.9 (M−H), t$_R$=2.0 min (99.5%); HRMS (FAB+) Calculated for C$_{14}$H$_{15}$NO$_2$S 261.0824; Found 2610.0827.

4-Propyl-N-(2-thiophen-2-yl-ethyl)-benzamide (STX1381, CCM01020)

Reaction of 2-thiopheneethylamine (50 μL, 0.42 mmol) in THF (2.5 mL) with 4-propylbenzoyl chloride (92 μL, 0.55 mmol) in presence of triethylamine (78 μL, 0.55 mmol) according to method A gave 4-propyl-N-(2-thiophen-2-yl-ethyl)-benzamide (100 mg, 0.36 mmol, 85% yield) as a off-white powder after purification on silica gel (eluent: EtOAc/hexane 5/95 to 20/80).

R$_f$: 0.4 (EtOAc/DCM 5/95); M.p.: 97-99° C.; $^1$H NMR (270 MHz, CDCl$_3$) δ$_H$ 0.93 (t, 3H, J=7.4 Hz, CH$_3$), 1.55-1.69 (m, 2H, CH$_2$—CH$_3$), 2.60 (t, 2H, J=7.4 Hz, CH$_2$Ar), 3.13 (t, 2H, J=6.4 Hz, CH$_2$thiophene), 3.70 (dt, 2H, J=6.4, 6.4 Hz, CH$_2$NH), 6.22 (bs, 1H, NH), 6.85 (d, 1H, J=3.4 Hz, H$_{Ar}$thiophene), 6.94 (dd, 1H, J=3.5, 5.0 Hz, H$_{Ar}$thiophene), 7.16 (dd, 1H, J=1.0, 5.2. Hz, H$_{Ar}$thiophene), 7.20 (d, 2H, J=8.1 Hz, H$_{Ar}$), 7.62 (d, 2H, J=8.1 Hz, H$_{Ar}$); LC/MS (AP−) m/z 271.8 (M−H); t$_R$=2.4 min (95.8%); HRMS (FAB+) Calculated for C$_{16}$H$_{19}$NOS 273.1187; Found 273.1176.

2,5-Dichloro-N-(2-thiophen-2-yl-ethyl)-benzamide (STX1382, CCM01021)

Reaction of 2,5-dichlorobenzoic acid (164 mg, 0.85 mmol) in thionyl chloride (2 mL) then with 2-thiophene-ethylamine (50 μL, 0.42 mmol) in presence of triethylamine (0.5 mL) in THF (3 mL) according to method B gave 2,5-dichloro-N-(2-thiophen-2-yl-ethyl)-benzamide (83 mg, 0.28 mmol, 66% yield) as a off-white powder after purification on silica gel (eluent: EtOAc/hexane 5/95 to 20/80).

R$_f$: 0.2 (EtOAc/hexane 2/8); M.p.: 99-100° C.; $^1$H NMR (270 MHz, CDCl$_3$) δ$_H$ 3.15 (t, 2H, J=6.6 Hz, CH$_2$thiophene), 3.73 (dt, 2H, J=6.6, 6.6 Hz, CH$_2$NH), 6.33 (bs, 1H, NH), 6.86 (d, 1H, J=3.4 Hz, H$_{Ar}$thiophene), 6.94 (dd, 1H, J=3.5, 5.1 Hz, H$_{Ar}$thiophene), 7.15 (dd, 1H, J=1.2, 5.1. Hz, H$_{Ar}$thiophene), 7.28 (d, 2H, J=8.1 Hz, H$_{Ar}$), 7.58-7.59 (m, 1H, H$_{Ar}$); $^{13}$C NMR (400 MHz, CDCl$_3$) δ$_C$ 29.7 (CH$_2$-thiophene), 41.6 (CH$_2$NH), 124.2 (CH$_{Ar}$), 125.7 (CH$_{Ar}$), 127.2 (CH$_{Ar}$), 128.9 (C$_q$), 130.2 (CH$_{Ar}$), 131.3 (CH$_{Ar}$), 131.5 (CH$_{Ar}$), 133.3 (C$_q$), 136.2 (C$_q$), 140.9 (C$_q$), 165.1 (C=O); LC/MS (AP−) m/z298.0 (M−H); t$_R$=2.2 min (99.9%); HRMS (FAB+) Calculated for C$_{13}$H$_{11}$Cl$_2$NOS 298.9938; Found 298.9933

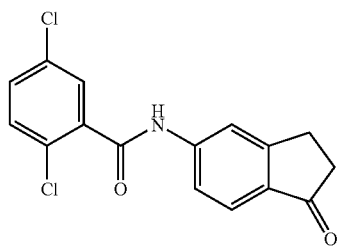

STX1397, CCM01023

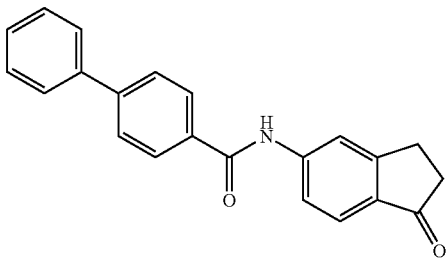

STX1398, CCM0101624

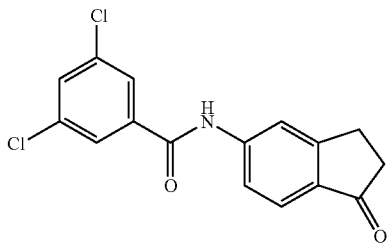

STX1399, CCM01025

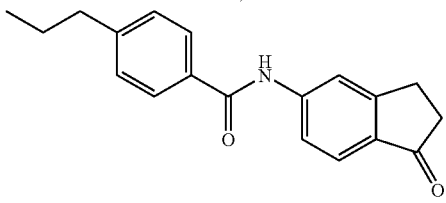

STX1400, CCM01026

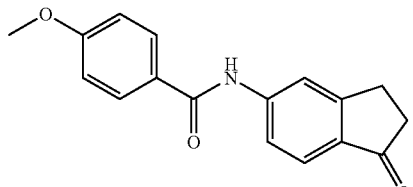

STX1401, CCM01027

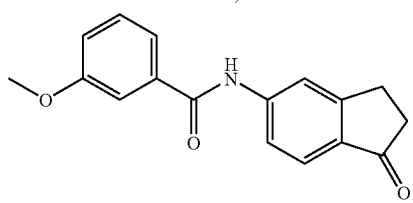

STX1402, CCM01028

General method for synthesis of
N-(5-indanone)-benzamide derivatives
(STX1397-1402)

Method A: to a stirred solution of the amine (n mmol) in THF are added triethylamine (1.2 n mmol) and the acyl chloride (1.2 n mmol) at room temperature. After completion, ethyl acetate and water are added. The aqueous layer is extracted by ethyl acetate. The combined organic layers are washed with brine, dried (MgSO4), filtered and evaporated under reduce pressure. The crude product is then purified to give the amide.

Method B: A solution of the acid (3 n mmol) in thionyl chloride is refluxed 3 hours. Thionyl chloride is then removed under reduced pressure. The crude product is diluted in dry THF and added to a solution of the amine (n mmol) and triethylamine in THF. After completion, ethyl acetate and water are added. The aqueous layer is extracted by EtOAc. The combined organic layers are then washed with brine, dried (MgSO4), filtered and evaporated under reduce pressure. The crude product is purified to give the amide.

2,5-Dichloro-N-(1-oxo-indan-5-yl)-benzamide
(STX1397, CCM01023)

Reaction of 2,5dichlorobenzoic acid (287 mg, 1.50 mmol) in thionyl chloride (3.5 mL) then with 5-amino-indan-1-one (74 mg, 0.50 mmol) in presence of triethylamine (0.5 mL) in THF (6 mL) according to method B gave 2,5-dichloro-N-(1-oxo-indan-5-yl)-benzamide (33 mg, 0.09 mmol, 35% yield) as a green powder after purification by chromatography on silica gel (eluent: DCM).

$R_f$ 0.4 (EtOAc/DCM 1/9); M.p.: 218-221° C.; $^1$H NMR (270 MHz, DMSO-$d_6$) $\delta_H$ 2.58-2.62 (m, 2H, $CH_2$), 3.06-3.10 (m, 2H, $CH_2$), 7.57-7.60 (m, 4H, $H_{Ar}$), 7.77-7.78 (m, 1H, $H_{Ar}$), 8.01 (s, 1H, $H_{Ar}$), 10.94 (s, 1H, NH); LC/MS (AP−) m/z317.7 (M−H); $t_R$=2.1 min (98.0%).

Biphenyl-4-carboxylic acid (1-oxo-indan-5-yl)-amide (SXT1398, CCM01024)

Reaction of 0.5-amino-indan-1-one (73 mg, 0.50 mmol) in THF (6 mL) with 4-biphenylcarbonyl chloride (140 mg, 0.65 mmol) in presence of triethylamine (90 μL, 0.65 mmol) according to method A gave biphenyl-4-carboxylic acid (1-oxo-indan-5-yl)-amide (100 mg, 0.30 mmol, 60% yield) as a brown powder after purification by washing the crude product with ethyl acetate.

$R_f$: 0.4 (EtOAc/DCM 1/9); M.p.: 217-219° C.; $^1$H NMR (270 MHz, DMSO-$d_6$) $\delta_H$ 2.58-2.62 (m, 2H, $CH_2$), 3.07-3.11 (m, 2H, $CH_2$), 7.41-7.45 (m, 1H, $H_{Ar}$), 7.48-7.54 (m, 1H, $H_{Ar}$), 7.63 (d, 1H, J=8.4 Hz, $H_{Ar}$), 7.75-7.80 (m, 3H, $H_{Ar}$), 7.84-7.87 (m, 2H, $H_{Ar}$), 8.05-8.08 (m, 2H, $H_{Ar}$), 8.12 (bs, 1H, $H_{Ar}$), 10.62 (s, 1H, NH); LC/MS (AP−) m/z325.9 (M−H); $t_R$=2.3 min (97.4%); HRMS (FAB+) Calculated for $C_{22}H_{17}NO_2$ 327.1259; Found 327.1266.

3,5-Dichloro-N-(1-oxo-indan-5-yl)-benzamide
(STX1399, CCM01025)

Reaction of 5-amino-indan-1-one (73 mg, 0.50 mmol) in THF (6 mL) with 3,5-dichlorobenzoyl chloride (136 mg, 0.65 mmol) in presence of triethylamine (90 μL, 0.65 mmol) according to method A gave biphenyl-4-carboxylic acid (1-oxo-indan-5-yl)-amide (115 mg, 0.36 mmol, 72% yield) as a brown powder after purification by washing the crude product with ethyl acetate.

$R_f$: 10.4 (EtOAc/DCM 1/9); M.p.: 261-263° C.; $^1$H NMR (270 MHz, DMSO-$d_6$) $\delta_H$ 2.58-2.62 (m, 2H, $CH_2$), 3.06-3.10 (m, 2H, $CH_2$), 7.63 (d, 1H, J=8.4 Hz, $CH_{Ar}$—C—CO), 7.72 (dd, 1H, J 1.7, 8.4 Hz, N—C—CH$_{Ar}$—CH$_{Ar}$), 7.88 (t, 1H, J=2.0 Hz, CCl—CH$_{Ar}$—CCl), 7.97 (d, 2H, J=2 Hz, H$_{Ar}$), 8.05 (d, 1H, J=1.7 Hz, CH$_{Ar}$—CH$_{Ar}$—C—CO), 10.70 (s, 1H, NH); $^{13}$C NMR (400 MHz, DMSO-d$_6$) δ$_C$ 26.0 (CH$_2$), 36.5 (CH$_2$), 117.5 (CH$_{Ar}$), 120.0 (CH$_{Ar}$), 124.2 (CH$_{Ar}$), 127.1 (CH$_{Ar}$), 131.7 (CH$_{Ar}$), 132.9 (C$_q$), 134.8 (C$_q$), 138.2 (C$_q$), 144.9 (C$_q$), 157.1 (C$_q$), 163.8 (C=O), 205.4 (C=O);LC/MS (AP–) m/z318.0 (M–H); t$_R$=2.5 min (99.9%); HRMS (FAB+) Calculated for C$_{16}$H$_{11}$Cl$_2$NO$_2$ 319.0167; Found 319.0156.

N-(1-Oxo-indan-5-yl)-4-propyl-benzamide (STX1400. CCM01026)

Reaction of 5-amino-indan-1-one (75 mg, 0.50 mmol) in THF (6 mL) with 4-propylbenzoyl chloride (108 µL, 0.65 mmol) in presence of triethylamine (90 µL, 0.65 mmol) according to method A gave N-(1-oxo-indan-5-yl)-4-propyl-benzamide (94 mg, 0.32 mmol, 64% yield) as a white powder after purification on silica gel (eluent EtOAc/DCM 0/10 to 1/9).

R$_f$: 0.4 (EtOAc/DCM 1/9); M.p.: 181-184° C.; $^1$H NMR (270 MHz, DMSO-d$_6$) δ$_H$ 0.88 (t, 3H, J=7.2 Hz, CH$_3$), 1.56-1.65 (m, 2H, CH$_2$—CH$_3$), 2.57-2.65 (m, 4H, 2*CH$_2$), 3.08 (bt, 2H, J=5.4 Hz, CH$_2$CO), 7.35 (d, 2H, J=8.1 Hz, H$_{Ar}$), 7.60 (d, 1H, J=8.4 Hz, CH$_{Ar}$—C—CO), 7.74 (d, 1H, J=8.4 Hz, N—C—CH$_{Ar}$—CH$_{Ar}$), 7.87 (d, 2H, J=8.1 Hz, CH$_{Ar}$), 8.09 (d, 1H, J=8.1 Hz, CH$_{Ar}$—CH$_{Ar}$—C—CO), 10.50 (s, 1H, NH); LC/MS (AP–) m/z291.9 (M–H); t$_R$=2.4 min (99.1%).

4-Methoxy-N-(1-oxo-indan-5-yl)-benzamide (STX1401, CCM01027)

Reaction of 5-amino-indan-1-one (73 mg, 0.50 mmol) in THF (6 mL) with p-anisoyl chloride (88 µL, 0.65 mmol) in presence of triethylamine (90 µL, 0.65 mmol) according to method A gave 4-methoxy-N-(1-oxo-indan-5-yl)-benzamide (107 mg, 0.38 mmol, 76% yield) as a yellow powder after purification by chromatography on silica gel (eluent EtOAc/DCM 0/10 to 2/8).

R$_f$: 0.2 (EtOAc/DCM 1/9); M.p.: 237-238° C.; $^1$H NMR (270 MHz, DMSO-d$_6$) δ$_H$ 2.57-2.62 (m, 2H, CH$_2$), 3.08 (bt, 2H, J=5.5 Hz, CH$_2$CO), 3.83 (s, 3H, OCH$_3$), 7.07 (d, 2H; J=8.9 Hz, H$_{Ar}$), 7.60 (d, 1H, J=8.4 Hz, CH$_{Ar}$—C—CO), 7.74 (d, 1H, J=1.6 Hz, N—C—CH$_{Ar}$—CH$_{Ar}$), 7.96 (d, 2H, J=8.9 Hz, CH$_{Ar}$), 8.08 (d, 1H, J=1.6 Hz, CH$_{Ar}$—CH$_{Ar}$—C—CO), 10.42 (s, 1H, NH); $^{13}$C NMR (400 MHz, DMSO-d$_6$) δ$_C$ 26.0 (CH$_2$), 36.5 (CH$_2$), 56.0 (OCH$_3$), 114.2 (CH$_{Ar}$), 117.1 (CH$_{Ar}$), 119.8 (CH$_{Ar}$), 124.1 (CH$_{Ar}$), 127.0 (C$_q$), 130.3 (CH$_{Ar}$), 132.3 (C$_q$), 145.8 (C$_q$), 157.1 (C$_q$), 162.7 (C$_q$), 165.9 (C$_q$), 205.3 (C=O); LC/MS (AP–) m/z279.9 (M–H); t$_R$=2.0 min (99.9%).

3-Methoxy-N-(1-oxo-indan-5-yl)-benzamide (STX1402. CCM01028)

Reaction of 5-amino-indan-1-one (73 mg, 0.50 mmol) in THF (6 mL) with m-anisoyl chloride (90 µL, 0.65 mmol) in presence of triethylamine (90 µL, 0.65 mmol) according to method A gave 3-methoxy-N-(1-oxo-indan-5-yl)-benzamide (73 mg, 0.26 mmol, 52% yield) as a yellow powder after purification by chromatography on silica gel (eluent EtOAc/DCM 0/10 to 1/9).

R$_f$: 0.2 (EtOAc/DCM 1/9); M.p.: 203-204° C.; $^1$H NMR (270 MHz, DMSO-d$_6$) δH 2.59-2.63 (m, 2H, CH$_2$), 3.09 (bt, 2H, J=5.7 Hz, CH$_2$CO), 3.84 (s, 3H, OCH$_3$), 7.16-7.21 (m, 1H, H$_{Ar}$), 7.44-7.49 (m, 2H, H$_{Ar}$), 7.52-7.56 (m, 1H, H$_{Ar}$), 7.62 (d, 0.1H. J -8.4 Hz, CHAr—C—CO), 7.76 (dd, 1H, J=1.8, 8.4 Hz, N—C—CHAr—CH$_{Ar}$), 8.09 (d, 1H, J=1.8 Hz, CHAr—CHAr—C—CO), 10.55 (s, 1H, NH); $^{13}$C NMR (400 MHz, DMSO-d$_6$) δ$_C$ 26.0 (CH$_2$), 36.5 (CH$_2$), 55.9 (OCH$_3$), 113.6 (CH$_{Ar}$); 117.3 (CH$_{Ar}$), 118.1 (CH$_{Ar}$), 119.9 (CH$_{Ar}$), 120.5 (CH$_{Ar}$), 124.2 (CH$_{Ar}$), 130.2 (CH$_{Ar}$), 132.5 (C$_q$), 136.5 (C$_q$), 145.4 (C$_q$), 157.1 (C$_q$), 159.7 (C$_q$), 166.3 (C=O), 205.3 (C=O); LC/MS (AP–) m/z 280.0 (M–H); t$_R$=2.0 min (99.7%

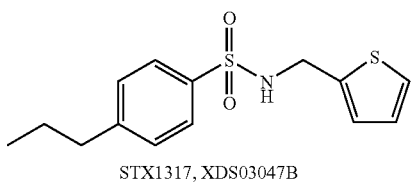

STX1317, XDS03047B

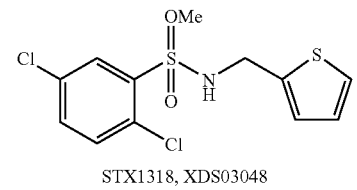

STX1318, XDS03048

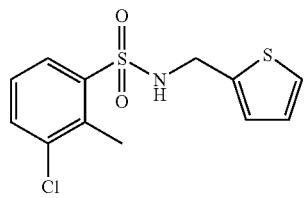

STX1319, XDS03049

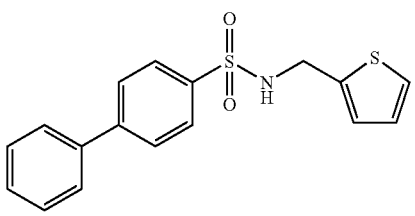

STX1320, XDS03050

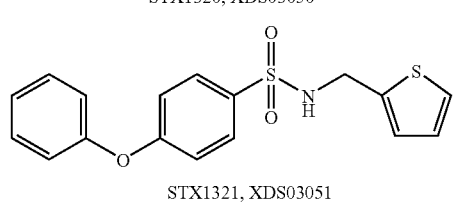

STX1321, XDS03051

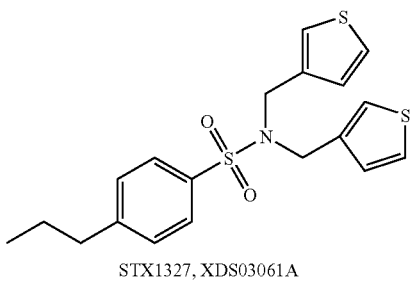

STX1327, XDS03061A

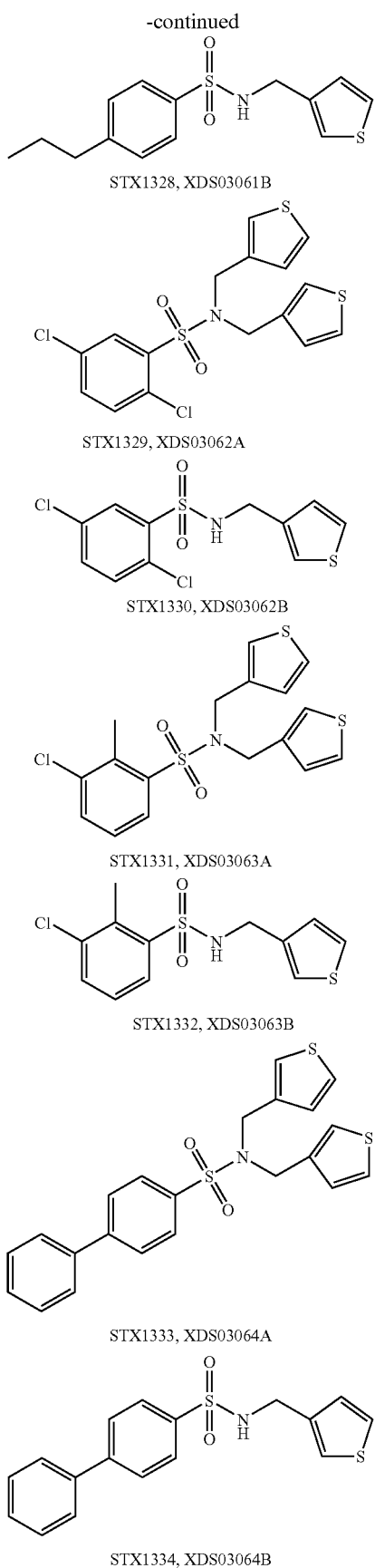
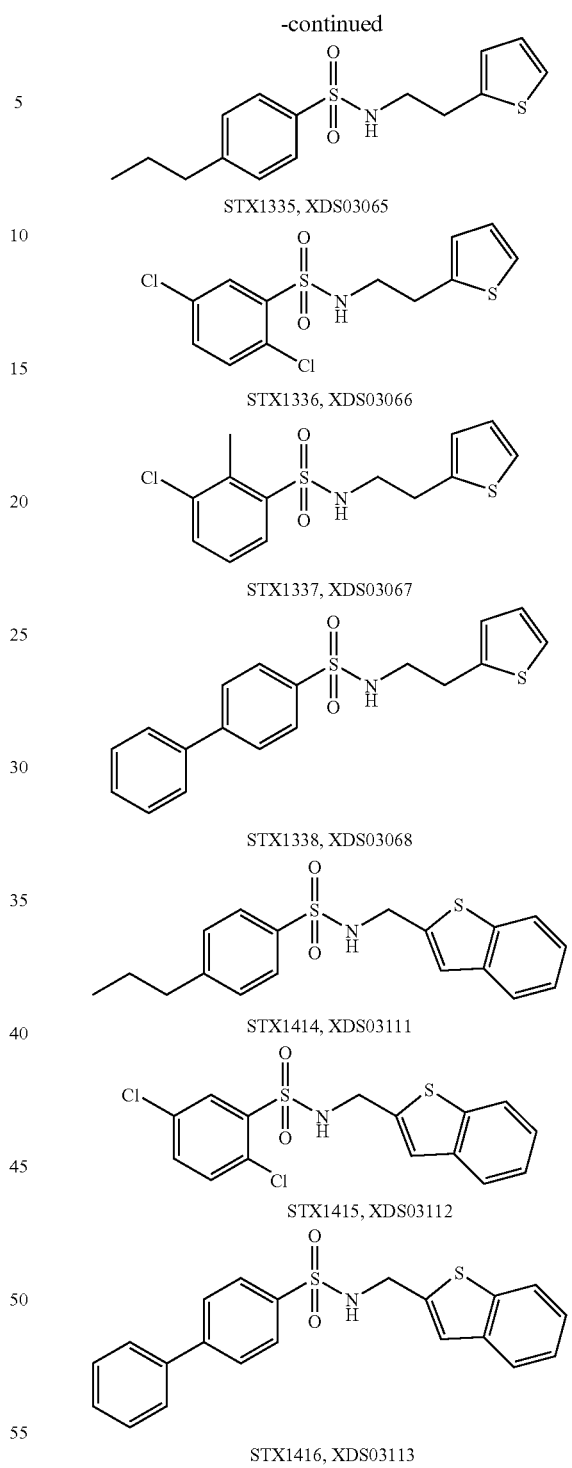

General Method for Synthesis of Thiophene or Benzothiophene Arylsulphonamide Derivatives (STX1317-1321, STX1327-1338, STX1414-1416):

To a solution of arylsulphonyl chloride (1.1 eq.) in DCM was added pyridine (2.2 eq.), followed by the corresponding amine (1 eq.). The reaction mixture was stirred at ambient temperature under nitrogen for 3-6 h. After TLC showed completion of the reaction, the mixture was partitioned between ethyl acetate and 5% sodium bicarbonate solution.

The organic layer was washed with brine, dried over sodium sulfate, and concentrated in vacuo to give the crude product as solid or thick syrup. The compound was then purified by flash chromatography (Ethyl acetate-hexane gradient elution) to give desired arylsulphonamide as crystalline solid or amorphous solid. Yield ranged from 35-65%.

4-Propyl-N-thiophen-2-ylmethyl-benzenesulfonamide (STX1317, XDS03047B)

White solid. TLC single spot at $R_f$ 0.25 (20% ethyl acetate/hexane); HPLC purity >99% ($t_R$ 3.1 min in 30% water-acetonitrile); $^1$H NMR (270 MHz, DMSO): δ 8.20 (1H, broad, NH), 7.70 (2H, d, J=8.4 Hz, ArH), 7.37-7.40 (3H, m, ArH), 6.89 (2H, m, ArH), 4.15 (2H, s, NCH$_2$), 2.65 (2H, t, J=7.4 Hz, CH$_2$), 1.61 (2H, sextet, J=7.4 Hz, CH$_2$), 0.89 (3H, t, J=7.4 Hz, CH$_3$); FAB-MS 296 (MH$^+$); FAB-HRMS calcd for C$_{14}$H$_{18}$NO$_2$S$_2$ (MH$^+$) 296.0779, found 296.0776.

2,5-Dichloro-N-thiophen-2-ylmethyl-benzene-sulfonamide (STX1318, XDS03048)

White crystalline solid. TLC single spot at $R_f$ 0.29 (20% ethyl acetate/hexane); HPLC purity>99% ($t_R$ 2.8 min in 30% water-acetonitrile); $^1$H NMR (270 MHz, DMSO): δ 8.73 (1H, s, NH), 7.80 (1H, d, J=2.5 Hz, ArH), 7.60-7.69 (2H, m, ArH), 7.33 (1H, dd, J.=5.0, 1.5 Hz, ArH), 6.82-6.87 (2H, m, ArH), 4.36 (2H, s, NCH$_2$); FAB-MS 322 (MH$^+$); FAB-HRMS calcd for C$_{11}$H$_{10}$Cl$_2$NO$_2$S$_2$ (MH$^+$) 321.9530, found 321.9426.

3-Chloro-2-methyl-N-thiophen-2-ylmethyl-benzene-sulfonamide (STX1319, XDS03049)

White crystalline solid. TLC single spot at $R_f$ 0.28 (20% ethyl acetate/hexane); HPLC purity>99% ($t_R$ 3.1 min in 30% water-acetonitrile); $^1$H NMR (270 MHz, DMSO): δ 8.58 (1H, s, NH), 7.82 (1H, d, J=7.9 Hz, ArH), 7.70 (1H, d, J=7.9 Hz, ArH), 7.35-7.40 (2H, m, ArH), 6.84-6.87 (2H, m, ArH), 4.26 (2H, s, NCH$_2$), 2.57 (3H, s, CH$_3$); FAB-MS 302 (MH$^+$); FAB-HRMS calcd for C$_{12}$H$_{13}$ClNO$_2$S$_2$ (MH$^+$) 302.0076, found 301.9988.

Biphenyl-4-sulfonic acid (thiophen-2-ylmethyl)-amide (STX1320, XDS03050)

White solid. TLC single spot at $R_f$ 0.29 (20% ethyl acetate/hexane); HPLC purity >99% ($t_R$ 2.5 min in 30% water-acetonitrile); $^1$H NMR (270 MHz, DMSO): δ 8.32 (1H, s, NH), 7.87 (4H, s, ArH), 7.73-7.76 (2H, m, ArH), 7.39-7.55 (4H, m, ArH), 6.91 (2H, m, ArH), 4.21 (2H, s, NCH$_2$); FAB-MS 330 (MH$^+$); FAB-HRMS calcd for C$_{17}$H$_{16}$NO$_2$S$_2$ (MH$^+$) 330.0622, found 330.0601.

4-Phenoxy-N-thiophen-2-ylmethyl-benzenesulfonamide (STX1321 XDS03051

White solid. TLC single spot at $R_f$ 0.29 (20% ethyl acetate/hexane); HPLC purity>99% ($t_R$ 2.4 min in 20% water-acetonitrile); $^1$H NMR (270 MHz, DMSO): δ 8.22 (1H, s, NH), 7.75-7.80 (2H, m, ArH), 7.39-7.51 (3H, m, ArH), 7.07-7.28 (5H, m, ArH), 6.90-6.92 (2H, m, ArH), 4.18 (2H, s, NCH$_2$); FAB-MS 346 (MH$^+$); FAB-HRMS calcd for C$_{17}$H$_{16}$NO$_3$S$_2$ (MH$^+$) 346.0572, found 346.0574.

4-Propyl-N,N-bis-thiophen-3-ylmethyl-benzene-sulfonamide (STX1327 XDS03061A)

White solid. TLC single spot at $R_f$ 0.56 (20% ethyl acetate/hexane); HPLC purity>99% ($t_R$ 4.5 min in 20% water-acetonitrile); $^1$H NMR (270 MHz, CDCl$_3$): δ 7.72 (2H, dt, J.=8.4, 2.0 Hz, ArH), 7.29 (2H, dt, J=8.5, 1.9 Hz, ArH), 7.17 (2H, dd, J=5.0, 3.0 Hz, ArH), 6.90 (2H, dd, J=3.0, 1.5 Hz, ArH), 6.74 (2H, dd, J=5.0, 1.5 Hz, ArH), 4.31 (4H, s, 2×NCH$_2$), 2.66 (2H, t, J=7.1 Hz, CH$_2$), 1.67 (2H, sextet, J=7.5 Hz, CH$_2$), 0.95 (3H, t, J=7.3 Hz, CH$_3$); APCI-MS 392 (MH$^+$); FAB-HRMS calcd for C$_{19}$H$_{22}$NO$_2$S$_3$ (MH$^+$) 392.0813, found 392.0805.

4-Propyl-N-thiophen-3-ylmethyl-benzenesulfonamide (STX1328, XDS03061B)

White solid. TLC single spot at $R_f$ 0.29 (20% ethyl acetate/hexane); HPLC purity 92% ($t_R$ 2.6 min in 20% water-acetonitrile); $^1$H NMR (270 MHz, CDCl$_3$): δ 7.75 (2H, dt, J=8.5, 2.0 Hz, ArH), 7.29 (2H, dt, J=8.4, 1.8 Hz, ArH), 7.20 (1H, dd, J=5.2, 3.2 Hz, ArH), 7.03 (1H, dd, J=3.1, 1.1 Hz, ArH), 6.86 (1H, dd, J=5.1, 1.1 Hz, ArH), 4.73 (1H, t, J=6.1 Hz, NH), 4.15 (2H, d, J=5.9 Hz, NCH$_2$), 2.65 (2H, t, J=7.9 Hz CH$_2$), 1.67 (2H, sextet, J=8.0 Hz, CH$_2$), 0.94 (3H, t, J=7.3 Hz, CH$_3$); APCI-MS 294 (M–H$^+$); FAB-HRMS calcd for C$_{14}$H$_{18}$NO$_2$S$_2$ (MH$^+$) 296.0779, found 296.0784.

2,5-Dichloro-N,N-bis-thiophen-3-ylmethyl-benzene-sulfonamide (STX1329, XDS03062A)

White crystalline solid. TLC single spot at $R_f$ 0.50 (20% ethyl acetate/hexane); HPLC purity>98% ($t_R$ 4.0 min in 20% water-acetonitrile); $^1$H NMR (270 MHz, CDCl$_3$): δ 8.02 (1H, rm, ArH), 7.42-7.45 (2H, m, ArH), 7.23 (2H, dd, J=5.0, 3.0 Hz, ArH), 7.01 (2H, dd, J=3.0, 1.0 Hz, ArH), 6.82 (2H, dd, J=5.0, 1.3 Hz, ArH), 4.41 (4H, s, 2×NCH$_2$); APCI-MS 418 (MH$^+$); FAB-HRMS calcd for C$_{16}$H$_{14}$Cl$_2$NO$_2$S$_3$ (MH$^+$) 417.9564, found 417.9510.

2,5-Dichloro-N-thiophen-3-ylmethyl-benzene-sulfonamide (STX1330, XDS03062B)

White crystalline solid. TLC single spot at $R_f$ 0.25 (20% ethyl acetate/hexane); HPLC purity>99% ($t_R$ 2.4 min in 20% water-acetonitrile); $^1$H NMR (270 MHz, CDCl$_3$): δ 7.99 (1H, d, J=2.0 Hz, ArH), 7.36-7.45 (2H, m, ArH), 7.17 (1H, dd, J=5.2, 3.2 Hz, ArH), 7.06 (1H, dd, J=3.0, 1.0 Hz, ArH), 6.86 (1H, dd, J=5.0, 1.3 Hz, ArH), 5.25 (1H, t, J=6.1 Hz, NH), 4.19 (2H, d, J=6.2 Hz, NCH$_2$); APCI-MS 320 (M–H$^+$); FAB-HRMS calcd for C$_{11}$H$_{10}$Cl$_2$NO$_2$S$_2$ (MH$^+$) 321.9530, found 321.9473.

3-Chloro-2-methyl-N,N-bis-thiophen-3-ylmethyl-benzenesulfonamide (STX1331, XDS03063A)

White solid. TLC single spot at $R_f$ 0.55 (20% ethyl acetate/hexane); HPLC purity>98% ($t_R$ 6.8 min in 30% water-acetonitrile); $^1$H NMR (270 MHz, CDCl$_3$): δ 7.90 (1H, dd, J=7.8, 1.2 Hz; ArH), 7.60 (1H, dd, J=7.8, 1.1 Hz, ArH), 7.20-7.27 (3H, m, ArH), 7.00 (2H, dd, J=3.0, 1.0 Hz, ArH), 6.76 (2H, dd, J=5.0, 1.3 Hz, ArH), 4.32 (4H, s, 2×NCH$_2$), 2.61 (3H, s, CH$_3$); APCI-MS 398 (MH$^+$); FAB-HRMS calcd for C$_{17}$H$_{17}$ClNO$_2$S$_3$ (MH$^+$) 398.0110, found 398.0098.

3-Chloro-2-methyl-N-thiophen-3-ylmethyl-benzene-sulfonamide (STX1332, XDS03063B)

White solid. TLC single spot at $R_f$ 0.30 (20% ethyl acetate/hexane); HPLC purity>99% ($t_R$ 2.5 min in 20% water-acetonitrile); $^1$H NMR (270 MHz, CDCl$_3$): δ 7.91 (1H, dd, J=7.9, 1.0 Hz, ArH), 7.57 (1H, dd, J=7.8, 1.0 Hz, ArH), 7.20-7.27 (2H, m, ArH), 7.02 (1H, m, ArH), 6.84 (2H, dd, J=5.1, 1.3 Hz, ArH), 4.79 (1H, t, J=5.9 Hz, NH), 4.16 (2H, d, J=5.9 Hz, NCH$_2$); 2.62 (3H, s, CH$_3$); APCI-MS 302 (MH$^+$); FAB-HRMS calcd for C$_{12}$H$_{13}$ClNO$_2$S$_2$ (MH$^+$) 302.0076, found 302.0056.

Biphenyl-4-sulfonic acid bis-thiophen-3-ylmethyl-amide (STX1333, XDS03064A)

White solid. TLC single spot at $R_f$ 0.45 (20% ethyl acetate/hexane); HPLC purity>99% ($t_R$ 4.3 min in 20% water-acetonitrile); $^1$H NMR (270 MHz, CDCl$_3$): δ 7.86 (2H, dt, J=8.6, 1.8 Hz, ArH), 7.70 (2H, dt, J=8.5, 1.8 Hz, ArH), 7.59-7.63 (2H, m, ArH), 7.39-7.52 (3H, m, ArH), 7.19 (2H, dd, J=5.3, 3.3 Hz, ArH), 6.95 (2H, dd, J=3.2, 1.2 Hz, ArH), 6.80 (2H, dd, J=5.3, 1.4 Hz, ArH), 4.36 (4H, s, 2×NCH$_2$);APCI-MS 426 (MH$^+$); FAB-HRMS calcd for C$_{22}$H$_{20}$NO$_2$S$_3$ (MH$^+$) 426.0656, found 426.0628.

Biphenyl-4-sulfonic Acid (thiophen-3-ylmethyl)-amide (STX1334, XDS03064B)

White solid. TLC single spot at $R_f$ 0.45 (20% ethyl acetate/hexane); HPLC purity>99% ($t_R$ 3.1 min in 30% water-acetonitrile); $^1$H NMR (270 MHz, CDCl$_3$): δ 7.91 (2H, dt, J=8.5, 1.7 Hz, ArH), 7.71 (2H, dt, J=8.8, 1.8 Hz, ArH), 7.57-7.62 (2H, m, ArH), 7.42-7.52 (3H, m, ArH), 7.22 (1H, dd, J=5.2, 3.2 Hz, ArH), 7.08 (1H, m, ArH), 6.90 (1H, dd, J=5.2, 1.2 Hz, ArH), 4.61 (1H, t, J=6.4 Hz, NH), 4.22 (2H, d, J=6.5 Hz, NCH$_2$); APCI-MS 330 (MH$^+$); FAB-HRMS calcd for C$_{17}$H$_{16}$NO$_2$S$_2$ (MH$^+$) 330.0622, found 330.0627.

4-Propyl-N-(2-thiophen-2-yl-ethyl)-benzenesulfonamide (STX1335, XDS03065)

White solid. TLC single spot at $R_f$ 0.40 (25% ethyl acetate/hexane); HPLC purity>99% ($t_R$ 3.5 min in 30% water-acetonitrile); $^1$H NMR (270 MHz, CDCl$_3$): δ 7.72 (2H, dt, J=8.2, 1.1 Hz, ArH), 7.28 (2H, m, ArH), 7.11 (1H, dd, J=5.2, 1.2 Hz, ArH), 6.88 (1H, dd, J=5.2, 3.2 Hz, ArH), 6.73 (1H, dd, J=3.0, 1.0 Hz, ArH), 4.78 (1H, t, J=6.2 Hz, NH), 3.21 (2H, q, J=6.4 Hz, CH$_2$) 2.95 (2H, t, J=6.8 Hz, CH$_2$), 2.64 (2H, t, J=6.5 Hz, CH$_2$), 1.65 (2H, sextet, J=6.3 Hz, CH$_2$), 0.90 (3H, t, J=6.5 Hz, CH$_3$); APCI-MS 308 (M–H$^+$).

2,5-Dichloro-N-(2-thiophen-2-yl-ethyl)-benzene-sulfonamide (STX1336, XDS03066)

Off-white crystalline solid. TLC single spot at $R_f$ 0.37 (25% ethyl acetate/hexane); HPLC-purity>99% ($t_R$ 3.3 min 30% water-acetonitrile); $^1$H NMR (270 MHz, CDCl$_3$): δ 8.06 (1H, d, J=2.5 Hz, ArH), 7.39-7.49 (2H, rm, ArH), 7.16 (1H, dd, J=5.2, 1.2 Hz, ArH), 6.91 (1H, dd, J=5.2, 3.2 Hz, ArH), 6.79 (1H, dd, J=3.2, 1.1 Hz, ArH), 5.06 (1H, t, J=5.8 Hz, NH), 3.24 (2H, q, J=5.9 Hz, CH$_2$) 3.01 (2H, t, J=5.8 Hz, CH$_2$); APCI-MS 334 (M–H$^+$).

3-Chloro-2-nmethyl-N-(2-thiophen-2-yl-ethyl)-benzenesulfonamide (STX1337, XDS03067)

White crystalline solid. TLC single spot at $R_f$ 0.34 (25% ethyl acetate/hexane); HPLC purity>99% ($t_R$ 3.3 min in 30% water-acetonitrile); $^1$H NMR (270 MHz, CDCl$_3$): δ 7.90 (1H, dd, J=7.9, 1.2 Hz, ArH), 7.57 (1H, dd, J=7.8, 1.2 Hz, ArH), 7.25 (1H, t, J=7.7 Hz, ArH), 7.16 (1H, dd, J=5.2, 1.3 Hz, ArH), 6.92 (1H, dd, J=5.2, 3.3 Hz, ArH), 6.73 (1H, dd, J=3.2, 1.2 Hz, ArH), 4.54 (1H, t, J=6.5 Hz, NH), 3.24 (2H, q, J=6.4 Hz, CH$_2$), 2.98 (2H, t, J=6.4 Hz, CH$_2$), 2.50 (3H, s, CH$_3$); APCI-MS 314 (M–H$^+$).

Biphenyl-4-sulfonic acid (2-thiophen-2-yl-ethyl)-amide (STX1338, XDS03068)

Off-white crystalline solid. TLC single spot at $R_f$ 0.29 (25% ethyl acetate/hexane); HPLC purity>99% ($t_R$ 2.7 min in 30% water-acetonitrile); $^1$H NMR (270 MHz, CDCl$_3$): δ 7.87 (2H, dt, J=7.9, 1.2 Hz, ArH), 7.70 (2H, dt, J=8.1, 1.2 Hz, ArH), 7.58-7.62 (2H, m, ArH), 7.41-7.50 (3H, m, ArH), 7.15 (1H, dd, J=5.1, 1.2 Hz, ArH), 6.91 (1H, dd, J=5.2, 3.2 Hz, ArH), 6.77 (1H, dd, J=3.0, 1.0 Hz, ArH), 4.50 (1H, t, J=6.5 Hz, NH), 3.29 (2H, q, J=6.5 Hz, CH$_2$), 3.00 (2H, t, J=6.5 Hz, CH$_2$); APCI-MS 342 (M–H$^+$).

N-Benzo[b]thiophen-2-ylmethyl-4-propyl-benzene-sulfonamide (STX1414, XDS03111)

Off-white solid. TLC single spot at $R_f$ 0.47 (25% ethyl acetate/hexane); HPLC purity>99% ($t_R$ 2.4 min in 20% water-acetonitrile); $^1$H NMR (270 MHz, CDCl$_3$): δ 7.76 (2H, dt, J=7.9, 1.7 Hz, ArH), 7.61-7.72 (2H, m, ArH), 7.24-7.32 (4H, m, ArH), 7.05 (1H, d, J=1.2 Hz, ArH), 4.73 (1H, t, J=6.7 Hz, NH), 4.43 (2H, d, J=6.5 Hz, NCH$_2$), 2.61 (2H, t, J=7.6 Hz, CH$_2$), 1.62 (2H, sextet, J=7.4 Hz, CH$_2$), 0.92 (3H, t, J=7.3 Hz, CH$_3$); APCI-MS 344 (M–H$^+$).

N-Benzo[b]thiophen-2-ylmethyl-2,5-dichloro-benzenesulfonamide (STX1415, XDS03112)

Off-white solid. TLC single spot at $R_f$ 0.46 (20% ethyl acetate/hexane); HPLC purity>99% ($t_R$ 2.4 min in 30% water-acetonitrile); $^1$H NMR (270 MHz, CDCl$_3$): δ 7.98 (1H, dd, J=1.5, 0.5 Hz, ArH), 7.61-7.69 (2H, m, ArH), 7.26-7.30 (4H, m, ArH), 7.05 (1H, d, J=0.8 Hz, ArH), 5.41 (1H, t, J=5.9 Hz, NH), 4.47 (2H, d, J=5.7 Hz, NCH$_2$); APCI-MS 370 (M–H$^+$).

Biphenyl-4-sulfonic acid (benzo[b]thiophen-2-ylmethyl)-amide (STX1415, XDS030113)

Off-white solid. TLC single spot at $R_f$ 0.58 (30% ethyl acetate/hexane); HPLC purity>99% ($t_R$ 2.4 min in 30% water-acetonitrile); $^1$H NMR (270 MHz, CDCl$_3$): δ 7.92 (2H, dt, J=7.9, 1.7 Hz, ArH), 7.61-7.72 (4H, m, ArH), 7.40-7.55 (5H, m, ArH), 7.24-7.30 (2H, m, ArH), 7.08 (1H, d, J=1.2 Hz, ArH), 4.81 (1H, t, J=5.2 Hz, NH), 4.48 (2H, d, J=5.4 Hz, NCH$_2$); APCI-MS 378 (M–H$^+$).

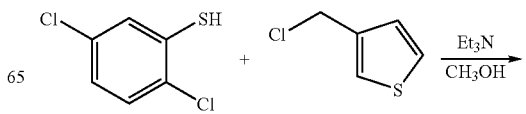

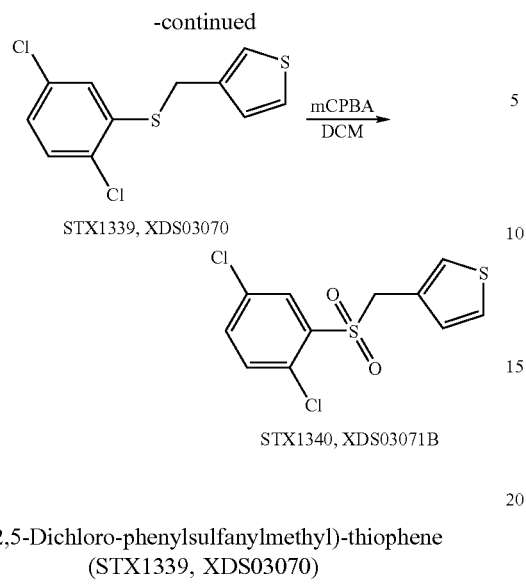

STX1339, XDS03070

STX1340, XDS03071B

3-(2,5-Dichloro-phenylsulfanylmethyl)-thiophene (STX1339, XDS03070)

To a solution of 2,5-dichlorobenzenethiol (420 mg, 2.35 mmol) in methanol (8 mL) was added triethylamine (0.4 mL), followed by 3-chloromethyl-thiophene (266 mg, 2.00 mmol). The reaction mixture was stirred at ambient temperature under nitrogen for 4 hours, and then partitioned between ethyl acetate and water. The organic layer was washed with 1N HCl, 5% sodium carbonate solution and brine, dried over sodium sulphate, and concentrated in vacuo to give the crude product. The compound was purified by flash chromatography (Ethyl acetate-hexane gradient elution). White crystalline solid (440 mg, yield 80%) was obtained. TLC single spot at $R_f$ 0.49 (8% ethyl acetate/hexane); HPLC purity>99% ($t_R$ 7.1 min in 0.30% water-acetonitrile); $^1$H NMR (270 MHz, CDCl$_3$): δ 7.27-7.30 (2H, m, ArH), 7.16-7.19 (2H, m, ArH), 7.04-7.09 (2H, m, ArH), 4.16 (2H, s, CH$_2$); FAB-MS 274 (M$^+$); FAB-HRMS calcd for C$_{11}$H$_8$Cl$_2$S$_2$ (M$^+$) 273.9444, found 273.9439.

3-(2,5-Dichloro-benzenesulfonylmethyl)-thiophene (STX1340, XDS03071B)

To a cold solution (−5° C.) of 3-(2,5-Dichloro-phenylsulfanylmethyl)-thiophene (360 mg, 1.31 mmol) in DCM (10 mL) was added 3-chloroperoxy benzoic acid (800 mg, 57-86% pure). The reaction mixture was stirred at −5-0° C. for 6 hours, and then partitioned between DCM and 5% sodium carbonate solution. The organic layer was washed with brine, dried over sodium sulphate, and concentrated in vacuo to give a yellow residue which was purified by flash chromatography (Ethyl acetate-hexane gradient elution). White crystalline solid (295 mg, 73%) was obtained. TLC single spot at $R_f$ 0.52 (20% ethyl acetate/hexane); HPLC purity>99% ($t_R$ 3.0 min in 30% water-acetonitrile); $^1$H NMR (270 MHz, CDCl$_3$): δ 7.68 (1H, t, J=1.3 Hz, ArH), 7.46 (2H, d, J=1.2 Hz, ArH), 7.23 (1H, m, ArH), 7.17 (1H, m, ArH), 6.96 (1H, dd, J=5.0, 1.2 Hz, ArH), 4.70 (2H, s, CH$_2$); FAB-MS 307 (MH$^+$); FAB-HRMS calcd for C$_{11}$H$_9$Cl$_2$O$_2$S$_2$ (MH$^+$) 306.9421, found 306.9397

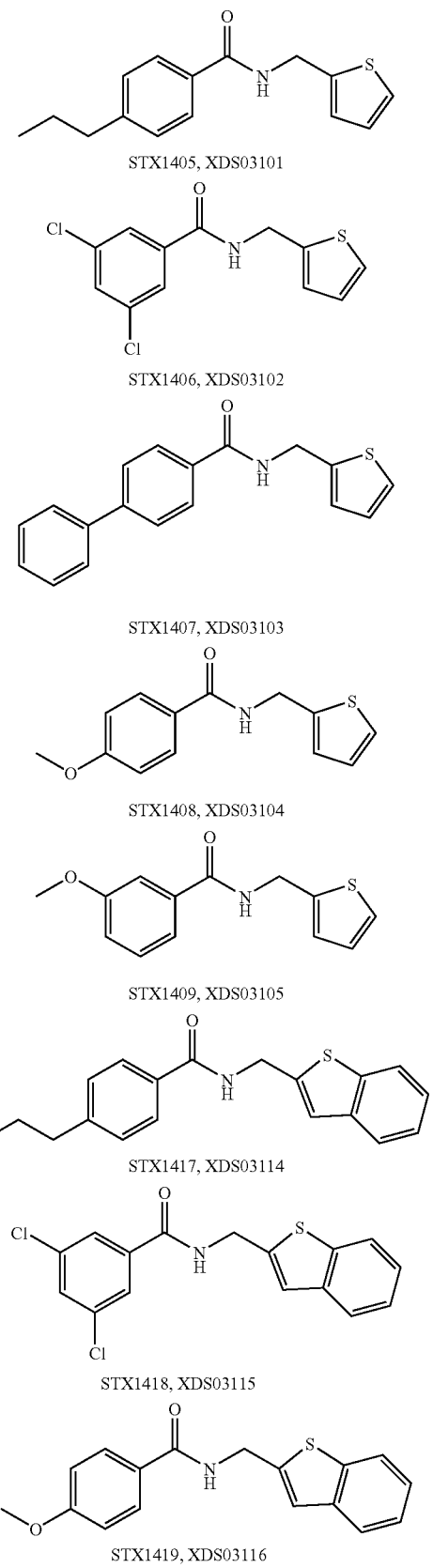

STX1405, XDS03101

STX1406, XDS03102

STX1407, XDS03103

STX1408, XDS03104

STX1409, XDS03105

STX1417, XDS03114

STX1418, XDS03115

STX1419, XDS03116

General Method for Synthesis of Thiophene or Benzothiophene Benzamide Derivatives (STX1405-1409, STX1417-1419):

To a solution of substituted benzoyl chloride (1.1 eq.) in DCM was added triethylamine (2.2 eq.), followed by the corresponding amine (1 eq.). The reaction mixture was stirred at ambient temperature under nitrogen overnight. PS-Trisamine (0.2 eq.) was added and the mixture was stirred for another 3 hours at ambient temperature, filtered. The solution was concentrated in vacuo to give crude product as solid or thick syrup. The compound was then purified by flash chromatography (Ethyl acetate-hexane gradient elution) to give desired benzamide as crystalline solid. Yield ranged from 70-96%.

4-Propyl-N-thiophen-2-ylmethyl-benzamide (STX1405, XDS03101)

White crystalline solid. TLC single spot at $R_f$ 0.49 (20% ethyl acetate/hexane); HPLC purity>99% ($t_R$ 2.3 min in 20% water-acetonitrile); $^1$H NMR (270 MHz, CDCl$_3$): δ 7.68 (2H, m, ArH), 7.20-7.25 (3H, m, ArH), 7.02 (1H, dd, J=3.0, 1.3 Hz, ArH), 6.96 (1H, dd, J=5.2, 3.2 Hz, ArH), 6.37 (1H, broad, NH), 4.80 (2H, d, J=5.4 Hz, CH$_2$), 2.61 (2H, t, J=7.7 Hz, CH$_2$), 1.61 (2H, sextet, J=7.4 Hz, CH$_2$), 0.92 (3H, t, J=7.3 Hz, CH$_3$); APCI-MS 258 (M–H$^+$).

3,5-Dichloro-N-thiophen-2-ylmethyl-benzamide (STX1406, XDS03102)

White crystalline solid. TLC single spot at $R_f$ 0.45 (20% ethyl acetate/hexane); HPLCG purity>99% ($t_R$ 2.4 min in 20% water-acetonitrile); $^1$H NMR (270 MHz, CDCl$_3$): δ 7.62 (2H, d, J=2.0 Hz, ArH), 7.46 (1H, t, J=1.9 Hz, ArH), 7.25 (1H, dd, J=5.0, 1.2 Hz, ArH), 7.03 (1H, dd, J=3.6, 0.9 Hz, ArH), 6.96 (1H, dd, J=5.0, 3.5 Hz, ArH), 6.38 (1H, broad, NH), 4.77 (2H, d, J=5.7 Hz, NCH$_2$); APCI-MS 284 (M–H$^+$).

Biphenyl-4-carboxylic acid (thiophen-2-ylmethyl)-amide (STX1407, XDS03103)

White crystalline solid. TLC single spot at $R_f$ 0.52 (20% ethyl acetate/hexane); HPLC purity >99% ($t_R$ 2.2 min in 20% water-acetonitrile); $^1$H NMR (270 MHz, CDCl$_3$): δ 7.85 (2H, dt, J=8.9, 2.0 Hz, ArH), 7.57-7.66 (4H, m, ArH), 7.35-7.48 (3H, m, ArH), 7.25 (1H, dd, J=5.1, 1.3 Hz, ArH), 7.06 (1H, dd, J=3.5, 1.0 Hz, ArH), 6.97 (1H, dd, J=5.0, 3.5 Hz, ArH), 6.46 (1H, broad, NH), 4.84 (2H, d, J=5.7 Hz, NCH$_2$); APCI-MS 294 (MH$^+$).

4-Methoxy-N-thiophen-2-ylmethyl-benzamide (STX1408, XDS03104)

White crystalline solid. TLC single spot at $R_f$ 0.35 (20% ethyl acetate/hexane); HPLC purity>99% ($t_R$ 1.9 min in 20% water-acetonitrile); $^1$H NMR (270 MHz, CDCl$_3$): δ 7.74 (2H, dt, J=9.0, 2.3 Hz, ArH), 7.23 (1H, dd, J=5.2, 1.2 Hz, ArH), 7.02 (1H, dd, J=3.5, 1.0 Hz, ArH), 6.96 (1H, dd, J=5.1, 3.6 Hz, ArH), 6.31 (1H, broad, NH), 4.79 (2H, d, J=5.7 Hz, CH$_2$), 3.83 (3H, s, OCH$_3$); APCI-MS 246 (M–H$^+$).

3-Methoxy-N-thiophen-2-ylmethyl-benzamide (STX1409, XDS03105)

White crystalline solid. TLC single spot at $R_f$ 0.35 (20% ethyl acetate/hexane); HPLC purity>99% ($t_R$ 2.0 min in 20% water-acetonitrile); $^1$H NMR (270 MHz, CDCl$_3$): δ7.38 (2H, dd, J=2.3, 1.7 Hz, ArH), 7.24-7.32 (3H, m, ArH), 7.01-7.05 (2H, m, ArH), 6.97 (1H, dd, J=5.2, 3.4 Hz, ArH), 6.39 (1H, broad, NH), 4.82 (2H, d, J=5.5 Hz, CH$_2$), 3.84 (3H, s, OCH$_3$); APCI-MS 246 (M–H$^+$).

N-Benzo[b]thiophen-2-ylmethyl-4-propyl-benzamide (STX1417, XDS03114)

White crystalline solid. TLC single spot at $R_f$ 0.49 (30% ethyl acetate/hexane);

HPLC purity>99% ($t_R$ 2.5 min in 20% water-acetonitrile); $^1$H NMR (270 MHz, CDCl$_3$): δ 7.77 (1H, m, ArH), 7.69-7.73 (3H, m, ArH), 7.28-7.36 (2H, m, ArH), 7.21-7.25 (3H, m, ArH), 6.48 (1H, broad, NH), 4.88 (2H, dd, J=5.6, 1.0 Hz, CH$_2$), 2.61 (2H, t, J=7.2 Hz, CH$_2$), 1.63 (2H, sextet, J=7.5 Hz, CH$_2$), 0.92 (3H, t, J=7.4 Hz, CH$_3$); APCI-MS 308 (M–H$^+$).

N-Benzo[b]thiophen-2-ylmethyl-3,5-dichloro-benzamide (STX1418, XDS03115)

White crystalline solid. TLC single spot at $R_f$ 0.45 (20% ethyl acetate/hexane); HPLC purity>98% ($t_R$ 2.7 min in 20% water-acetonitrile); $^1$H NMR (270 MHz, CDCl$_3$): δ 7.76-7.80 (1H, m, ArH), 7.69-7.73 (1H, m, ArH), 7.65 (2H, d, J=1.7 Hz, ArH), 7.48 (1H, t, J=1.9 Hz, ArH), 7.30-7.35 (2H, m, ArH), 7.25 (1H, m, ArH), 6.45 (1H, broad, NH), 4.87 (2H, d, J=5.6 Hz, CH$_2$); APCI-MS 334 (M–H$^+$).

N-Benzo[b]thiophen-2-ylmethyl-4-methoxy-benzamide (STX1419, XDS03116)

White crystalline solid. TLC single spot at $R_f$ 0.52 (40% ethyl acetate/hexane); HPLC purity>99% ($t_R$ 2.1 min in 20% water-acetonitrile); $^1$H NMR (270 MHz, CDCl$_3$) δ 7.69-7.79 (4H, m, ArH), 7.24-7.33 (3H, m, ArH), 6.92 (2H, dt, J=8.8, 2.2 Hz, ArH), 6.43 (1H, broad, NH), 4.88 (2H, dd, J=5.6, 1.0 Hz, CH$_2$), 3.84 (3H, s, OCH$_3$); APCI-MS 296 (M–H$^+$).

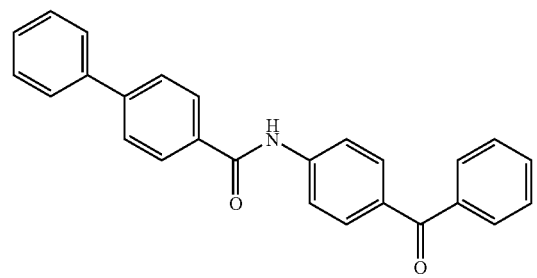

STX1430, CCM01029

-continued

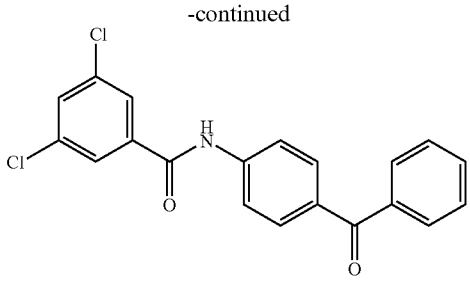

STX1431, CCM01031

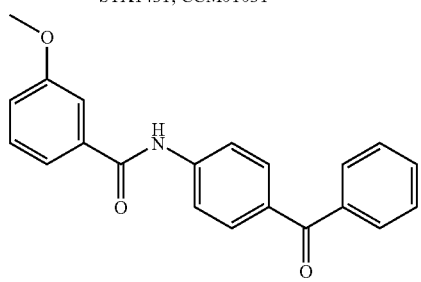

STX1432, CCM01032

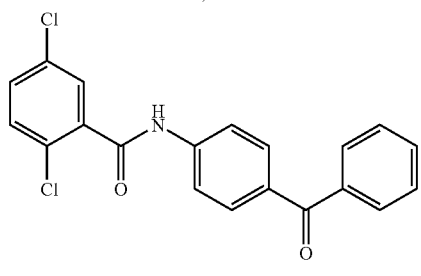

STX1433, CCM01034

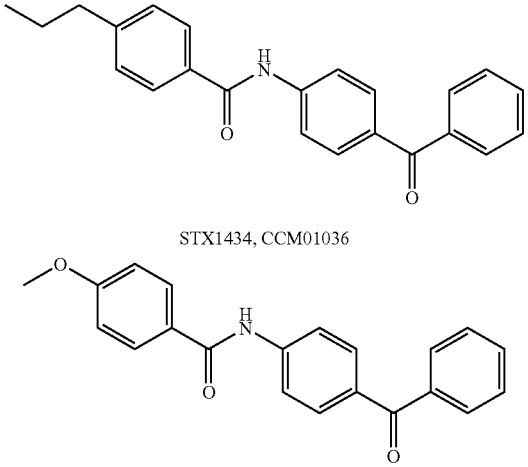

STX1434, CCM01036

STX1435, CCM01037

General Method for Synthesis of
N-(4-benzophenone)-benzamide Derivatives
(STX1430-1435)

Method A: to a stirred solution of the amine (n mmol) in THF are added triethylamine (1.2 n mmol) and the acyl chloride (1.2 n mmol) at room temperature. After completion, ethyl acetate and water are added. The aqueous layer is extracted by ethyl acetate. The combined organic layers are washed with brine, dried (MgSO4), filtered and evaporated under reduce pressure. The crude product is then purified to give the amide.

Method B: A solution of the acid (3 n mmol) in thionyl chloride is refluxed 3 hours. Thionyl chloride is then removed under reduced pressure. The crude product is diluted in dry THF and added to a solution of the amine (n mmol) and triethylamine in THF. After completion, ethyl acetate and water are added. The aqueous layer is extracted by EtOAc. The combined organic layers are then washed with brine, dried (MgSO4), filtered and evaporated under reduce pressure. The crude product is purified to give the amide.

Biphenyl-4-carboxylic acid
(4-benzoyl-phenyl)-amide (STX1430, CCM01029)

Reaction of 4-aminobenzophenone (102 mg, 0.52 mmol) in THF (6 mL) with 4-biphenylcarbonyl chloride (143 mg, 0.65 mmol) in presence of triethylamine (90 μL, 0.65 mmol) according to method A gave biphenyl-4-carboxylic acid (4-benzoyl-phenyl)-amide (125 mg, 0.33 mmol, 63% yield) as a yellow powder after purification by crystallisation in DCM/EtOAc.

$R_f$: 0.2 (DCM); M.p.: 212-213° C.; $^1$H NMR (270 MHz, DMSO-$d_6$) $\delta_H$ 7.40-7.45 (m, 1H, $H_{Ar}$), 7.49 (bs, 1H, $H_{Ar}$), 7.52 (bs, 1H, $H_{Ar}$), 7.54-7.59 (m, 2H, $H_{Ar}$), 7.64-7.68 (m, 1H, $H_{Ar}$), 7.72 (d, 1H, J=1.54 Hz, $H_{Ar}$), 7.74-7.76 (m, 2H, $H_{Ar}$), 7.77-7.79 (m, 2H, $H_{Ar}$), 7.81 (s, 1H, $H_{Ar}$), 7.87 (d, 2H, J=8.4 Hz, $H_{Ar}$), 8.02 (d, 2H, J=8.4 Hz, $H_{Ar}$), 8.09 (d, 2H, J=8.4 Hz, $H_{Ar}$),10.70 (s, 1H, NH); LC/MS (AP−) m/z 376.0 (M−H); $t_R$=2.7 min (99.9%).

N-(4-Benzoyl-phenyl)-3,5-dichloro-benzamide
(STX1431, CCM01031)

Reaction of 4-aminobenzophenone (100 mg, 0.51 mmol) in THF (6 mL) with 3,5-dicchlorobenzoyl chloride (1.36 mg, 0.65 mmol) in presence of triethylamine (90 μL, 0.65 mmol) according to method A gave N-(4-benzoyl-phenyl)-3,5-dichloro-benzamide (160 mg, 0.33 mmol, 63% yield) as a white powder after purification by crystallisation in DCM.

$R_f$: 0.3 (DCM); M.p.: 219-220° C.; $^1$H NMR (270 MHz, DMSO-$d_6$) $\delta_H$ 7.52-7.58 (m, 2H, $H_{Ar}$), 7.63-7.67 (m, 1H, $H_{Ar}$), 7.69-7.71 (m, 1H, $H_{Ar}$), 7.72-7.73 (m, 1H, $H_{Ar}$), 7.79 (d, 2H, J=8.6 Hz, $H_{Ar}$), 7.89 (t, 1H, J=2.0 Hz, CCl—$CH_{Ar}$—CCl), 7.94 (d, 2H, J=8.6 Hz, $H_{Ar}$), 7.99 (d, 2H, J=2.0 Hz, $H_{Ar}$), 10.74 (s, 1H, NH); $^{13}$C NMR (400 MHz, DMSO-$d_6$) $\delta_c$ 120.1 ($CH_{Ar}$), 127.2 ($CH_{Ar}$), 129.0 ($CH_{Ar}$), 129.9 ($CH_{Ar}$), 131.5 ($CH_{Ar}$), 131.7 ($CH_{Ar}$), 132.7 ($C_q$), 132.9 ($CH_{Ar}$), 134.8 ($C_q$), 137.9 ($C_q$), 138.2 ($C_q$), 143.3 ($C_q$), 163.7 (C=O), 195.2 (C=O); LC/MS (AP−) m/z 367.3 (M−H); $t_R$=3.0 min (99.9%).

N-(4-Benzoyl-phenyl)-3-methoxy-benzamide
(STX1432, CCM01032)

Reaction of 4-aminobenzophenone (100 mg, 0.51 mmol) in THF (6 mL) with m-anisoyl chloride (136 mg, 0.65 mmol) in presence of triethylamine (90 μL, 0.65 mmol) according to method A gave N-(4-benzoyl-phenyl)-3-methoxy-benzamide (160 mg, 0.48 mmol, 94% yield) as a white powder after purification by chromatography on silica gel (eluent EtOAc/DCM 0/100 to 5/95.

$R_f$: 0.4 (EtOAc/DCM 5/95); M.p.: 139-141° C.; $^1$H NMR (270 MHz, CDCl$_3$) $\delta_H$ 3.76 (s, 3H, OCH$_3$), 7.00 (ddd, 1H, J=1.4, 2.8, 8.0 Hz, $H_{Ar}$), 7.28 (t, 1H, J=7.7 Hz, $H_{Ar}$), 7.33

7.38 (m, 2H, H$_{Ar}$), 7.41 (dt, 2H, J=1.5, 7.7 Hz, H$_{Ar}$), 7.48-7.52 (m, 1H, H$_{Ar}$), 7.67-7.70 (m, 2H, H$_{Ar}$), 7.72-7.77 (m, 4H, H$_{Ar}$), 8.29 (s, 1H, NH); $^{13}$C NMR (400 MHz, DMSO-d$_6$) δ$_C$ 55.5 (OCH$_3$), 112.6 (CH$_{Ar}$), 118.4 (CH$_{Ar}$), 118.9 (CH$_{Ar}$), 119.3 (CH$_{Ar}$), 128.3 (CH$_{Ar}$), 129.9 (CH$_{Ar}$), 129.9 (CH$_{Ar}$), 131.7 (CH$_{Ar}$), 132.4 (CH$_{Ar}$), 133.2 (C$_q$), 1.36.0 (C$_q$), 137.8 (C$_q$), 142.1 (C$_q$), 160.0 (C$_q$), 166.0 (C=O), 195.9 (C=O); LC/MS (AP−) m/z 330.0 (M−H); t$_R$=2.2 min (99.9%).

N-(4-Benzoyl-phenyl)-2,5-dichloro-benzamide
(STX1433, CCM01034)

Reaction of 2,5-dichlorobenzoic acid (300 mg, 1.50 mmol) in thionyl chloride (3.5 mL) then with 4-aminobenzophenone (100 mg, 0.51 mmol) in presence of triethylamine (90 μL) in THF (6 mL) according to method B gave N-(4-benzoyl-phenyl)-2,5-dichloro-benzamide (160 mg, 0.43 mmol, 84% yield) as a off-white powder after purification by chromatography on silica gel (eluent:EtOAc/exane 1/9 to 3/7).

R$_f$: 0.3 (DCM); M.p.: 150-153° C.; $^1$H NMR (270 MHz, DMSO-d$_6$) δ$_H$ 7.51-7.55 (m, 1H, H$_{Ar}$), 7.57-7.58 (m, 1H, H$_{Ar}$), 7.59-7.61 (m, 2H, H$_{Ar}$), 7.62-7.66 (m, 1H, H$_{Ar}$), 7.68-7.70 (m, 1H, H$_{Ar}$), 7.72-7.76 (m, 1H, H$_{Ar}$), 7.77-7.80 (m, 2H, H$_{Ar}$), 7.85-7.88 (m, 3H, H$_{Ar}$), 10.96 (s, 1H, NH); LC/MS (AP−) m/z 367.8 (M−H), t$_R$=2.3 min (98.4%).

N-(4-Benzoyl-phenyl)-4-propyl-benzamide
(STX1434, CCM01036)

Reaction of 4-aminobenzophenone (99 mg, 0.51 mmol) in THF (6 mL) with 4-propylbenzoyl chloride (100 μL, 0.65 mmol) in presence of triethylamine (90 μL, 0.65 mmol) according to method A gave N-(4-benzoyl-phenyl)-4-propyl-benzamide (136 mg, 0.40 mmol, 78% yield) as a white powder after purification by chromatography on silica gel (eluent EtOAc/DCM 0/100 to 5/95).

R$_f$: 0.3 (DCM); M.p.: 119-122° C.; $^1$H NMR (270 MHz, CDCl$_3$) δ$_H$ 0.94 (t, 1H, J=7.2 Hz, CH$_3$), 1.59-1.72 (m, 2H, CH$_2$—CH$_3$), 2.65 (t, 2H, J=7.7 Hz, CH$_2$—Ar), 7.27-7.30 (m, 2H, H$_{Ar}$), 7.44-7.50 (m, 2H, H$_{Ar}$), 7.54-7.60 (m, 1H, H$_{Ar}$), 7.74-7.76 (m, 2H, H$_{Ar}$), 7.76-7.79 (m, 3H, H$_{Ar}$), 7.80-7.87 (m, 3H, H$_{Ar}$), 8.02 (s, 1H, NH); $^{13}$C NMR (400 MHz, CDCl$_3$) δ$_C$ 13.8 (CH$_3$), 24.3 (CH$_2$), 37.9 (CH$_2$), 119.1 (CH$_{Ar}$), 127.2 (CH$_{Ar}$), 128.3 (CH$_{Ar}$), 129.0 (CH$_{Ar}$), 129.9 (CH$_{Ar}$), 131.7 (CH$_{Ar}$), 131.8 (C$_q$), 132.3 (CH$_{Ar}$), 133.1 (C$_q$), 137.9 (C$_q$), 142.1 (C$_q$), 147.7 (C$_q$), 165.9 (C=O), 195.7 (C=O); LC/MS (AP−) m/z 341.5 (M−H); t$_R$=2.8 min (99.1%).

N-(4-Benzoyl-phenyl)-4-methoxy-benzamide
(STX1435, CCM01037)

Reaction of 4-aminobenzophenone (98 mg, 0.51 mmol) in THF (6 mL) with p-anisoyl chloride (90 μL, 0.65 mmol) in presence of triethylamine (90 μL, 0.65 mmol) according to method A gave N-(4-benzoyl-phenyl)-4-methoxy-benzamide (165 mg, 0.50 mmol, 98% yield) as a white powder after purification by washing the crude product with ethyl acetate and hexane.

R$_f$: 0.4 (EtOAc/DCM 5/95); M.p.: 171-174° C.; $^1$H NMR (270 MHz, DMSO-d$_6$) δ$_H$ 3.84 (s, 3H, OCH$_3$), 7.08 (d, 2H, J=8.6 Hz, H$_{Ar}$), 7.53-7.58 (m, 2H, H$_{Ar}$), 7.64-7.66 (m, 1H, H$_{Ar}$), 7.71-7.79 (m, 4H, H$_{Ar}$), 7.97-8.01 (m, 4H, H$_{Ar}$), 10.45 (s, 1H, NH); $^{13}$C NMR (400 MHz, , DMSO-d$_6$) δ$_c$ 56.0 (OCH$_3$), 114.2 (CH$_{Ar}$), 119.8 (CH$_{Ar}$), 127.0 (C$_q$), 129.0 (CH$_{Ar}$), 129.9 (CH$_{Ar}$), 130.3 (CH$_{Ar}$), 131.5 (CH$_{Ar}$), 131.9 (C$_q$), 132.8 (CH$_{Ar}$), 138.1 (C$_q$), 144.2 (C$_q$), 162.7 (C$_q$), 165.8 (C=O), 195.1 (C=O); LC/MS (AP−) m/z 330.0 (M−H); t$_R$=3.6 min (97.2%)

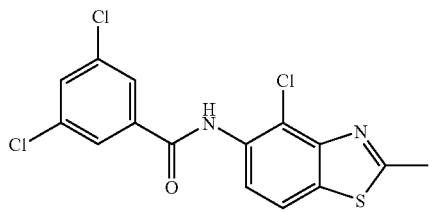

STX1355, CCM01002

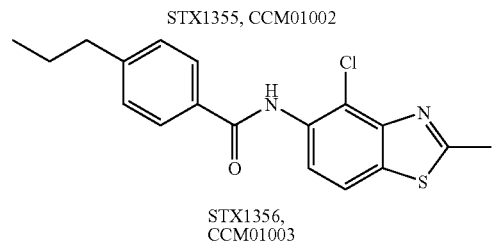

STX1356, CCM01003

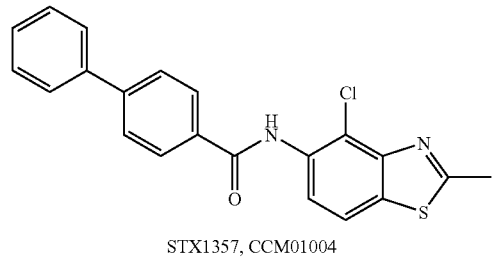

STX1357, CCM01004

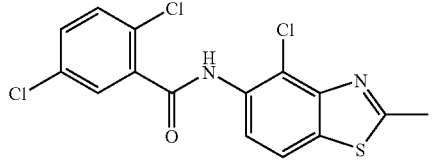

STX1358, CCM01006

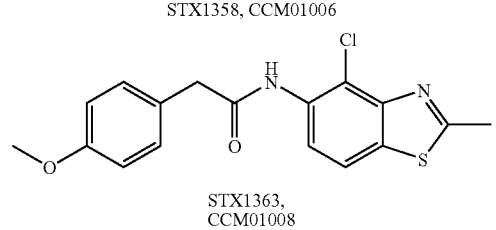

STX1363, CCM01008

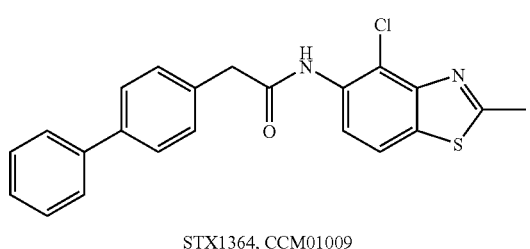

STX1364, CCM01009

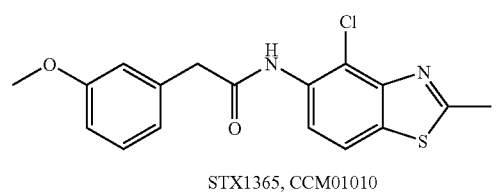

STX1365, CCM01010

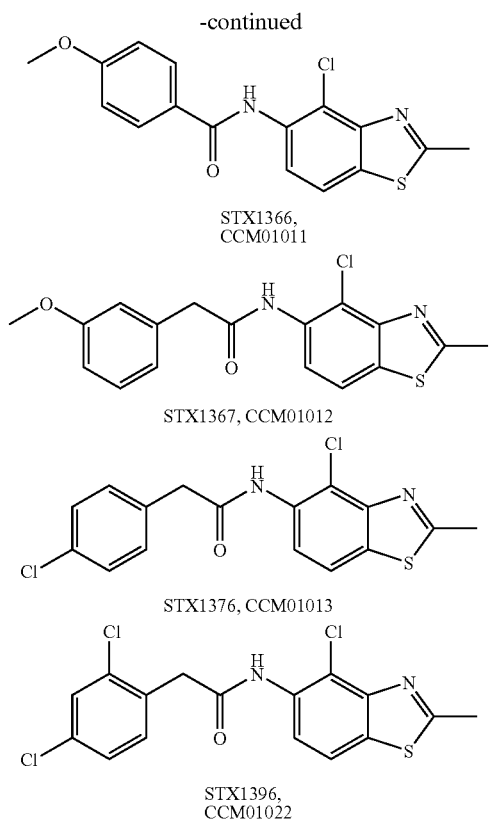

STX1366, CCM01011

STX1367, CCM01012

STX1376, CCM01013

STX1396, CCM01022

General Method for Synthesis of N-Benzothiazole Benzamide, Acetamide and Sulfonamide Derivatives (STX1355-1358, STX1363-1367, STX1376, STX1396)

Method A: to a stirred solution of the amine (n mmol) in THF are added triethylamine (1.2 n mmol) and the acyl chloride (1.2 n mmol) at room temperature. After completion, ethyl acetate and water are added. The aqueous layer is extracted by ethyl acetate. The combined organic layers are washed with brine, dried (MgSO4), filtered and evaporated under reduce pressure. The crude product is then purified to give the amide.

Method B: A solution of the acid (3 n mmol) in thionyl chloride is refluxed 3 hours. Thionyl chloride is then removed under reduced pressure. The crude product is diluted in dry THF and added to a solution of the amine (n mmol) and triethylamine in THF. After completion, ethyl acetate and water are added. The aqueous layer is extracted by EtOAc. The combined organic layers are then washed with brine, dried (MgSO4), filtered and evaporated under reduce pressure. The crude product is purified to give the amide.

3,5-Dichloro-N(4-chloro-2-methyl-benzothiazol-5-yl)-benzamide (STX1355, CCM01002)

Reaction of 4-chloro-2-methyl-benzothiazol-5-ylamine (50 mg, 0.25 mmol) in THF (1.5 mL) with 3,5-dichlorobenzoyl chloride (122 mg, 0.56 mmol) in presence of triethylamine (0.5 mL) according to method A gave 3,5-Dichloro-N-(4-chloro-2-methyl-benzothiazol-5-yl)-benzamide (66 mg, 0.15 mmol, 60% yield) as a off-white powder after crystallisation in hexane/DCM.

$R_f$ 0.3 (DCM); M.p. (° C.) 252-253; $^1$H NMR (270 MHz, DMSO-$d_6$) 2.85 (s, 3H, $CH_3$), 7.54 (d, 1H, J=8.7 Hz, $H_{Ar}$benzothiazole), 7.92-7.94 (m, 1H, $H_{Ar}$), 8.03-8.04 (m, 2H, $H_{Ar}$), 8.06 (d, 1H, J=8.7 Hz, $H_{Ar}$benzothiazole), 10.55 (s, 1H, NH); $^{13}$C NMR (400 MHz, DMSO-$d_6$) 20.4 ($CH_3$), 120.8 ($CH_{Ar}$benzothiazole), 123.2 ($C_q$), 125.6 ($CH_{Ar}$benzothiazole), 127.1 ($CH_{Ar}$), 131.8 ($CH_{Ar}$), 133.2 ($C_q$), 134.8 ($C_q$), 135.0 ($C_q$), 137.6 ($C_q$), 150.8 ($C_q$), 163.5 ($C_q$), 170.4 (C=O); LC/MS (AP−) m/z 368.7 (M−H); $t_R$=3.0 min (99.9%); HRMS (FAB+) Calculated for $C_{15}H_9Cl_3N_2OS$ 369.9501; Found 369.9504.

N-(4-Chloro-2-methyl-benzothiazol-5-yl)-4-propyl-benzamide (STX1356, CCM01003)

Reaction of 4-chloro-2-methyl-benzothiazol-5-ylamine (50 mg, 0.25 mmol) in THF (1.5 mL) with 4-propylbenzoyl chloride (90 μL, 0.56 mmol) in presence of triethylamine (0.5 mL) according to method A gave N-(4-Chloro-2-methyl-benzothiazol-5-yl)-4-propyl-benzamide (44 mg, 0.13 mmol, 52% yield) as a orange powder after crystallisation in hexane and methanol.

$R_f$ 0.3 (DCM); M.p. 184° C.; $^1$H NMR (270 MHz, DMSO-$d_6$) 0.91 (t, 3H, J=7.3 Hz, $CH_2$—$CH_3$), 1.59-1.68 (m, 2H, $CH_2$—$CH_3$), 2.65 (t, 2H, J=7.6 Hz, $CH_2$—Ar), 2.85 (s, 3H, $CH_3$), 7.36 (d, 2H, J=8.2 Hz, $H_{Ar}$), 7.58 (d, 1H, J=8.6 Hz, $H_{Ar}$benzothiazole), 7.95 (m, 2H, J=8.2 Hz, $H_{Ar}$), 8.03 (d, 1H, J=8.6 Hz, $H_{Ar}$benzothiazole), 10.18 (s, 1H, NH); $^{13}$C NMR (400 MHz, DMSO-$d_6$) 14.1 ($CH_2$—$CH_3$), 20.4 ($CH_3$), 24.4 ($CH_2$—$CH_3$), 37.5 (Ar—$CH_2$), 120.6 ($CH_{Ar}$benzothiazole), 125.5 ($CH_{Ar}$benzothiazole), 128.3 ($CH_{Ar}$), 128.9 ($CH_{Ar}$), 131.9 ($C_q$), 133.9 ($C_q$), 134.2 ($C_q$), 146.9 ($C_q$), 150.8 ($C_q$), 165.9 ($C_q$), 170.1 (C=O); LC/MS (AP−) m/z 343.0 (M−H); $t_R$=2.9 min (98.8%); HRMS (FAB+) Calculated for $C_{18}H_{17}ClN_2OS$ 344.0750; Found 344.0744; IR (v, cm$^{-1}$) (CCl$_4$) 3429w, 2962w, 2933w, 1692s (CO), 1611 w, 1598, 1561 w, 1520s, 1505s, 1430w, 1405, 1308, 1253, 1176w, 1122w, 1097w.

Biphenyl-4-carboxylic acid (4-chloro-2-methyl-benzothiazol-5-yl)-amide (STX1357, CCM01004

Reaction of 4-chloro-2-methyl-benzothiazol-5-ylamine (50 mg, 0.25 mmol) in THF (1.5 mL) with 4-biphenylcarbonyl chloride (50 μL, 0.30 mmol) in presence of triethylamine (42 μL, 0.30 mmol) according to method A gave biphenyl-4-carboxylic acid (4-chloro-2-methyl-benzothiazol-5-yl)-amide (79 mg, 0.21 mmol, 84% yield) as a pale pink powder after crystallisation in hexane/DCM.

$R_f$ 0.3 (DCM); M.p. 210-211° C.; $^1$H NMR (270 MHz, DMSO-$d_6$) 2.86 (s, 3H, $CH_3$), 7.42-7.47 (m, 1H, $H_{Ar}$), 7.49-7.52 (m, 2H, $H_{Ar}$), 7.61 (d, 1H, J=8.4 Hz, $H_{Ar}$benzothiazole), 7.77 (d, 2H, J=7.4 Hz, $H_{Ar}$), 7.88 (d, 2H, J=8.4 Hz, $H_{Ar}$), 8.04 (d, 1H, J=8.4 Hz, $H_{Ar}$benzothiazole), 8.13 (d, 2H, J=8.4 Hz, $H_{Ar}$), 10.33 (s, 1H, NH); $^{13}$C NMR (400 MHz, DMSO-$d_6$) 20.4 ($CH_3$), 120.7 ($CH_{Ar}$benzothiazole), 123.1 ($C_q$), 125.6 ($CH_{Ar}$benzothiazole), 127.2 ($CH_{Ar}$), 127.4 ($CH_{Ar}$), 128.7 ($CH_{Ar}$), 129.0 ($CH_{Ar}$), 129.6 ($CH_{Ar}$), 133.1 ($C_q$), 133.8 ($C_q$), 134.3 ($C_q$), 139.5 ($C_q$), 143.9 ($C_q$), 150.8 ($C_q$), 165.7 ($C_q$), 170.2 (C=O); LC/MS (AP+) rnz379.02 (M+H); $t_R$=2.8 min (99.4%); HRMS (FAB+) Calculated for $C_{21}H_{15}ClN_2OS$ 378.0594; Found 378.0590.

2,5-Dichloro-AN(4-chloro-2-methyl-benzothiazol-5-yl)-benzamide (STX1358, CCM01006)

Reaction of 2,5-dichlorobenzoic acid (145 mg, 0.76 mmol) in thionyl chloride (5 mL) then with 4-chloro-2-methyl-benzothiazol-5-ylamine (50 mg, 0.25 mmol) in presence of triethylamine (0.5 mL) in THF (2 mL) according to method B gave 2,5-dichloro-N-(4-chloro-2-methyl-benzothiazol-5-yl)-benzamide (50 mg, 0.13 mmol, 52% yield) as a white powder after purification by chromatography on silica gel(eluent: DCM).

$R_f$ 0.35 (DCM); M.p. 175° C.; $^1$H NMR (270 MHz, DMSO-$d_6$) 2.85 (s, 3H, $CH_3$), 7.61-7.62 (m, 2H, $H_{Ar}$), 7.66 (d, 1H, J=8.6 Hz, $H_{Ar}$benzothiazole), 7.76 (m, 1H, $H_{Ar}$), 8.05 (d, 1H, J=8.6 Hz, $H_{Ar}$benzothiazole), 10.52 (s, 1H, NH); LC/MS (AP+) m/z 370.8 (M+H); $t_R$=2.4 min (99.5%) HRMS (FAB+) Calculated for $C_{15}H_9Cl_3N_2OS$ 369.9501; Found 369.9503.

N-(4-Chloro-2-methyl-benzothiazol-5-yl)-2-(4-methoxy-phenyl)-acetamide (STX1363, CCM01008)

Reaction of 4-chloro-2-methyl-benzothiazol-5-ylamine (50 mg, 0.25 mmol) in THF (1.5 mL) with 4-methoxyphenylacetyl chloride (46 µL, 0.30 mmol) in presence of triethylamine (42 µL, 0.30 mmol) according to method A gave N-(4-chloro-2methyl-benzothiazol-5-yl)-2-(4-methoxy-phenyl)-acetamide (50 mg, 0.14 mmol, 56% yield) as a white powder after crystallisation in hexane/DCM.

$R_f$ 0.4 (EtOAc/DCM 1/9); M.p. 173-174° C.; $^1$H NMR (270 MHz, CDCl$_3$) 2.83 (s, 3H, $CH_3$), 3.76 (s, 2H, $CH_2$), 3.82 (s, 3H, $OCH_3$), 6.95 (d, 2H, J=8.6 Hz, $H_{Ar}$), 7.30 (d, 2H, J=8.6 Hz, $H_{Ar}$), 7.65 (d, 1H, J=8.9 Hz, $H_{Ar}$benzothiazole), 7.80 (s, 1H, NH), 8.40 (d, 1H, J=8.9 Hz, $H_{Ar}$benzothiazole); LC/MS (AP+) m/z 347.0 (M+H); $t_R$=2.1 min (99.2%); HRMS (FAB+) Calculated for $C_{17}H_{15}ClN_2O_2S$ 346.0543; Found 346.0542.

Biphenyl-4-carboxylic acid (4-chloro-2-methyl-benzothiazol-5-yl)-amide (STX1364, CCM01009)

Reaction of 4-biphenylacetic acid (160 mg, 0.76 mmol) in thionyl chloride (1 mL) then with 4-chloro-2-methyl-benzothiazol-5-ylamine (50 mg, 0.25 mmol) in presence of triethylamine (0.5 mL) in THF (2 mL) according to method B gave biphenyl-4-carboxylic acid (4-chloro-2-methyl-benzothiazol-5-yl)-amide (60 mg, 0.15 mmol, 60% yield) as a pink powder after purification by chromatography on silica gel (eluent: DCM).

$R_f$: 0.2 (DCM); M.p.:168-169° C.; $^1$H NMR (270 MHz, CDCl$_3$) $\delta_H$ 2.83 (s, 3H, $CH_3$), 3.87 (s, 2H, $CH_2$), 7.35-7.38 (m, 1H, $H_{Ar}$), 7.41-7.48 (m, 4H, $H_{Ar}$), 7.57-7.61 (m, 2H, $H_{Ar}$), 7.64-7.69 (m, 3H, $H_{Ar}$), 7.82 (s, 1H, NH), 8.42 (d, 1H, J=9.1 Hz, $H_{Ar}$benzothiazole); LC/MS (AP+) m/z 393.3; $t_R$=3.2 min (99.8%); HRMS (FAB+) Calculated for $C_{22}H_{17}ClN_2OS$ 392.0750; Found 392.0742.

N-(4-Chloro-2-methyl-benzothiazol-5-yl)-3-methoxy-benzamide (STX1365, CCM01010)

Reaction of 4-chloro-2-methyl-benzothiazol-5-ylamine (50 mg, 0.25 mmol) in THF (1.5 mL) with m-anisoyl chloride (41 µL, 0.30 mmol) in presence of triethylamine (42 µL, 0.30 mmol) according to method A gave N-(4-chloro-2-methyl-benzothiazol-5-yl)-3-methoxy-benzamide (70 mg, 0.21 mmol, 84% yield) as a orange powder after crystallisation in hexane/DCM.

$R_f$: 0.4 (EtOAc/DCM 5/95); M.p.:177-179° C.; $^1$H NMR (270 MHz, DMSO-$d_6$) $\delta_H$ 2.83 (s, 3H, $CH_3$), 3.82 (s, 3H, $OCH_3$), 7.17 (ddd, 1H, J=1.3, 2.7, 8.1 Hz, $H_{Ar}$), 7.44 (dd, 1H, J=7.7, 8.1 Hz, $H_{Ar}$), 7.54-7.55 (m, 1H, $H_{Ar}$), 7.55 (d, 1H, J=8.4 Hz, $H_{Ar}$benzothiazole), 7.56-7.61 (m, 1H, $H_{Ar}$), 8.02 (d, 1H, J=8.4 Hz, $H_{Ar}$benzothiazole), 10.20 (s, 1H, NH); LC/MS (AP+) m/z 333.2;_$t_R$=2.6 min, (99.7%); HRMS (FAB+) Calculated for $C_{16}H_{13}ClN_2O_2S$ 332.0386; Found 332.0383.

N(4-Chloro-2-methyl-benzothiazol-5-yl)-4-methoxy-benzamide (STX1366, CCMo0011)

Reaction of 4-chloro-2-methyl-benzothiazol-5-ylamine (50 mg, 0.25 mmol) in THF (1.5 mL) with panisoyl chloride (41 µL, 0.30 mmol) in presence of triethylamine (42 µL, 0.30 mmol) according to method A gave N-(4-chloro-2-methyl-benzothiazol-5-yl)-4-methoxy-benzamide (65 mg, 0.19 mmol, 76% yield) as a white powder after crystallisation in hexane/DCM.

$R_f$: 0.4 (EtOAc/DCM 1/9); M.p.:182° C. $^1$H NMR (270 MHz, DMSO-$d_6$) $\delta_H$ 2.83 (s, 3H, $CH_3$), 3.83 (s,.3H, $OCH_3$), 7.06 (d, 2H, J=8.8 Hz, $H_{Ar}$), 7.55 (d, 1H, J=8.5 Hz, $H_{Ar}$benzothiazole), 7.99 (d, 1H, J=8.5 Hz, $H_{Ar}$benzothiazole), 8.00 (d, 2H, J=8.8 Hz, $H_{Ar}$), 10.06 (s, 1H, NH); LC/MS (AP+) m/z 333.2;_$t_R$=2.6 min (99.9%); HRMS: (FAB+) Calculated for $C_{16}H_{13}ClN_2O_2S$ 332.0386; Found 332.0383.

N-(4-Chloro-2-methyl-benzothiazol-5-yl)-2-(3-methoxy-phenyl)-acetamide (STX1367, CCM01012)

Reaction of 4-chloro-2-methyl-benzothiazol-5-ylamine (50 mg, 0.25 mmol) in THF (1.5 mL) with 3-methoxyphenylacetyl chloride (47 µL, 0.30 mmol) in presence of triethylamine (42 µL, 0.30 mmol) according to method A gave N-(4-chloro-2-methyl-benzothiazol-5-yl)-2-(3-methoxy-phenyl)-acetamide (40 mg, 0.11 mmol, 48% yield) as a white powder after crystallisation in hexane/DCM.

$R_f$: 0.4 (EtOAc/DCM 1/9); M.p.:147-148° C.; $^1$H NMR (270 MHz, DMSO-$d_6$) $\delta_H$ 2.82 (s, 3H, $CH_3$), 3.72 (s, 2H, $CH_2$), 3.75 (s, 3H, $OCH_3$), 6.80-6.84 (m, 1H, $H_{Ar}$), 6.93-6.96 (m, 2H, $H_{Ar}$), 7.25 (dd, 1H, J=8.2, 8.2 Hz, $H_{Ar}$), 7.65 (d, 1H, J=8.6 Hz, $H_{Ar}$benzothiazole), 7.95 (d, 1H, J=8.6 Hz, $H_{Ar}$benzothiazole), 9.90 (s, 1H, NH); LC/MS (AP+) m/z347.2 (M+H); $t_R$=2.5 min, (99.3%); HRMS (FAB+) Calculated for $C_{17}H_{15}ClN_2O_2S$ 346.0543; Found 346.0541.

N-(4-Chloro-2-methyl-benzothiazol-5-yl)-2-(4-chloro-phenyl)-acetamide (STX1376, CCM01013)

Reaction of 4-chloro-2-methyl-benzothiazol-5-ylamine (50 mg, 0.25 mmol) in THF (1.5 mL) with 4-chlorophenylacetyl chloride (65 mg, 0.30 mmol) in presence of triethylamine (42 µL, 0.30 mmol) according to method A gave N-(4-chloro-2-methyl-benzothiazol-5-yl)-2-(4-chloro-phenyl)-acetamide (65 mg, 0.19 mmol, 80% yield) as a white powder after crystallisation in hexane/DCM.

$R_f$: 0.5 (EtOAc/DCM 1/9); M.p.:227-229° C.; $^1$H NMR (270 MHz, DMSO-$d_6$) $\delta_H$ 2.82 (s, 3H, $CH_3$), 3.76 (s, 2H, $CH_2$), 7.38 (s, 4H, $H_{Ar}$), 7.63 (d, 1H, J=8.5 Hz, $H_{Ar}$benzothiazole), 7.95 (d, 1H, J=8.5 Hz, $H_{Ar}$benzothiazole), 9.96 (s, 1H, NH); LC/MS (AP-) m/z 350.8 (M-H); $t_R$=2.5 min, (96.5%) HRMS (FAB+) Calculated for $C_{16}H_{12}Cl_2N_2OS$ 350.0047; Found 350.0048.

N-(4-Chloro-2-methyl-benzothiazol-5-yl)-2-(2,4-dichloro-phenyl)-acetamide (STX1396, CCM01022)

Reaction of 2,4-dichlorophenylacetic acid (163 mg, 0.79 mmol) in thionyl chloride (2 mL) then with 4-chloro-2-methyl-benzothiazol-5-ylamine (52 mg, 0.26 mmol) in presence of triethylamine (0.5 mL) in THF (3 mL) according to method B gave N-(4-chloro-2-methyl-benzothiazol-5-yl)-2-(2,4-dichloro-phenyl)-acetamide (33 mg, 0.09 mmol, 35% yield) as a white powder after crystallisation in hexane/DCM.

$R_f$: 0.4 (EtOAc/DCM 1/9); M.p.:257-258° C.; $^1$H NMR (270 MHz, DMSO-$d_6$) $\delta_H$ 2.81 (s, 3H, $CH_3$), 3.93 (s, 2H, $CH_2$), 7.38-7.42 (m, 1H, $H_{Ar}$), 7.47-7.52 (m, 1H, $H_{Ar}$), 7.59-7.60 (m, 1H, $H_{Ar}$), 7.62 (d, 1H, J=8.7 Hz, $H_{Ar}$benzothiazole), 7.95 (d, 1H, J=8.7 Hz, $H_{Ar}$benzothiazole), 10.05 (bs, 1H, NH); LC/MS (AP−) m/z 382.8 (M−H); $t_R$=2.6 min (95.1%); HRMS (FAB+) Calculated for $C_{16}H_{11}Cl_3N_2OS$ 383.9658; Found 383.9653

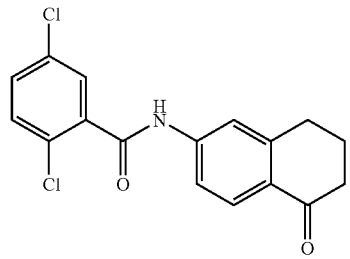

STX1465, CCM01044

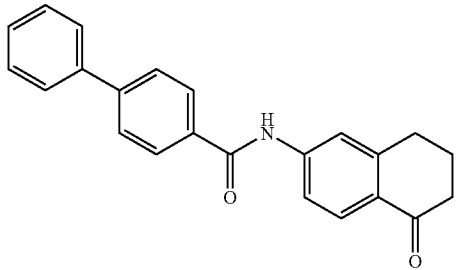

STX1470, CCM01049

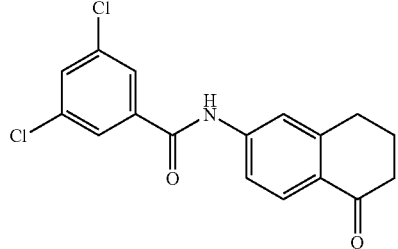

STX142, CCM01050

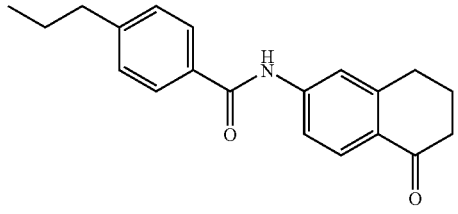

STX1473, CCM01051

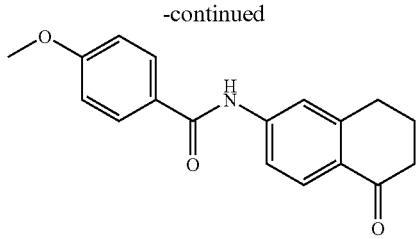

STX1474, CCM01052

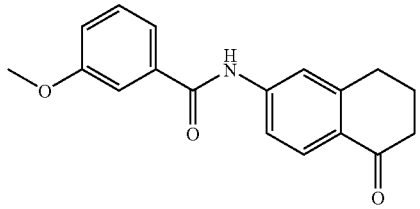

STX1475, CCM01053

General Method for Synthesis of V(5-tetralone)-benzamide Derivatives (STX1465 and STX1470-1475):

Method A: to a stirred solution of the amine (n mmol) in THF are added triethylamine (1.2 n mmol) and the acyl chloride (1.2 n mmol) at room temperature. After completion, ethyl acetate and water are added. The aqueous layer is extracted by ethyl acetate. The combined organic layers are washed with brine, dried (MgSO4), filtered and evaporated under reduce pressure. The crude product is then purified to give the amide.

Method B: A solution of the acid (3 n mmol) in thionyl chloride is refluxed 3 hours. Thionyl chloride is then removed under reduced pressure. The crude product is diluted in dry THF and added to a solution of the amine (n mmol) and triethylamine in THF. After completion, ethyl acetate and water are added. The aqueous layer is extracted by EtOAc. The combined organic layers are then washed with brine, dried (MgSO$_4$), filtered and evaporated under reduce pressure. The crude product is purified to give the amide.

2,5-Dichloro-N-(5-oxo-5,6,7,8-tetrahydro-naphthalen-2-yl)-benzamide (CCM01044, STX1465)

Reaction of 2,5-dichlorobenzoic acid (300 mg, 1.50 mmol) in thionyl chloride (3.5 mL) then with 6-Amino-3,4-dihydro-2H-naphthalen-1-one (80 mg, 0.50 mmol) in presence of triethylamine (90 µL, 0.65 mmol) in THF (6 mL) according to method B gave 2,5-dichloro-N-(5-oxo-5,6,7,8-tetrahydro-naphthalen-2-yl)-benzamide (150 mg, 0.48 mmol, 76% yield) as a grey powder after purification by crystallisation in DCM.

$^1$H NMR (270 MHz, DMSO-$d_6$) $\delta_H$ 1.92-1.97 (2H, m, $CH_2$), 2.46-2.50 (2H, m $CH_2$), 2.84 (2H, t, J=5.7 Hz, $CH_2$), 7.48-7.52 (3H, m, $H_{Ar}$), 7.67 (2H, bs, $H_{Ar}$), 7.78 (1H, d, J=8.6 Hz, $H_{Ar}$), 10.78 (1H, s, NH); LC/MS (AP−) $t_r$=2.2 min (93.5%), m/z 315.2 (M−H).

Biphenyl-4-carboxylic acid (5-oxo-5,6,7,8-tetrahydro-naphthalen-2-yl)-amide (CCM01049, STX1470)

Reaction of 6-Amino-3,4-dihydro-2H-naphthalen-1-one (80 mg, 0.50 mmol) in THF (6 mL) with 4-biphenylcarbonyl chloride (143 mg, 0.65 mmol) in presence of triethylamine (90 µL, 0.65 mmol) according to method A gave biphenyl-4-carboxylic acid (5-oxo-5,6,7,8-tetrahydro-naphthalen-2-yl)-amide (150 mg, 0.43 mmol, 86% yield) as a white powder after purification by flash chromatography on silica gel (EtOAc/DCM 1/9 to 2/8).

$^1$H NMR (270 MHz, DMSO-$d_6$) $\delta_H$ 1.92-1.98 (2H, m, $CH_2$), 2.44-2.51 (2H, m, $CH_2$), 2.85 (2H, t, J=5.9 Hz, $CH_2$), 7.34-7.45 (3H, m, $H_{Ar}$), 7.65-7.70 (3H, m, $H_{Ar}$), 7.75-7.80 (4H, m, $H_{Ar}$), 7.98 (2H, d, J=8.6 Hz, $H_{Ar}$), 10.48 (1H, s, NH).

3,5-Dichloro-N-(5-oxo-5,6,7,8-tetrahydro-naphthalen-2-yl)-benzamide (CCM01050, STX1472)

Reaction of 6-Amino-3,4-dihydro-2H-naphthalen-1-one (80 mg, 0.50 mmol) in THF (6mL) with 3,5-dichlorobenzoyl chloride (136 mg, 0.65 mmol) in presence of triethylamine (90 µL, 0.65 mmol) according to method A gave 3,5-dichloro-N-(5-oxo-5,6,7,8-tetrahydro-naphthalen-2-yl)-benzamide. (140 mg, 0.42 mmol, 84% yield) as a brown powder after washing by DCM.

Mp 226-228° C.; $^1$H NMR (270 MHz, DMSO-$d_6$) $\delta_H$ 1.92-1.97 (2H, m, $CH_2$), 2.49 (2H, t, J=6.0 Hz, $CH_2$), 2.85 (2H, t, J=6.0 Hz, $CH_2$), 7.62 (1H, dd, J=2.1;8.4 Hz, $H_{Ar}$tetralone), 7.71 (1H, d, J=1.7 Hz, $H_{Ar}$), 7.79 (1H, d, J=8.4 Hz, $H_{Ar}$tetralone), 7.81 (1H, d, J=2.1 Hz, $H_{Ar}$tetralone), 7.90 (2H, d, J=1.7 Hz, $H_{Ar}$), 8.08 (2H, d, J=8.4 Hz, $H_{Ar}$), 10.61 (1H, s, NH); $^{13}$C NMR (50 MHz, DMSO-$d_6$) $\delta_C$ 23.4 ($CH_2$), 29.8 ($CH_2$), 38.9 ($CH_2$), 118.7 ($CH_{Ar}$), 119.6 ($CH_{Ar}$), 127.1 ($CH_{Ar}$), 128.0 ($CH_{Ar}$), 128.6 ($C_q$), 131.7 ($C_q$), 134.8 ($CH_{Ar}$), 138.2 ($C_q$), 143.5 ($C_q$), 146.2 ($C_q$), 163.6 (CO), 196.8 (CO).

N-(5-Oxo-5,6,7,8-tetrahydro-naphthalen-2-yl)-4-propyl-benzamide (CCM01051, STX1473)

Reaction of 6-Amino-3,4-dihydro-2H-naphthalen-1-one (80 mg, 0.50 mmol) in THF (6 mL) with 4-propylbenzoyl chloride (100 µL, 0.65 mmol) in presence of triethylamine (90 µL, 0.65 mmol) according to method A gave N-(5-oxo-5,6,7,8-tetrahydro-naphthalen-2-yl)-4-propyl-benzamide (140 mg, 0.45 mmol, 90% yield) as a white powder after purification by flash chromatography on silica gel (eluent :EtOAc/hexane 2/8 to 4/6).

Mp 168-170° C.; $^1$H NMR (270 MHz, DMSO-$d_6$) $\delta_H$ 0.89 (3H, t, J=7.4 Hz, CH3), 1.54-1.68 (2H, m, CH2propyl), 1.97-2.07 (2H, m, $CH_2$tetralone), 2.55 (2H, t, J=6.5 Hz, $CH_2$), 2.63 (2H, t, J=7.4 Hz, $CH_2$), 2.91 (2H, t, J=6.5 Hz, CH2), 7.35 (2H, d, J=8.4 Hz, $H_{Ar}$), 7.70 (1H, dd, J=1.7; 8.7 Hz, $H_{Ar}$tetralone), 7.83-7.89 (4H, m, $H_{Ar}$), 10.41 (1H, s, NH); $^{13}$C NMR (50 MHz, DMSO-$d_6$) $\delta_C$ 14.1 ($CH_3$), 23.4 ($CH_2$tetralone), 24.4 ($CH_2$), 29.8 ($CH_2$tetralone), 37.5 ($CH_2$), 38.9 ($CH_2$tetralone), 118.5 ($CH_{Ar}$), 119.3 ($CH_{Ar}$), 127.9 ($CH_{Ar}$), 128.2 ($C_q$), 128.3 ($CH_{Ar}$), 128.9 ($CH_{Ar}$),132.5 ($C_q$), 144.2 ($C_q$), 146.2 ($C_q$), 147.0 ($C_q$), 166.4 (CO), 196.8 (CO)

4-Methoxy-N-(5-oxo-5,6,7,8-tetrahydro-naphthalen-2-yl)-benzamide (CCM01052, STX1474)

Reaction of 6-Amino-3,4-dihydro-2H-naphthalen-1-one (80 mg, 0.50 mmol) in THF (6 mL) with p-anisoyl chloride (90 mg, 0.65 mmol) in presence of triethylamine (90 µL, 0.65 mmol) according to method A gave 4-methoxy-N-(5-oxo-5,6,7,8-tetrahydro-naphthalen-2-yl)-benzamide (135 mg, 0.46 mmol, 92% yield) as a white powder after purification by flash chromatography on silica gel (eluent: EtOAc/DCM 0/10 to 2/8).

Mp 163-166° C.; $^1$H NMR (270 MHz, DMSO-$d_6$) $\delta_H$ 1.99-2.06 (2H, m, $CH_2$), 2.54 (2H, t, J=6.0 Hz, $CH_2$), 2.90 (2H, t, J=5.8 Hz, $CH_2$), 3.82 (3H, s, $OCH_3$), 7.06 (2H, d, J=8.7 Hz, $H_{Ar}$), 7.70 (1H, dd, J=2.0;8.7 Hz, $H_{Ar}$tetralone), 7.81-7.84 (2H, m, $H_{Ar}$), 7.95 (2H, d, J=8.7 Hz, $H_{Ar}$), 10.32 (1H, s, NH).

3-Methoxy-N-(5-oxo-5,6,7,8-tetrahydro-naphthalen-2-yl)-benzamide (CCM01053, STX1475)

Reaction of 6-Amino-3,4-dihydro-2H-naphthalen-1-one (80 mg, 0.50 mmol) in THF (6 mL) with m-anisoyl chloride (90 µL, 0.65 mmol) in presence of triethylamine (90 µL, 0.65 mmol) according to method A gave 3-methoxy-N-(5-oxo-5,6,7,8-tetrahydro-naphthalen-2-yl)-benzamide (135 mg, 0.46 mmol, 92% yield) as a white powder after purification by flash chromatography on silica gel (eluent:EtOAc/DCM 0/10 to 2/8).

Mp 142-143° C.; $^1$H NMR (270 MHz, DMSO-$d_6$) $\delta_H$ 2.01-2.09 (2H, m, $CH_2$), 2.57 (2H, t, J=6.3 Hz, $CH_2$), 2.93 (2H, t, J=6.0 Hz, $CH_2$), 3.84 (3H, s, $OCH_3$), 7.18 (1H, ddd, J=1.0;2.5;7.9 Hz, $H_{Ar}$), 7.43-7.56 (3H, m, HAr), 7.73 (1H, dd, J=2.0;8.7 Hz, $H_{Ar}$tetralone), 7.83 (1H, d, J=1.0 Hz, $H_{Ar}$tetralone), 7.86 (1H, d, J=8.7 Hz, $H_{Ar}$tetralone), 10.32 (1H, s, NH).

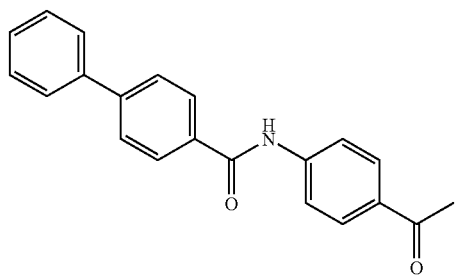

STX1461, CCM01040

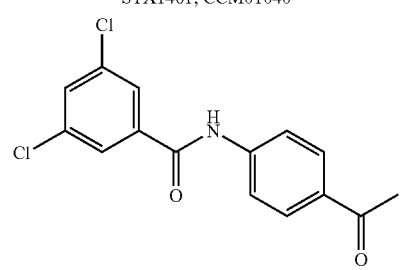

STX1462, CCM01041

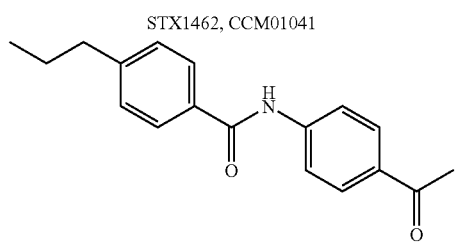

STX1463, CCM01042

-continued

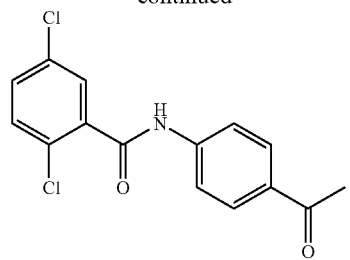

STX1464, CCM01043

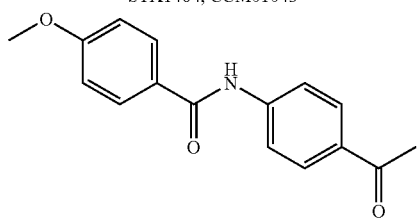

STX1468, CCM01047

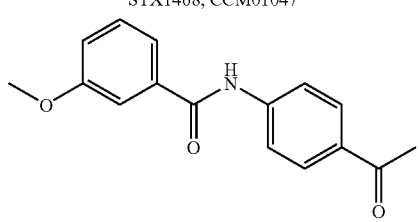

STX1469, CCM01048

General Method for Synthesis of
N-(5-acetophenone)-benzamide Derivatives
(STX1461-1464 and STX1468-1469):

Method A: to a stirred solution of the amine (n mmol) in THF are added triethylamine (1.2 n mmol) and the acyl chloride (1.2 n mmol) at room temperature. After completion, ethyl acetate and water are added. The aqueous layer is extracted by ethyl acetate. The combined organic layers are washed with brine, dried (MgSO4), filtered and evaporated under reduce pressure. The crude product is then purified to give the amide.

Method B: A solution of the acid (3n mmol) in thionyl chloride is refluxed 3 hours. Thionyl chloride is then removed under reduced pressure. The crude product is diluted in dry THF and added to a solution of the amine (n mmol) and triethylamine in THF. After completion, ethyl acetate and water are added. The aqueous layer is extracted by EtOAc. The combined organic layers are then washed with brine, dried (MgSO4), filtered and evaporated under reduce pressure. The crude product is purified to give the amide.

Biphenyl-4-carboxylic acid (4-acetyl-phenyl)-amide
(CCM01040, STX1461)

Reaction of 4-aminoacetophenone (75 mg, 0.55 mmol) in THF (6 mL) with 4-biphenylcarbonyl chloride (147 mg, 0.68 mmol) in presence of triethylamine (90 μL, 0.65 mmol) according to method A gave biphenyl-4-carboxylic acid (4-acetyl-phenyl)-amide (90 mg, 0.28 mmol, 50% yield) as a white powder after washing by water and ethyl acetate.

Mp 283-285° C.; $^1$H NNMR (270 MHz, DMSO-d$_6$) $\delta_H$ 2.55 (3H, s, CH$_3$), 7.42-7.45 (1H, m, H$_{Ar}$), 7.48-7.54 (2H, m, H$_{Ar}$), 7.75-7.78 (2H, m, H$_{Ar}$), 7.86 (2H, d, J=8.4 Hz, H$_{Ar}$), 7.97 (4H, s, H$_{Ar}$), 8.08 (2H, d, J=8.4 Hz, H$_{Ar}$), 10.61 (1H, s, NH); LC/MS (AP−) t$_r$=2.3 min (99.2%), m/z 314.3 (M−H)

N-(4-Acetyl-phenyl)-3,5-dichloro-benzamide
(CCM01041, STX1462)

Reaction of 4-aminoacetophenone (76 mg, 0.56 mmol) in THF (6 mL) with 3,5-dichlorobenzoyl chloride (145 mg, 0.69 mmol) in presence of triethylamine (90 μL, 0.65 mmol) according to method A gave N-(4-acetyl-phenyl)-3,5-dichloro-benzamide (145 mg, 0.47 mmol, 84% yield) as a white powder after washing by dichloromethane.

Mp 199-200° C.; R$_f$: 0.3 (Ethyl acetate/hexane, 3:7); $^1$H NMR (270 MHz, DMSO-d$_6$) $\delta_H$ 2.55 (3H, s, CH$_3$), 7.86-7.92 (3H, m, H$_{Ar}$), 7.97-8.00 (4H, m, H$_{Ar}$), 10.69 (1H, s, NH); $^{13}$C NMR (50 MHz, DMSO-d$_6$) $\delta_C$ 27.2 (CH$_3$), 120.3 (CH$_{Ar}$), 127.3 (CH$_{Ar}$), 130.0 (CH$_{Ar}$), 131.9 (C$_q$), 133.1 (C$_q$), 135.0 (CH$_{Ar}$), 138.4 (C$_q$), 143.7 (C$_q$), 163.8 (CO), 197.3 (CO); LC/MS (AP−) t$_r$=2.5 min (99.5%), m/z 306.1 (M−H).

N-(4-Acetyl-phenyl)-4-propyl-benzamide
(CCM01042, STX1463)

Reaction of 4-aminoacetophenone (76 mg, 0.56 mmol) in THF (6 mL) with 4-propylbenzoyl chloride (100 μL, 0.65 mmol) in presence of triethylamine (90 μL, 0.65 mmol) according to method A gave N-(4-acetyl-phenyl)-4-propyl-benzamide (125 mg, 0.44 mmol, 78% yield) as a white powder after washing by dichloromethane and hexane.

Mp 174-176° C.; R$_f$: 0.2 (Ethyl acetate/hexane, 4:8); $^1$H NMR (270 MHz, DMSO-d$_6$) $\delta_H$ 0.89 (3H, t, J=7.2 Hz, CH$_3$), 1.55-1.59 (2H, m, CH$_2$-CH$_3$), 2.54 (3H, s, CH$_3$), 2.63 (2H, t, J=7.2 Hz, ArCH$_2$), 7.35 (2H, d, J=8.3 Hz, H$_{Ar}$), 7.89 (2H, d, J=8.3 Hz, H$_{Ar}$), 7.94-7.98 (4H, m, H$_{Ar}$), 10.47 (1H, s, NH); $^{13}$C NMR (50 MHz, DMSO-d$_6$) $\delta_C$ 14.3 (CH$_3$), 24.6 (CH$_2$), 27.1 (CH$_3$CO), 37.7 (CH$_2$), 120.0 (CH$_{Ar}$), 128.5 (CH$_{Ar}$), 129.1 (CH$_{Ar}$), 130.0 (CH$_{Ar}$), 132.5 (C$_q$), 132.7 (C$_q$), 144.4 (C$_q$), 147.2 (C$_q$), 166.6 (CO), 197.3 (CO); LC/MS (AP−) t$_r$=2.4 min (99.1%), m/z 280.2 (M−H).

N-(4-Acetyl-phenyl)-2,5-dichloro-benzamide
(CCM01043, STX1464)

Reaction of 2,5-dichlorobenzoic acid (300 mg, 1.50 mmol) in thionyl chloride (3.5 mL) then with 4-aminoacetophenone (85 mg, 0.63 mmol) in presence of triethylamine (90 μL, 0.65 mmol) in THF (6 mL) according to method B gave N-(4-acetyl-phenyl)-2,5-dichloro-benzamide (150 mg, 0.48 mmol, 76% yield) as a orange powder after purification by crystallisation in DCM.

R$_f$: 0.35 (Ethyl acetate/hexane, 4:6); $^1$H NMR (270 MHz, DMSO-d$_6$) $\delta_H$ 2.49 (3H, s, CH$_3$), 7.55-7.56 (2H, m, H$_{Ar}$), 7.73 (1H, dd, J=1.0; 2.0 Hz, H$_{Ar}$), 7.75-7.78 (2H, m, H$_{Ar}$), 7.91-7.94 (2H, m, H$_{Ar}$), 10.86 (1H, s, NH).

N-(4-Acetyl-phenyl)-4-methoxy-benzamide
(CCM01047, STX1468)

Reaction of 4-aminoacetophenone (74 mg, 0.55 mmol) in THF (6 mL) with p-anisoyl chloride (90 mg, 0.65 mmol) in presence of triethylamine (90 μL, 0.65 mmol) according to method A gave N-(4-acetyl-phenyl)-4-methoxy-benzamide (110 mg, 0.41 mmol, 75% yield) as a white powder after washing by dichloromethane.

Mp 222-223° C.; $R_f$: 0.35 (Ethyl acetate/DCM, 1:9); $^1$H NMR (270 MHz, DMSO-d$_6$) $\delta_H$ 2.53 (3H, s, CH$_3$), 3.83 (3H, s, OCH$_3$), 7.05-7.08 (2H, m, H$_{Ar}$), 7.93-7.98 (6H, m, H$_{Ar}$), 10.38 (1H, s, NH); $^{13}$C NMR (50 MHz, DMSO-d$_6$) $\delta_C$ 27.1 (CH$_3$CO), 56.1 (CH$_3$), 114.4 (CH$_{Ar}$), 120.0 (CH$_{Ar}$), 127.2 (C$_q$), 130.0 (CH$_{Ar}$), 130.5 (CH$_{Ar}$), 132.4 (C$_q$), 144.5 (C$_q$), 162.8 (C$_q$), 166.0 (CO), 197.3 (CO).

N-(4-Acetyl-phenyl)-3-methoxy-benzamide (CCM01048, STX1469)

Reaction of 4-aminoacetophenone (72 mg, 0.53 mmol) in THF (6 mL) with m-anisoyl chloride (90 µL, 0.65 mmol) in presence of triethylamine (90 µL, 0.65 mmol) according to method A gave N-(4-acetyl-phenyl)-3-methoxy-benzamide (110 mg, 0.41 mmol, 77% yield) as a white powder after washing by dichloromethane.

Mp 152-154° C.; $R_f$: 0.35 (Ethyl acetate/DCM, 1:9); $^1$H NMR (270 MHz, DMSO-d$_6$) $\delta_H$ 2.49 (3H, s, CH$_3$), 3.78 (3H, s, OCH$_3$), 7.12 (1H, ddd, J=1.0; 2.7; 8.1 Hz, H$_{Ar}$), 7.37-7.44 (2H, m, H$_{Ar}$), 7.49 (1H, ddd, J=1.0; 1.5; 7.4 Hz, H$_{Ar}$), 7.85 7.94 (4H, m, H$_{Ar}$), 10.48 (1H, s, NH); $^{13}$C NMR (50 MHz, DMSO-d$_6$) $\delta_C$ 27.4 (CH$_3$CO), 56.2 (OCH$_3$), 113.9 (CH$_{Ar}$), 118.5 (CH$_{Ar}$), 120.4 (CH$_{Ar}$), 120.9 (CH$_{Ar}$), 130.2 (CH$_{Ar}$), 130.5 (CH$_{Ar}$), 132.9 (C$_q$), 136.8 (C$_q$), 144.4 (C$_q$), 160.1 (C$_q$), 166.6 (CO), 197.5 (CO).

DETAILED DESCRIPTION OF FIGURES

Separation of Cortisone and Cortisol

Several solvent systems claiming to separate cortisone from cortisol are detailed in the literature[30, 31]. Before running an assay, 10 mg/ml solutions of cortisone and cortisol were prepared in IMS and 50 µl aliquots were spotted separately onto a silica gel TLC plate 3 cm from the bottom edge and 2.5 cm apart. The plate was run in a TLC tank in 200 ml of CH$_2$Cl$_2$: IMS 92: 8 v/v [30] until the solvent front reached the top of the plate. The plate was air dried and sprayed with 0.1% Rhodamine B in IMS to visualise the spots. The Table below describes the separation obtained.

TABLE

Separation of cortisone from cortisol by TLC

| Steroid | Distance run from origin (cm) | Solvent front migration/ steroid migration (cm) |
|---|---|---|
| Cortisone | 7.5 | 2.3 |
| Cortisol | 4.5 | 3.8 |

The separation was considered adequate for use in an enzyme assay.

FIG. 1 (Extraction Efficiencies Obtained with Four Extraction Methods)

The literature details several methods of extracting cortisol from aqueous solution[30, 31]. In order to select a method for use, a $^{14}$C-labelled cortisol was obtained from NEN. A stock was prepared in PBS containing 4000 DPM in 50 µl with cold cortisol (1 µg) added as a carrier. The final ethanol concentration was 0.4%. Aliquots of this solution were added to glass tubes (100 µl) and the following extractions were carried out: 1.1 ml CH$_2$Cl$_2$, vortex and pass through phase separating filter paper (Whatman, IPS) 2.1 ml ethyl acetate, vortex and pass through phase separating filter paper 3.1 ml CH$_2$Cl$_2$ and 200 µl 0.05% CaCl$_2$, vortex, centrifuge (500×g for 5 min) and remove upper aqueous phase 4.1 ml ethyl acetate and 200 µl 0.05% CaCl$_2$, vortex, centrifuge (500×g for 5 min) and collect upper organic phase. The organic phases were dried and the residues were taken up in 100 µl IMS. An aliquot of this (50 µl) was spotted onto a TLC plate and run as before. Following visualisation with Rhodamine B, the spots were scraped into scintillation vials and counted on a liquid scintillation counter (TriCarb) in 5 ml Ultima gold scintillant. Extraction efficiencies were calculated and are given in FIG. 1.

Figure 2:
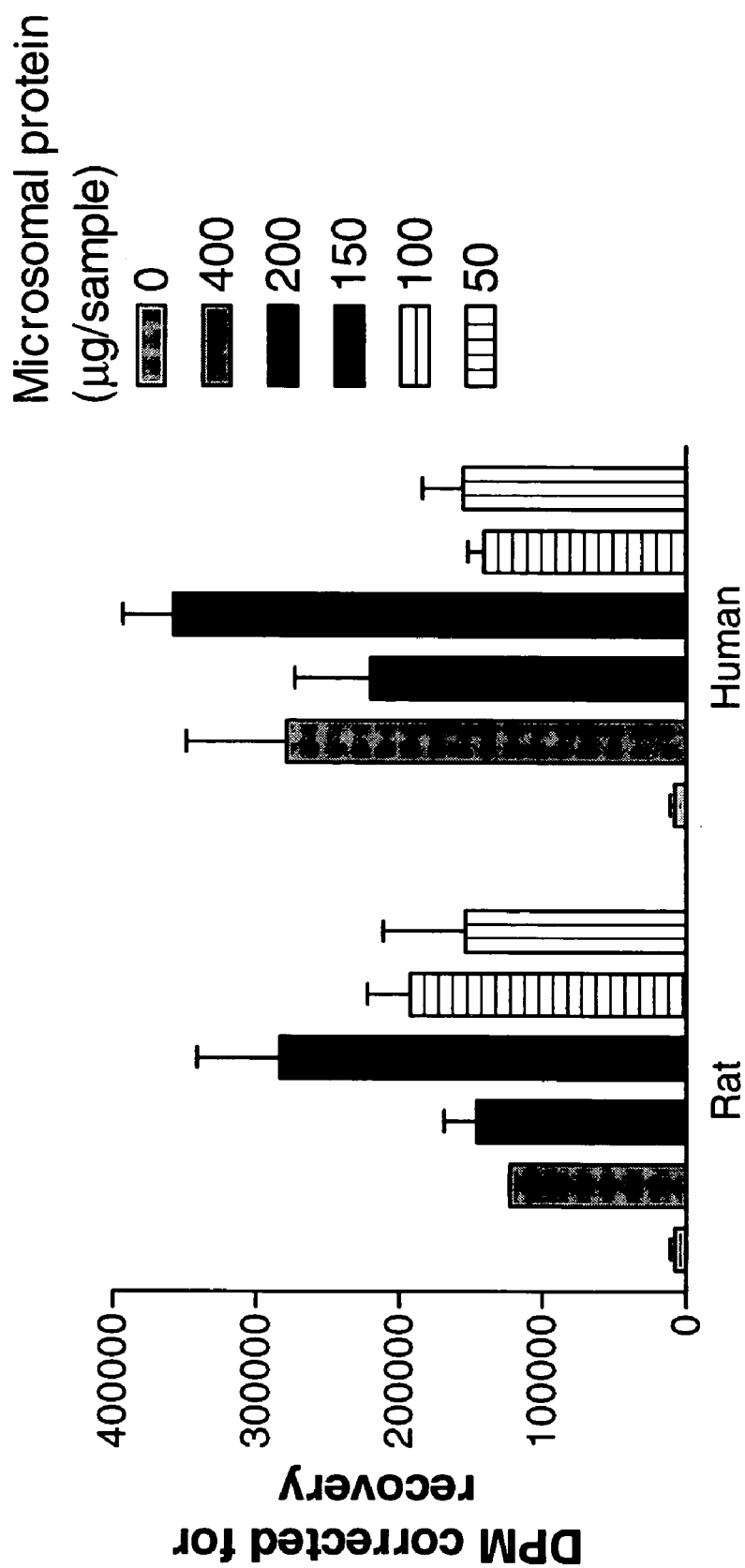
FIG. 2 is a graph showing a comparison of 11β-HSD1 activity in rat and human hepatic microsomes.

Assay of Human and Rat Hepatic Microsomal 11β-HSD1 Activity using a TLC Separation of Substrate from Product FIG. 2 (Comparison of 11β-HSD1 Activity in Rat and Human Hepatic Microsomes)

This experiment was carried out to compare the enzyme activity in hepatic microsomes from human and rat and to assess minimum microsomal protein concentrations necessary for reasonable measurement of enzyme activity. The assay was carried out in Buffer 2 and the cortisone concentration used was 2 µM containing 0.5 µCi per incubation $^3$H-cortisone. Rat and human hepatic microsomes were tested at concentrations ranging from 400 µg to 50 µg microsomal protein per incubation in a final incubation volume of 100 µl in glass tubes. Buffer was substituted for microsomal protein for blanks. Samples were incubated for 1 h in a shaking water bath at 37° C. and the assay was stopped by the addition of 1 ml ethyl acetate. To correct for recovery, 50 µl $^{14}$C-cortisol (approximately 4000 DPM per tube) was added to the samples followed by 200 µl 0.05% CaCl$_2$. The samples were vortexed and centrifuged as detailed in 2.1. The upper organic phase was removed into clean tubes and dried down. The residue was taken up in 100 µl IMS and 50 µl aliquots were spotted onto TLC plates which were run as described in 2.1. DPM were measured on a TriCarb liquid scintillation counter using a dual label programme. Recovery was determined from the DPM obtained in 50 µl $^{14}$C-cortisol solution which was counted with the samples. The results are given in FIG. 2.

It had been expected that there would be higher activity in the rat microsomes but this was not the case. Using 50 µg microsomal protein per well the activities of the rat and human enzymes were quite similar, rat microsomal activity was 0.7 pmol/mg/min and human was 0.5 pmol/mg/min. Good activity was detected in the human microsomes although this was not particularly related to microsomal protein concentration. It was suspected that the concentration range examined was too high so in the next experiment a lower range was tested. Also, the dependence of apparent enzyme activity with incubation time was looked at. A linear relationship between DPM and incubation time would indicate that increases over blank were due to enzyme activity and not due to an artefact.

Figure 3:
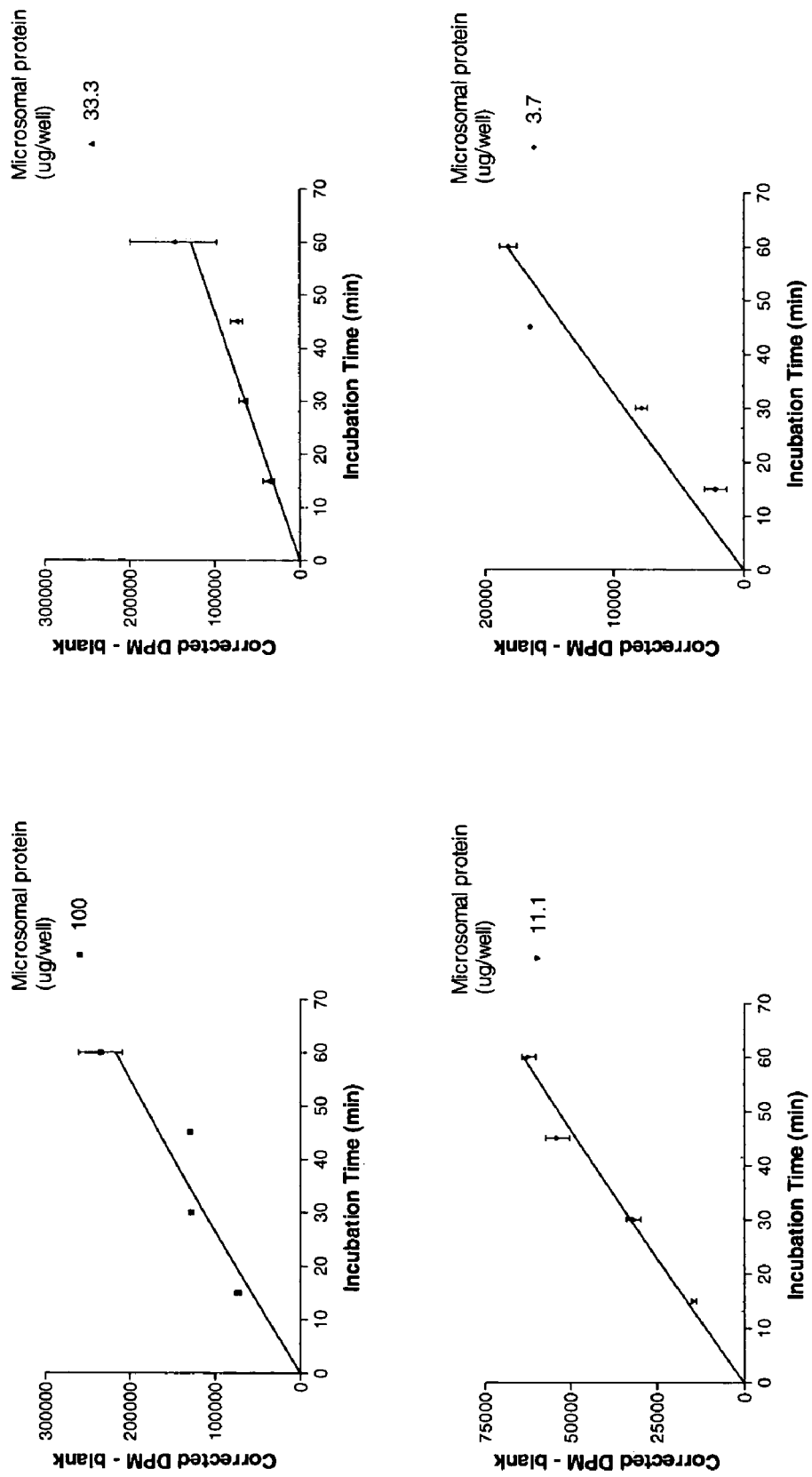
FIG. 3 is a series of graphs showing the effect of incubation time on human microsomal 11β-HSD1 activity
Figure 4:
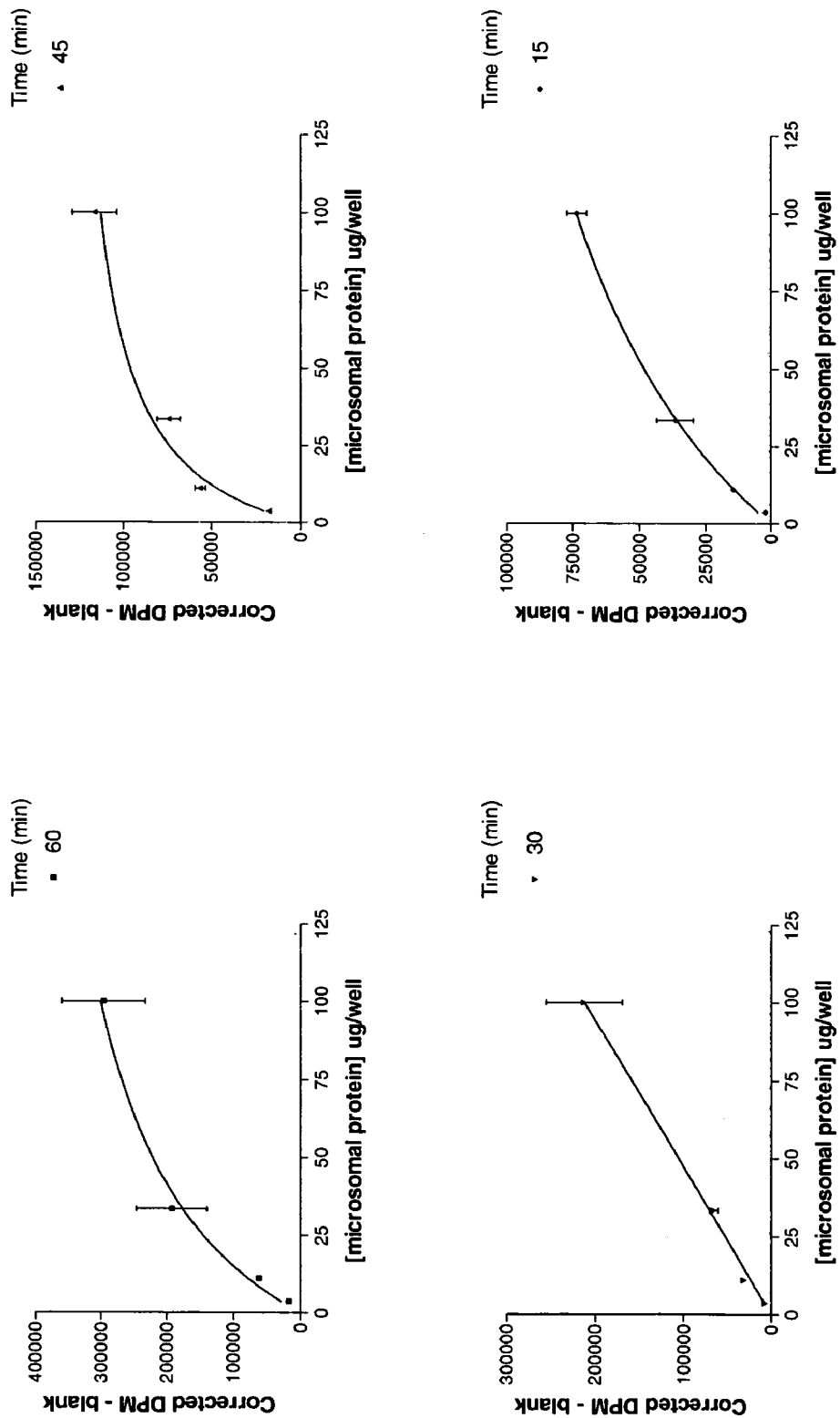
FIG. 4 is a series of graphs showing the effect of microsomal protein concentration on human microsomal 11β-HSD1 activity.

FIG. 3 (Effect of Incubation Time on Human Microsomal 11β-HSD1 Activity) and FIG. 4 (Effect of Microsomal Protein Concentration on Human Microsomal 11β-HSD1 activity)

In the next test, the same assay method was followed except that only human hepatic microsomes were examined and the concentration range of these was from 3.7 µg per sample to 100 µg per sample. The samples were incubated for 60 min, 45 min, 30 min or 15 min in a shaking water bath at 37° C. and were stopped, extracted and the substrate and product were separated as detailed above. FIG. 3 and FIG. 4 illustrate the results:

Conclusion (FIG. 3):
There is linearity of enzyme activity with incubation times up to 30 min with all microsomal protein concentrations tested.

Conclusion (FIG. 4):
Enzyme activity is linear with microsomal protein concentrations below 30 µg per sample FIG. 5 (Substrate (Cortisone) Saturation Curve for Human Hepatic Microsomal 11β HSD1)

Figure 5:
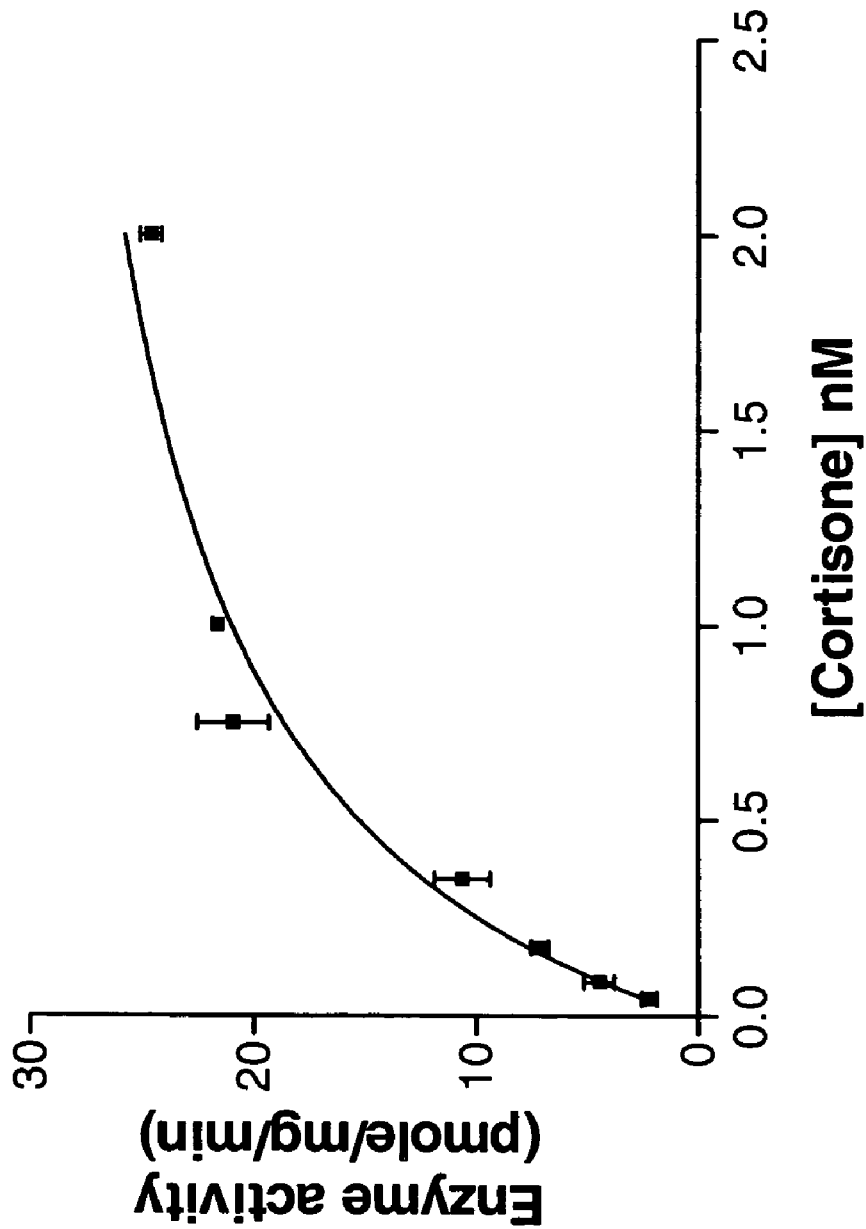
FIG. 5 is a graph showing the substrate (cortisone) saturation curve for human hepatic microsomal 11β HSD1.

Substrate requirement was examined using the classical assay. The DPM in each group was kept constant (0.5 µCi/sample) and the cold cortisone was varied from 2 µM down to 43.8 nM. The assay was carried out with 10 µg microsomal protein per sample and the incubation time was 30 min at 37° C. The buffer used for this assay was Buffer 1 FIG. 5 shows the data obtained.

Figure 6:
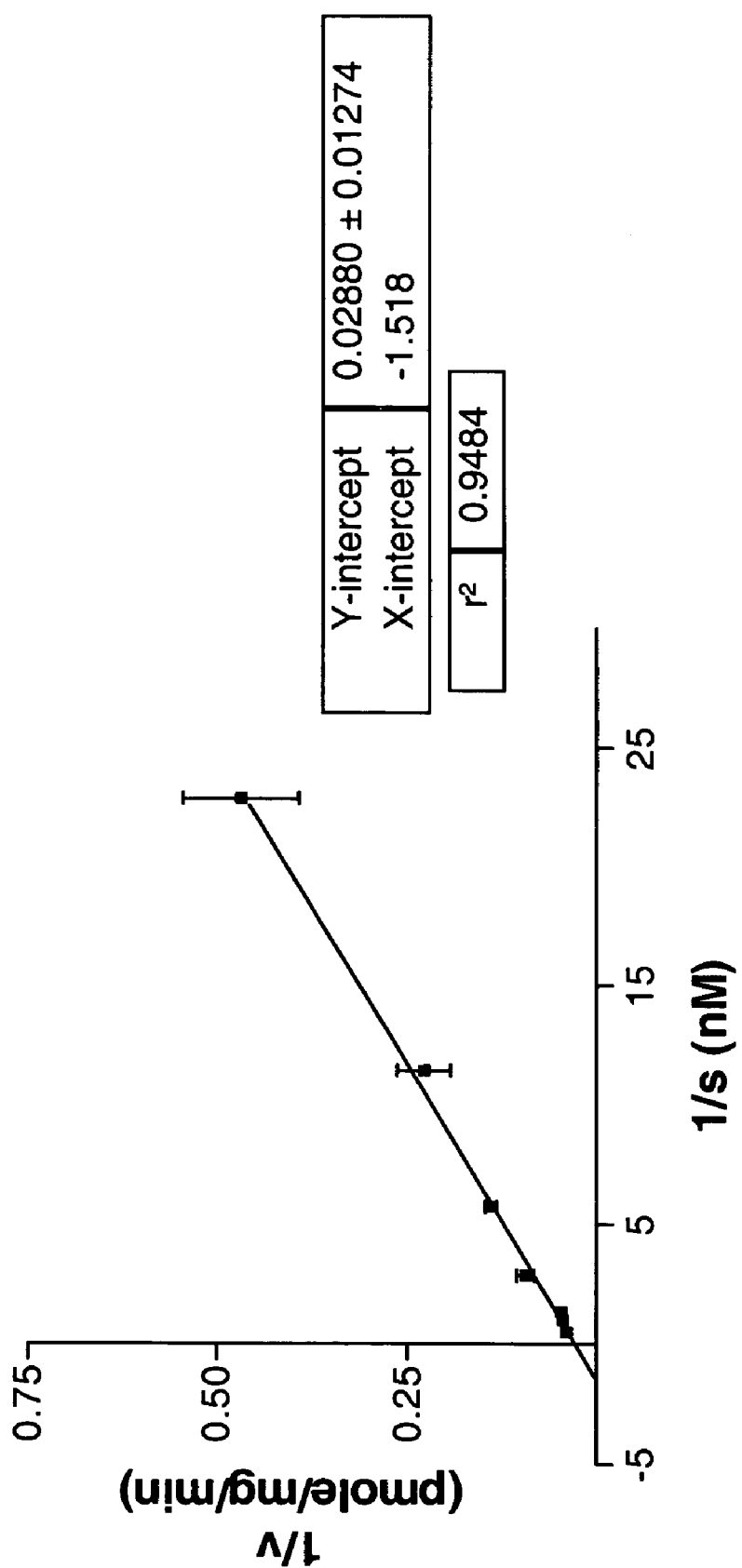
FIG. 6 is a Lineweaver-Burke plot.

FIG. 6 (Lineweaver-Burke Plot)

Figure 7:
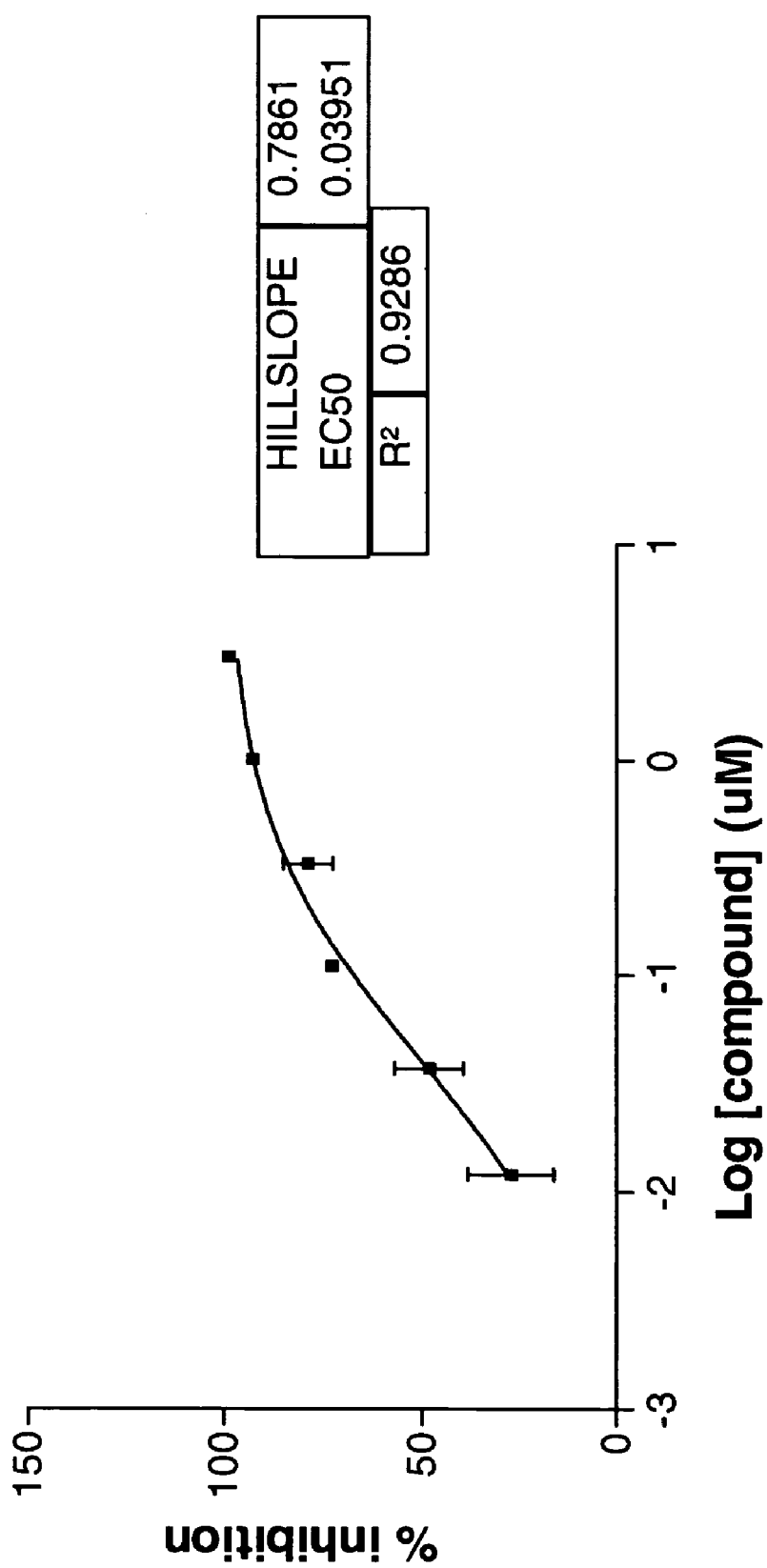
FIG. 7 is a graph showing the IC$_{50}$ determination for Glycyrrhetinic acid.
Figure 8:
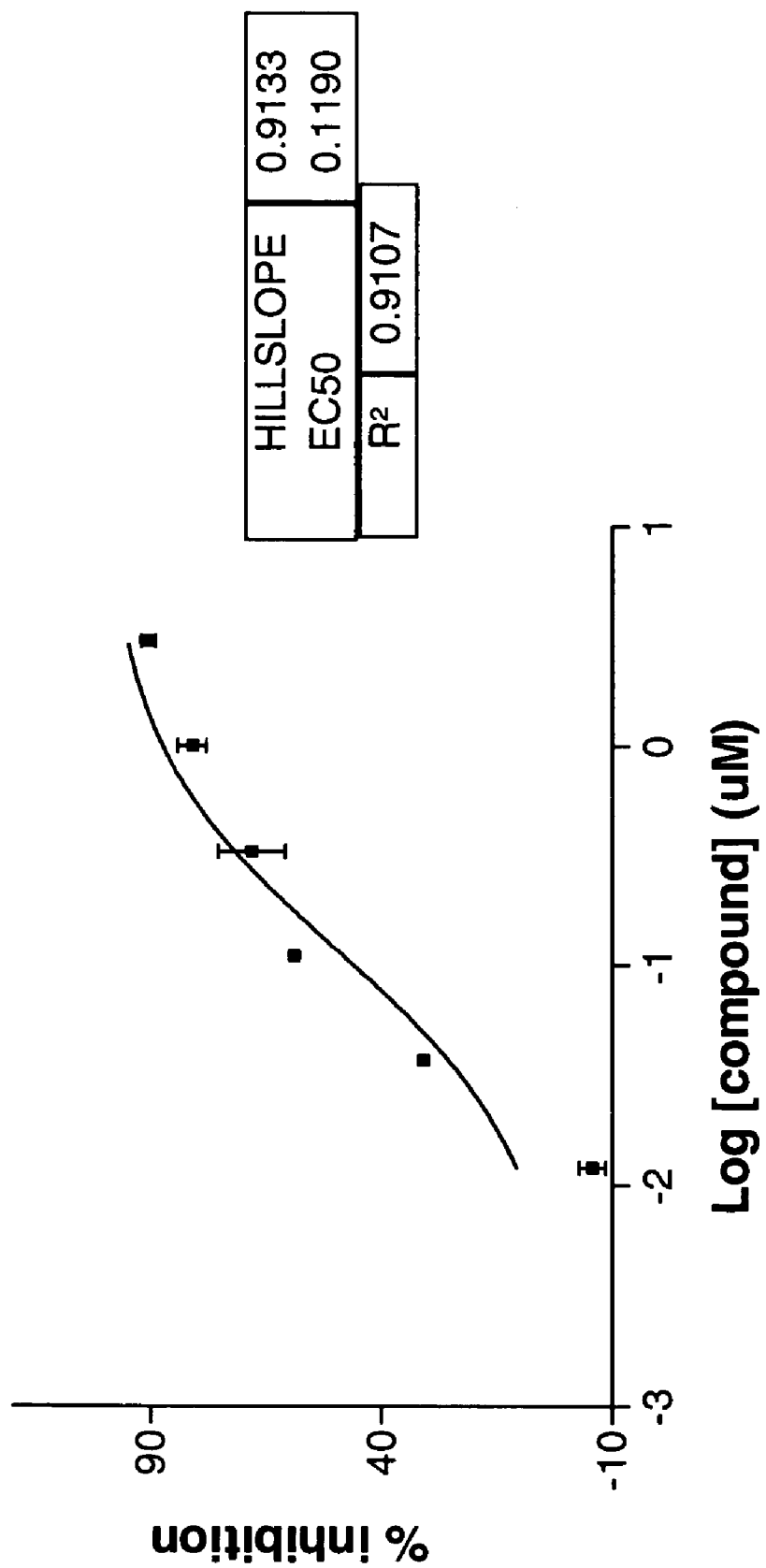
FIG. 8 is a graph showing the IC$_{50}$ determination for Carbenoxolone.

A double reciprocal plot of these data (Lineweaver-Burke) gives an apparent Km for cortisone of 660 nM, but it should be noted that it is unlikely that initial enzyme activity rates were measured at the lower [cortisone] over a 30 mins incubation. FIG. 6 shows the Lineweaver-Burke plot obtained:

FIG. 7 ($IC_{50}$ Determination for Glvcvrrhetinic Acid) and FIG. 8 ($IC_{50}$ Determination for Carberioxolone)

In order to reproduce the inhibition data given in [14], it was decided to use the cortisone concentration quoted in the reference (175 nM) to examine compound activity, even though FIG. 5 and FIG. 6 suggest that this concentration is not saturating with 10 µg microsomal protein per 30 mins incubation at 37° C. The following experiment was carried out with a lower microsomal protein concentration (5 µg) in the same buffer conditions as in the last experiment (Buffer 1) over a 30 mins incubation at 37° C. in the presence of 175 nM cortisone (0.5 µCi/sample). Glycyrrhetinic acid and carbenoxolone were examined at concentrations from 3 µM to 0.012 µM (DMSO concentration 1% throughout) and the data are shown in FIG. 7 and FIG. 8.

The reported $IC_{50}$ for carbenoxolone is 330 nM [14], which is approximately three times less active than observed in the above experiment. It appears that these assay conditions support good enzyme activity which should be measurable in a 96 well plate method.

Cortisol Immunoassay

An enzyme immunoassay kit was obtained from Assay Designs, Inc. The antibody provided in the kit is a mouse monoclonal reported to cross react 100% with cortisol (the enzyme product) and <0.1% with cortisone (the enzyme substrate). The kit is designed for theanalysis of cortisol levels in saliva, urine, serum and plasma and also in tissue culture media, not for microsomal enzyme activity.

FIG. 9 (11β-HSD1 Activity Measured by Immunoassay)

Figure 9A:
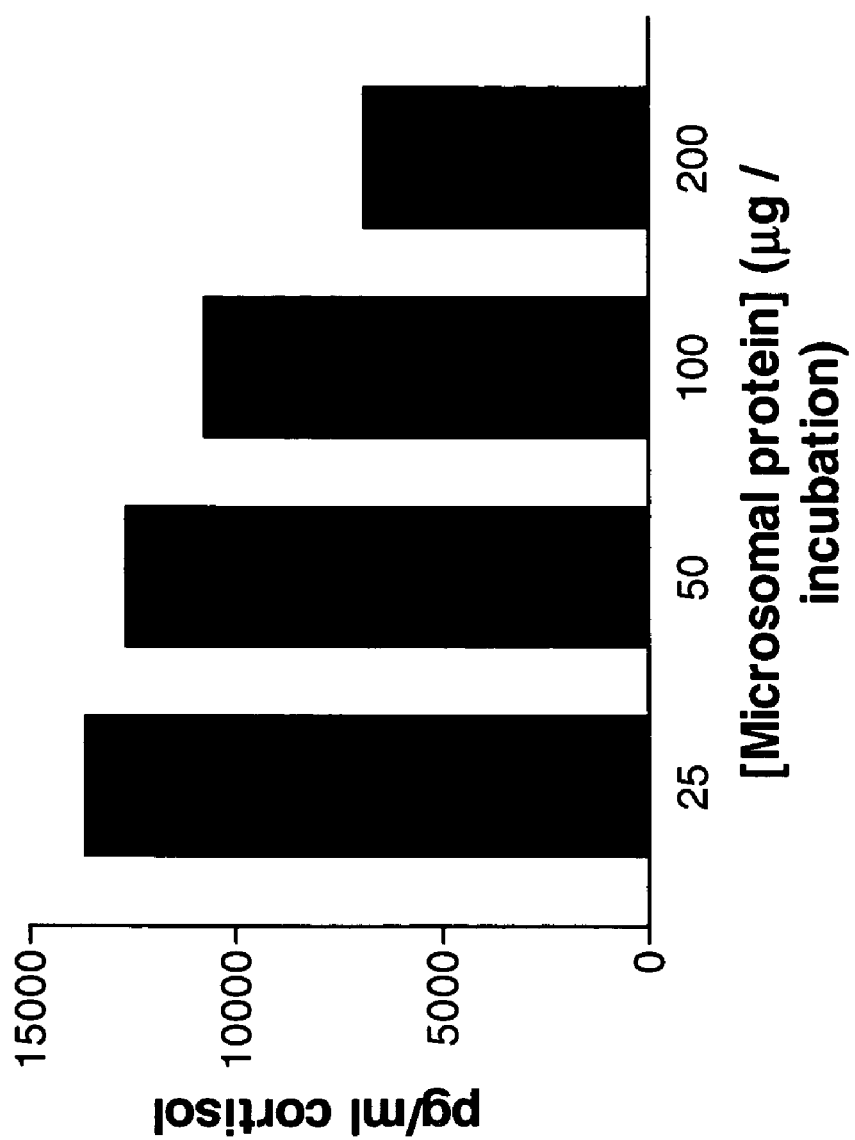
FIGS. 9(A), 9(B) and 9(C) are graphs showing the 11β-HSD1 activity measured by Immunoassay.
Figure 9B:
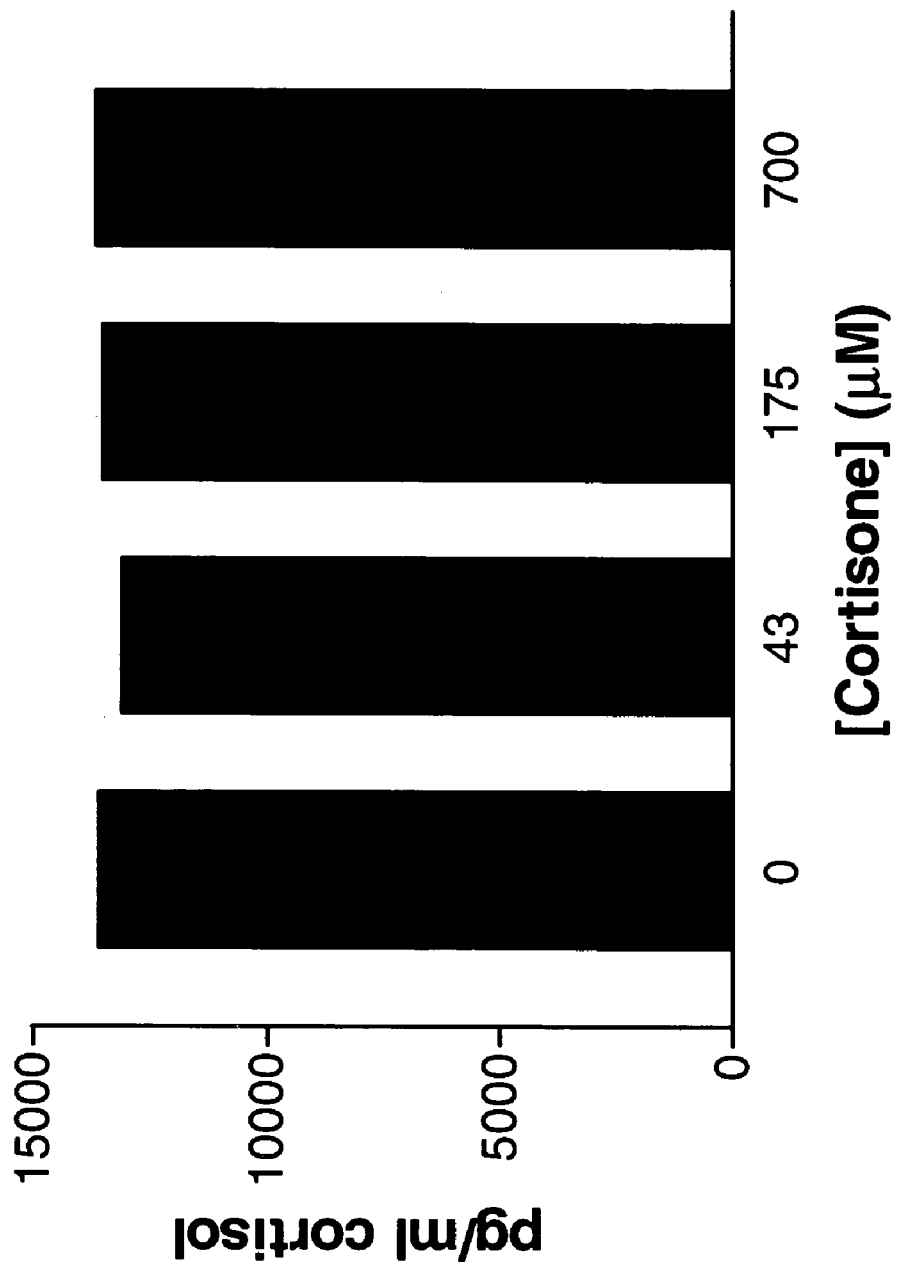
Figure 9C:
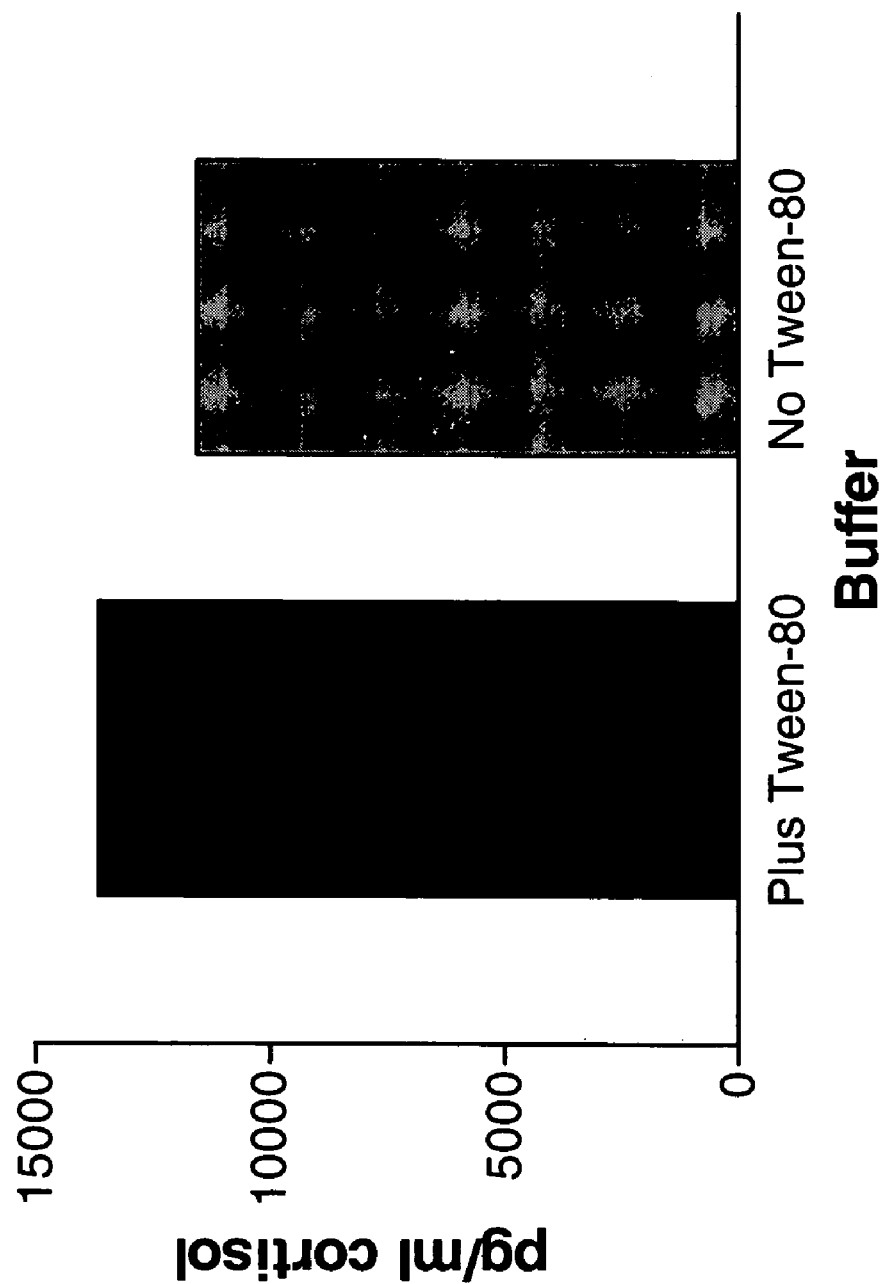

The methodology for the enzyme assay used with the kit was based on the paper by Barf et al. [14] Human hepatic microsomes were incubated in Buffer 1 at concentrations ranging from 25 µg protein per point to 200 µg protein per point in the presence of cortisone ranging from 44 nM to 700 nM for 1 h. Also, these groups were tested in the presence and absence of 0.9% Tween 80 since this detergent may improve the activity of enzymes involved in steroid metabolism. The basis of the assay is one of competition between the sample cortisol binding and the detector-cortisol binding. The assay detected the cortisol in the standard curve (313 pg/ml to 10,000 pg/ml) as expected but the signal obtained from the enzyme assay samples decreased with increasing microsomal protein concentration, suggesting that the presence of microsomes interfered with the immunoassay. FIGS. 9(A), 9(B) and 9(C) shows some of the data obtained.

FIG. 9(A) shows the effect of protein. Data taken from 700 µM cortisone group tested in the presence of Tween-80

FIG. 9(B) shows the effect of cortisone. Data taken from the 25 µg microsomal protein group tested in the presence of Tween-80

FIG. 9(C) shows the effect of Tween-80. Data taken from the 25 µg microsomal protein group tested in the presence of 700 µM cortisone.

Conclusions:
Microsomal protein may interfere with the immunoassay (FIG. 9(A))
Addition of exogenous cortisone had no effect on levels of cortisol detected in the enzyme assay samples (FIG. 9(B))
Inclusion of detergent in the enzyme assay buffer had only a slight effect (FIG. 9(C))

Figure 10:
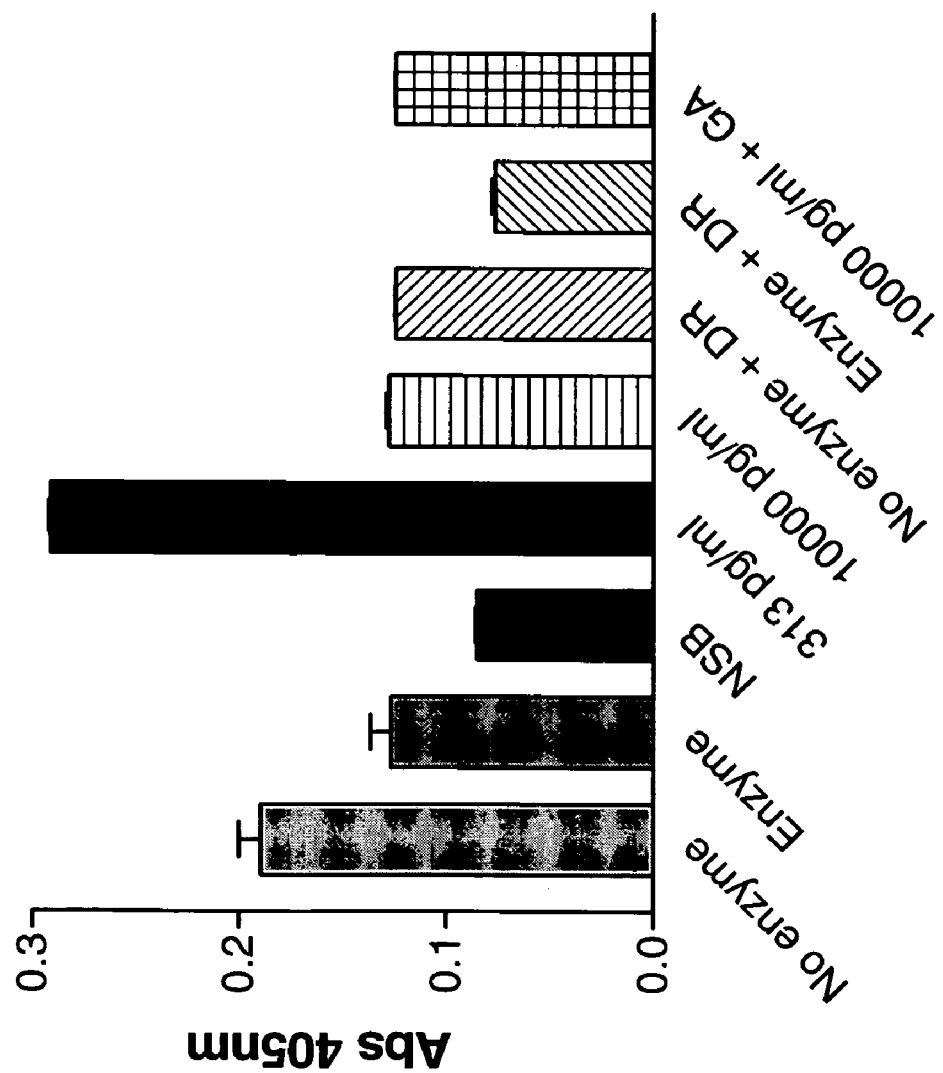
FIG. 10 is a graph showing the performance of the cortisol immunoassay: various experimental designs.

FIG. 10 (Performance of the Cortisol Immunoassay: Various Experimental Designs)

An 11β-HSD1 assay was carried out with 24 µg microsomal protein/sample and 2 µM cortisone substrate in buffer 2 Enzyme activity was also measured in samples following the addition of steroid displacement reagent (kit component) which releases cortisol from cortisol binding protein, if present in.the sample. The assay detected the cortisol in the standard curve.(313 pg/ml to 10,000 pg/ml). FIG. 10 shows the absorbance at 405 nm obtained for the different groups:

Conclusions:
The lowest and highest concentrations of the cortisol standard have been included in FIG. 10 as 313 pg/ml and 1000 pg/ml together with the NSB absorbance to show the dynamic range obtained in the assay.
Absorbance obtained in the presence of reaction mixture taken from samples incubatedwith microsomal protein ("Enzyme") are lower than those in the presence:
of reaction mixture not containing microsomal protein ("No enzyme") indicating increases in levels of cortisol.
In the presence of the kit steroid displacement reagent ("DR") these two reaction mixtures show the same pattern but the signal is depressed.
Glycyrrhetinic acid ("GA") in the presence of the top concentration of cortisol standard has no effect on the ability of the kit to measure cortisol concentrations.

Figure 11:
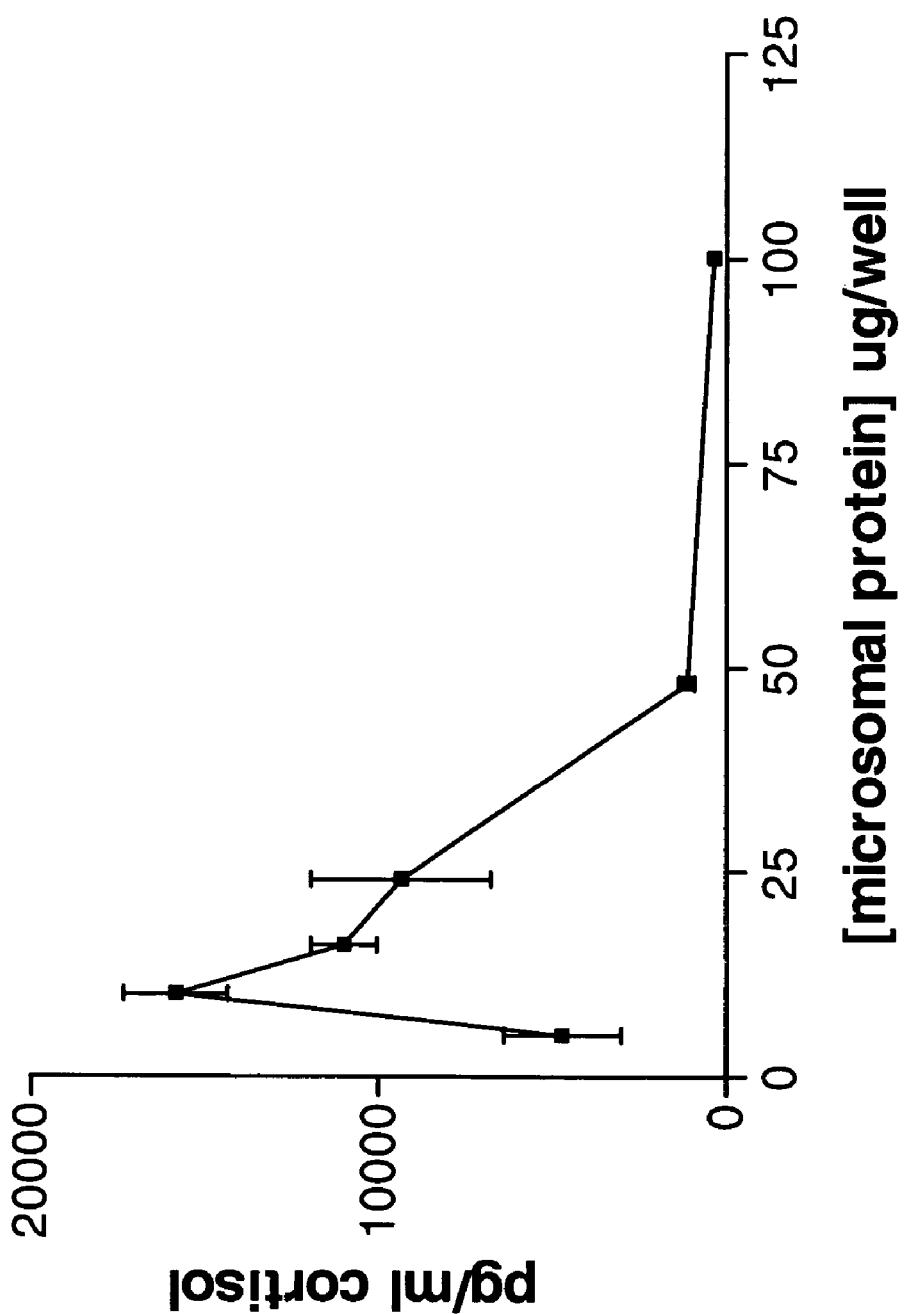
FIG. 11 is a graph showing the effect of increasing microsomal protein on measurement of 11β HSD1 activity detected by Assay Designs Immunoassay.

FIG. 11 (Effect of Increasing Microsomal Protein on Measurement of 1113 HSDβ Activity Detected by Assay Designs Immunoassay)

When the enzyme assay data was calculated as enzyme activity using the pg/ml cortisol indicated by the standard curve, the blank value was 47 pg/ml/min incubation and the enzyme activity was 119 pg/ml/min, a signal to noise of 2.5. Although the signal to noise obtained is rather poor, these data demonstrate that the antibody can bind the cortisol:AP conjugate and that this can be displaced by cortisol. An experiment was carried out to examine the effect of slightly increasing the microsomal protein concentration in an attempt to improve the signal to noise obtained. Microsomal protein was tested from 100 µg/incubation down to 5 µg/incubation using 2 µM cortisone in buffer 2. All other, conditions were identical to those detailed above. The results are shown in FIG. 11.

Conclusions:
Decreasing microsomal protein from 10 µg/incubation to 5 µg/incubation results in a corresponding decrease in enzyme activity.
Increasing microsomal protein above 10 µg/incubation results in a quenching of signal which may be due to the colour of the microsomes.
The dynamic range of this assay cannot be improved by increasing the microsomal protein concentration.

Figure 12:
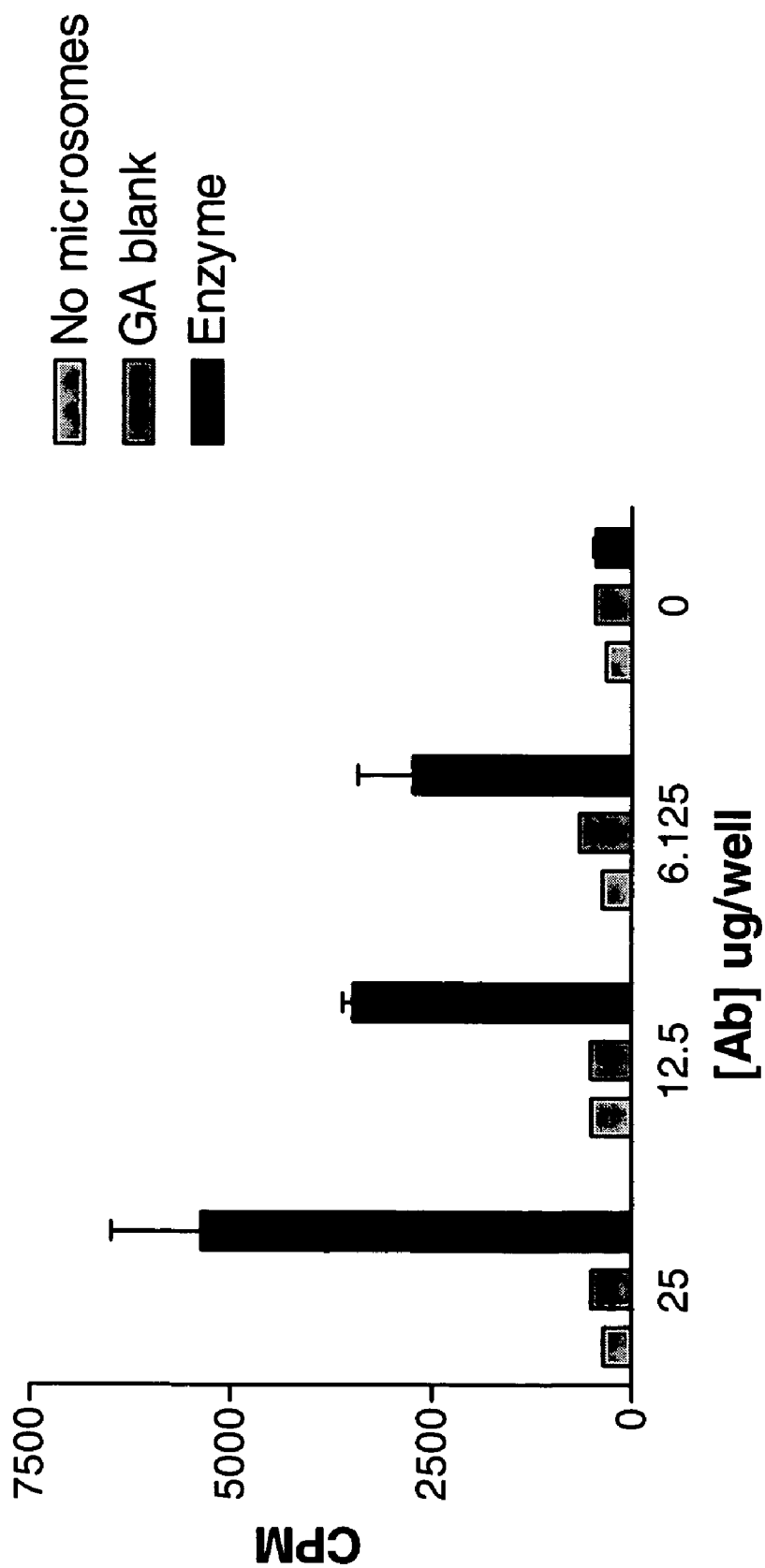
FIG. 12 is a graph showing the detection of 11β HSD1 activity by RIA using the Immunotech anti-cortisol antibody.

FIG. 12 (Detection of 11β HSD1 Activity by RIA Using the Immunotech Anti-Cortisol Antibody)

The next experiment was carried out to assess the Immunotech antibody. The enzyme assay was carried out in Buffer 2. The substrate (cortisone) concentration of 175 nM was chosen from the SPA method described by Barf et al. [14] with 0.5 µCi/well $^3$H-cortisone. The enzyme assay was carried out in a polypropylene plate in a final incubation volume of 100 µl containing 10 µg/well human hepatic microsomal protein. Blanks had either buffer substituted for microsomal protein or had 10 µl stop solution added prior to the microsomes. The assay was incubated at 37° C. for 30 mins and the reaction was terminated by the addition of the stop solution to all remaining wells. The Immunotech antibody was diluted in Buffer 3 to give 25 µg /100 µl down to 6.25 µg /100 µl. The antibody (100 µl) was added to test wells, 100 µl Buffer 3 was added to the antibody blank wells. The remainder of the procedures followed the 96 well plate RIA protocol exactly. Results demonstrating 11 β HSD1 activity using the Immunotech are shown in FIG. 12.

Conclusions:
Good enzyme activity was detected with this antibody.
The signal to noise with 12.5 and 6.1 µg antibody per well was similar hence it may be possible to reduce the antibody concentration.

Figure 13:
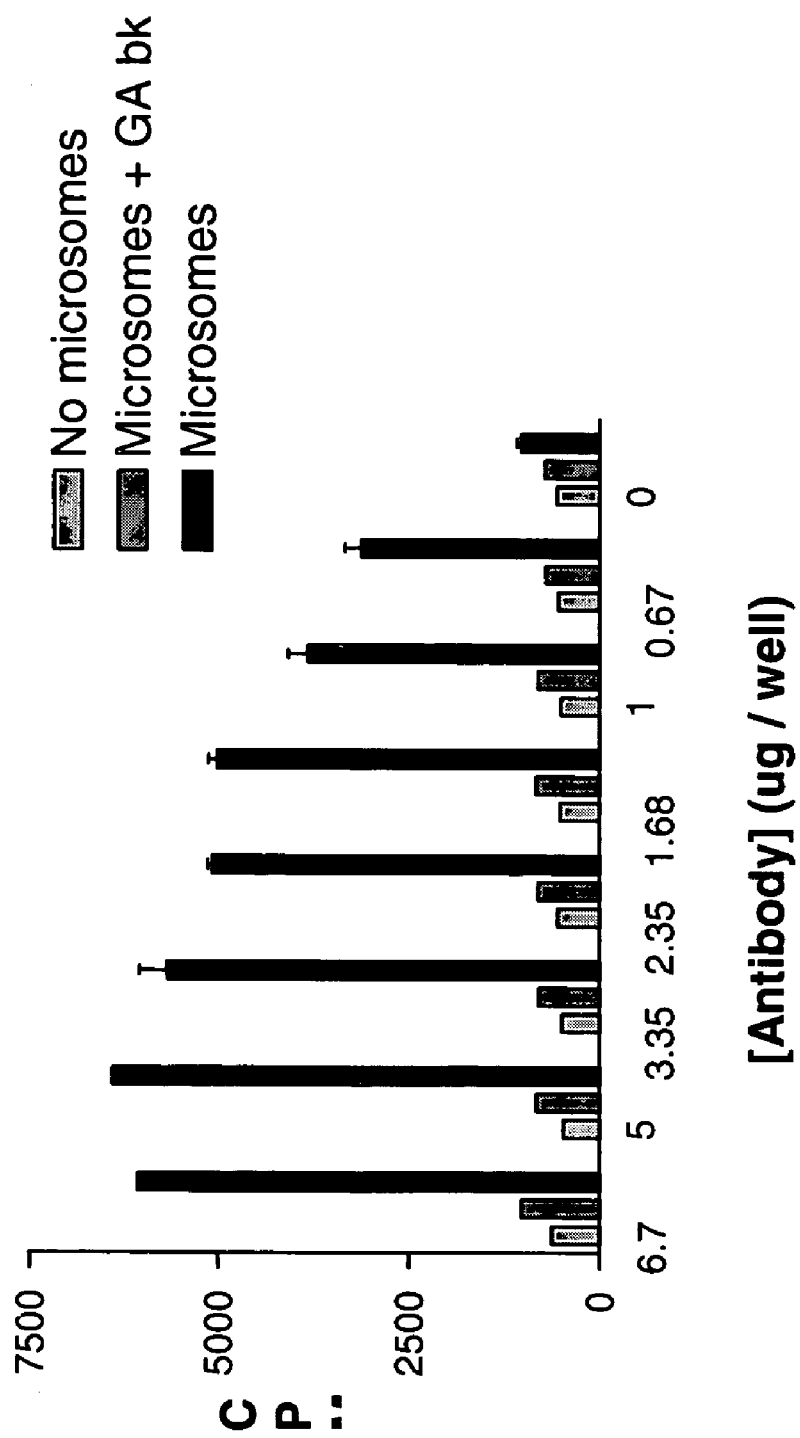
FIG. 13 is a graph showing the effect of lowering the Immunotech antibody concentration on the signal to noise (microsome group compared to GA blank group).
Figure 14:
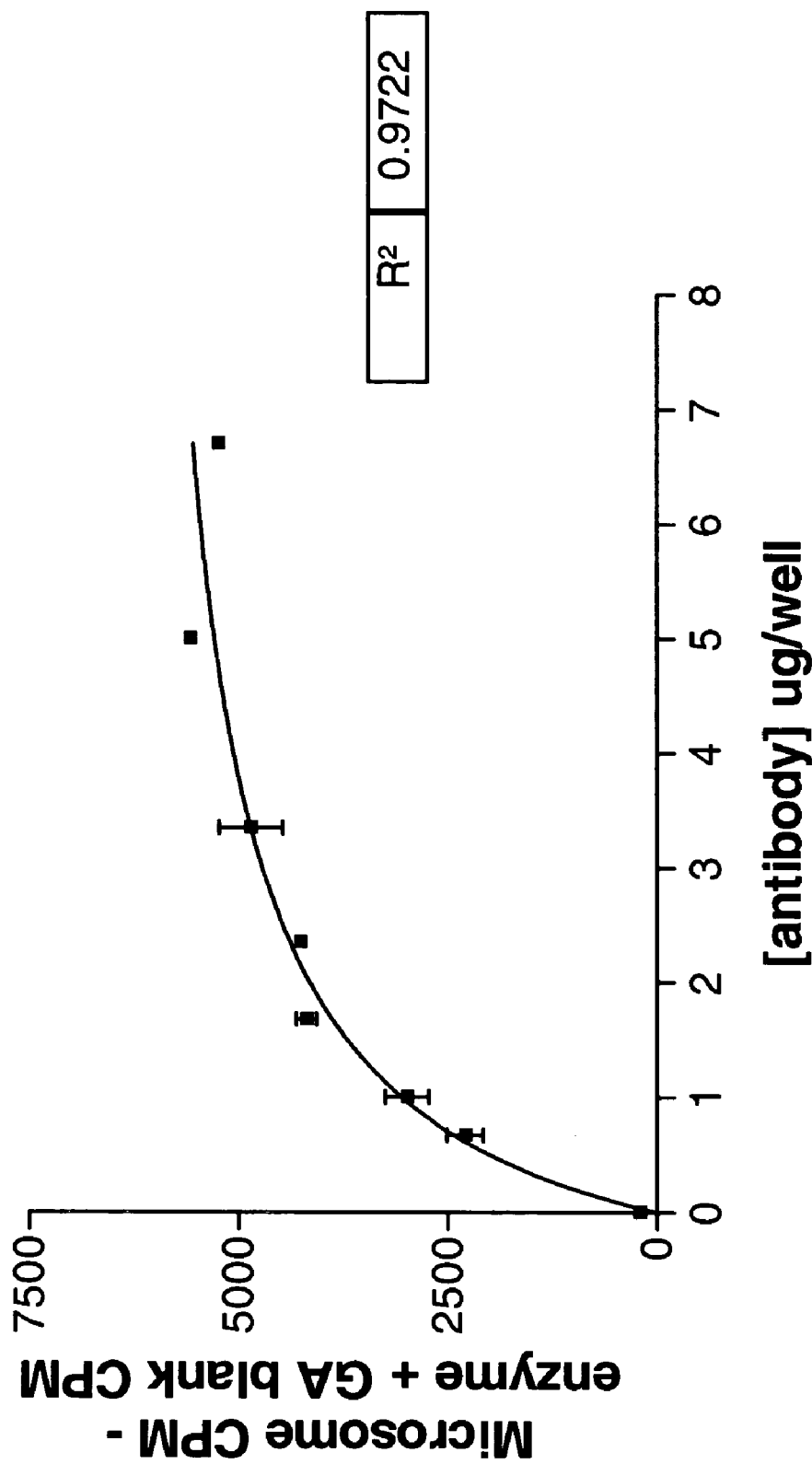
FIG. 14 is a graph showing the Immunotech antibody saturation curve for detection of 11β HSD1 activity by RIA.

FIG. 13 (Effect of Lowering the Immunotech Antibody Concentration on the Signal to Noise (Microsome Group Compared to GA Blank Group)) and FIG. 14 (Immunotech Antibody Saturation Curve for Detection of 11β HSD1 Activity by RIA)

The antibody titre was examined in the next test, investigating concentrations per well from 6.7 µg down to 0.67 µg. The usual 11β HSD1 assay was carried out except that the microsomal protein concentration was doubled to 20 µg/well in order to get the best signal to noise. The cortisone concentration was 175 nM and the enzyme assay buffer was Buffer 2. Each antibody concentration was tested against a "no enzyme" blank (buffer substituted for microsomes) and a "GA blank" (10 SIt stop solution added prior to microsomes) and a control group. The RIA was carried out exactly as indicated in the methods for assay in 96 wells. These results are shown in FIG. 13 and FIG. 14.

Conclusion:
The Immunotech antibody performed very well.
The saturation curve indicates that there is no difference in the detection of enzyme activity above 1.68 µg/well.
The antibody will be used at 1.7 µg/well.
The signal to noise ratio (microsome CPM/microsome+ GA blank CPM) with this concentration of antibody was 6 fold.

Figure 15:
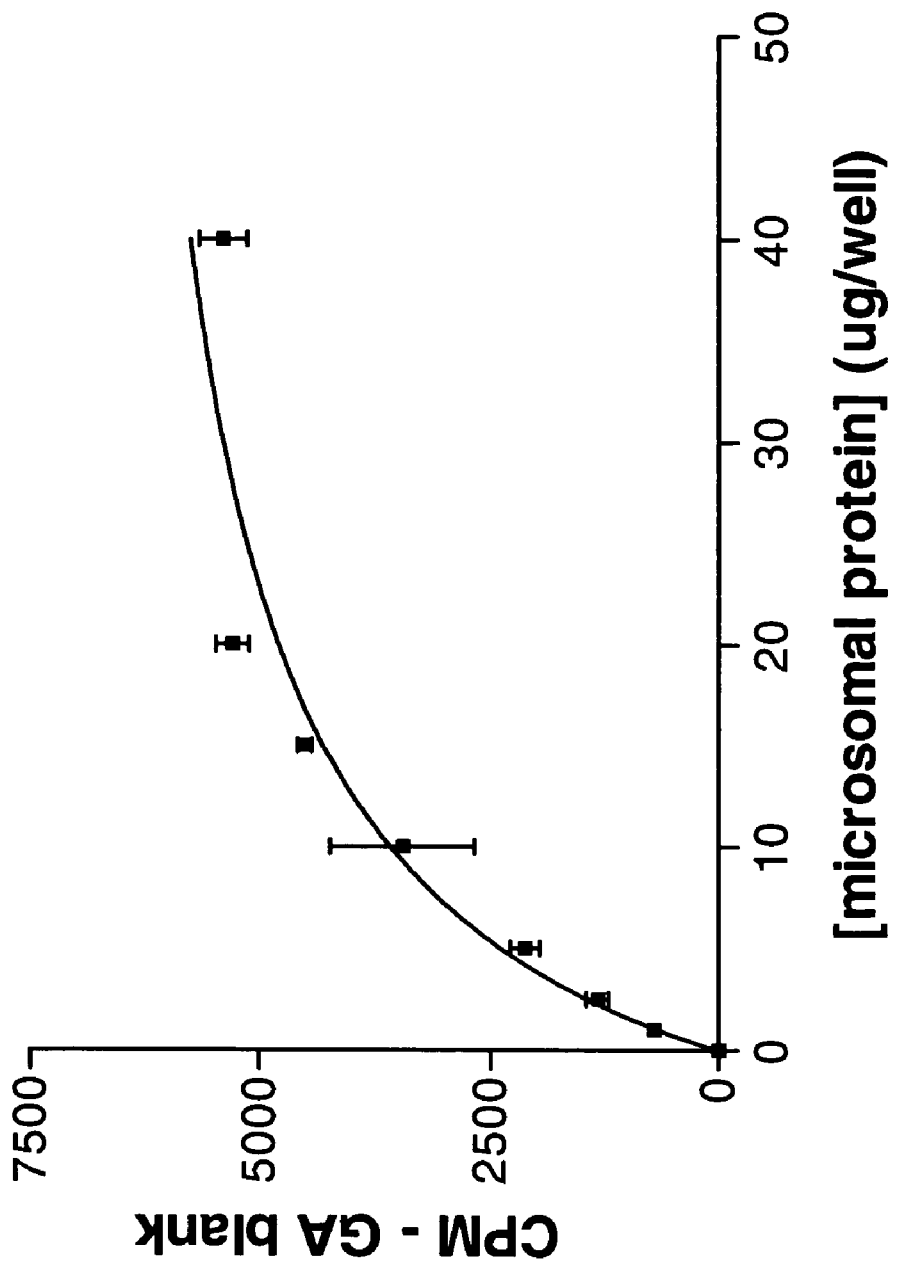
FIG. 15 is a graph showing the linearity of human hepatic microsomal 11β HSD1 activity detected by RIA.

FIG. 15 (Linearity of Human Hepatic Microsomal 11β HSD1 Activity Detected by RIA)

Linearity of enzyme activity with human hepatic microsomal protein concentration using RIA detection was examined in the next test. The usual 11β HSD1 assay was carried out except that the microsomal protein concentration was varied from 40 µg/well down to 1 µg/well. The cortisone concentration was 175 nM and the enzyme assay buffer was Buffer 2. 11β HSD1 activity was linear with protein up to concentrations of 20 µg /well confirming the results obtained with the classical enzyme assay (FIG. 4). Data from these experiments are shown in FIG. 15.

Figure 16:
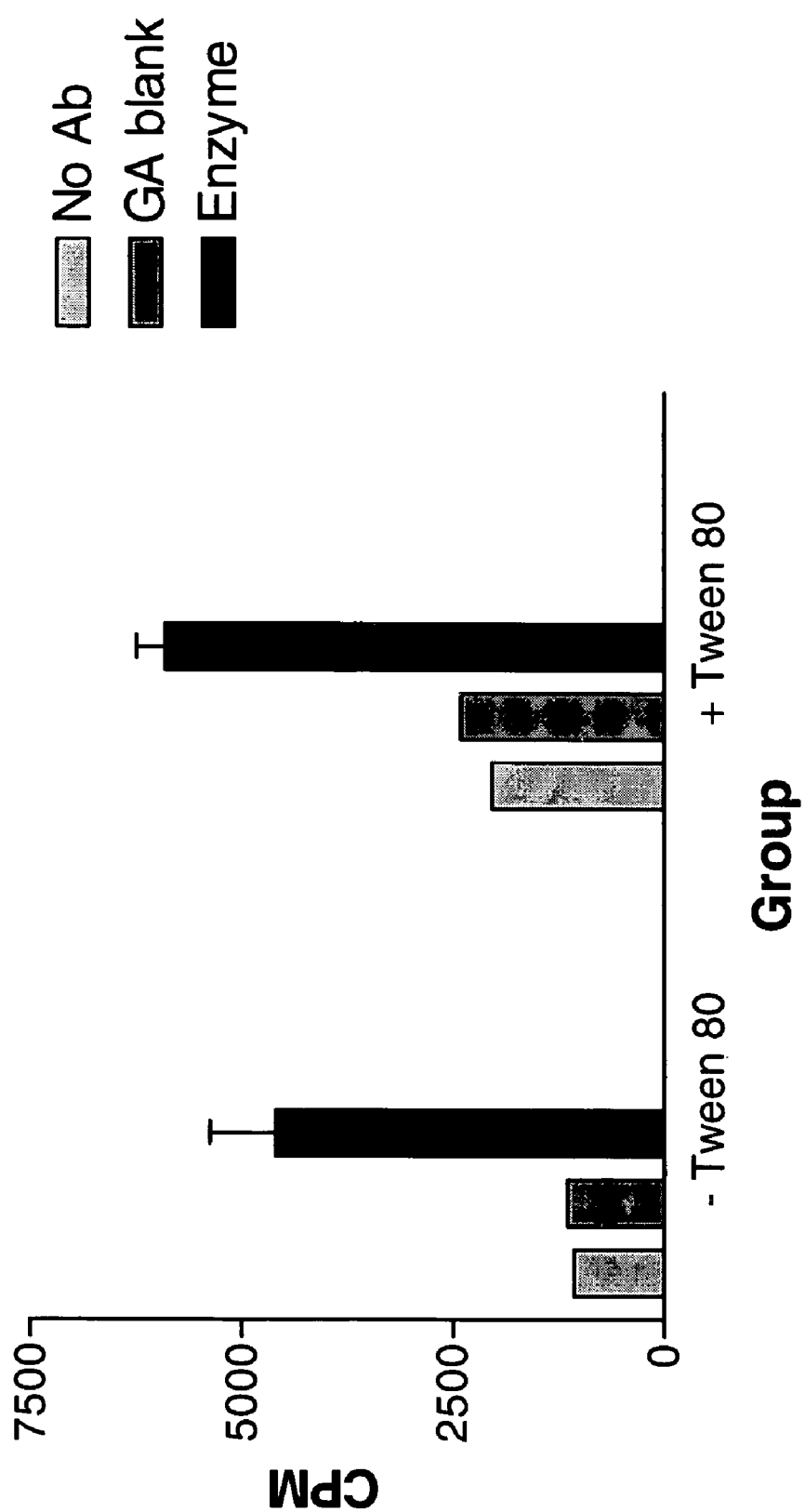
FIG. 16 is a graph showing the effect of Tween 80 on detection of human hepatic microsomal 11β HSD1 activity by RIA.

FIG. 16 (Effect of Tween 80 on Detection of Human Hepatic Microsomal 11β HSD1 Activity by RIA)

The effect of including Tween 80 in the enzyme assay buffer was also investigated. This assay was carried out in parallel with the assay above and under the same conditions except that the enzyme assay buffer (Buffer 2) contained 0.05% Tween 80. Microsomal protein was tested at four concentrations. Tween 80 was found to increase the blank CPM, reducing the signal to noise of the assay. The data in FIG. 16 are taken from the group tested with 10 µg/well microsomal protein, but the same effect was seen with all protein concentrations examined.

Conclusion:
Including 0.05% Tween 80 in the enzyme assay buffer increases the CPM obtained in the blanks thereby reducing the signal to noise to 3 fold (compared to 5 fold in the absence of Tween 80).

Figure 17:
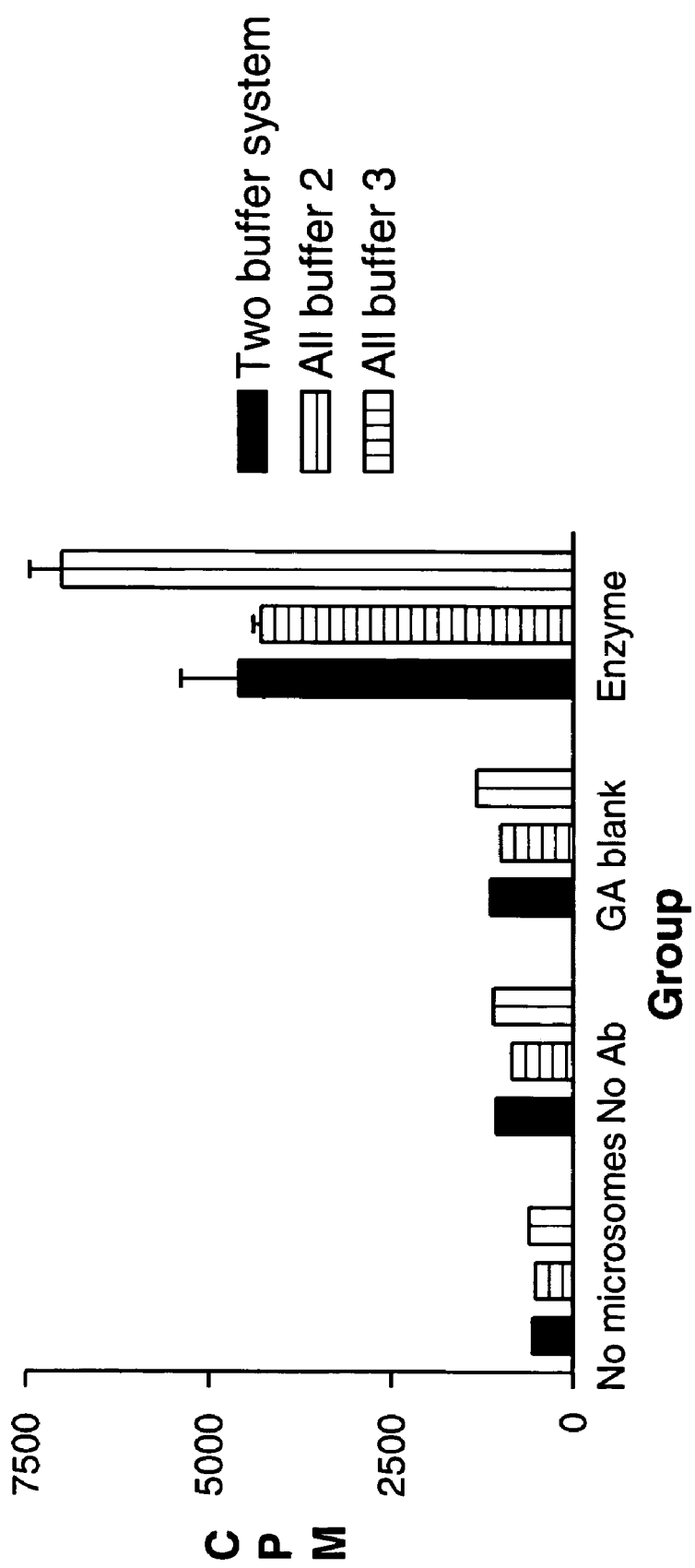
FIG. 17 is a graph showing the effect of buffer systems on detection of human hepatic microsomal 11β HDS1 activity by RIA.

FIG. 17 (Effect of Buffer Systems on Detection of Human Hepatic Microsomal 11β HDS1 Activity by RIA)

To simplify the protocol such that both enzyme assay and RIA stages are carried out in the same buffer, both phases were carried out in either enzyme assay buffer (buffer 2) or buffer 3 (RIA buffer). The microsomal protein concentration used was 10 µg/well and the cortisoneconcentration was 175 nM. Performing both enzyme assay and RIA in enzyme assay buffer gave similar data to the two buffers system but performing both enzyme assay and RIA in Buffer 3 appeared to improve the data slightly. These results are highlighted in FIG. 17.

Figure 18:
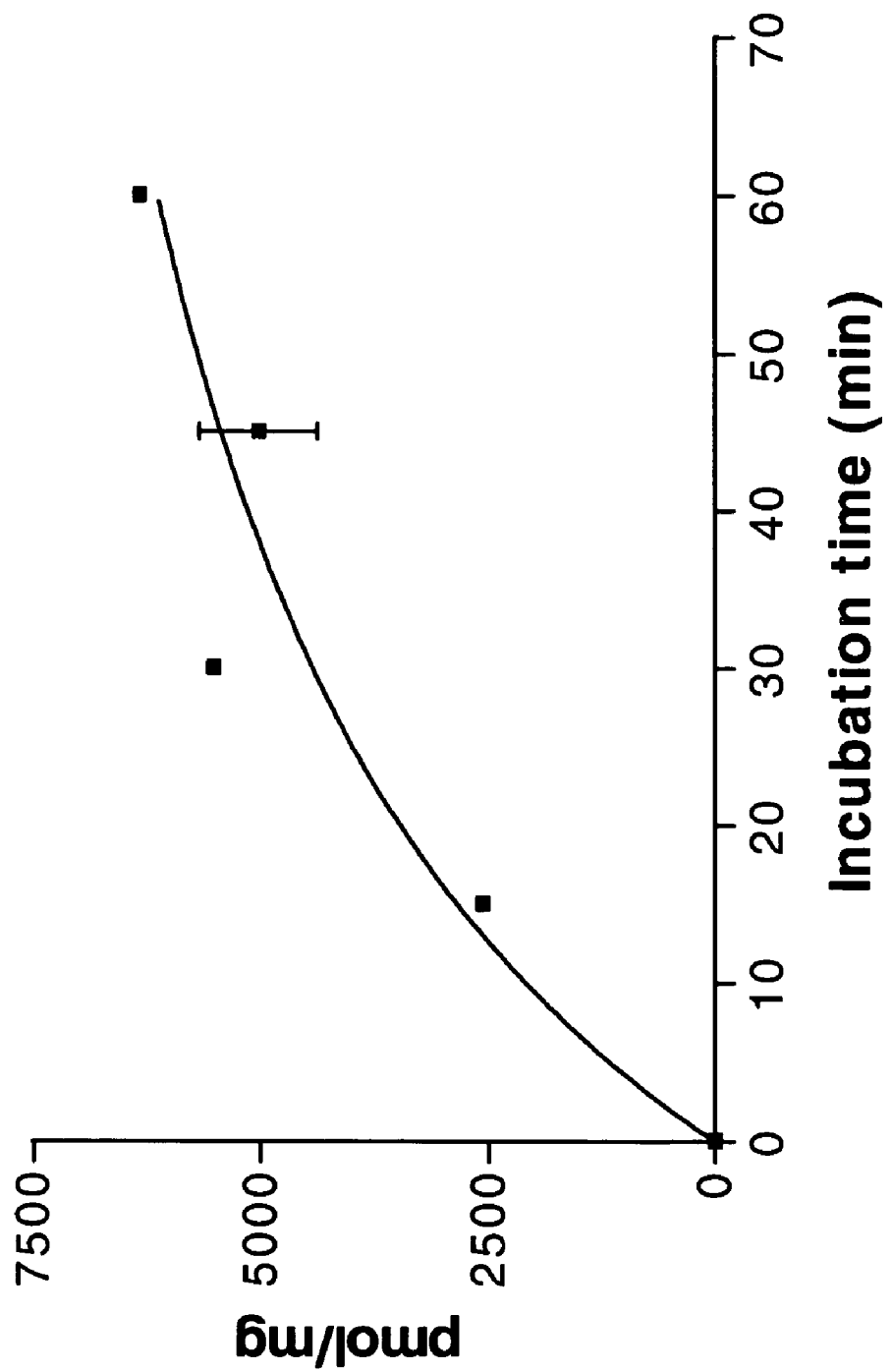
FIG. 18 is a graph showing the linearity of human hepatic microsomal 11β HSD1 activity with incubation time detected by RIA.

FIG. 18 (Linearity of Human Hepatic Microsomal 11β HSD1 Activity with Incubation Time Detected by RIA)

Linearity of enzyme activity with incubation time was investigated. The enzyme assay was carried out exactly as indicated in the methods section in buffer 3 with 10 µg/well microsomal protein and with 175 nM cortisone. The reaction was stopped at the times indicated in FIG. 18 by the addition of 10 µl stop solution. The RIA was carried out exactly as indicated in the methods section. FIG. 18 illustrates these results.

Conclusion:
30 min incubation is within the linear range of enzyme activity with 10 µg/well microsomal protein and 175 nM substrate.

It is possible that 175 nM substrate is low. The apparent Km observed in the classical 11β HSD1 assay was 660 nM (FIG. 5 and FIG. 6), although these assays are end-point measurement, hence it is not certain that initial rates were measured in the low substrate groups with a 30 min incubation time. However, there are published Km values which suggest that the actual µm for cortisone in human hepatic microsomal 11β HSD1 assays is in the micromolar range [31, 32]. Even though 175 nM substrate is well below the apparent Km, it may not be possible to increase the concentration significantly for two reasons:

(i) If the compounds are competitive with cortisone, the measured inhibiton will fall if the substrate is increased above the concentration used in Reference [14].

Figure 19:
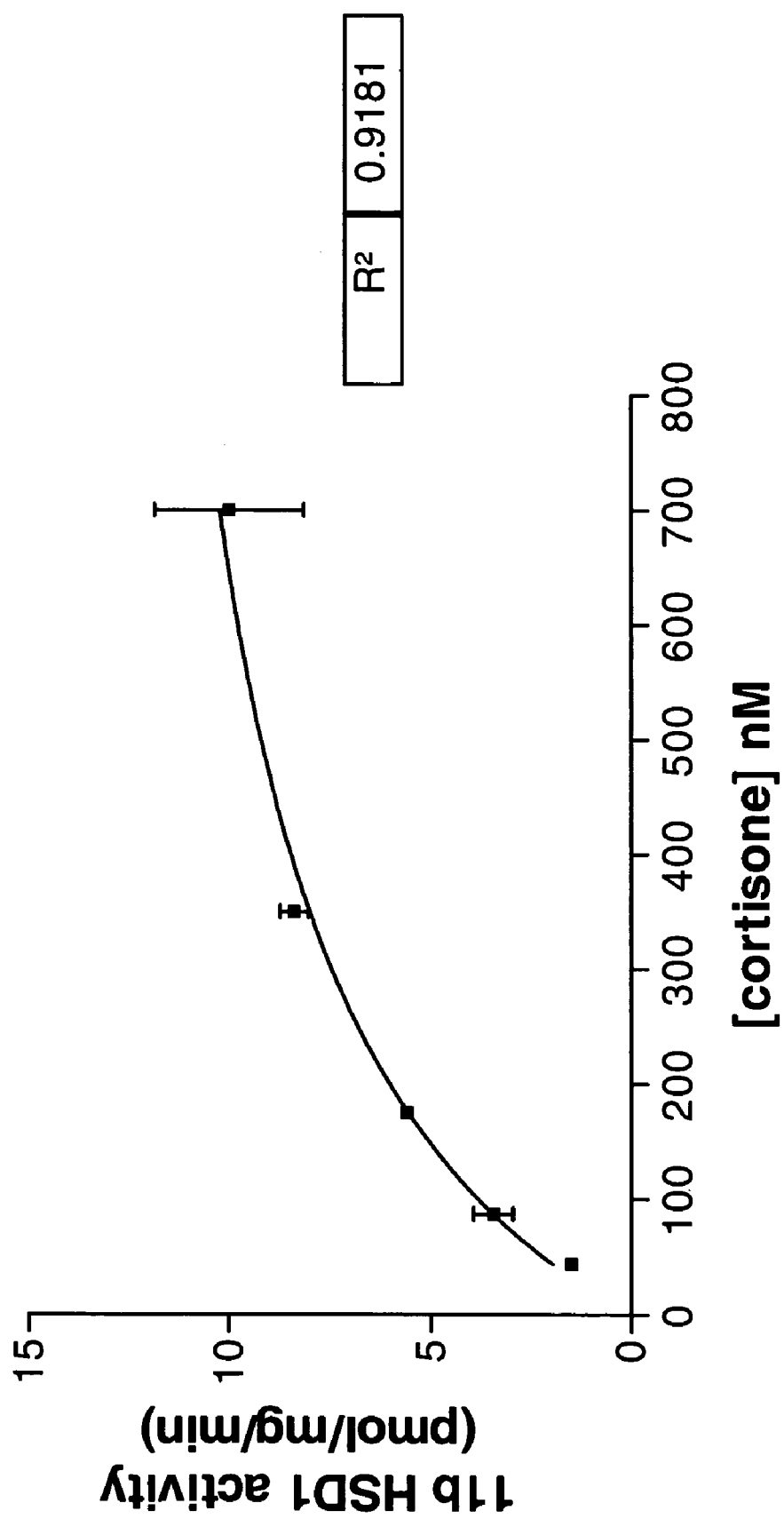
FIG. 19 is a graph showing the substrate saturation curve for human hepatic microsomal 11β HDS1 activity detected by RIA.

(ii) Increasing the substrate will reduce the specific activity of the label, reducing the CPM and the sensitivity of the assay—this could be overcome by adding higher concentrations of $^3$H-cortisone FIG. 19 (Substrate Saturation Curve for Human Hepatic Microsomal 11β HDS1 Activity Detected by RIA)

The substrate saturation effects were examined in the next assay. The enzyme assay was carried out exactly as indicated in the methods section in buffer 3 with 10 µg/well microsomal protein and with [cold cortisone] as indicated. 3H-cortisone was 0.5 µCi/sample throughout. The reaction was stopped after 30 min by the addition of 10 µl stop solution. The RIA was carried out exactly as indicated in the methods section. Results are shown in FIG. 19.

Inspection of the data shown in FIG. 19 shows that 10 µg microsomal protein is not saturated with 175 nM cortisone over an incubation period of 30 mins. The apparent Km (700 nM), determined from the Lineweaver-Burke plot of these data shown in FIG. 20 is very similar to that determined in the classical 11β HSD1 assay (FIG. 6, apparent Km~660 nM).

Figure 20:
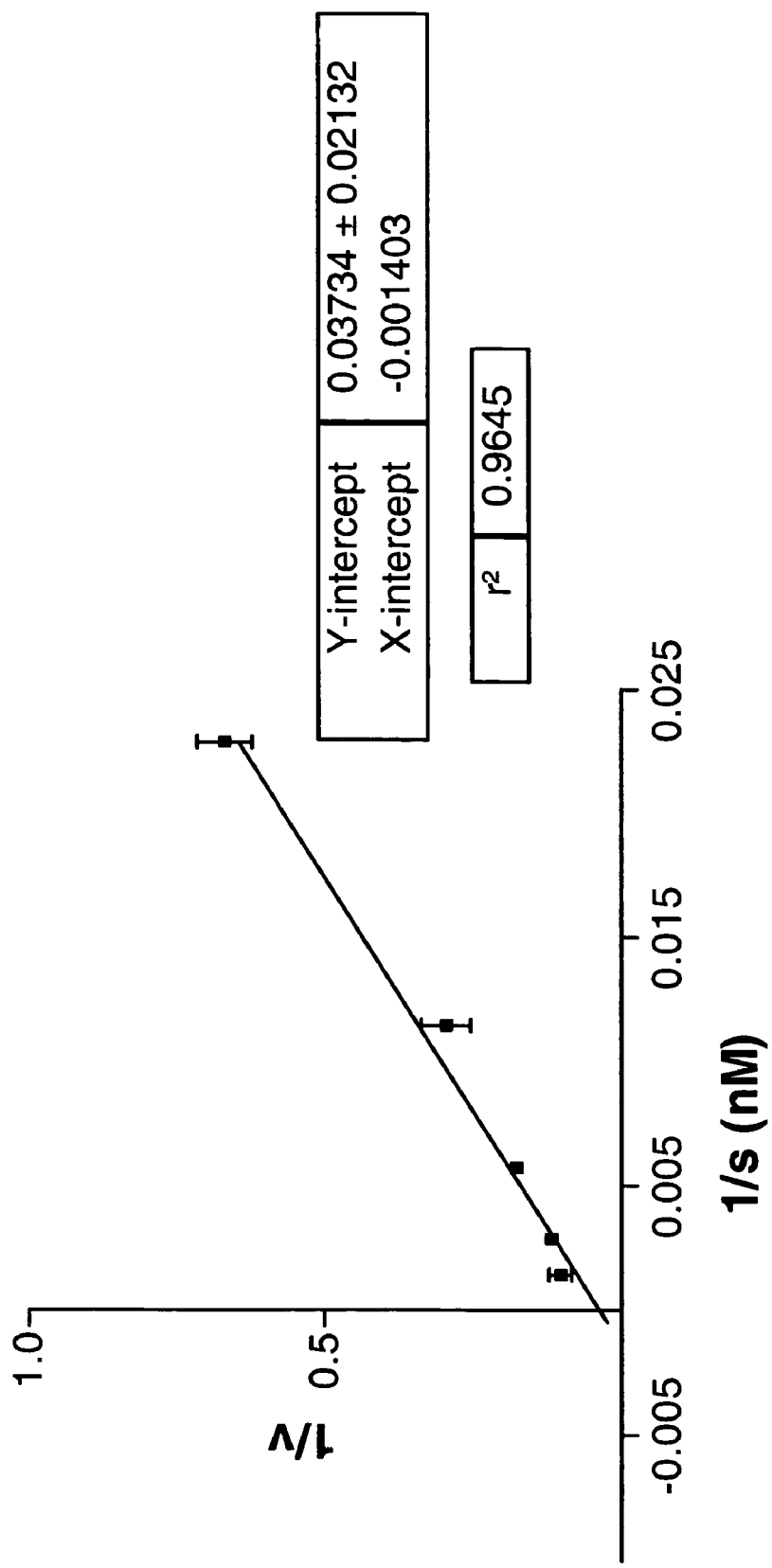
FIG. 20 is a Lineweaver-Burke plot

FIG. 20 (Lineweaver-Burke Plot)

Lowering the microsomal protein concentration or the incubation time to fit well within the linear range would partly overcome the problem, but both adjustments would decrease the assay sensitivity. All of the tests carried out so far suggest that even if increasing the microsomal, protein from 10 µg/sample to 20 µg/sample does not result in a doubling of enzyme activity, decreasing it from 10 µg/sample to 5 µg/sample does result in a twofold decrease in enzyme activity. Since the purpose of the assay is to monitor inhibitory effects of compounds it is probably a better course of action to leave the assay parameters as they are.

Figure 21:
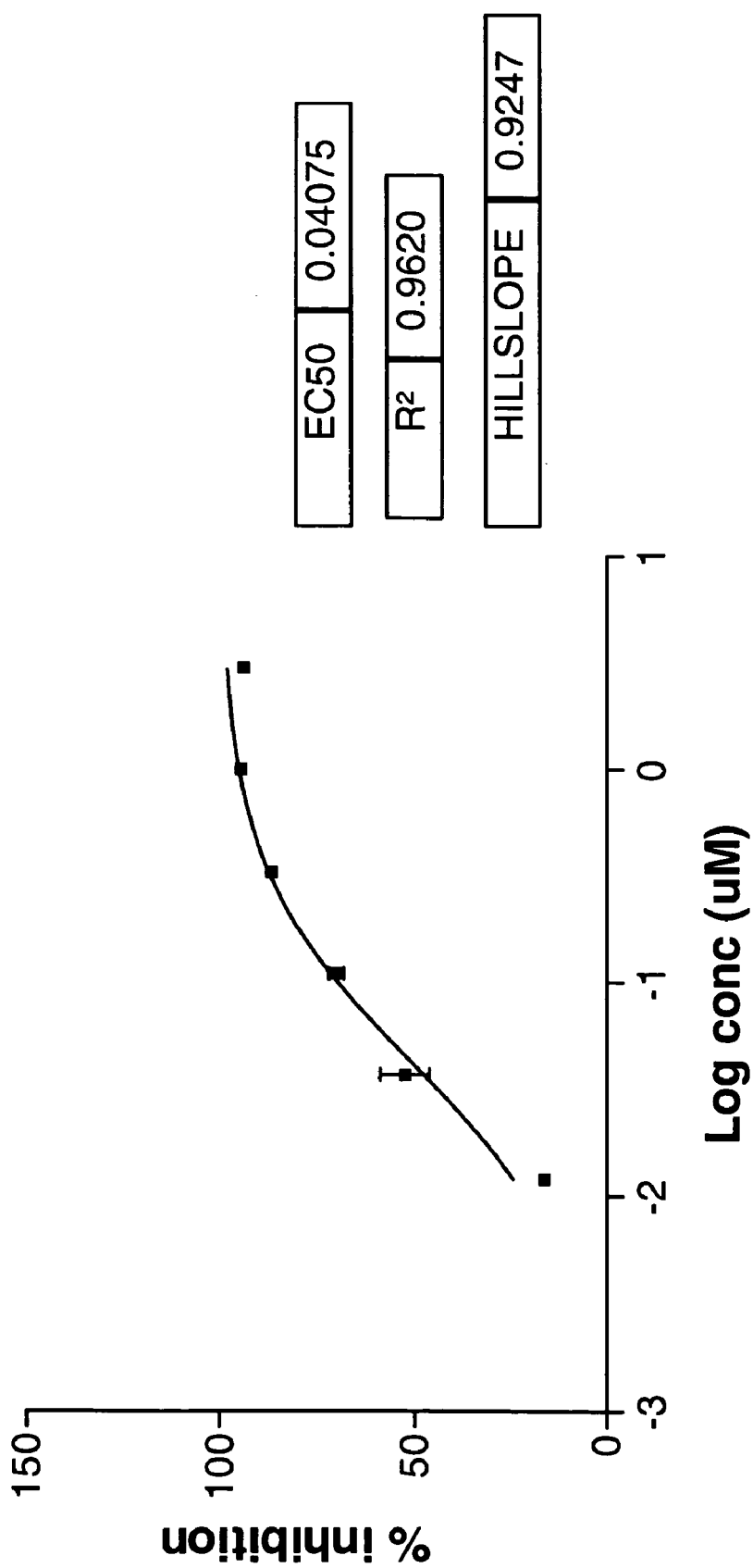
FIG. 21 is an IC$_{50}$ curve for inhibition of human hepatic microsomal 11β HSD1 activity by Glycyrrhetinic acid.

FIG. 21 ($IC_{50}$ Curve for Inhibition of Human Hepatic Microsomal 11β HSD1 Activity by Glycyrrhetinic Acid)

In order to assess the quality of compound inhibition data obtained in this assay format, an $IC_{50}$ for Glycyrrhetinic acid was determined in the next test. A 10 mM stock solution of Glycyrrhetinic acid was prepared in 100% DMSO and was further diluted in 100% DMSO to 0.3 mM. This solution was serially diluted in 100% DMSO 1 in 3 to obtain the test range and each solution was diluted in assay buffer (Buffer 3) 1 in 25. These solutions were diluted into the final enzyme reaction 1 in 4 to give assay concentrations from 3 µM down to 0.012 µM in a final [DMSO] of 1%. Controls, NSB (no antibody) and GA blanks (addition of 10 µl stop solution prior to the addition of microsomes) were included with and without the addition of 1% DMSO. Human hepatic microsomal protein was tested at 10 µg/well and the substrate concentration (cortisone) was 175 nM, 0.5 µCi/well. All other procedures were as indicated in the methods section. GA inhibition data are shown in FIG. 21.

The assay control and blank CPM are given in the Table below.

TABLE

Control and blank CPM obtained in the Glycyrrhetinic acid $IC_{50}$ assay showing effect of 1% DMSO and signal to noise ratio obtained.

| Group | 1% DMSO | No DMSO |
| --- | --- | --- |
| NSB | 670 | 661 |
| GA blank | 640 | 660 |
| Control | 3515 | 2583 |
| Signal to noise | 5 fold | 4 fold |

Conclusion

Glycyrrhetinic acid gives a concentration-related inhibition of the enzyme with reasonable fit values ($r^2$=0.962) and Hillslope (FIG. 21).

In th eclassical enzyme assay (FIG. 7) an $IC_{50}$ of nm was determined for this inhibitor, which is similar to the data given in FIG. 21

Glycyrrhetinic acid inhibition of human hepatic microsomal 11β HSD1 using dehydro-dexamethasone as the substrate has ben reported to have an $IC_{50}$ of 30 nM [32]

However, the compound appears more active than suggested by Barf et al., (2002) [14]

Inclusion of DMSO at 1% in the enzyme assay does not affect NSB or blank values but may slightly increase enzyme activity and the signal to noise ratio These data suggest that RIA detection of 11β HSD1 activity can generate acceptable compound inhibition data.

Figure 22:
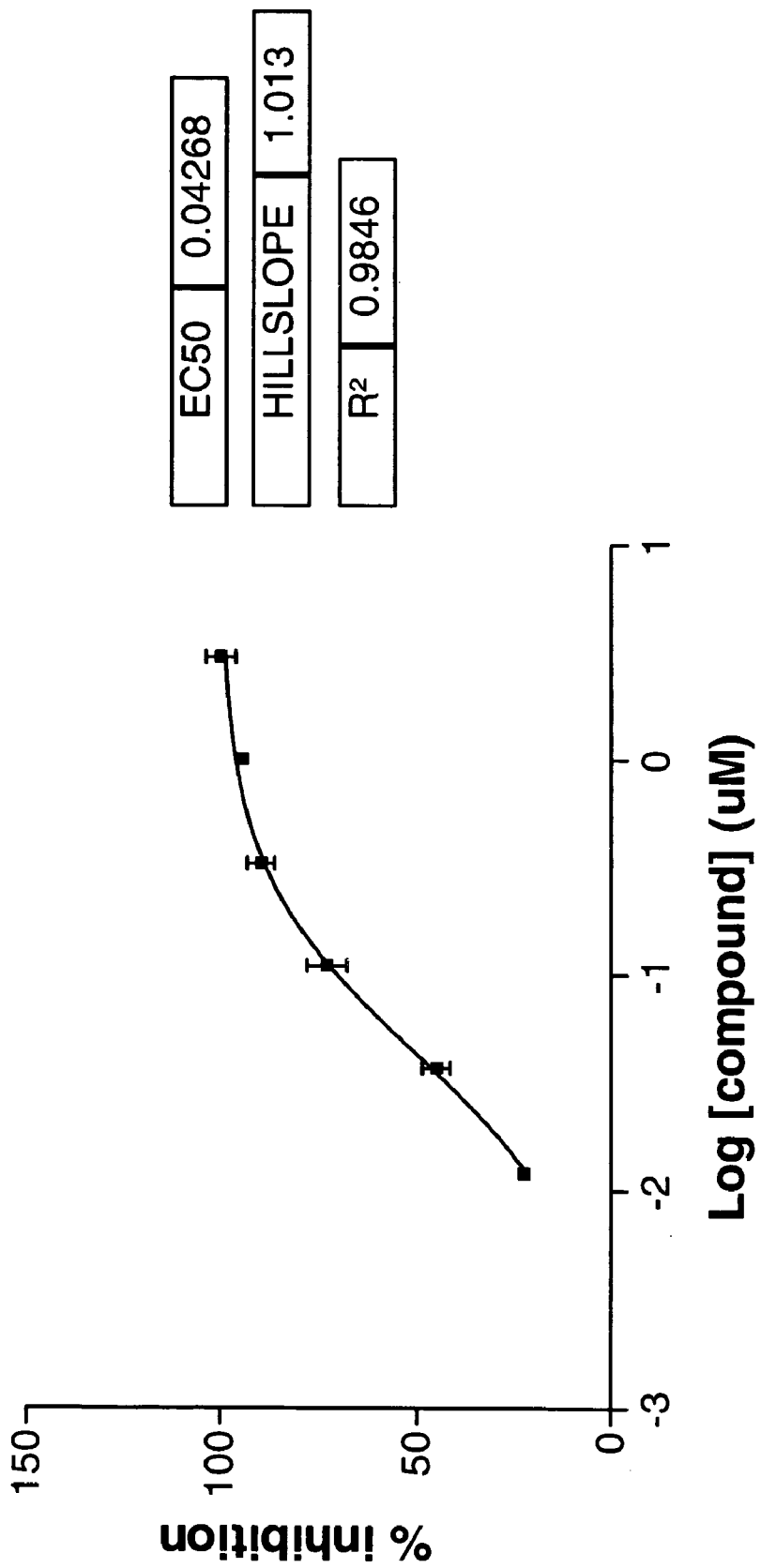
FIG. 22 is an IC$_{50}$ curve for inhibition of human hepatic microsomal 11β HSD1 activity by Glycyrrhetinic acid in the presence of 350 nM cortisone.
Figure 23:
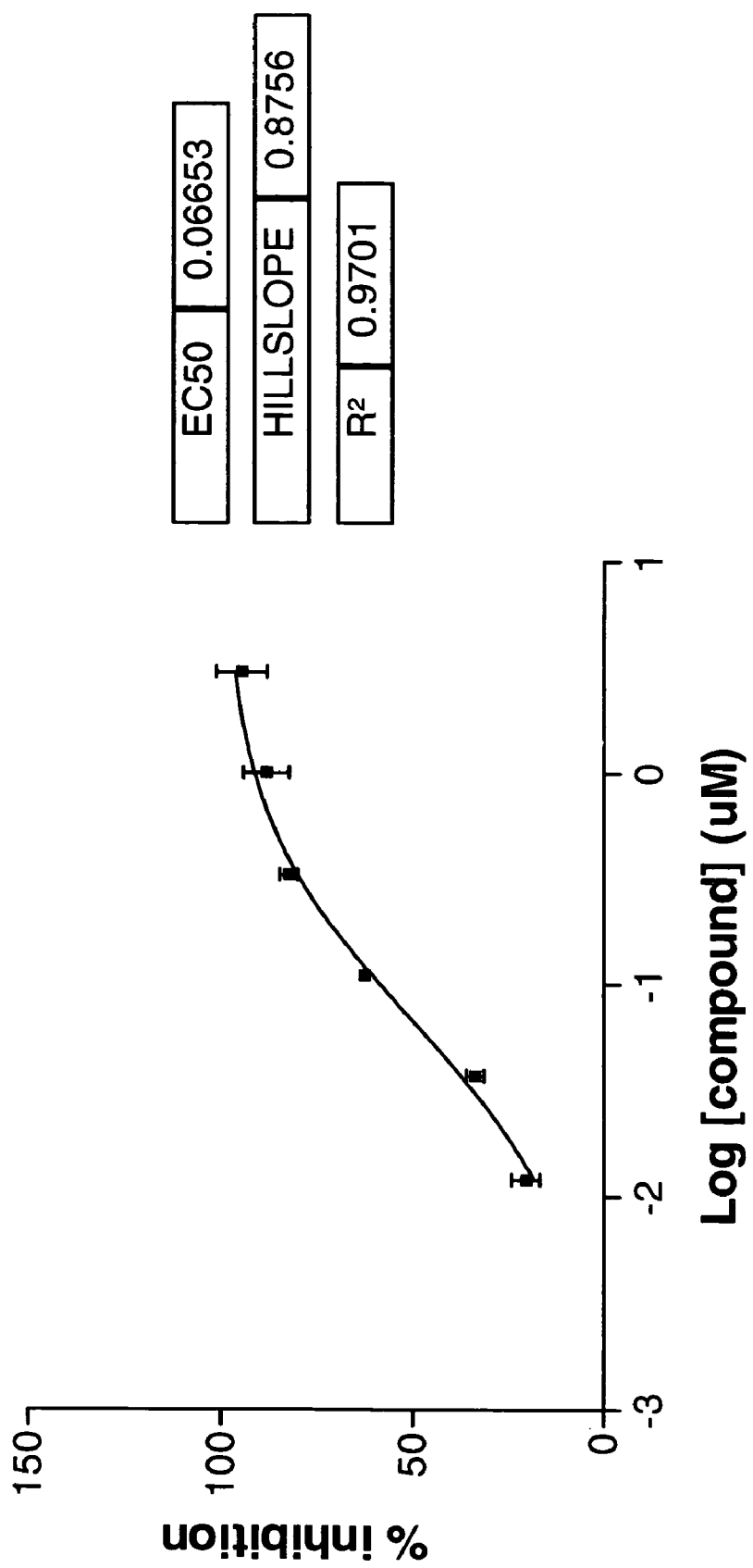
FIG. 23 is an IC$_{50}$ curve for inhibition of human hepatic microsomal 11β HSD1 activity by Carbenoxolone in the presence of 350 nM cortisone.

FIG. 22 ($IC_{50}$ Curve for Inhibition of Hepatic Micromisal 11β HSD1 Activity by Glycyrrhetinic Acid in the Presence of 350 nM Cortisone) and FIG. 23 ($IC_{50}$ curve for Inhibition of Human Microsomal 11β HSD1 Activity by Carbenoxolone in the Presence of 350 nM Cortisone In the next experiment, Glycyrrhetinic acid and its hemisuccinate ester, carbenoxolone, were tested for $IC_{50}$ determination. In view of the higher than expected inhibitory activity obtained with Glycyrrhetinic acid (FIG. 22 in the last test and the apparent non-saturation obtained with 175 nM cortisone (FIG. 19), the substrate concentration was increased to 350 nM (0.5 µci/well). In addition, the final DMSO concentration was reduced to 0.3%. The assay was performed as indicated in the Methods in RIA buffer. Results with some of these compounds are shown in FIG. 22 and FIG. 23.

Conclusion (FIG. 22):

Increasing the substrate concentration and decreasing the DMSO concentration has little effect on Glycyrrhetinic acid inhibitory activity.

Conclusion (FIG. 23):

Even in the presence of a higher concentration of cortisone, carbenoxolone is about 5 times more active than is suggested Barf et al. [14]. This could be due to an effect of the buffer system used here (Buffer 3) since it differs from that Barf et al., [14] (Buffer 1). This compound was less active ($IC_{50}$ of 119 nM) in the classical enzyme assay, which used the buffer described by Barf et al. [14] (FIG. 8).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

REFERENCES

1. Hammond, G H (1990): Molecular properties of corticosteroid binding globulin and sex-steroid binding proteins. Endocr. Rev. 11, 65-79.
2. Gomez-Sanchez E P, Gomex-Sanchez C E (1997): First there was one, then two . . . why not more 11 β-Hydroxysteroid Dehydrogenases? Endocrinology vol. 138, 12.
3. Krozowski Z S, Funder J W (1983): Renal mineralocorticosterone receptors and hippocampal corticosterone binding species have identical intrinsic steroid specificity Proc. Natl. Sci. USA 80: 6056-60
4. Ulick S, Levine L S, Gunczler P, Zanconato G, Rarnirez L C, Rauh W, Rosler A, Bradlow H L, Mew M I (1979): A syndrome of apparent mineralocorticoid excess associated with defects in the peripheral metabolism of cortisol. J. Clin. Endo. And Metab. 49: 757-64.
5. Edwards C R W, Stewart P M, Burt D, Brett L, Mcintyre M A, Sutanto W S, Kloet E R, Monder C (1998): Localisation of 11 β-HSD-tissue specific protector of the mineralocorticoid receptor. Lancet 2: 986-989.
6. Moore C C D, Melloh S H, Murai I, Siiteri P K, Miller W L (1993): Structure and function of the hepatic form of 11β-HSD in the squirrel monkey, an animal model of glucocorticoid resistance. Endocrinology 133: 368-375.
7. Kotelevtsev Y V, larnieson P M, Best R, Stewart F, Edwards C R W, Seckl J R, Mullins II (1996): Inactivation of 11 β-HSD type 1 by gene targeting in mice. Endocrinology Res. 22: 791-792.
8. Ricketts M L, Verhaeg J M, Bujalska I, Howie A J, Rainey W E, Stewart P M (1998): Immunohistochemicallocalisation of type 11 β-HSD in human tissues. I. Clin. Endoc. Metab. 83: 1325-35.
9. Stewart P M, Sheppard M C (1992): Novel aspects ofhormone action: intracellular ligand supply and its control by a series of tissue specific enzymes. Molecular and Cellular Endocrinology 83: C13-C18.
10. Seckl J R, Chapman K E (1997): The 11 β-HSD system, a determinant of glucocorticoid and mineralocorticoid action. Medical and physiological aspects. European I. Biochem. 249: 361-364.
11. Maser E (1998): 11 β-HSD responsible for carbonyl reduction of the tobacco-specific nitrosoamine in mouse lung microsomes. Cancer Res. 58: 2996-3003.
12. Walker B R, Stewart P M, Shackleton C H L, Padfield P L, Edwards C R W (1993): Deficient inactivation of cortisol by 11β-HSD in essential hypertension. Clin. Endocr. 38: 221-227.
13. Daynes R A, Araneo B A (1998): Contrasting effects of glucocorticoids on the capacity of T-cells to produce the growth factors interleukin-2 and interleukin-4. Eur. J. Immunol. 19: 2319-2324.
14. Barf, T. et al., (2002), Arylsulfonamidothiazoles as a new class of potential antidiabetic drugs. Discovery of potent and selective inhibitors of the 11β-Hydroxysteroid Dehydrogenase Type 1. J. Med. Chem., 45, 3813-3815.
15. Matassa, Victor G. et. al. *J. Med. Chem.*; 33(9); 1990; 2621.
16. This compound is synthesized in the literature and the NMR spectrum is reported, however the spectrum obtained here differs from that in the literature. Baraldi, Pier Giovanni et. al.; *Bioorg. & Med. Chem. Lett.*; 10; 2002, 1611.
17. Horaguchi, Takaaki; Matsuda, Shinichi; Tanemura, Kiyoshi; Suzuki, Tsuneo. *J. Heterocyclic Chem.*; 24; 1987; 965.
18. Plé, Patrick A., Marnett, Lawrence J.; *J. Heterocyclic Chem.*; 25; 1988; 1271.
19. Rao, U. and Balasubramanian, K.K.; *Tetrahedron Lett.*; 24; 1983; 5023.
20. Bordwell, F. G. and Stange, Hugo; *J. Amer. Chem. Soc.*; 77; 1955; 5939.
21. Elderfield, Robert C.; Williamson, Thurmond A.; Gensler, Walter J.; Kremer, Chester B.; *J. Org. Chem;* 12; 1947; 405.
22. For 6-nitro-2,3-dimethylquinoxaline see: Barluenga, Jose; Aznar, Fernando; Liz, Ramon; Cabal, Maria-Paz; *Synthesis;* 3; 1985; 313, then for 6-amino-2,3-dimethylquinoxaline: Salon, Jozef; Milata, Viktor; Pronayova, Nadezda; Lesko, Jan; *Collect. Czech. Chem. Commun.;* 66; 11; 2001; 1691.
23. Klicnar, J.; and Kosek, F.; *Collect. Czech. Chem. Commun.;* 30; 1965; 3102.
24. Gloster, Daniel F.; Cincotta, Louis; Foley, James W.; *J. Heterocyclic Chem.*; 36; 1999; 25.
25. The same reduction was carried out using $SnCl_2$ by: Case et al.; *J. Amer. Chem. Soc.;* 81; 1959; 6297.
26. Modified procedure from similar compound described in U.S. Pat. No. 6,355,796 (Example 20)
27. Hollfelder, F.; Kirby, A. J.; Tawfik, D. S.; Kikuchi, K.; Hilvert, D.; *J. Amer. Chem. Soc.;* 122 (6); 2000; 1022-1029
28. Fujimoto, M.; Okabe, K.; Chem. Pharm. Bull.; 10; 1962; 572-575.
29: Kawamura, T.; Yagi, N.; Sugawara, H.; Yamahata, K.;. Takada, M.; Chem.Pharm.Bull.; 28; 1; 1980; 268-276.
30. Stewart, P. M. and Mason, J. I., (1995), Cortisol to cortisone: Glucocorticoid to mineralocortcoid. Steriods, 60,143-146.
31. Escher, G. et al., (1995), Furosemide inhibits 11 β-Hydroxysteroid Dehydrogenase in vitro and in vivo. Endocrinology, 136, 1759-1765.
32. Hult, M. et. al., (1998), Selective inhibition of human type 11β-hydroxysteroid dehydrogenase by synthetic steroids and xenobiotics. FEBS Letters, 441, 25-28.
33. Diederich S, Grossmann C, Hanke B, Quinkler M, Herrrnann M, Bahr V, Oelkers W (2000): In the search for specific inhibitors ofhuman 11β-HSD: chenodeoxycholic acid selectively inhibits 11β-HSD type 1. Europ. J. Endocrin. 142: 200-207.

The invention claimed is:
1. A compound having Formula

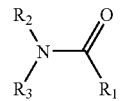

Wherein
$R_1$ is an optionally substituted phenyl ring wherein the optional substituents are selected from hydrocarbon groups, oxyhydrocarbon groups, halogens, amines and amides; $R_2$ is an optionally substituted aromatic ring of formula

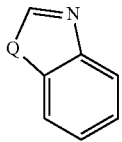

wherein the optional substituents are selected from alkyl groups, oxyalkyl groups, halogens, amines and amides; and $R_3$ is selected from H and $C_{1-10}$ alkyl;

Q is an atom selected from the group consisting of S and O; or a salt thereof.

2. A compound according to claim 1, wherein $R_1$ is substituted.

3. A compound according to claim 1, wherein is $R_1$ is substituted with one or more substituents selected from phenyl groups, $C_{1-5}$ alkyl groups, oxy- $C_{1-5}$ alkyl groups, chloro and bromo.

4. A compound according to claim 1, wherein the optionally substituted aromatic ring of $R_2$ is a heterocyclic ring.

5. A compound according to claim 1 wherein the optionally substituted aromatic ring of $R_2$ is a heterocyclic ring comprising a carbon and a hetero atom selected form O and N.

6. A compound according to claim 1, wherein $R_2$ is

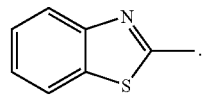

7. A compound according to claim 1 wherein $R_3$ is selected from H and $C_{1-5}$ alkyl groups.

8. A compound according to claim 1 wherein $R_3$ is H.

9. A pharmaceutical composition comprising a compound according to claim 1 optionally admixed with a pharmaceutically acceptable carrier, diluent, excipient or adjuvant.

10. A compound according to claim 1 which is one of:
N-(2-methylbenzothiazol -5-yl)-4-propylbenzamide;
3,5-dichloro-N-(2-methylbenzothiazol-5-yl)-benzamide;
N-methyl-N-(2-methylbenzothiazol-5-yl)-4-propylbenzamide;
3,5-dichloro-N-(4-chloro-2-methyl-benzothiazol-5-yl)-benzamide;
N-(4-chloro-2-methyl-benzothiazol-5-yl)-4-propyl-benzamide;
biphenyl-4-carboxylic acid (4-chloro-2-methyl-benzothiazol-5-yl)-amide;
2,5-dichloro-N-(4-chloro-2-methyl-benzothiazol-5-yl)-benzamide;
N-(4-chloro-2-methyl-benzothiazol-5-yl)-3-methoxybenzamide; or
N-(4-chloro-2-methyl-benzothiazol-5-yl)-4-methoxybenzamide.

* * * * *